US012383570B2

(12) United States Patent
Duval et al.

(10) Patent No.: US 12,383,570 B2
(45) **Date of Patent: *Aug. 12, 2025**

(54) METHODS OF SELECTIVELY MODULATING GASTROINTESTINAL MICROBIAL GROWTH

(71) Applicant: DSM IP Assets B.V., Heerlen (NL)

(72) Inventors: Stephane Duval, Carspach (FR); John Michael Geremia, Watertown, MA (US); Lisa Ann Laprade, Dedham, MA (US); April Waguespack-Levy, Ankeny, IA (US); Estefania Perez Calvo, Rosenau (FR); Ghislain Schyns, Waltham, MA (US); Viviane Verlhac, Dietwiller (FR); Joshua Thomas Claypool, Cambridge, MA (US)

(73) Assignee: DSM IP Assets B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 18/420,540

(22) Filed: Jan. 23, 2024

(65) Prior Publication Data

US 2024/0293437 A1 Sep. 5, 2024

Related U.S. Application Data

(63) Continuation of application No. 17/292,132, filed as application No. PCT/US2019/060488 on Nov. 8, 2019, now Pat. No. 11,911,405.

(60) Provisional application No. 62/757,439, filed on Nov. 8, 2018, provisional application No. 62/757,438, filed on Nov. 8, 2018.

(51) Int. Cl.

| | |
|---|---|
| ***A61K 31/702*** | (2006.01) |
| ***A23K 20/163*** | (2016.01) |
| ***A23K 50/30*** | (2016.01) |
| ***A23K 50/75*** | (2016.01) |

(52) U.S. Cl.

CPC .......... *A61K 31/702* (2013.01); *A23K 20/163* (2016.05); *A23K 50/30* (2016.05); *A23K 50/75* (2016.05)

(58) Field of Classification Search

None

See application file for complete search history.

(56) References Cited

U.S. PATENT DOCUMENTS

| | | | |
|---|---|---|---|
| 2011/0061645 | A1 | 3/2011 | Fosdick |
| 2016/0007642 | A1 | 1/2016 | Geremia |
| 2016/0213702 | A1 | 7/2016 | Von Maltzahn |
| 2016/0366909 | A1 | 12/2016 | Geremia |
| 2018/0000146 | A1 | 1/2018 | Geremia |

FOREIGN PATENT DOCUMENTS

| | | |
|---|---|---|
| WO | 2017/125929 | 7/2017 |

OTHER PUBLICATIONS

International Search Report issue in International Application No. PCT/US2019/060488, dated Feb. 6, 2020 (4 pages).

Written Opinion issue in international Application No. PCT/US2019/060488, dated Feb. 6, 2020 (7 pages).

*Primary Examiner* — Dale R Miller

(74) *Attorney, Agent, or Firm* — Nixon & Vanderhye P.C.

(57) ABSTRACT

Methods of feeding animals are disclosed wherein providing feed additives are provided that modulate the gut microbiome to improve the health, nutrition, and growth performance. Methods of modulating the microbial species present in the gastrointestinal tract of an animal are also disclosed. Such modulation includes, for example, modulating the level or function of microbial species.

9 Claims, 37 Drawing Sheets

Levoglucosane
CAS 498-07-7

1,6-anhydro-β-D Glucofuranose
CAS 7425-74-3,

Anhydro-cellobiose,

Anhydro DP2

Anhydro DP1

DP2

DP2

Anhydro DP1

Anhydro DP2

1,6-Anhydro-beta-D-glucofuranose 1,6-Anhydro-beta-D-glucopyranose

METHODS OF SELECTIVELY MODULATING GASTROINTESTINAL MICROBIAL GROWTH

RELATED APPLICATIONS

This application is a continuation of U.S. application Ser. No. 17/292,132 filed on May 7, 2021 (now U.S. Pat. No. 11,911,405), which in turn is a U.S. National Stage Application of International Application No. PCT/US2019/060488, filed Nov. 8, 2019, which claims the benefit of U.S. Provisional Patent Application No. 62/757,438 filed on Nov. 8, 2018, and U.S. Provisional Patent Application No. 62/757,439 filed on Nov. 8, 2018, the entire contents of which are hereby expressly incorporated by reference herein.

BACKGROUND

Global population growth places continuous pressure on agriculture and animal farming to improve the yield and sustainability of animal production. Meeting this demand requires continuous improvements to the growth performance of animals raised for protein. For example, increasing the feed efficiency of an animal allows the animal to achieve the same weight or productivity while consuming less feed than a comparable animal with lower feed efficiency. Since the production of feed requires the consumption of resources and energy to obtain, formulate, and transport its ingredients, improving animal growth performance reduces the amount of resources and energy required to grow the animal. Furthermore, since feed is the largest cost of raising animals, improved feed efficiency provides an economic advantage to the producer.

Feed additives have been developed to improve the body weight gain and feed efficiency of animals. For example, antibiotic growth promoters (AGPs) saw widespread use for their ability to increase weight gain and feed efficiency. However, increasing regulatory and consumer pressure have moved the animal production industry away from antibiotic feed additives, which exhibit a poor sustainability profile. In particular, non-therapeutic use of antibiotics contributes to increased microbial resistance and multi-drug-resistant strains of dangerous pathogens.

Direct fed microbials (DFMs) have been explored by the animal production industry as an alternative to AGPs. Unlike antibiotics, DFMs attempt to support the host animal by providing probiotic species that exert a positive influence on the animal's digestive system. DFMs, such as commensal bacteria or yeasts, are generally restricted to spore-forming microbes so that they can withstand formulation into a dry product and incorporation into conventional feed manufacturing processes. It is however, challenging to formulate probiotic organisms into dry product forms without compromising the viability of the active strains. The resulting dose variability, i.e. the number of viable organisms delivered to the digestive track, translates to inconsistent performance under commercial production conditions. Furthermore, many of the most prominent commensal gastrointestinal microbes, i.e., taxa with the greatest beneficial impact on growth performance, are either non-spore forming or unculturable, making it essentially impossible to form them into a stable feed additive.

Thus, there is a need for novel feed additives and nutritional compositions that improve animal growth, feed efficiency, and health, including feed additives that promote growth of beneficial gastrointestinal microbes not readily formulated into DFM animal feed additives or inhibit the growth of detrimental gastrointestinal microbes.

SUMMARY

In one aspect, provided herein are methods of increasing the body weight of an animal, the method comprising: administering a nutritional composition comprising a base nutritional composition and a synthetic oligosaccharide preparation to an animal, wherein said synthetic oligosaccharide preparation comprises at least n fractions of oligosaccharides each having a distinct degree of polymerization selected from 1 to n (DP1 to DPn fractions), wherein n is an integer greater than 3; and wherein each of a DP1 and DP2 fraction independently comprises from about 0.5% to about 15% of anhydro-subunit containing oligosaccharides by relative abundance as determined by mass spectrometry, and wherein the body weight of said animal is increased relative to the body weight of said animal prior to said administering said nutritional composition to said animal, and wherein the increase in the body weight of said animal is a larger increase relative to an increase in body weight of a comparable control animal administered a comparable nutritional composition lacking said oligosaccharide preparation.

In some embodiments, said body weight of said animal is at least 10 g, 20 g, 30 g, 40 g, 50 g, 60 g, 70 g, 80 g, 90 g, or 100 g higher than said body weight of said animal prior to administration of said nutritional composition comprising said synthetic oligosaccharide preparation.

In some embodiments, said body weight of said animal is at least at least 10 g, 20 g, 30 g, 40 g, 50 g, 60 g, 70 g, 80 g, 90 g, or 100 g higher than said body weight of said animal prior to administration of said nutritional composition comprising said synthetic oligosaccharide preparation, as measured after at least 30 days, 35 days, 40 days, 45 days, 50 days, 60 days, 70 days, 80 days, or 90 days after first administration of said nutritional composition comprising said synthetic oligosaccharide preparation, and wherein said animal ingests said nutritional composition at least once during every twenty-four-hour period.

In some embodiments, said nutritional composition comprising said synthetic oligosaccharide preparation is administered to said animal for at least 1, 7, 10, 14, 30, 45, 60, 90, or 120 days.

In some embodiments, said nutritional composition comprising said synthetic oligosaccharide preparation is administered to said animal at least once, twice, three, four, or five times a day.

In some embodiments, said administering comprises providing said nutritional composition to said animal to ingest at will.

In some embodiments, said animal ingests at least a portion of said nutritional composition in over at least 1, 2, 3, 4, 5, 6, 7, 8, 9, 10, 20, 30, 40, 50, 60, 90, or 120 twenty-four-hour periods.

In some embodiments, said nutritional composition comprises at least 100 ppm, 200 ppm, 300 ppm, 400 ppm, 500 ppm, 600 ppm, 700 ppm, 800 ppm, 900 ppm, 1000 ppm, 1500 ppm, or 2000 ppm oligosaccharide preparation. In some embodiments, said nutritional composition comprises about 100 ppm, 200 ppm, 300 ppm, 400 ppm, 500 ppm, 600 ppm, 700 ppm, 800 ppm, 900 ppm, 1000 ppm, 1500 ppm, or 2000 ppm oligosaccharide preparation. In some embodiments, said nutritional composition comprises about 500 ppm oligosaccharide preparation. In some embodiments, said nutritional composition comprises from about 100 ppm-2000 ppm, 100 ppm-1500 ppm, 100 ppm-1000 ppm, 100 ppm-900 ppm, 100 ppm-800 ppm, 100 ppm-700 ppm, 100 ppm-600 ppm, 100 ppm-500 ppm, 100 ppm-400 ppm, 100 ppm-300 ppm, 100 ppm-200 ppm, 200 ppm-1000 ppm, 200 ppm-800 ppm, 200 ppm-700 ppm, 200 ppm-600 ppm, 200 ppm-500 ppm, 300 ppm-1000 ppm, 300 ppm-700 ppm, 300 ppm-600 ppm, or 300 ppm-500 ppm oligosaccharide preparation. In some embodiments, said nutritional composition comprises from about 300 ppm-600 ppm oligosaccharide preparation.

In some embodiments, said animal is a poultry, seafood, sheep, cow, cattle, buffalo, bison, pig, cat, dog, rabbit, goat, guinea pig, donkey, camel, horse, pigeon, ferret, gerbil, hamster, mouse, rat, fish, or bird. In some embodiments, said animal is poultry. In some embodiments, said animal is a chicken, turkey, duck, or goose. In some embodiments, said chicken is a broiler chicken, a layer chicken, or a breeder chicken. In some embodiments, said animal is a pig. In some embodiments, said pig is a nursery pig, a grower pig, or a finisher pig. In some embodiments, said animal is a fish. In some embodiments, said fish is a salmon, a tilapia, or a tropical fish.

In some embodiments, said nutritional composition is an animal feed composition. In some embodiments, said base nutritional composition is base animal feed.

In some embodiments, said relative abundance is determined by LC-MS/MS.

In some embodiments, said relative abundance of oligosaccharides in at least 5, 10, 20, or 30 DP fractions decreases monotonically with its degree of polymerization. In some embodiments, said relative abundance of oligosaccharides in each of the n fractions decreases monotonically with its degree of polymerization.

In some embodiments, n is at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100.

In some embodiments, said DP2 fraction comprises less than 12%, less than 11%, less than 10%, less than 9%, less than 8%, less than 7%, less than 6%, less than 5%, less than 4%, less than 3%, less than 2%, or less than 1% anhydro-subunit containing oligosaccharides by relative abundance.

In some embodiments, said DP2 fraction comprises from about 5% to about 10% of anhydro-subunit containing oligosaccharides by relative abundance. In some embodiments, said DP2 fraction comprises from about 1% to about 10% of anhydro-subunit containing oligosaccharides by relative abundance. In some embodiments, said DP2 fraction comprises from about 0.5% to about 10% of anhydro-subunit containing oligosaccharides by relative abundance. In some embodiments, said DP2 fraction comprises from about 2% to about 12% of anhydro-subunit containing oligosaccharides by relative abundance.

In some embodiments, said DP1 fraction comprises less than 12%, less than 11%, less than 10%, less than 9%, less than 8%, less than 7%, less than 6%, less than 5%, less than 4%, less than 3%, less than 2%, or less than 1% anhydro-subunit containing oligosaccharides by relative abundance. In some embodiments, said DP1 fraction comprises from about 2% to about 12% of anhydro-subunit containing oligosaccharides by relative abundance. In some embodiments, said DP1 fraction comprises from about 1% to about 10% of anhydro-subunit containing oligosaccharides by relative abundance.

In some embodiments, said DP1 fraction comprises from about 0.5% to about 10% of anhydro-subunit containing oligosaccharides by relative abundance. In some embodiments, said DP1 fraction comprises from about 5% to about 10% of anhydro-subunit containing oligosaccharides by relative abundance.

In some embodiments, said DP3 fraction comprises less than 15%, less than 12%, less than 11%, less than 10%, less than 9%, less than 8%, less than 7%, less than 6%, less than 5%, less than 4%, less than 3%, less than 2%, or less than 1% anhydro-subunit containing oligosaccharides by relative abundance. In some embodiments, said DP3 fraction comprises from about 2% to about 12% of anhydro-subunit containing oligosaccharides by relative abundance. In some embodiments, said DP3 fraction comprises from about 1% to about 10% of anhydro-subunit containing oligosaccharides by relative abundance. In some embodiments, said DP3 fraction comprises from about 0.5% to about 10% of anhydro-subunit containing oligosaccharides by relative abundance. In some embodiments, said DP3 fraction comprises from about 5% to about 10% of anhydro-subunit containing oligosaccharides by relative abundance.

In some embodiments, said oligosaccharide preparation comprises from about 2% to about 12% anhydro-subunit containing oligosaccharides by relative abundance. In some embodiments, said oligosaccharide preparation comprises from about 0.5% to about 10% anhydro-subunit containing oligosaccharides by relative abundance. In some embodiments, said oligosaccharide preparation comprises from about 1% to about 10% anhydro-subunit containing oligosaccharides by relative abundance. In some embodiments, said oligosaccharide preparation comprises from about 5% to about 10% anhydro-subunit containing oligosaccharides by relative abundance.

In some embodiments, said DP2 fraction comprises greater than 0.6%, greater than 0.8%, greater than 1.0%, greater than 1.5%, greater than 2%, greater than 3%, greater than 4%, greater than 5%, greater than 6%, greater than 7%, greater than 8%, greater than 9%, greater than 10%, greater than 11%, or greater than 12% anhydro-subunit containing oligosaccharides by relative abundance.

In some embodiments, said DP1 fraction comprises greater than 0.6%, greater than 0.8%, greater than 1.0%, greater than 1.5%, greater than 2%, greater than 3%, greater than 4%, greater than 5%, greater than 6%, greater than 7%, greater than 8%, greater than 9%, greater than 10%, greater than 11%, or greater than 12% anhydro-subunit containing oligosaccharides by relative abundance.

In some embodiments, said DP3 fraction comprises greater than 0.6%, greater than 0.8%, greater than 1.0%, greater than 1.5%, greater than 2%, greater than 3%, greater than 4%, greater than 5%, greater than 6%, greater than 7%, greater than 8%, greater than 9%, greater than 10%, greater than 11%, or greater than 12% anhydro-subunit containing oligosaccharides by relative abundance.

In some embodiments, said oligosaccharide preparation comprises greater than 0.5%, 0.6%, greater than 0.8%, greater than 1.0%, greater than 1.5%, greater than 2%, greater than 3%, greater than 4%, greater than 5%, greater than 6%, greater than 7%, greater than 8%, greater than 9%, greater than 10%, greater than 11%, or greater than 12% anhydro-subunit containing oligosaccharides by relative abundance.

In some embodiments, said oligosaccharide preparation has a DP1 fraction content of from about 1% to about 40% by weight as determined by liquid chromatography.

In some embodiments, said oligosaccharide preparation has a DP2 fraction content of from about 1% to about 35% by weight as determined by liquid chromatography.

In some embodiments, said oligosaccharide preparation has a DP3 fraction content of from about 1% to about 30% by weight as determined by liquid chromatography.

In some embodiments, said oligosaccharide preparation has a DP4 fraction content of from about 0.1% to about 20% by weight as determined by liquid chromatography In some embodiments, said oligosaccharide preparation has a DP5 fraction content of from about 0.1% to about 15% by weight as determined by liquid chromatography.

In some embodiments, a ratio of the DP2 fraction to the DP1 fraction is from about 0.02 to about 0.40 as determined by liquid chromatography.

In some embodiments, a ratio of the DP3 fraction to the DP2 fraction is from about 0.01 to about 0.30 as determined by liquid chromatography.

In some embodiments, an aggregate content of the DP1 and the DP2 fractions in the oligosaccharide preparation is less than 50%, less than 40%, or less than 30% as determined by liquid chromatography.

In some embodiments, said oligosaccharide preparation comprises at least 103, at least 104, at least 105, at least 106 or at least 109 different oligosaccharide species.

In some embodiments, two or more independent oligosaccharides comprise different anhydro-subunits.

In some embodiments, each of said anhydro-subunit containing oligosaccharides comprises one or more anhydro-subunits that are products of thermal dehydration of monosaccharides.

In some embodiments, said oligosaccharide preparation comprises one or more anhydro-subunits selected from anhydro-glucose, anhydro-galactose, anhydro-mannose, anhydro-allose, anhydro-altrose, anhydro-gulose, anhydro-indose, anhydro-talose, anhydro-fructose, anhydro-ribose, anhydro-arabinose, anhydro-rhamnose, anhydro-lyxose, and anhydro-xylose.

In some embodiments, said oligosaccharide preparation comprises one or more anhydro-glucose, anhydro-galactose, anhydro-mannose, or anhydro-fructose subunits.

In some embodiments, said DP1 fraction comprises 1,6-anhydro-β-D-glucofuranose or 1,6-anhydro-β-D-glucopyranose anhydro-subunits. In some embodiments, said DP1 fraction comprises both 1,6-anhydro-β-D-glucofuranose and 1,6-anhydro-β-D-glucopyranose anhydro-subunits.

In some embodiments, a ratio of the 1,6-anhydro-β-D-glucofuranose to the 1,6-anhydro-β-D-glucopyranose is from about 10:1 to 1:10, from about 9:1 to about 1:10, from about 8:1 to about 1:10, from about 7:1 to about 1:10, from about 6:1 to about 1:10, from about 5:1 to about 1:10, from about 4:1 to about 1:10, from about 3:1 to about 1:10, from about 2:1 to about 1:10, from about 10:1 to about 1:9, from about 10:1 to about 1:8, from about 10:1 to about 1:7, from about 10:1 to about 1:6, from about 10:1 to about 1:5, from about 10:1 to about 1:4, from about 10:1 to about 1:3, from about 10:1 to about 1:2, or from about 1:1 to about 3:1 in the oligosaccharide reparation. In some embodiments, a ratio of the 1,6-anhydro-β-D-glucofuranose to the 1,6-anhydro-β-D-glucopyranose is about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, or about 1:10 in the oligosaccharide preparation. In some embodiments, a ratio of the 1,6-anhydro-β-D-glucofuranose to the 1,6-anhydro-β-D-glucopyranose is about 2:1 in the oligosaccharide preparation.

In some embodiments, said DP2 fraction comprises at least 5 species of anhydro-subunit containing oligosaccharides. In some embodiments, said DP2 fraction comprises about 5 to 10 species of anhydro-subunit containing oligosaccharides.

In some embodiments, said oligosaccharide preparation comprises one or more sugar caramelization products. In some embodiments, said sugar caramelization products are selected from a group consisting of: methanol; ethanol; furan; methyl glyoxal; 2-methyl furan; vinyl acetate; glycolaldehyde; acetic acid; acetol; furfural; 2-furanmethanol; 3-furanmethanol; 2-hydroxy cyclopent-2-en-1-one; 5-methyl furfural; 2(5H)-furanone; 2 methyl cyclopentenolone; levoglucosenone; cyclic hydroxyl lactone; 1,4,3,6-dianhydro-α-D-glucopyranose; dianhydro glucopyranose; and 5-hydroxy methyl furfural (5-hmf).

In some embodiments, greater than 50%, 60%, 70%, 80%, 90%, 95%, or 99% of the anhydro-subunit containing oligosaccharides comprise a chain-end anhydro-subunit.

In some embodiments, said oligosaccharide preparation has a weight average molecular weight of from about 300 to about 5000 g/mol as determined by high-performance liquid chromatography (HPLC). In some embodiments, said oligosaccharide preparation has a weight average molecular weight of from about 300 to about 2500 g/mol as determined by HPLC. In some embodiments, said oligosaccharide preparation has a weight average molecular weight of from about 500 to about 2000 g/mol as determined by HPLC. In some embodiments, said oligosaccharide preparation has a weight average molecular weight of from about 500 to about 1500 g/mol as determined by HPLC. In some embodiments, said oligosaccharide preparation has a number average molecular weight of from about 300 to about 5000 g/mol as determined by HPLC. In some embodiments, said oligosaccharide preparation has a number average molecular weight of from about 300 to about 2500 g/mol as determined by HPLC. In some embodiments, said oligosaccharide preparation has a number average molecular weight of from about 500 to about 2000 g/mol as determined by HPLC. In some embodiments, said oligosaccharide preparation has a number average molecular weight of from about 500 to about 1500 g/mol as determined by HPLC.

In some embodiments, said oligosaccharide preparation has a weight average molecular weight of from about 2000 to about 2800 g/mol. In some embodiments, said oligosaccharide preparation has a number average molecular weight of from about 1000 to about 2000 g/mol.

In one aspect, provided herein are methods of decreasing the feed conversion ratio of an animal, the method comprising: administering a nutritional composition comprising a base nutritional composition and a synthetic oligosaccharide preparation to an animal, wherein said synthetic oligosaccharide preparation comprises at least n fractions of oligosaccharides each having a distinct degree of polymerization selected from 1 to n (DP1 to DPn fractions), wherein n is an integer greater than 3; and wherein each of a DP1 and DP2 fraction independently comprises from about 0.5% to about 15% of anhydro-subunit containing oligosaccharides by relative abundance as determined by mass spectrometry, and wherein the feed conversion ratio (FCR) of said animal is decreased relative to the FCR of said animal prior to said administering said nutritional composition to said animal.

In some embodiments, said feed conversion ratio (FCR) of said animal is at least 1%, 2%, 3%, 4%, 5%, 6%, 7%, 8%, 9%, or 10% lower than said FCR of said animal prior to administration of said nutritional composition comprising said synthetic oligosaccharide preparation.

In some embodiments, said feed conversion ratio (FCR) of said animal is at least 1%, 2%, 3%, 4%, 5%, 6%, 7%, 8%, 9%, or 10% lower than said FCR of said animal prior to administration of said nutritional composition comprising said synthetic oligosaccharide preparation, as measured after at least 30 days, 35 days, 40 days, 45 days, 50 days, 60 days, 70 days, 80 days, or 90 days after first administration of said nutritional composition comprising said synthetic oligosaccharide preparation, and wherein said animal ingests said nutritional composition at least once during every twenty-four-hour period.

In some embodiments, the decrease in the feed conversion ratio of said animal is a larger decrease relative to a decrease in feed conversion ratio of a comparable control animal administered a comparable nutritional composition lacking said oligosaccharide preparation.

In some embodiments, said nutritional composition comprising said synthetic oligosaccharide preparation is administered to said animal for at least 1, 7, 10, 14, 30, 45, 60, 90, or 120 days.

In some embodiments, said nutritional composition comprising said synthetic oligosaccharide preparation is administered to said animal at least once, twice, three, four, or five times a day.

In some embodiments, said administering comprises providing said nutritional composition to said animal to ingest at will.

In some embodiments, said animal ingests at least a portion of said nutritional composition in over at least 1, 2, 3, 4, 5, 6, 7, 8, 9, 10, 20, 30, 40, 50, 60, 90, or 120 twenty-four-hour periods.

In some embodiments, said nutritional composition comprises at least 100 ppm, 200 ppm, 300 ppm, 400 ppm, 500 ppm, 600 ppm, 700 ppm, 800 ppm, 900 ppm, 1000 ppm, 1500 ppm, or 2000 ppm oligosaccharide preparation. In some embodiments, said nutritional composition comprises about 100 ppm, 200 ppm, 300 ppm, 400 ppm, 500 ppm, 600 ppm, 700 ppm, 800 ppm, 900 ppm, 1000 ppm, 1500 ppm, or 2000 ppm oligosaccharide preparation. In some embodiments, said nutritional composition comprises about 500 ppm oligosaccharide preparation. In some embodiments, said nutritional composition comprises from about 100 ppm-2000 ppm, 100 ppm-1500 ppm, 100 ppm-1000 ppm, 100 ppm-900 ppm, 100 ppm-800 ppm, 100 ppm-700 ppm, 100 ppm-600 ppm, 100 ppm-500 ppm, 100 ppm-400 ppm, 100 ppm-300 ppm, 100 ppm-200 ppm, 200 ppm-1000 ppm, 200 ppm-800 ppm, 200 ppm-700 ppm, 200 ppm-600 ppm, 200 ppm-500 ppm, 300 ppm-1000 ppm, 300 ppm-700 ppm, 300 ppm-600 ppm, or 300 ppm-500 ppm oligosaccharide preparation. In some embodiments, said nutritional composition comprises from about 300 ppm-600 ppm oligosaccharide preparation.

In some embodiments, said animal is a poultry, seafood, sheep, cow, cattle, buffalo, bison, pig, cat, dog, rabbit, goat, guinea pig, donkey, camel, horse, pigeon, ferret, gerbil, hamster, mouse, rat, fish, or bird. In some embodiments, said animal is poultry. In some embodiments, said animal is a chicken, turkey, duck, or goose. In some embodiments, said chicken is a broiler chicken, a layer chicken, or a breeder chicken. In some embodiments, said animal is a pig. In some embodiments, said pig is a nursery pig, a grower pig, or a finisher pig. In some embodiments, said animal is a fish. In some embodiments, said fish is a salmon, a tilapia, or a tropical fish.

In some embodiments, said nutritional composition is an animal feed composition. In some embodiments, said base nutritional composition is base animal feed.

In some embodiments, said relative abundance is determined by LC-MS/MS.

In some embodiments, said relative abundance of oligosaccharides in at least 5, 10, 20, or 30 DP fractions decreases monotonically with its degree of polymerization. In some embodiments, said relative abundance of oligosaccharides in each of the n fractions decreases monotonically with its degree of polymerization.

In some embodiments, n is at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100.

In some embodiments, said DP2 fraction comprises less than 12%, less than 11%, less than 10%, less than 9%, less than 8%, less than 7%, less than 6%, less than 5%, less than 4%, less than 3%, less than 2%, or less than 1% anhydro-subunit containing oligosaccharides by relative abundance.

In some embodiments, said DP2 fraction comprises from about 5% to about 10% of anhydro-subunit containing oligosaccharides by relative abundance. In some embodiments, said DP2 fraction comprises from about 1% to about 10% of anhydro-subunit containing oligosaccharides by relative abundance. In some embodiments, said DP2 fraction comprises from about 0.5% to about 10% of anhydro-subunit containing oligosaccharides by relative abundance. In some embodiments, said DP2 fraction comprises from about 2% to about 12% of anhydro-subunit containing oligosaccharides by relative abundance.

In some embodiments, said DP1 fraction comprises less than 12%, less than 11%, less than 10%, less than 9%, less than 8%, less than 7%, less than 6%, less than 5%, less than 4%, less than 3%, less than 2%, or less than 1% anhydro-subunit containing oligosaccharides by relative abundance. In some embodiments, said DP1 fraction comprises from about 2% to about 12% of anhydro-subunit containing oligosaccharides by relative abundance. In some embodiments, said DP1 fraction comprises from about 1% to about 10% of anhydro-subunit containing oligosaccharides by relative abundance. In some embodiments, said DP1 fraction comprises from about 0.5% to about 10% of anhydro-subunit containing oligosaccharides by relative abundance. In some embodiments, said DP1 fraction comprises from about 5% to about 10% of anhydro-subunit containing oligosaccharides by relative abundance.

In some embodiments, said DP3 fraction comprises less than 15%, less than 12%, less than 11%, less than 10%, less than 9%, less than 8%, less than 7%, less than 6%, less than 5%, less than 4%, less than 3%, less than 2%, or less than 1% anhydro-subunit containing oligosaccharides by relative abundance. In some embodiments, said DP3 fraction comprises from about 2% to about 12% of anhydro-subunit containing oligosaccharides by relative abundance. In some embodiments, said DP3 fraction comprises from about 1% to about 10% of anhydro-subunit containing oligosaccharides by relative abundance. In some embodiments, said DP3 fraction comprises from about 0.5% to about 10% of anhydro-subunit containing oligosaccharides by relative abundance. In some embodiments, said DP3 fraction comprises from about 5% to about 10% of anhydro-subunit containing oligosaccharides by relative abundance.

In some embodiments, said oligosaccharide preparation comprises from about 2% to about 12% anhydro-subunit containing oligosaccharides by relative abundance. In some embodiments, said oligosaccharide preparation comprises from about 0.5% to about 10% anhydro-subunit containing oligosaccharides by relative abundance. In some embodiments, said oligosaccharide preparation comprises from about 1% to about 10% anhydro-subunit containing oligosaccharides by relative abundance. In some embodiments, said oligosaccharide preparation comprises from about 5% to about 10% anhydro-subunit containing oligosaccharides by relative abundance.

In some embodiments, said DP2 fraction comprises greater than 0.6%, greater than 0.8%, greater than 1.0%, greater than 1.5%, greater than 2%, greater than 3%, greater than 4%, greater than 5%, greater than 6%, greater than 7%, greater than 8%, greater than 9%, greater than 10%, greater than 11%, or greater than 12% anhydro-subunit containing oligosaccharides by relative abundance.

In some embodiments, said DP1 fraction comprises greater than 0.6%, greater than 0.8%, greater than 1.0%, greater than 1.5%, greater than 2%, greater than 3%, greater than 4%, greater than 5%, greater than 6%, greater than 7%, greater than 8%, greater than 9%, greater than 10%, greater than 11%, or greater than 12% anhydro-subunit containing oligosaccharides by relative abundance.

In some embodiments, said DP3 fraction comprises greater than 0.6%, greater than 0.8%, greater than 1.0%, greater than 1.5%, greater than 2%, greater than 3%, greater than 4%, greater than 5%, greater than 6%, greater than 7%, greater than 8%, greater than 9%, greater than 10%, greater than 11%, or greater than 12% anhydro-subunit containing oligosaccharides by relative abundance.

In some embodiments, said oligosaccharide preparation comprises greater than 0.5%, 0.6%, greater than 0.8%, greater than 1.0%, greater than 1.5%, greater than 2%, greater than 3%, greater than 4%, greater than 5%, greater than 6%, greater than 7%, greater than 8%, greater than 9%, greater than 10%, greater than 11%, or greater than 12% anhydro-subunit containing oligosaccharides by relative abundance.

In some embodiments, said oligosaccharide preparation has a DP1 fraction content of from about 1% to about 40% by weight as determined by liquid chromatography.

In some embodiments, said oligosaccharide preparation has a DP2 fraction content of from about 1% to about 35% by weight as determined by liquid chromatography.

In some embodiments, said oligosaccharide preparation has a DP3 fraction content of from about 1% to about 30% by weight as determined by liquid chromatography.

In some embodiments, said oligosaccharide preparation has a DP4 fraction content of from about 0.1% to about 20% by weight as determined by liquid chromatography In some embodiments, said oligosaccharide preparation has a DP5 fraction content of from about 0.1% to about 15% by weight as determined by liquid chromatography.

In some embodiments, a ratio of the DP2 fraction to the DP1 fraction is from about 0.02 to about 0.40 as determined by liquid chromatography.

In some embodiments, a ratio of the DP3 fraction to the DP2 fraction is from about 0.01 to about 0.30 as determined by liquid chromatography.

In some embodiments, an aggregate content of the DP1 and the DP2 fractions in the oligosaccharide preparation is less than 50%, less than 40%, or less than 30% as determined by liquid chromatography.

In some embodiments, said oligosaccharide preparation comprises at least 103, at least 104, at least 105, at least 106 or at least 109 different oligosaccharide species.

In some embodiments, two or more independent oligosaccharides comprise different anhydro-subunits.

In some embodiments, each of said anhydro-subunit containing oligosaccharides comprises one or more anhydro-subunits that are products of thermal dehydration of monosaccharides.

In some embodiments, said oligosaccharide preparation comprises one or more anhydro-subunits selected from anhydro-glucose, anhydro-galactose, anhydro-mannose, anhydro-allose, anhydro-altrose, anhydro-gulose, anhydro-indose, anhydro-talose, anhydro-fructose, anhydro-ribose, anhydro-arabinose, anhydro-rhamnose, anhydro-lyxose, and anhydro-xylose.

In some embodiments, said oligosaccharide preparation comprises one or more anhydro-glucose, anhydro-galactose, anhydro-mannose, or anhydro-fructose subunits.

In some embodiments, said DP1 fraction comprises 1,6-anhydro-β-D-glucofuranose or 1,6-anhydro-β-D-glucopyranose anhydro-subunits. In some embodiments, said DP1 fraction comprises both 1,6-anhydro-β-D-glucofuranose and 1,6-anhydro-β-D-glucopyranose anhydro-subunits.

In some embodiments, a ratio of the 1,6-anhydro-β-D-glucofuranose to the 1,6-anhydro-β-D-glucopyranose is from about 10:1 to 1:10, from about 9:1 to about 1:10, from about 8:1 to about 1:10, from about 7:1 to about 1:10, from about 6:1 to about 1:10, from about 5:1 to about 1:10, from about 4:1 to about 1:10, from about 3:1 to about 1:10, from about 2:1 to about 1:10, from about 10:1 to about 1:9, from about 10:1 to about 1:8, from about 10:1 to about 1:7, from about 10:1 to about 1:6, from about 10:1 to about 1:5, from about 10:1 to about 1:4, from about 10:1 to about 1:3, from about 10:1 to about 1:2, or from about 1:1 to about 3:1 in the oligosaccharide reparation. In some embodiments, a ratio of the 1,6-anhydro-β-D-glucofuranose to the 1,6-anhydro-β-D-glucopyranose is about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, or about 1:10 in the oligosaccharide preparation. In some embodiments, a ratio of the 1,6-anhydro-β-D-glucofuranose to the 1,6-anhydro-β-D-glucopyranose is about 2:1 in the oligosaccharide preparation.

In some embodiments, said DP2 fraction comprises at least 5 species of anhydro-subunit containing oligosaccharides. In some embodiments, said DP2 fraction comprises about 5 to 10 species of anhydro-subunit containing oligosaccharides.

In some embodiments, said oligosaccharide preparation comprises one or more sugar caramelization products. In some embodiments, said sugar caramelization products are selected from a group consisting of: methanol; ethanol; furan; methyl glyoxal; 2-methyl furan; vinyl acetate; glycolaldehyde; acetic acid; acetol; furfural; 2-furanmethanol; 3-furanmethanol; 2-hydroxy cyclopent-2-en-1-one; 5-methyl furfural; 2(5H)-furanone; 2 methyl cyclopentenolone; levoglucosenone; cyclic hydroxyl lactone; 1,4,3,6-dianhydro-α-D-glucopyranose; dianhydro glucopyranose; and 5-hydroxy methyl furfural (5-hmf).

In some embodiments, greater than 50%, 60%, 70%, 80%, 90%, 95%, or 99% of the anhydro-subunit containing oligosaccharides comprise a chain-end anhydro-subunit.

In some embodiments, said oligosaccharide preparation has a weight average molecular weight of from about 300 to about 5000 g/mol as determined by high-performance liquid chromatography (HPLC). In some embodiments, said oligosaccharide preparation has a weight average molecular weight of from about 300 to about 2500 g/mol as determined by HPLC. In some embodiments, said oligosaccharide preparation has a weight average molecular weight of from about 500 to about 2000 g/mol as determined by HPLC. In some embodiments, said oligosaccharide preparation has a weight average molecular weight of from about 500 to about 1500 g/mol as determined by HPLC. In some embodiments, said oligosaccharide preparation has a number average molecular weight of from about 300 to about 5000 g/mol as determined by HPLC. In some embodiments, said oligosaccharide preparation has a number average molecular weight of from about 300 to about 2500 g/mol as determined by HPLC. In some embodiments, said oligosaccharide preparation has a number average molecular weight of from about 500 to about 2000 g/mol as determined by HPLC. In some embodiments, said oligosaccharide preparation has a number average molecular weight of from about 500 to about 1500 g/mol as determined by HPLC.

In some embodiments, said oligosaccharide preparation has a weight average molecular weight of from about 2000 to about 2800 g/mol. In some embodiments, said oligosaccharide preparation has a number average molecular weight of from about 1000 to about 2000 g/mol.

In one aspect, provided herein are methods of increasing the feed efficacy of an animal, the method comprising: administering a nutritional composition comprising a base nutritional composition and a synthetic oligosaccharide preparation to an animal, wherein said synthetic oligosaccharide preparation comprises at least n fractions of oligosaccharides each having a distinct degree of polymerization selected from 1 to n (DP1 to DPn fractions), wherein n is an integer greater than 3; and wherein each of a DP1 and DP2 fraction independently comprises from about 0.5% to about 15% of anhydro-subunit containing oligosaccharides by relative abundance as determined by mass spectrometry, and wherein the feed efficiency of said animal is increased relative to the feed efficiency of said animal prior to said administering said nutritional composition to said animal.

In some embodiments, said feed efficiency of said animal is at least 1%, 2%, 3%, 4%, 5%, 6%, 7%, 8%, 9%, or 10% higher than said feed efficiency of said animal prior to administration of said nutritional composition comprising said synthetic oligosaccharide preparation.

In some embodiments, said feed efficiency of said animal is at least 1%, 2%, 3%, 4%, 5%, 6%, 7%, 8%, 9%, or 10% higher than said feed efficiency of said animal prior to administration of said nutritional composition comprising said synthetic oligosaccharide preparation, as measured after at least 30 days, 35 days, 40 days, 45 days, 50 days, 60 days, 70 days, 80 days, or 90 days after first administration of said nutritional composition comprising said synthetic oligosaccharide preparation, and wherein said animal ingests said nutritional composition at least once during every twenty-four-hour period.

In some embodiments, the increase in the feed efficiency of said animal is a larger increase relative to an increase in feed efficiency of a comparable control animal administered a comparable nutritional composition lacking said oligosaccharide preparation.

In some embodiments, said nutritional composition comprising said synthetic oligosaccharide preparation is administered to said animal for at least 1, 7, 10, 14, 30, 45, 60, 90, or 120 days.

In some embodiments, said nutritional composition comprising said synthetic oligosaccharide preparation is administered to said animal at least once, twice, three, four, or five times a day.

In some embodiments, said administering comprises providing said nutritional composition to said animal to ingest at will.

In some embodiments, said animal ingests at least a portion of said nutritional composition in over at least 1, 2, 3, 4, 5, 6, 7, 8, 9, 10, 20, 30, 40, 50, 60, 90, or 120 twenty-four-hour periods.

In some embodiments, said nutritional composition comprises at least 100 ppm, 200 ppm, 300 ppm, 400 ppm, 500 ppm, 600 ppm, 700 ppm, 800 ppm, 900 ppm, 1000 ppm, 1500 ppm, or 2000 ppm oligosaccharide preparation. In some embodiments, said nutritional composition comprises about 100 ppm, 200 ppm, 300 ppm, 400 ppm, 500 ppm, 600 ppm, 700 ppm, 800 ppm, 900 ppm, 1000 ppm, 1500 ppm, or 2000 ppm oligosaccharide preparation. In some embodiments, said nutritional composition comprises about 500 ppm oligosaccharide preparation. In some embodiments, said nutritional composition comprises from about 100 ppm-2000 ppm, 100 ppm-1500 ppm, 100 ppm-1000 ppm, 100 ppm-900 ppm, 100 ppm-800 ppm, 100 ppm-700 ppm, 100 ppm-600 ppm, 100 ppm-500 ppm, 100 ppm-400 ppm, 100 ppm-300 ppm, 100 ppm-200 ppm, 200 ppm-1000 ppm, 200 ppm-800 ppm, 200 ppm-700 ppm, 200 ppm-600 ppm, 200 ppm-500 ppm, 300 ppm-1000 ppm, 300 ppm-700 ppm, 300 ppm-600 ppm, or 300 ppm-500 ppm oligosaccharide preparation. In some embodiments, said nutritional composition comprises from about 300 ppm-600 ppm oligosaccharide preparation.

In some embodiments, said animal is a poultry, seafood, sheep, cow, cattle, buffalo, bison, pig, cat, dog, rabbit, goat, guinea pig, donkey, camel, horse, pigeon, ferret, gerbil, hamster, mouse, rat, fish, or bird. In some embodiments, said animal is poultry. In some embodiments, said animal is a chicken, turkey, duck, or goose. In some embodiments, said chicken is a broiler chicken, a layer chicken, or a breeder chicken. In some embodiments, said animal is a pig. In some embodiments, said pig is a nursery pig, a grower pig, or a finisher pig. In some embodiments, said animal is a fish. In some embodiments, said fish is a salmon, a tilapia, or a tropical fish.

In some embodiments, said nutritional composition is an animal feed composition. In some embodiments, said base nutritional composition is base animal feed.

In some embodiments, said relative abundance is determined by LC-MS/MS.

In some embodiments, said relative abundance of oligosaccharides in at least 5, 10, 20, or 30 DP fractions decreases monotonically with its degree of polymerization. In some embodiments, said relative abundance of oligosaccharides in each of the n fractions decreases monotonically with its degree of polymerization.

In some embodiments, n is at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100.

In some embodiments, said DP2 fraction comprises less than 12%, less than 11%, less than 10%, less than 9%, less than 8%, less than 7%, less than 6%, less than 5%, less than 4%, less than 3%, less than 2%, or less than 1% anhydro-subunit containing oligosaccharides by relative abundance.

In some embodiments, said DP2 fraction comprises from about 5% to about 10% of anhydro-subunit containing oligosaccharides by relative abundance. In some embodiments, said DP2 fraction comprises from about 1% to about 10% of anhydro-subunit containing oligosaccharides by relative abundance. In some embodiments, said DP2 fraction comprises from about 0.5% to about 10% of anhydro-subunit containing oligosaccharides by relative abundance. In some embodiments, said DP2 fraction comprises from about 2% to about 12% of anhydro-subunit containing oligosaccharides by relative abundance.

In some embodiments, said DP1 fraction comprises less than 12%, less than 11%, less than 10%, less than 9%, less than 8%, less than 7%, less than 6%, less than 5%, less than 4%, less than 3%, less than 2%, or less than 1% anhydro-subunit containing oligosaccharides by relative abundance. In some embodiments, said DP1 fraction comprises from about 2% to about 12% of anhydro-subunit containing oligosaccharides by relative abundance. In some embodiments, said DP1 fraction comprises from about 1% to about 10% of anhydro-subunit containing oligosaccharides by relative abundance.

In some embodiments, said DP1 fraction comprises from about 0.5% to about 10% of anhydro-subunit containing oligosaccharides by relative abundance. In some embodiments, said DP1 fraction comprises from about 5% to about 10% of anhydro-subunit containing oligosaccharides by relative abundance.

In some embodiments, said DP3 fraction comprises less than 15%, less than 12%, less than 11%, less than 10%, less than 9%, less than 8%, less than 7%, less than 6%, less than 5%, less than 4%, less than 3%, less than 2%, or less than 1% anhydro-subunit containing oligosaccharides by relative abundance. In some embodiments, said DP3 fraction comprises from about 2% to about 12% of anhydro-subunit containing oligosaccharides by relative abundance. In some embodiments, said DP3 fraction comprises from about 1% to about 10% of anhydro-subunit containing oligosaccharides by relative abundance. In some embodiments, said DP3 fraction comprises from about 0.5% to about 10% of anhydro-subunit containing oligosaccharides by relative abundance. In some embodiments, said DP3 fraction comprises from about 5% to about 10% of anhydro-subunit containing oligosaccharides by relative abundance.

In some embodiments, said oligosaccharide preparation comprises from about 2% to about 12% anhydro-subunit containing oligosaccharides by relative abundance. In some embodiments, said oligosaccharide preparation comprises from about 0.5% to about 10% anhydro-subunit containing oligosaccharides by relative abundance. In some embodiments, said oligosaccharide preparation comprises from about 1% to about 10% anhydro-subunit containing oligosaccharides by relative abundance. In some embodiments, said oligosaccharide preparation comprises from about 5% to about 10% anhydro-subunit containing oligosaccharides by relative abundance.

In some embodiments, said DP2 fraction comprises greater than 0.6%, greater than 0.8%, greater than 1.0%, greater than 1.5%, greater than 2%, greater than 3%, greater than 4%, greater than 5%, greater than 6%, greater than 7%, greater than 8%, greater than 9%, greater than 10%, greater than 11%, or greater than 12% anhydro-subunit containing oligosaccharides by relative abundance.

In some embodiments, said DP1 fraction comprises greater than 0.6%, greater than 0.8%, greater than 1.0%, greater than 1.5%, greater than 2%, greater than 3%, greater than 4%, greater than 5%, greater than 6%, greater than 7%, greater than 8%, greater than 9%, greater than 10%, greater than 11%, or greater than 12% anhydro-subunit containing oligosaccharides by relative abundance.

In some embodiments, said DP3 fraction comprises greater than 0.6%, greater than 0.8%, greater than 1.0%, greater than 1.5%, greater than 2%, greater than 3%, greater than 4%, greater than 5%, greater than 6%, greater than 7%, greater than 8%, greater than 9%, greater than 10%, greater than 11%, or greater than 12% anhydro-subunit containing oligosaccharides by relative abundance.

In some embodiments, said oligosaccharide preparation comprises greater than 0.5%, 0.6%, greater than 0.8%, greater than 1.0%, greater than 1.5%, greater than 2%, greater than 3%, greater than 4%, greater than 5%, greater than 6%, greater than 7%, greater than 8%, greater than 9%, greater than 10%, greater than 11%, or greater than 12% anhydro-subunit containing oligosaccharides by relative abundance.

In some embodiments, said oligosaccharide preparation has a DP1 fraction content of from about 1% to about 40% by weight as determined by liquid chromatography.

In some embodiments, said oligosaccharide preparation has a DP2 fraction content of from about 1% to about 35% by weight as determined by liquid chromatography.

In some embodiments, said oligosaccharide preparation has a DP3 fraction content of from about 1% to about 30% by weight as determined by liquid chromatography.

In some embodiments, said oligosaccharide preparation has a DP4 fraction content of from about 0.1% to about 20% by weight as determined by liquid chromatography In some embodiments, said oligosaccharide preparation has a DP5 fraction content of from about 0.1% to about 15% by weight as determined by liquid chromatography.

In some embodiments, a ratio of the DP2 fraction to the DP1 fraction is from about 0.02 to about 0.40 as determined by liquid chromatography.

In some embodiments, a ratio of the DP3 fraction to the DP2 fraction is from about 0.01 to about 0.30 as determined by liquid chromatography.

In some embodiments, an aggregate content of the DP1 and the DP2 fractions in the oligosaccharide preparation is less than 50%, less than 40%, or less than 30% as determined by liquid chromatography.

In some embodiments, said oligosaccharide preparation comprises at least 103, at least 104, at least 105, at least 106 or at least 109 different oligosaccharide species.

In some embodiments, two or more independent oligosaccharides comprise different anhydro-subunits.

In some embodiments, each of said anhydro-subunit containing oligosaccharides comprises one or more anhydro-subunits that are products of thermal dehydration of monosaccharides.

In some embodiments, said oligosaccharide preparation comprises one or more anhydro-subunits selected from anhydro-glucose, anhydro-galactose, anhydro-mannose, anhydro-allose, anhydro-altrose, anhydro-gulose, anhydro-indose, anhydro-talose, anhydro-fructose, anhydro-ribose, anhydro-arabinose, anhydro-rhamnose, anhydro-lyxose, and anhydro-xylose.

In some embodiments, said oligosaccharide preparation comprises one or more anhydro-glucose, anhydro-galactose, anhydro-mannose, or anhydro-fructose subunits.

In some embodiments, said DP1 fraction comprises 1,6-anhydro-β-D-glucofuranose or 1,6-anhydro-β-D-glucopyranose anhydro-subunits. In some embodiments, said DP1 fraction comprises both 1,6-anhydro-β-D-glucofuranose and 1,6-anhydro-β-D-glucopyranose anhydro-subunits.

In some embodiments, a ratio of the 1,6-anhydro-β-D-glucofuranose to the 1,6-anhydro-β-D-glucopyranose is from about 10:1 to 1:10, from about 9:1 to about 1:10, from about 8:1 to about 1:10, from about 7:1 to about 1:10, from about 6:1 to about 1:10, from about 5:1 to about 1:10, from about 4:1 to about 1:10, from about 3:1 to about 1:10, from about 2:1 to about 1:10, from about 10:1 to about 1:9, from about 10:1 to about 1:8, from about 10:1 to about 1:7, from about 10:1 to about 1:6, from about 10:1 to about 1:5, from about 10:1 to about 1:4, from about 10:1 to about 1:3, from about 10:1 to about 1:2, or from about 1:1 to about 3:1 in the oligosaccharide reparation. In some embodiments, a ratio of the 1,6-anhydro-β-D-glucofuranose to the 1,6-anhydro-β-D-glucopyranose is about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, or about 1:10 in the oligosaccharide preparation. In some embodiments, a ratio of the 1,6-anhydro-β-D-glucofuranose to the 1,6-anhydro-β-D-glucopyranose is about 2:1 in the oligosaccharide preparation.

In some embodiments, said DP2 fraction comprises at least 5 species of anhydro-subunit containing oligosaccharides. In some embodiments, said DP2 fraction comprises about 5 to 10 species of anhydro-subunit containing oligosaccharides.

In some embodiments, said oligosaccharide preparation comprises one or more sugar caramelization products. In some embodiments, said sugar caramelization products are selected from a group consisting of: methanol; ethanol; furan; methyl glyoxal; 2-methyl furan; vinyl acetate; glycolaldehyde; acetic acid; acetol; furfural; 2-furanmethanol; 3-furanmethanol; 2-hydroxy cyclopent-2-en-1-one; 5-methyl furfural; 2(5H)-furanone; 2 methyl cyclopentenolone; levoglucosenone; cyclic hydroxyl lactone; 1,4,3,6-dianhydro-α-D-glucopyranose; dianhydro glucopyranose; and 5-hydroxy methyl furfural (5-hmf).

In some embodiments, greater than 50%, 60%, 70%, 80%, 90%, 95%, or 99% of the anhydro-subunit containing oligosaccharides comprise a chain-end anhydro-subunit.

In some embodiments, said oligosaccharide preparation has a weight average molecular weight of from about 300 to about 5000 g/mol as determined by high-performance liquid chromatography (HPLC). In some embodiments, said oligosaccharide preparation has a weight average molecular weight of from about 300 to about 2500 g/mol as determined by HPLC. In some embodiments, said oligosaccharide preparation has a weight average molecular weight of from about 500 to about 2000 g/mol as determined by HPLC. In some embodiments, said oligosaccharide preparation has a weight average molecular weight of from about 500 to about 1500 g/mol as determined by HPLC. In some embodiments, said oligosaccharide preparation has a number average molecular weight of from about 300 to about 5000 g/mol as determined by HPLC. In some embodiments, said oligosaccharide preparation has a number average molecular weight of from about 300 to about 2500 g/mol as determined by HPLC. In some embodiments, said oligosaccharide preparation has a number average molecular weight of from about 500 to about 2000 g/mol as determined by HPLC. In some embodiments, said oligosaccharide preparation has a number average molecular weight of from about 500 to about 1500 g/mol as determined by HPLC.

In some embodiments, said oligosaccharide preparation has a weight average molecular weight of from about 2000 to about 2800 g/mol. In some embodiments, said oligosaccharide preparation has a number average molecular weight of from about 1000 to about 2000 g/mol.

In one aspect, provided herein are methods of modulating the growth of at least one microbial species in the gastrointestinal tract of an animal, said method comprising: administering a nutritional composition comprising a base nutritional composition and a synthetic oligosaccharide preparation to an animal, wherein said synthetic oligosaccharide preparation comprises at least n fractions of oligosaccharides each having a distinct degree of polymerization selected from 1 to n (DP1 to DPn fractions), wherein n is an integer greater than 3; and wherein each of a DP1 and DP2 fraction independently comprises from about 0.5% to about 15% of anhydro-subunit containing oligosaccharides by relative abundance as determined by mass spectrometry, and wherein a level of at least one microbial species in a gastrointestinal sample from said animal is increased or decreased relative to a level of said at least one microbial species in a gastrointestinal sample from said animal prior to said administering said nutritional composition to said animal.

In some embodiments, said increase or decrease in said least one microbial species in a gastrointestinal sample from said animal is a larger increase or decrease relative to an increase or decrease in said at least one microbial species in a gastrointestinal sample from a comparable control animal that has been administered a comparable nutritional composition lacking said synthetic oligosaccharide preparation.

In some embodiments, said at least one microbial species is an archaea, a bacteria, a protozoan, a virus, a bacteriophage, a parasite, or a fungus. In some embodiments, said microbial species is a bacteria.

In some embodiments, said gastrointestinal sample is a biopsy of a gastrointestinal tissue, a fecal sample, or a cloacal swab. In some embodiments, said gastrointestinal tissue is cecal tissue or ileum tissue. In some embodiments, said method further comprises obtaining said sample.

In some embodiments, said method further comprises detecting the level of said at least one microbial species in said gastrointestinal sample. In some embodiments, said method further comprises detecting a level of at least 2, 3, 4, 5, 6 microbial species in said gastrointestinal sample. In some embodiments, a level of at least 2, 3, 4, 5, or 6 microbial species in said gastrointestinal sample from said animal are increased or decreased relative to a level of said at least 2, 3, 4, 5, or 6 microbial species in a gastrointestinal sample from said animal prior to said administering said nutritional composition to said animal. In some embodiments, a level of at least 2, 3, 4, 5, or 6 microbial species in a gastrointestinal sample from said animal are increased or decreased relative to a level of said at least 2, 3, 4, 5, or 6, or more microbial species in a gastrointestinal sample from a control animal that has been administered a comparable nutritional composition lacking said synthetic oligosaccharide preparation.

In some embodiments, said method comprises promoting the growth of said at least one microbial species, and wherein said level of at least one microbial species in said gastrointestinal sample is increased relative to a level of said at least one microbial species in a gastrointestinal sample from said animal prior to said administering said nutritional composition to said animal. In some embodiments, said increase in said least one microbial species in a gastrointestinal sample from said animal is a larger increase relative to an increase in said at least one microbial species in a gastrointestinal sample from a comparable control animal that has been administered a comparable nutritional composition lacking said synthetic oligosaccharide preparation.

In some embodiments, said method comprises promoting the growth of said at least one microbial species, and wherein said level of at least one microbial species in said gastrointestinal sample is increased relative to a level of said at least one microbial species in a gastrointestinal sample from a comparable control animal that has been administered a comparable nutritional composition lacking said synthetic oligosaccharide preparation.

In some embodiments, said microbial species is beneficial to the health of the animal. In some embodiments, said microbial species is beneficial to the gastrointestinal health of the animal. In some embodiments, said microbial species is non-pathogenic to said animal. In some embodiments, said microbial species is non-pathogenic to humans.

In some embodiments, said microbial species belongs to the genus *Bacteroides, Odoribacter, Oscillibacter, Subdoligranulum, Biophila*, or *Barnesiella*. In some embodiments, said microbial species is selected from the group consisting of: *Bacteroides clarus, Bacteroides dorei, Odoribacter splanchinicus*, and *Barnesiella intestinihominis*. In some embodiments, said microbial species is selected from Group 1 as listed in Table 26. In some embodiments, said microbial species is selected from Group 2 as listed in Table 26. In some embodiments, said microbial species is selected from Group 3 as listed in Table 26.

In some embodiments, each of said at least 2, 3, 4, 5, or 6 microbial species improve the health of the animal. In some embodiments, each of said at least 2, 3, 4, 5, or 6 microbial species improve the gastrointestinal health of the animal. In some embodiments, each of said at least 2, 3, 4, 5, or 6 microbial species are non-pathogenic to said animal. In some embodiments, each of said at least 2, 3, 4, 5, or 6 microbial species are non-pathogenic to humans. In some embodiments, each of said at least 2, 3, 4, 5, or 6 microbial species in said gastrointestinal sample from said animal are increased relative to a level of said at least 2, 3, 4, 5, or 6 microbial species in a gastrointestinal sample from said animal prior to administration of said nutritional composition to said animal. In some embodiments, each of said at least 2, 3, 4, 5, or 6 microbial species in a gastrointestinal sample from said animal are increased relative to a level of said at least 2, 3, 4, 5, or 6 microbial species in a gastrointestinal sample from a control animal that has been administered a comparable nutritional composition lacking said synthetic oligosaccharide preparation. In some embodiments, at least one of said at least 2, 3, 4, 5, or 6 microbial species belongs to the genus *Bacteroides, Odoribacter, Oscillibacter, Subdoligranulum, Biophila*, or *Barnesiella*. In some embodiments, at least one of said at least 2, 3, 4, 5, or 6 microbial species is selected from the group consisting of: *Bacteroides clarus, Bacteroides dorei, Odoribacter splanchinicus*, and *Barnesiella intestinihominis*. In some embodiments, said gastrointestinal sample comprises at least 0.1%, 1%, 2%, 3%, 4%, 5%, 6%, 7%, 8%, 9%, or 10% of at least one microbial species that belongs to the genus *Bacteroides, Odoribacter, Oscillibacter, Subdoligranulum, Biophila*, or *Barnesiella*. In some embodiments, said gastrointestinal sample comprises at least 0.1%, 1%, 2%, 3%, 4%, 5%, 6%, 7%, 8%, 9%, or 10% of at least one of *Bacteroides clarus, Bacteroides dorei, Odoribacter splanchinicus*, and *Barnesiella intestinihominis*.

In some embodiments, said method comprises inhibiting the growth the growth of said at least one microbial species, and wherein said level of at least one microbial species in a gastrointestinal sample is decreased relative to a level of said at least one microbial species in a gastrointestinal sample from said animal prior to said administering said nutritional composition to said animal. In some embodiments, said decrease in said least one microbial species in a gastrointestinal sample from said animal is a larger decrease relative to an increase in said at least one microbial species in a gastrointestinal sample from a comparable control animal that has been administered a comparable nutritional composition lacking said synthetic oligosaccharide preparation.

In some embodiments, said method comprises inhibiting the growth the growth of said at least one microbial species, and wherein said level of at least one microbial species in a gastrointestinal sample is decreased relative to a level of said at least one microbial species in a gastrointestinal sample from a comparable control animal that has been administered a comparable nutritional composition lacking said synthetic oligosaccharide preparation.

In some embodiments, said microbial species is detrimental to the health of said animal. In some embodiments, said microbial species is detrimental to the gastrointestinal health of said animal.

In some embodiments, said microbial species is pathogenic to said animal. In some embodiments, said microbial species is pathogenic to humans but not pathogenic to said animal.

In some embodiments, said microbial species is *Helicobacter pullorum*. In some embodiments, said microbial species belongs to the phylum Proteobacteria. In some embodiments, said microbial species belongs to the genus *Helicobacter, Escherichia, Salmonella, Vibrio*, or *Yersinia*.

In some embodiments, said microbial species is selected from the group consisting of: *Helicobacter pullorum, Proteobacteria johnsonii, Escherichia coli, Camplobacter jejuni*, and *Lactobacillus crispatus*. In some embodiments, said microbial species is selected from Group 2 as listed in Table 26. In some embodiments, said microbial species is selected from Group 3 as listed in Table 26. In some embodiments, said microbial species is selected from Group 4 as listed in Table 26.

In some embodiments, each of said at least 2, 3, 4, 5, or 6 microbial species is detrimental to the health of the animal. In some embodiments, each of said at least 2, 3, 4, 5, or 6 microbial species in said gastrointestinal sample from said animal is decreased relative to a level of said at least 2, 3, 4, 5, or 6, or more microbial species in a gastrointestinal sample from said animal prior to said administering said nutritional composition to said animal. In some embodiments, each of said at least 2, 3, 4, 5, or 6 microbial species in a gastrointestinal sample from said animal are decreased relative to a level of said at least 2, 3, 4, 5, or 6 microbial species in a gastrointestinal sample from a control animal that has been administered a comparable nutritional composition lacking said synthetic oligosaccharide preparation. In some embodiments, at least one of said at least 2, 3, 4, 5, or 6 microbial species belongs to the phylum Proteobacteria. In some embodiments, at least one of said at least 2, 3, 4, 5, or 6 microbial species belongs to the genus *Helicobacter, Escherichia, Salmonella, Vibrio*, or *Yersinia*. In some embodiments, at least one of said at least 2, 3, 4, 5, or 6 microbial species is selected from the group consisting of: *Helicobacter pullorum, Proteobacteria johnsonii, Escherichia coli, Camplobacter jejuni*, and *Lactobacillus crispatus*. In some embodiments, said gastrointestinal sample comprises less than 0.1%, 1%, 2%, 3%, 4%, 5%, 6%, 7%, 8%, 9%, or 10% of at least one microbial species that belongs to the genus *Helicobacter, Escherichia, Salmonella, Vibrio*, or *Yersinia*. In some embodiments, said gastrointestinal sample comprises at less than 0.1%, 1%, 2%, 3%, 4%, 5%, 6%, 7%, 8%, 9%, or 10% of at least one of *Helicobacter pullorum, Proteobacteria johnsonii, Escherichia coli, Camplobacter jejuni*, and *Lactobacillus crispatus*.

In some embodiments, said nutritional composition comprising said synthetic oligosaccharide preparation is administered to said animal for at least 1, 7, 10, 14, 30, 45, 60, 90, or 120 days.

In some embodiments, said nutritional composition comprising said synthetic oligosaccharide preparation is administered to said animal at least once, twice, three, four, or five times a day.

The method of any preceding claim, wherein said administering comprises providing the nutritional composition to said animal to ingest at will.

In some embodiments, said animal ingests at least a portion of said nutritional composition in over at least 1, 2, 3, 4, 5, 6, 7, 8, 9, 10, 20, 30, 40, 50, 60, 90, or 120 twenty-four-hour periods.

In some embodiments, said nutritional composition comprises at least 100 ppm, 200 ppm, 300 ppm, 400 ppm, 500 ppm, 600 ppm, 700 ppm, 800 ppm, 900 ppm, 1000 ppm, 1500 ppm, or 2000 ppm oligosaccharide preparation. In some embodiments, said nutritional composition comprises about 100 ppm, 200 ppm, 300 ppm, 400 ppm, 500 ppm, 600 ppm, 700 ppm, 800 ppm, 900 ppm, 1000 ppm, 1500 ppm, or 2000 ppm oligosaccharide preparation. In some embodiments, said nutritional composition comprises about 500 ppm oligosaccharide preparation. In some embodiments, said nutritional composition comprises from about 100 ppm-2000 ppm, 100 ppm-1500 ppm, 100 ppm-1000 ppm, 100 ppm-900 ppm, 100 ppm-800 ppm, 100 ppm-700 ppm, 100 ppm-600 ppm, 100 ppm-500 ppm, 100 ppm-400 ppm, 100 ppm-300 ppm, 100 ppm-200 ppm, 200 ppm-1000 ppm, 200 ppm-800 ppm, 200 ppm-700 ppm, 200 ppm-600 ppm, 200 ppm-500 ppm, 300 ppm-1000 ppm, 300 ppm-700 ppm, 300 ppm-600 ppm, or 300 ppm-500 ppm oligosaccharide preparation. In some embodiments, said nutritional composition comprises from about 300 ppm-600 ppm oligosaccharide preparation.

In some embodiments, said animal is a poultry, seafood, sheep, cow, cattle, buffalo, bison, pig, cat, dog, rabbit, goat, guinea pig, donkey, camel, horse, pigeon, ferret, gerbil, hamster, mouse, rat, fish, or bird. In some embodiments, said animal is poultry. In some embodiments, said animal is a chicken, turkey, duck, or goose. In some embodiments, said chicken is a broiler chicken, a layer chicken, or a breeder chicken. In some embodiments, said animal is a pig. In some embodiments, said pig is a nursery pig, a grower pig, or a finisher pig. In some embodiments, said animal is a fish. In some embodiments, said fish is a salmon, a tilapia, or a tropical fish.

In some embodiments, said nutritional composition is an animal feed composition. In some embodiments, said base nutritional composition is base animal feed.

In some embodiments, said relative abundance is determined by LC-MS/MS.

In some embodiments, said relative abundance of oligosaccharides in at least 5, 10, 20, or 30 DP fractions decreases monotonically with its degree of polymerization. In some embodiments, said relative abundance of oligosaccharides in each of the n fractions decreases monotonically with its degree of polymerization.

In some embodiments, n is at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100.

In some embodiments, said DP2 fraction comprises less than 12%, less than 11%, less than 10%, less than 9%, less than 8%, less than 7%, less than 6%, less than 5%, less than 4%, less than 3%, less than 2%, or less than 1% anhydro-subunit containing oligosaccharides by relative abundance.

In some embodiments, said DP2 fraction comprises from about 5% to about 10% of anhydro-subunit containing oligosaccharides by relative abundance. In some embodiments, said DP2 fraction comprises from about 1% to about 10% of anhydro-subunit containing oligosaccharides by relative abundance. In some embodiments, said DP2 fraction comprises from about 0.5% to about 10% of anhydro-subunit containing oligosaccharides by relative abundance. In some embodiments, said DP2 fraction comprises from about 2% to about 12% of anhydro-subunit containing oligosaccharides by relative abundance.

In some embodiments, said DP1 fraction comprises less than 12%, less than 11%, less than 10%, less than 9%, less than 8%, less than 7%, less than 6%, less than 5%, less than 4%, less than 3%, less than 2%, or less than 1% anhydro-subunit containing oligosaccharides by relative abundance. In some embodiments, said DP1 fraction comprises from about 2% to about 12% of anhydro-subunit containing oligosaccharides by relative abundance. In some embodiments, said DP1 fraction comprises from about 1% to about 10% of anhydro-subunit containing oligosaccharides by relative abundance. In some embodiments, said DP1 fraction comprises from about 0.5% to about 10% of anhydro-subunit containing oligosaccharides by relative abundance. In some embodiments, said DP1 fraction comprises from about 5% to about 10% of anhydro-subunit containing oligosaccharides by relative abundance.

In some embodiments, said DP3 fraction comprises less than 15%, less than 12%, less than 11%, less than 10%, less than 9%, less than 8%, less than 7%, less than 6%, less than 5%, less than 4%, less than 3%, less than 2%, or less than 1% anhydro-subunit containing oligosaccharides by relative abundance. In some embodiments, said DP3 fraction comprises from about 2% to about 12% of anhydro-subunit containing oligosaccharides by relative abundance. In some embodiments, said DP3 fraction comprises from about 1% to about 10% of anhydro-subunit containing oligosaccharides by relative abundance. In some embodiments, said DP3 fraction comprises from about 0.5% to about 10% of anhydro-subunit containing oligosaccharides by relative abundance. In some embodiments, said DP3 fraction comprises from about 5% to about 10% of anhydro-subunit containing oligosaccharides by relative abundance.

In some embodiments, said oligosaccharide preparation comprises from about 2% to about 12% anhydro-subunit containing oligosaccharides by relative abundance. In some embodiments, said oligosaccharide preparation comprises from about 0.5% to about 10% anhydro-subunit containing oligosaccharides by relative abundance. In some embodiments, said oligosaccharide preparation comprises from about 1% to about 10% anhydro-subunit containing oligosaccharides by relative abundance. In some embodiments, said oligosaccharide preparation comprises from about 5% to about 10% anhydro-subunit containing oligosaccharides by relative abundance.

In some embodiments, said DP2 fraction comprises greater than 0.6%, greater than 0.8%, greater than 1.0%, greater than 1.5%, greater than 2%, greater than 3%, greater than 4%, greater than 5%, greater than 6%, greater than 7%, greater than 8%, greater than 9%, greater than 10%, greater than 11%, or greater than 12% anhydro-subunit containing oligosaccharides by relative abundance.

In some embodiments, said DP1 fraction comprises greater than 0.6%, greater than 0.8%, greater than 1.0%, greater than 1.5%, greater than 2%, greater than 3%, greater than 4%, greater than 5%, greater than 6%, greater than 7%, greater than 8%, greater than 9%, greater than 10%, greater than 11%, or greater than 12% anhydro-subunit containing oligosaccharides by relative abundance.

In some embodiments, said DP3 fraction comprises greater than 0.6%, greater than 0.8%, greater than 1.0%, greater than 1.5%, greater than 2%, greater than 3%, greater than 4%, greater than 5%, greater than 6%, greater than 7%, greater than 8%, greater than 9%, greater than 10%, greater than 11%, or greater than 12% anhydro-subunit containing oligosaccharides by relative abundance.

In some embodiments, said oligosaccharide preparation comprises greater than 0.5%, 0.6%, greater than 0.8%, greater than 1.0%, greater than 1.5%, greater than 2%, greater than 3%, greater than 4%, greater than 5%, greater than 6%, greater than 7%, greater than 8%, greater than 9%, greater than 10%, greater than 11%, or greater than 12% anhydro-subunit containing oligosaccharides by relative abundance.

In some embodiments, said oligosaccharide preparation has a DP1 fraction content of from about 1% to about 40% by weight as determined by liquid chromatography.

In some embodiments, said oligosaccharide preparation has a DP2 fraction content of from about 1% to about 35% by weight as determined by liquid chromatography.

In some embodiments, said oligosaccharide preparation has a DP3 fraction content of from about 1% to about 30% by weight as determined by liquid chromatography.

In some embodiments, said oligosaccharide preparation has a DP4 fraction content of from about 0.1% to about 20% by weight as determined by liquid chromatography In some embodiments, said oligosaccharide preparation has a DP5 fraction content of from about 0.1% to about 15% by weight as determined by liquid chromatography.

In some embodiments, a ratio of the DP2 fraction to the DP1 fraction is from about 0.02 to about 0.40 as determined by liquid chromatography.

In some embodiments, a ratio of the DP3 fraction to the DP2 fraction is from about 0.01 to about 0.30 as determined by liquid chromatography.

In some embodiments, an aggregate content of the DP1 and the DP2 fractions in the oligosaccharide preparation is less than 50%, less than 40%, or less than 30% as determined by liquid chromatography.

In some embodiments, said oligosaccharide preparation comprises at least 103, at least 104, at least 105, at least 106 or at least 109 different oligosaccharide species.

In some embodiments, two or more independent oligosaccharides comprise different anhydro-subunits.

In some embodiments, each of said anhydro-subunit containing oligosaccharides comprises one or more anhydro-subunits that are products of thermal dehydration of monosaccharides.

In some embodiments, said oligosaccharide preparation comprises one or more anhydro-subunits selected from anhydro-glucose, anhydro-galactose, anhydro-mannose, anhydro-allose, anhydro-altrose, anhydro-gulose, anhydro-indose, anhydro-talose, anhydro-fructose, anhydro-ribose, anhydro-arabinose, anhydro-rhamnose, anhydro-lyxose, and anhydro-xylose.

In some embodiments, said oligosaccharide preparation comprises one or more anhydro-glucose, anhydro-galactose, anhydro-mannose, or anhydro-fructose subunits.

In some embodiments, said DP1 fraction comprises 1,6-anhydro-β-D-glucofuranose or 1,6-anhydro-β-D-glucopyranose anhydro-subunits. In some embodiments, said DP1 fraction comprises both 1,6-anhydro-β-D-glucofuranose and 1,6-anhydro-β-D-glucopyranose anhydro-subunits.

In some embodiments, a ratio of the 1,6-anhydro-β-D-glucofuranose to the 1,6-anhydro-β-D-glucopyranose is from about 10:1 to 1:10, from about 9:1 to about 1:10, from about 8:1 to about 1:10, from about 7:1 to about 1:10, from about 6:1 to about 1:10, from about 5:1 to about 1:10, from about 4:1 to about 1:10, from about 3:1 to about 1:10, from about 2:1 to about 1:10, from about 10:1 to about 1:9, from about 10:1 to about 1:8, from about 10:1 to about 1:7, from about 10:1 to about 1:6, from about 10:1 to about 1:5, from about 10:1 to about 1:4, from about 10:1 to about 1:3, from about 10:1 to about 1:2, or from about 1:1 to about 3:1 in the oligosaccharide reparation. In some embodiments, a ratio of the 1,6-anhydro-β-D-glucofuranose to the 1,6-anhydro-β-D-glucopyranose is about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, or about 1:10 in the oligosaccharide preparation. In some embodiments, a ratio of the 1,6-anhydro-β-D-glucofuranose to the 1,6-anhydro-β-D-glucopyranose is about 2:1 in the oligosaccharide preparation.

In some embodiments, said DP2 fraction comprises at least 5 species of anhydro-subunit containing oligosaccharides. In some embodiments, said DP2 fraction comprises about 5 to 10 species of anhydro-subunit containing oligosaccharides.

In some embodiments, said oligosaccharide preparation comprises one or more sugar caramelization products. In some embodiments, said sugar caramelization products are selected from a group consisting of: methanol; ethanol; furan; methyl glyoxal; 2-methyl furan; vinyl acetate; glycolaldehyde; acetic acid; acetol; furfural; 2-furanmethanol; 3-furanmethanol; 2-hydroxy cyclopent-2-en-1-one; 5-methyl furfural; 2(5H)-furanone; 2 methyl cyclopentenolone; levoglucosenone; cyclic hydroxyl lactone; 1,4,3,6-dianhydro-α-D-glucopyranose; dianhydro glucopyranose; and 5-hydroxy methyl furfural (5-hmf).

In some embodiments, greater than 50%, 60%, 70%, 80%, 90%, 95%, or 99% of the anhydro-subunit containing oligosaccharides comprise a chain-end anhydro-subunit.

In some embodiments, said oligosaccharide preparation has a weight average molecular weight of from about 300 to about 5000 g/mol as determined by high-performance liquid chromatography (HPLC). In some embodiments, said oligosaccharide preparation has a weight average molecular weight of from about 300 to about 2500 g/mol as determined by HPLC. In some embodiments, said oligosaccharide preparation has a weight average molecular weight of from about 500 to about 2000 g/mol as determined by HPLC. In some embodiments, said oligosaccharide preparation has a weight average molecular weight of from about 500 to about 1500 g/mol as determined by HPLC. In some embodiments, said oligosaccharide preparation has a number average molecular weight of from about 300 to about 5000 g/mol as determined by HPLC. In some embodiments, said oligosaccharide preparation has a number average molecular weight of from about 300 to about 2500 g/mol as determined by HPLC. In some embodiments, said oligosaccharide preparation has a number average molecular weight of from about 500 to about 2000 g/mol as determined by HPLC. In some embodiments, said oligosaccharide preparation has a number average molecular weight of from about 500 to about 1500 g/mol as determined by HPLC.

In some embodiments, said oligosaccharide preparation has a weight average molecular weight of from about 2000 to about 2800 g/mol. In some embodiments, said oligosaccharide preparation has a number average molecular weight of from about 1000 to about 2000 g/mol.

In one aspect, provided herein are methods of modulating the growth of at least one microbial species in the gastrointestinal tract of an animal, said method comprising: administering a nutritional composition comprising a base nutritional composition and a synthetic oligosaccharide preparation to an animal, wherein said synthetic oligosaccharide preparation comprises at least n fractions of oligosaccharides each having a distinct degree of polymerization selected from 1 to n (DP1 to DPn fractions), wherein n is an integer greater than 3; and wherein each of a DP1 and DP2 fraction independently comprises from about 0.5% to about 15% of anhydro-subunit containing oligosaccharides by relative abundance as determined by mass spectrometry, and wherein a level of at least one microbial species in a gastrointestinal sample from said animal is increased or decreased relative to a level of said at least one microbial species in a gastrointestinal sample from a comparable control animal that has been administered a comparable nutritional composition lacking said synthetic oligosaccharide preparation.

In some embodiments, said at least one microbial species is an archaea, a bacteria, a protozoan, a virus, a bacteriophage, a parasite, or a fungus. In some embodiments, said microbial species is a bacteria.

In some embodiments, said gastrointestinal sample is a biopsy of a gastrointestinal tissue, a fecal sample, or a cloacal swab. In some embodiments, said gastrointestinal tissue is cecal tissue or ileum tissue. In some embodiments, said method further comprises obtaining said sample.

In some embodiments, said method further comprises detecting the level of said at least one microbial species in said gastrointestinal sample. In some embodiments, said method further comprises detecting a level of at least 2, 3, 4, 5, 6 microbial species in said gastrointestinal sample. In some embodiments, a level of at least 2, 3, 4, 5, or 6 microbial species in said gastrointestinal sample from said animal are increased or decreased relative to a level of said at least 2, 3, 4, 5, or 6 microbial species in a gastrointestinal sample from said animal prior to said administering said nutritional composition to said animal. In some embodiments, a level of at least 2, 3, 4, 5, or 6 microbial species in a gastrointestinal sample from said animal are increased or decreased relative to a level of said at least 2, 3, 4, 5, or 6, or more microbial species in a gastrointestinal sample from a control animal that has been administered a comparable nutritional composition lacking said synthetic oligosaccharide preparation.

In some embodiments, said method comprises promoting the growth of said at least one microbial species, and wherein said level of at least one microbial species in said gastrointestinal sample is increased relative to a level of said at least one microbial species in a gastrointestinal sample from said animal prior to said administering said nutritional composition to said animal. In some embodiments, said increase in said least one microbial species in a gastrointestinal sample from said animal is a larger increase relative to an increase in said at least one microbial species in a gastrointestinal sample from a comparable control animal that has been administered a comparable nutritional composition lacking said synthetic oligosaccharide preparation.

In some embodiments, said method comprises promoting the growth of said at least one microbial species, and wherein said level of at least one microbial species in said gastrointestinal sample is increased relative to a level of said at least one microbial species in a gastrointestinal sample from a comparable control animal that has been administered a comparable nutritional composition lacking said synthetic oligosaccharide preparation.

In some embodiments, said microbial species is beneficial to the health of the animal. In some embodiments, said microbial species is beneficial to the gastrointestinal health of the animal. In some embodiments, said microbial species is non-pathogenic to said animal. In some embodiments, said microbial species is non-pathogenic to humans.

In some embodiments, said microbial species belongs to the genus *Bacteroides, Odoribacter, Oscillibacter, Subdoligranulum, Biophila*, or *Barnesiella*. In some embodiments, said microbial species is selected from the group consisting of: *Bacteroides clarus, Bacteroides dorei, Odoribacter splanchinicus*, and *Barnesiella intestinihominis*. In some embodiments, said microbial species is selected from Group 1 as listed in Table 26. In some embodiments, said microbial species is selected from Group 2 as listed in Table 26. In some embodiments, said microbial species is selected from Group 3 as listed in Table 26.

In some embodiments, each of said at least 2, 3, 4, 5, or 6 microbial species improve the health of the animal. In some embodiments, each of said at least 2, 3, 4, 5, or 6 microbial species improve the gastrointestinal health of the animal. In some embodiments, each of said at least 2, 3, 4, 5, or 6 microbial species are non-pathogenic to said animal. In some embodiments, each of said at least 2, 3, 4, 5, or 6 microbial species are non-pathogenic to humans. In some embodiments, each of said at least 2, 3, 4, 5, or 6 microbial species in said gastrointestinal sample from said animal are increased relative to a level of said at least 2, 3, 4, 5, or 6 microbial species in a gastrointestinal sample from said animal prior to administration of said nutritional composition to said animal. In some embodiments, each of said at least 2, 3, 4, 5, or 6 microbial species in a gastrointestinal sample from said animal are increased relative to a level of said at least 2, 3, 4, 5, or 6 microbial species in a gastrointestinal sample from a control animal that has been administered a comparable nutritional composition lacking said synthetic oligosaccharide preparation. In some embodiments, at least one of said at least 2, 3, 4, 5, or 6 microbial species belongs to the genus *Bacteroides, Odoribacter, Oscillibacter, Subdoligranulum, Biophila*, or *Barnesiella*. In some embodiments, at least one of said at least 2, 3, 4, 5, or 6 microbial species is selected from the group consisting of: *Bacteroides clarus, Bacteroides dorei, Odoribacter splanchinicus*, and *Barnesiella intestinihominis*. In some embodiments, said gastrointestinal sample comprises at least 0.1%, 1%, 2%, 3%, 4%, 5%, 6%, 7%, 8%, 9%, or 10% of at least one microbial species that belongs to the genus *Bacteroides, Odoribacter, Oscillibacter, Subdoligranulum, Biophila*, or *Barnesiella*. In some embodiments, said gastrointestinal sample comprises at least 0.1%, 1%, 2%, 3%, 4%, 5%, 6%, 7%, 8%, 9%, or 10% of at least one of *Bacteroides clarus, Bacteroides dorei, Odoribacter splanchinicus*, and *Barnesiella intestinihominis*.

In some embodiments, said method comprises inhibiting the growth the growth of said at least one microbial species, and wherein said level of at least one microbial species in a gastrointestinal sample is decreased relative to a level of said at least one microbial species in a gastrointestinal sample from said animal prior to said administering said nutritional composition to said animal. In some embodiments, said decrease in said least one microbial species in a gastrointestinal sample from said animal is a larger decrease relative to an increase in said at least one microbial species in a gastrointestinal sample from a comparable control animal that has been administered a comparable nutritional composition lacking said synthetic oligosaccharide preparation.

In some embodiments, said method comprises inhibiting the growth the growth of said at least one microbial species, and wherein said level of at least one microbial species in a gastrointestinal sample is decreased relative to a level of said at least one microbial species in a gastrointestinal sample from a comparable control animal that has been administered a comparable nutritional composition lacking said synthetic oligosaccharide preparation.

In some embodiments, said microbial species is detrimental to the health of said animal. In some embodiments, said microbial species is detrimental to the gastrointestinal health of said animal. In some embodiments, said microbial species is pathogenic to said animal. In some embodiments, said microbial species is pathogenic to humans but not pathogenic to said animal.

In some embodiments, said microbial species is *Helicobacter pullorum*. In some embodiments, said microbial species belongs to the phylum Proteobacteria. In some embodiments, said microbial species belongs to the genus *Helicobacter, Escherichia, Salmonella, Vibrio*, or *Yersinia. In some embodiments, said microbial species is selected from the group consisting of: Helicobacter pullorum, Proteobacteria johnsonii, Escherichia coli, Camplobacter jejuni*, and *Lactobacillus crispatus*. In some embodiments, said microbial species is selected from Group 2 as listed in Table 26. In some embodiments, said microbial species is selected from Group 3 as listed in Table 26. In some embodiments, said microbial species is selected from Group 4 as listed in Table 26.

In some embodiments, each of said at least 2, 3, 4, 5, or 6 microbial species is detrimental to the health of the animal. In some embodiments, each of said at least 2, 3, 4, 5, or 6 microbial species in said gastrointestinal sample from said animal is decreased relative to a level of said at least 2, 3, 4, 5, or 6, or more microbial species in a gastrointestinal sample from said animal prior to said administering said nutritional composition to said animal. In some embodiments, each of said at least 2, 3, 4, 5, or 6 microbial species in a gastrointestinal sample from said animal are decreased relative to a level of said at least 2, 3, 4, 5, or 6 microbial species in a gastrointestinal sample from a control animal that has been administered a comparable nutritional composition lacking said synthetic oligosaccharide preparation. In some embodiments, at least one of said at least 2, 3, 4, 5, or 6 microbial species belongs to the phylum Proteobacteria. In some embodiments, at least one of said at least 2, 3, 4, 5, or 6 microbial species belongs to the genus *Helicobacter, Escherichia, Salmonella, Vibrio*, or *Yersinia*. In some embodiments, at least one of said at least 2, 3, 4, 5, or 6 microbial species is selected from the group consisting of: *Helicobacter pullorum, Proteobacteria johnsonii, Escherichia coli, Camplobacter jejuni*, and *Lactobacillus crispatus*. In some embodiments, said gastrointestinal sample comprises less than 0.1%, 1%, 2%, 3%, 4%, 5%, 6%, 7%, 8%, 9%, or 10% of at least one microbial species that belongs to the genus *Helicobacter, Escherichia, Salmonella, Vibrio*, or *Yersinia*. In some embodiments, said gastrointestinal sample comprises at less than 0.1%, 1%, 2%, 3%, 4%, 5%, 6%, 7%, 8%, 9%, or 10% of at least one of *Helicobacter pullorum, Proteobacteria johnsonii, Escherichia coli, Camplobacter jejuni*, and *Lactobacillus crispatus*.

In some embodiments, said nutritional composition comprising said synthetic oligosaccharide preparation is administered to said animal for at least 1, 7, 10, 14, 30, 45, 60, 90, or 120 days.

In some embodiments, said nutritional composition comprising said synthetic oligosaccharide preparation is administered to said animal at least once, twice, three, four, or five times a day.

The method of any preceding claim, wherein said administering comprises providing the nutritional composition to said animal to ingest at will.

In some embodiments, said animal ingests at least a portion of said nutritional composition in over at least 1, 2, 3, 4, 5, 6, 7, 8, 9, 10, 20, 30, 40, 50, 60, 90, or 120 twenty-four-hour periods.

In some embodiments, said nutritional composition comprises at least 100 ppm, 200 ppm, 300 ppm, 400 ppm, 500 ppm, 600 ppm, 700 ppm, 800 ppm, 900 ppm, 1000 ppm, 1500 ppm, or 2000 ppm oligosaccharide preparation. In some embodiments, said nutritional composition comprises about 100 ppm, 200 ppm, 300 ppm, 400 ppm, 500 ppm, 600 ppm, 700 ppm, 800 ppm, 900 ppm, 1000 ppm, 1500 ppm, or 2000 ppm oligosaccharide preparation. In some embodiments, said nutritional composition comprises about 500 ppm oligosaccharide preparation. In some embodiments, said nutritional composition comprises from about 100 ppm-2000 ppm, 100 ppm-1500 ppm, 100 ppm-1000 ppm, 100 ppm-900 ppm, 100 ppm-800 ppm, 100 ppm-700 ppm, 100 ppm-600 ppm, 100 ppm-500 ppm, 100 ppm-400 ppm, 100 ppm-300 ppm, 100 ppm-200 ppm, 200 ppm-1000 ppm, 200 ppm-800 ppm, 200 ppm-700 ppm, 200 ppm-600 ppm, 200 ppm-500 ppm, 300 ppm-1000 ppm, 300 ppm-700 ppm, 300 ppm-600 ppm, or 300 ppm-500 ppm oligosaccharide preparation. In some embodiments, said nutritional composition comprises from about 300 ppm-600 ppm oligosaccharide preparation.

In some embodiments, said animal has an increased body weight relative to a body weight of said animal prior to administration of said nutritional composition comprising said synthetic oligosaccharide preparation. In some embodiments, said body weight of said animal is at least 1%, 2%, 3%, 4%, 5%, 5%, 7%, 8%, 9%, or 10% increased relative to said body weight of said animal prior to administration of said nutritional composition comprising said synthetic oligosaccharide preparation. In some embodiments, said increase in body weight is a larger increase relative to a comparable control animal administered a comparable nutritional composition lacking said synthetic oligosaccharide preparation. In some embodiments, said body weight of said animal is at least 1%, 2%, 3%, 4%, 5%, 5%, 7%, 8%, 9%, or 10% increased relative to said body weight of said comparable control animal administered a comparable nutritional composition lacking said synthetic oligosaccharide preparation.

In some embodiments, said animal has an increased feed efficiency relative to a feed efficiency of said animal prior to administration of said nutritional composition comprising said synthetic oligosaccharide preparation. In some embodiments, said feed efficiency of said animal is at least 1%, 2%, 3%, 4%, 5%, 5%, 7%, 8%, 9%, or 10% increased relative to said feed efficiency of said animal prior to administration of said nutritional composition comprising said synthetic oligosaccharide preparation. In some embodiments, said animal has said increase in feed efficiency is a larger increase relative to a comparable control animal administered a comparable nutritional composition lacking said synthetic oligosaccharide preparation. In some embodiments, said increase in feed efficiency of said animal is at least 1%, 2%, 3%, 4%, 5%, 5%, 7%, 8%, 9%, or 10% increased relative to said body weight of said comparable control animal administered a comparable nutritional composition lacking said synthetic oligosaccharide preparation.

In some embodiments, said animal has a decreased feed conversion ratio (FCR) relative to an FCR of said animal prior to administration of said nutritional composition comprising said synthetic oligosaccharide preparation. In some embodiments, said feed conversion ratio of said animal is at least 1%, 2%, 3%, 4%, 5%, 5%, 7%, 8%, 9%, or 10% decreased relative to the feed conversion ratio of said animal prior to administration of said nutritional composition comprising said synthetic oligosaccharide preparation. In some embodiments, said animal has said decrease in feed conversion ratio is a larger decrease relative to a comparable control animal administered a comparable nutritional composition lacking said synthetic oligosaccharide preparation. In some embodiments, said feed conversion ratio of said animal is at least 1%, 2%, 3%, 4%, 5%, 5%, 7%, 8%, 9%, or 10% decreased relative to the feed conversion ratio of said comparable control animal administered a comparable nutritional composition lacking said synthetic oligosaccharide preparation.

In some embodiments, a life expectancy or survival rate of said animal is increased relative to a comparable control animal that was administered a comparable nutritional composition lacking said synthetic oligosaccharide preparation.

In some embodiments, said level of said at least one microbial species is determined by DNA sequencing or RNA sequencing. In some embodiments, said level of said at least one microbial species is determined by shotgun DNA sequencing.

In some embodiments, said animal is a poultry, seafood, sheep, cow, cattle, buffalo, bison, pig, cat, dog, rabbit, goat, guinea pig, donkey, camel, horse, pigeon, ferret, gerbil, hamster, mouse, rat, fish, or bird. In some embodiments, said animal is poultry. In some embodiments, said animal is a chicken, turkey, duck, or goose. In some embodiments, said chicken is a broiler chicken, a layer chicken, or a breeder chicken. In some embodiments, said animal is a pig. In some embodiments, said pig is a nursery pig, a grower pig, or a finisher pig. In some embodiments, said animal is a fish. In some embodiments, said fish is a salmon, a tilapia, or a tropical fish.

In some embodiments, said nutritional composition is an animal feed composition. In some embodiments, said base nutritional composition is base animal feed.

In some embodiments, said relative abundance is determined by LC-MS/MS.

In some embodiments, said relative abundance of oligosaccharides in at least 5, 10, 20, or 30 DP fractions decreases monotonically with its degree of polymerization. In some embodiments, said relative abundance of oligosaccharides in each of the n fractions decreases monotonically with its degree of polymerization.

In some embodiments, n is at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100.

In some embodiments, said DP2 fraction comprises less than 12%, less than 11%, less than 10%, less than 9%, less than 8%, less than 7%, less than 6%, less than 5%, less than 4%, less than 3%, less than 2%, or less than 1% anhydro-subunit containing oligosaccharides by relative abundance.

In some embodiments, said DP2 fraction comprises from about 5% to about 10% of anhydro-subunit containing oligosaccharides by relative abundance. In some embodiments, said DP2 fraction comprises from about 1% to about 10% of anhydro-subunit containing oligosaccharides by relative abundance. In some embodiments, said DP2 fraction comprises from about 0.5% to about 10% of anhydro-subunit containing oligosaccharides by relative abundance. In some embodiments, said DP2 fraction comprises from about 2% to about 12% of anhydro-subunit containing oligosaccharides by relative abundance.

In some embodiments, said DP1 fraction comprises less than 12%, less than 11%, less than 10%, less than 9%, less than 8%, less than 7%, less than 6%, less than 5%, less than 4%, less than 3%, less than 2%, or less than 1% anhydro-subunit containing oligosaccharides by relative abundance. In some embodiments, said DP1 fraction comprises from about 2% to about 12% of anhydro-subunit containing oligosaccharides by relative abundance. In some embodiments, said DP1 fraction comprises from about 1% to about 10% of anhydro-subunit containing oligosaccharides by relative abundance.

In some embodiments, said DP1 fraction comprises from about 0.5% to about 10% of anhydro-subunit containing oligosaccharides by relative abundance. In some embodiments, said DP1 fraction comprises from about 5% to about 10% of anhydro-subunit containing oligosaccharides by relative abundance.

In some embodiments, said DP3 fraction comprises less than 15%, less than 12%, less than 11%, less than 10%, less than 9%, less than 8%, less than 7%, less than 6%, less than 5%, less than 4%, less than 3%, less than 2%, or less than 1% anhydro-subunit containing oligosaccharides by relative abundance. In some embodiments, said DP3 fraction comprises from about 2% to about 12% of anhydro-subunit containing oligosaccharides by relative abundance. In some embodiments, said DP3 fraction comprises from about 1% to about 10% of anhydro-subunit containing oligosaccharides by relative abundance. In some embodiments, said DP3 fraction comprises from about 0.5% to about 10% of anhydro-subunit containing oligosaccharides by relative abundance. In some embodiments, said DP3 fraction comprises from about 5% to about 10% of anhydro-subunit containing oligosaccharides by relative abundance.

In some embodiments, said oligosaccharide preparation comprises from about 2% to about 12% anhydro-subunit containing oligosaccharides by relative abundance. In some embodiments, said oligosaccharide preparation comprises from about 0.5% to about 10% anhydro-subunit containing oligosaccharides by relative abundance. In some embodiments, said oligosaccharide preparation comprises from about 1% to about 10% anhydro-subunit containing oligosaccharides by relative abundance. In some embodiments, said oligosaccharide preparation comprises from about 5% to about 10% anhydro-subunit containing oligosaccharides by relative abundance.

In some embodiments, said DP2 fraction comprises greater than 0.6%, greater than 0.8%, greater than 1.0%, greater than 1.5%, greater than 2%, greater than 3%, greater than 4%, greater than 5%, greater than 6%, greater than 7%, greater than 8%, greater than 9%, greater than 10%, greater than 11%, or greater than 12% anhydro-subunit containing oligosaccharides by relative abundance.

In some embodiments, said DP1 fraction comprises greater than 0.6%, greater than 0.8%, greater than 1.0%, greater than 1.5%, greater than 2%, greater than 3%, greater than 4%, greater than 5%, greater than 6%, greater than 7%, greater than 8%, greater than 9%, greater than 10%, greater than 11%, or greater than 12% anhydro-subunit containing oligosaccharides by relative abundance.

In some embodiments, said DP3 fraction comprises greater than 0.6%, greater than 0.8%, greater than 1.0%, greater than 1.5%, greater than 2%, greater than 3%, greater than 4%, greater than 5%, greater than 6%, greater than 7%, greater than 8%, greater than 9%, greater than 10%, greater than 11%, or greater than 12% anhydro-subunit containing oligosaccharides by relative abundance.

In some embodiments, said oligosaccharide preparation comprises greater than 0.5%, 0.6%, greater than 0.8%, greater than 1.0%, greater than 1.5%, greater than 2%, greater than 3%, greater than 4%, greater than 5%, greater than 6%, greater than 7%, greater than 8%, greater than 9%, greater than 10%, greater than 11%, or greater than 12% anhydro-subunit containing oligosaccharides by relative abundance.

In some embodiments, said oligosaccharide preparation has a DP1 fraction content of from about 1% to about 40% by weight as determined by liquid chromatography.

In some embodiments, said oligosaccharide preparation has a DP2 fraction content of from about 1% to about 35% by weight as determined by liquid chromatography.

In some embodiments, said oligosaccharide preparation has a DP3 fraction content of from about 1% to about 30% by weight as determined by liquid chromatography.

In some embodiments, said oligosaccharide preparation has a DP4 fraction content of from about 0.1% to about 20% by weight as determined by liquid chromatography In some embodiments, said oligosaccharide preparation has a DP5 fraction content of from about 0.1% to about 15% by weight as determined by liquid chromatography.

In some embodiments, a ratio of the DP2 fraction to the DP1 fraction is from about 0.02 to about 0.40 as determined by liquid chromatography.

In some embodiments, a ratio of the DP3 fraction to the DP2 fraction is from about 0.01 to about 0.30 as determined by liquid chromatography.

In some embodiments, an aggregate content of the DP1 and the DP2 fractions in the oligosaccharide preparation is less than 50%, less than 40%, or less than 30% as determined by liquid chromatography.

In some embodiments, said oligosaccharide preparation comprises at least 103, at least 104, at least 105, at least 106 or at least 109 different oligosaccharide species.

In some embodiments, two or more independent oligosaccharides comprise different anhydro-subunits.

In some embodiments, each of said anhydro-subunit containing oligosaccharides comprises one or more anhydro-subunits that are products of thermal dehydration of monosaccharides.

In some embodiments, said oligosaccharide preparation comprises one or more anhydro-subunits selected from anhydro-glucose, anhydro-galactose, anhydro-mannose, anhydro-allose, anhydro-altrose, anhydro-gulose, anhydro-indose, anhydro-talose, anhydro-fructose, anhydro-ribose, anhydro-arabinose, anhydro-rhamnose, anhydro-lyxose, and anhydro-xylose.

In some embodiments, said oligosaccharide preparation comprises one or more anhydro-glucose, anhydro-galactose, anhydro-mannose, or anhydro-fructose subunits.

In some embodiments, said DP1 fraction comprises 1,6-anhydro-β-D-glucofuranose or 1,6-anhydro-β-D-glucopyranose anhydro-subunits. In some embodiments, said DP1 fraction comprises both 1,6-anhydro-β-D-glucofuranose and 1,6-anhydro-β-D-glucopyranose anhydro-subunits.

In some embodiments, a ratio of the 1,6-anhydro-β-D-glucofuranose to the 1,6-anhydro-β-D-glucopyranose is from about 10:1 to 1:10, from about 9:1 to about 1:10, from about 8:1 to about 1:10, from about 7:1 to about 1:10, from about 6:1 to about 1:10, from about 5:1 to about 1:10, from about 4:1 to about 1:10, from about 3:1 to about 1:10, from about 2:1 to about 1:10, from about 10:1 to about 1:9, from about 10:1 to about 1:8, from about 10:1 to about 1:7, from about 10:1 to about 1:6, from about 10:1 to about 1:5, from about 10:1 to about 1:4, from about 10:1 to about 1:3, from about 10:1 to about 1:2, or from about 1:1 to about 3:1 in the oligosaccharide reparation. In some embodiments, a ratio of the 1,6-anhydro-β-D-glucofuranose to the 1,6-anhydro-β-D-glucopyranose is about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, or about 1:10 in the oligosaccharide preparation. In some embodiments, a ratio of the 1,6-anhydro-β-D-glucofuranose to the 1,6-anhydro-β-D-glucopyranose is about 2:1 in the oligosaccharide preparation.

In some embodiments, said DP2 fraction comprises at least 5 species of anhydro-subunit containing oligosaccharides. In some embodiments, said DP2 fraction comprises about 5 to 10 species of anhydro-subunit containing oligosaccharides.

In some embodiments, said oligosaccharide preparation comprises one or more sugar caramelization products. In some embodiments, said sugar caramelization products are selected from a group consisting of: methanol; ethanol; furan; methyl glyoxal; 2-methyl furan; vinyl acetate; glycolaldehyde; acetic acid; acetol; furfural; 2-furanmethanol; 3-furanmethanol; 2-hydroxy cyclopent-2-en-1-one; 5-methyl furfural; 2(5H)-furanone; 2 methyl cyclopentenolone; levoglucosenone; cyclic hydroxyl lactone; 1,4,3,6-dianhydro-α-D-glucopyranose; dianhydro glucopyranose; and 5-hydroxy methyl furfural (5-hmf).

In some embodiments, greater than 50%, 60%, 70%, 80%, 90%, 95%, or 99% of the anhydro-subunit containing oligosaccharides comprise a chain-end anhydro-subunit.

In some embodiments, said oligosaccharide preparation has a weight average molecular weight of from about 300 to about 5000 g/mol as determined by high-performance liquid chromatography (HPLC). In some embodiments, said oligosaccharide preparation has a weight average molecular weight of from about 300 to about 2500 g/mol as determined by HPLC. In some embodiments, said oligosaccharide preparation has a weight average molecular weight of from about 500 to about 2000 g/mol as determined by HPLC. In some embodiments, said oligosaccharide preparation has a weight average molecular weight of from about 500 to about 1500 g/mol as determined by HPLC. In some embodiments, said oligosaccharide preparation has a number average molecular weight of from about 300 to about 5000 g/mol as determined by HPLC. In some embodiments, said oligosaccharide preparation has a number average molecular weight of from about 300 to about 2500 g/mol as determined by HPLC. In some embodiments, said oligosaccharide preparation has a number average molecular weight of from about 500 to about 2000 g/mol as determined by HPLC. In some embodiments, said oligosaccharide preparation has a number average molecular weight of from about 500 to about 1500 g/mol as determined by HPLC.

In some embodiments, said oligosaccharide preparation has a weight average molecular weight of from about 2000 to about 2800 g/mol. In some embodiments, said oligosaccharide preparation has a number average molecular weight of from about 1000 to about 2000 g/mol.

In one aspect, provided herein are methods of modulating expression of at least one microbial protein within the gastrointestinal tract of an animal, said method comprising: administering a nutritional composition comprising a base nutritional composition and a synthetic oligosaccharide preparation to an animal, wherein said synthetic oligosaccharide preparation comprises at least n fractions of oligosaccharides each having a distinct degree of polymerization selected from 1 to n (DP1 to DPn fractions), wherein n is an integer greater than 3; and wherein each of a DP1 and DP2 fraction independently comprises from about 0.5% to about 15% of anhydro-subunit containing oligosaccharides by relative abundance as determined by mass spectrometry, and wherein a level of at least one microbial protein in a gastrointestinal sample is increased or decreased relative to a level of said at least one microbial protein in a gastrointestinal sample from said animal prior to administration of said nutritional composition to said animal.

In some embodiments, said increase or decrease in said least one microbial protein in a gastrointestinal sample from said animal is a larger increase or decrease relative to an increase or decrease in said at least one microbial protein in a gastrointestinal sample from a comparable control animal that has been administered a comparable nutritional composition lacking said synthetic oligosaccharide preparation.

In some embodiments, said level of said at least one microbial protein in said gastrointestinal sample is decreased relative to said level of said at least one microbial protein in a gastrointestinal sample from said animal prior to administration of said nutritional composition to said animal.

In some embodiments, said level of said at least one microbial protein in said gastrointestinal sample is decreased relative to said level of said at least one microbial protein in a gastrointestinal sample from a comparable control animal that has been administered a comparable nutritional composition lacking said synthetic oligosaccharide preparation.

In some embodiments, said level of said at least one microbial protein in said gastrointestinal sample is increased relative to said level of said at least one microbial protein in a gastrointestinal sample from said animal prior to administration of said nutritional composition to said animal. In some embodiments, said level of said at least one microbial protein in said gastrointestinal sample is increased relative to said level of said at least one microbial protein in a gastrointestinal sample from a comparable control animal that has been administered a comparable nutritional composition lacking said synthetic oligosaccharide preparation.

In some embodiments, said microbial protein is a hydrolytic enzyme, a protein involved in digestion (e.g. hydrolytic enzymatic digestion), or a protein involved in metabolism.

In some embodiments, said at least one microbial protein is an archaea protein, a bacterial protein, a protozoan protein, a viral protein, a bacteriophage protein, a parasite protein, or a fungal protein. In some embodiments, said microbial species is a bacterial protein.

In some embodiments, said gastrointestinal sample is a biopsy of a gastrointestinal tissue or a fecal sample. In some embodiments, said gastrointestinal tissue is cecal tissue or ileum tissue.

In some embodiments, said method further comprises obtaining said gastrointestinal sample.

In some embodiments, said method further comprises detecting the level of said at least one microbial protein in said gastrointestinal sample.

In some embodiments, said at least one microbial protein is a carbohydrate active enzyme (CAZymes). In some embodiments, said at least one microbial protein is a sus-like polysaccharide utilization loci (PULs) protein. In some embodiments, said at least one microbial protein is selected from the group consisting of: GH127 (CAZyme α-L-arabinofuranosidase), susC (outer membrane protein involved in starch binding) and susD (starch binding protein).

In some embodiments, said level of said at least one microbial protein is determined by analyzing RNA or protein expression.

In some embodiments, said animal is a poultry, seafood, sheep, cow, cattle, buffalo, bison, pig, cat, dog, rabbit, goat, guinea pig, donkey, camel, horse, pigeon, ferret, gerbil, hamster, mouse, rat, fish, or bird. In some embodiments, said animal is poultry. In some embodiments, said animal is a chicken, turkey, duck, or goose. In some embodiments, said chicken is a broiler chicken, a layer chicken, or a breeder chicken. In some embodiments, said animal is a pig. In some embodiments, said pig is a nursery pig, a grower pig, or a finisher pig. In some embodiments, said animal is a fish. In some embodiments, said fish is a salmon, a tilapia, or a tropical fish.

In some embodiments, said nutritional composition is an animal feed composition. In some embodiments, said base nutritional composition is base animal feed.

In some embodiments, said relative abundance is determined by LC-MS/MS.

In some embodiments, said relative abundance of oligosaccharides in at least 5, 10, 20, or 30 DP fractions decreases monotonically with its degree of polymerization. In some embodiments, said relative abundance of oligosaccharides in each of the n fractions decreases monotonically with its degree of polymerization.

In some embodiments, n is at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100.

In some embodiments, said DP2 fraction comprises less than 12%, less than 11%, less than 10%, less than 9%, less than 8%, less than 7%, less than 6%, less than 5%, less than 4%, less than 3%, less than 2%, or less than 1% anhydro-subunit containing oligosaccharides by relative abundance.

In some embodiments, said DP2 fraction comprises from about 5% to about 10% of anhydro-subunit containing oligosaccharides by relative abundance. In some embodiments, said DP2 fraction comprises from about 1% to about 10% of anhydro-subunit containing oligosaccharides by relative abundance. In some embodiments, said DP2 fraction comprises from about 0.5% to about 10% of anhydro-subunit containing oligosaccharides by relative abundance. In some embodiments, said DP2 fraction comprises from about 2% to about 12% of anhydro-subunit containing oligosaccharides by relative abundance.

In some embodiments, said DP1 fraction comprises less than 12%, less than 11%, less than 10%, less than 9%, less than 8%, less than 7%, less than 6%, less than 5%, less than 4%, less than 3%, less than 2%, or less than 1% anhydro-subunit containing oligosaccharides by relative abundance.

In some embodiments, said DP1 fraction comprises from about 2% to about 12% of anhydro-subunit containing oligosaccharides by relative abundance. In some embodiments, said DP1 fraction comprises from about 1% to about 10% of anhydro-subunit containing oligosaccharides by relative abundance. In some embodiments, said DP1 fraction comprises from about 0.5% to about 10% of anhydro-subunit containing oligosaccharides by relative abundance. In some embodiments, said DP1 fraction comprises from about 5% to about 10% of anhydro-subunit containing oligosaccharides by relative abundance.

In some embodiments, said DP3 fraction comprises less than 15%, less than 12%, less than 11%, less than 10%, less than 9%, less than 8%, less than 7%, less than 6%, less than 5%, less than 4%, less than 3%, less than 2%, or less than 1% anhydro-subunit containing oligosaccharides by relative abundance. In some embodiments, said DP3 fraction comprises from about 2% to about 12% of anhydro-subunit containing oligosaccharides by relative abundance. In some embodiments, said DP3 fraction comprises from about 1% to about 10% of anhydro-subunit containing oligosaccharides by relative abundance. In some embodiments, said DP3 fraction comprises from about 0.5% to about 10% of anhydro-subunit containing oligosaccharides by relative abundance. In some embodiments, said DP3 fraction comprises from about 5% to about 10% of anhydro-subunit containing oligosaccharides by relative abundance.

In some embodiments, said oligosaccharide preparation comprises from about 2% to about 12% anhydro-subunit containing oligosaccharides by relative abundance. In some embodiments, said oligosaccharide preparation comprises from about 0.5% to about 10% anhydro-subunit containing oligosaccharides by relative abundance. In some embodiments, said oligosaccharide preparation comprises from about 1% to about 10% anhydro-subunit containing oligosaccharides by relative abundance. In some embodiments, said oligosaccharide preparation comprises from about 5% to about 10% anhydro-subunit containing oligosaccharides by relative abundance.

In some embodiments, said DP2 fraction comprises greater than 0.6%, greater than 0.8%, greater than 1.0%, greater than 1.5%, greater than 2%, greater than 3%, greater than 4%, greater than 5%, greater than 6%, greater than 7%, greater than 8%, greater than 9%, greater than 10%, greater than 11%, or greater than 12% anhydro-subunit containing oligosaccharides by relative abundance.

In some embodiments, said DP1 fraction comprises greater than 0.6%, greater than 0.8%, greater than 1.0%, greater than 1.5%, greater than 2%, greater than 3%, greater than 4%, greater than 5%, greater than 6%, greater than 7%, greater than 8%, greater than 9%, greater than 10%, greater than 11%, or greater than 12% anhydro-subunit containing oligosaccharides by relative abundance.

In some embodiments, said DP3 fraction comprises greater than 0.6%, greater than 0.8%, greater than 1.0%, greater than 1.5%, greater than 2%, greater than 3%, greater than 4%, greater than 5%, greater than 6%, greater than 7%, greater than 8%, greater than 9%, greater than 10%, greater than 11%, or greater than 12% anhydro-subunit containing oligosaccharides by relative abundance.

In some embodiments, said oligosaccharide preparation comprises greater than 0.5%, 0.6%, greater than 0.8%, greater than 1.0%, greater than 1.5%, greater than 2%, greater than 3%, greater than 4%, greater than 5%, greater than 6%, greater than 7%, greater than 8%, greater than 9%, greater than 10%, greater than 11%, or greater than 12% anhydro-subunit containing oligosaccharides by relative abundance.

In some embodiments, said oligosaccharide preparation has a DP1 fraction content of from about 1% to about 40% by weight as determined by liquid chromatography.

In some embodiments, said oligosaccharide preparation has a DP2 fraction content of from about 1% to about 35% by weight as determined by liquid chromatography.

In some embodiments, said oligosaccharide preparation has a DP3 fraction content of from about 1% to about 30% by weight as determined by liquid chromatography.

In some embodiments, said oligosaccharide preparation has a DP4 fraction content of from about 0.1% to about 20% by weight as determined by liquid chromatography In some embodiments, said oligosaccharide preparation has a DP5 fraction content of from about 0.1% to about 15% by weight as determined by liquid chromatography.

In some embodiments, a ratio of the DP2 fraction to the DP1 fraction is from about 0.02 to about 0.40 as determined by liquid chromatography.

In some embodiments, a ratio of the DP3 fraction to the DP2 fraction is from about 0.01 to about 0.30 as determined by liquid chromatography.

In some embodiments, an aggregate content of the DP1 and the DP2 fractions in the oligosaccharide preparation is less than 50%, less than 40%, or less than 30% as determined by liquid chromatography.

In some embodiments, said oligosaccharide preparation comprises at least 103, at least 104, at least 105, at least 106 or at least 109 different oligosaccharide species.

In some embodiments, two or more independent oligosaccharides comprise different anhydro-subunits.

In some embodiments, each of said anhydro-subunit containing oligosaccharides comprises one or more anhydro-subunits that are products of thermal dehydration of monosaccharides.

In some embodiments, said oligosaccharide preparation comprises one or more anhydro-subunits selected from anhydro-glucose, anhydro-galactose, anhydro-mannose, anhydro-allose, anhydro-altrose, anhydro-gulose, anhydro-indose, anhydro-talose, anhydro-fructose, anhydro-ribose, anhydro-arabinose, anhydro-rhamnose, anhydro-lyxose, and anhydro-xylose.

In some embodiments, said oligosaccharide preparation comprises one or more anhydro-glucose, anhydro-galactose, anhydro-mannose, or anhydro-fructose subunits.

In some embodiments, said DP1 fraction comprises 1,6-anhydro-β-D-glucofuranose or 1,6-anhydro-β-D-glucopyranose anhydro-subunits. In some embodiments, said DP1 fraction comprises both 1,6-anhydro-β-D-glucofuranose and 1,6-anhydro-β-D-glucopyranose anhydro-subunits.

In some embodiments, a ratio of the 1,6-anhydro-β-D-glucofuranose to the 1,6-anhydro-β-D-glucopyranose is from about 10:1 to 1:10, from about 9:1 to about 1:10, from about 8:1 to about 1:10, from about 7:1 to about 1:10, from about 6:1 to about 1:10, from about 5:1 to about 1:10, from about 4:1 to about 1:10, from about 3:1 to about 1:10, from about 2:1 to about 1:10, from about 10:1 to about 1:9, from about 10:1 to about 1:8, from about 10:1 to about 1:7, from about 10:1 to about 1:6, from about 10:1 to about 1:5, from about 10:1 to about 1:4, from about 10:1 to about 1:3, from about 10:1 to about 1:2, or from about 1:1 to about 3:1 in the oligosaccharide reparation. In some embodiments, a ratio of the 1,6-anhydro-β-D-glucofuranose to the 1,6-anhydro-β-D-glucopyranose is about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, or about 1:10 in the oligosaccharide preparation. In some embodiments, a ratio of the 1,6-anhydro-β-D-glucofuranose to the 1,6-anhydro-β-D-glucopyranose is about 2:1 in the oligosaccharide preparation.

In some embodiments, said DP2 fraction comprises at least 5 species of anhydro-subunit containing oligosaccharides. In some embodiments, said DP2 fraction comprises about 5 to 10 species of anhydro-subunit containing oligosaccharides.

In some embodiments, said oligosaccharide preparation comprises one or more sugar caramelization products. In some embodiments, said sugar caramelization products are selected from a group consisting of: methanol; ethanol; furan; methyl glyoxal; 2-methyl furan; vinyl acetate; glycolaldehyde; acetic acid; acetol; furfural; 2-furanmethanol; 3-furanmethanol; 2-hydroxy cyclopent-2-en-1-one; 5-methyl furfural; 2(5H)-furanone; 2 methyl cyclopentenolone; levoglucosenone; cyclic hydroxyl lactone; 1,4,3,6-dianhydro-α-D-glucopyranose; dianhydro glucopyranose; and 5-hydroxy methyl furfural (5-hmf).

In some embodiments, greater than 50%, 60%, 70%, 80%, 90%, 95%, or 99% of the anhydro-subunit containing oligosaccharides comprise a chain-end anhydro-subunit.

In some embodiments, said oligosaccharide preparation has a weight average molecular weight of from about 300 to about 5000 g/mol as determined by high-performance liquid chromatography (HPLC). In some embodiments, said oligosaccharide preparation has a weight average molecular weight of from about 300 to about 2500 g/mol as determined by HPLC. In some embodiments, said oligosaccharide preparation has a weight average molecular weight of from about 500 to about 2000 g/mol as determined by HPLC. In some embodiments, said oligosaccharide preparation has a weight average molecular weight of from about 500 to about 1500 g/mol as determined by HPLC. In some embodiments, said oligosaccharide preparation has a number average molecular weight of from about 300 to about 5000 g/mol as determined by HPLC. In some embodiments, said oligosaccharide preparation has a number average molecular weight of from about 300 to about 2500 g/mol as determined by HPLC. In some embodiments, said oligosaccharide preparation has a number average molecular weight of from about 500 to about 2000 g/mol as determined by HPLC. In some embodiments, said oligosaccharide preparation has a number average molecular weight of from about 500 to about 1500 g/mol as determined by HPLC.

In some embodiments, said oligosaccharide preparation has a weight average molecular weight of from about 2000 to about 2800 g/mol. In some embodiments, said oligosaccharide preparation has a number average molecular weight of from about 1000 to about 2000 g/mol.

In one aspect, provided herein are methods of modulating expression of at least one microbial protein within the gastrointestinal tract of an animal, the method comprising: administering a nutritional composition comprising a base nutritional composition and a synthetic oligosaccharide preparation to an animal, wherein said synthetic oligosaccharide preparation comprises at least n fractions of oligosaccharides each having a distinct degree of polymerization selected from 1 to n (DP1 to DPn fractions), wherein n is an integer greater than 3; and wherein each of a DP1 and DP2 fraction independently comprises from about 0.5% to about 15% of anhydro-subunit containing oligosaccharides by relative abundance as determined by mass spectrometry, and wherein a level of at least one microbial protein in a gastrointestinal sample is increased or decreased relative to a level of said at least one microbial protein in a gastrointestinal sample from a comparable control animal that has been administered a comparable nutritional composition lacking said synthetic oligosaccharide preparation.

In some embodiments, said level of said at least one microbial protein in said gastrointestinal sample is decreased relative to said level of said at least one microbial protein in a gastrointestinal sample from said animal prior to administration of said nutritional composition to said animal.

In some embodiments, said level of said at least one microbial protein in said gastrointestinal sample is decreased relative to said level of said at least one microbial protein in a gastrointestinal sample from a comparable control animal that has been administered a comparable nutritional composition lacking said synthetic oligosaccharide preparation.

In some embodiments, said level of said at least one microbial protein in said gastrointestinal sample is increased relative to said level of said at least one microbial protein in a gastrointestinal sample from said animal prior to administration of said nutritional composition to said animal. In some embodiments, said level of said at least one microbial protein in said gastrointestinal sample is increased relative to said level of said at least one microbial protein in a gastrointestinal sample from a comparable control animal that has been administered a comparable nutritional composition lacking said synthetic oligosaccharide preparation.

In some embodiments, said microbial protein is a hydrolytic enzyme, a protein involved in digestion (e.g. hydrolytic enzymatic digestion), or a protein involved in metabolism.

In some embodiments, said at least one microbial protein is an archaea protein, a bacterial protein, a protozoan protein, a viral protein, a bacteriophage protein, a parasite protein, or a fungal protein. In some embodiments, said microbial species is a bacterial protein.

In some embodiments, said gastrointestinal sample is a biopsy of a gastrointestinal tissue or a fecal sample. In some embodiments, said gastrointestinal tissue is cecal tissue or ileum tissue.

In some embodiments, said method further comprises obtaining said gastrointestinal sample.

In some embodiments, said method further comprises detecting the level of said at least one microbial protein in said gastrointestinal sample.

In some embodiments, said at least one microbial protein is a carbohydrate active enzyme (CAZymes). In some embodiments, said at least one microbial protein is a sus-like polysaccharide utilization loci (PULs) protein. In some embodiments, said at least one microbial protein is selected from the group consisting of: GH127 (CAZyme α-L-arabinofuranosidase), susC (outer membrane protein involved in starch binding) and susD (starch binding protein).

In some embodiments, said level of said at least one microbial protein is determined by analyzing RNA or protein expression.

In some embodiments, said animal is a poultry, seafood, sheep, cow, cattle, buffalo, bison, pig, cat, dog, rabbit, goat, guinea pig, donkey, camel, horse, pigeon, ferret, gerbil, hamster, mouse, rat, fish, or bird. In some embodiments, said animal is poultry. In some embodiments, said animal is a chicken, turkey, duck, or goose. In some embodiments, said chicken is a broiler chicken, a layer chicken, or a breeder chicken. In some embodiments, said animal is a pig. In some embodiments, said pig is a nursery pig, a grower pig, or a finisher pig. In some embodiments, said animal is a fish. In some embodiments, said fish is a salmon, a tilapia, or a tropical fish.

In some embodiments, said nutritional composition is an animal feed composition. In some embodiments, said base nutritional composition is base animal feed.

In some embodiments, said relative abundance is determined by LC-MS/MS.

In some embodiments, said relative abundance of oligosaccharides in at least 5, 10, 20, or 30 DP fractions decreases monotonically with its degree of polymerization. In some embodiments, said relative abundance of oligosaccharides in each of the n fractions decreases monotonically with its degree of polymerization.

In some embodiments, n is at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100.

In some embodiments, said DP2 fraction comprises less than 12%, less than 11%, less than 10%, less than 9%, less than 8%, less than 7%, less than 6%, less than 5%, less than 4%, less than 3%, less than 2%, or less than 1% anhydro-subunit containing oligosaccharides by relative abundance.

In some embodiments, said DP2 fraction comprises from about 5% to about 10% of anhydro-subunit containing oligosaccharides by relative abundance. In some embodiments, said DP2 fraction comprises from about 1% to about 10% of anhydro-subunit containing oligosaccharides by relative abundance. In some embodiments, said DP2 fraction comprises from about 0.5% to about 10% of anhydro-subunit containing oligosaccharides by relative abundance. In some embodiments, said DP2 fraction comprises from about 2% to about 12% of anhydro-subunit containing oligosaccharides by relative abundance.

In some embodiments, said DP1 fraction comprises less than 12%, less than 11%, less than 10%, less than 9%, less than 8%, less than 7%, less than 6%, less than 5%, less than 4%, less than 3%, less than 2%, or less than 1% anhydro-subunit containing oligosaccharides by relative abundance. In some embodiments, said DP1 fraction comprises from about 2% to about 12% of anhydro-subunit containing oligosaccharides by relative abundance. In some embodiments, said DP1 fraction comprises from about 1% to about 10% of anhydro-subunit containing oligosaccharides by relative abundance.

In some embodiments, said DP1 fraction comprises from about 0.5% to about 10% of anhydro-subunit containing oligosaccharides by relative abundance. In some embodiments, said DP1 fraction comprises from about 5% to about 10% of anhydro-subunit containing oligosaccharides by relative abundance.

In some embodiments, said DP3 fraction comprises less than 15%, less than 12%, less than 11%, less than 10%, less than 9%, less than 8%, less than 7%, less than 6%, less than 5%, less than 4%, less than 3%, less than 2%, or less than 1% anhydro-subunit containing oligosaccharides by relative abundance. In some embodiments, said DP3 fraction comprises from about 2% to about 12% of anhydro-subunit containing oligosaccharides by relative abundance. In some embodiments, said DP3 fraction comprises from about 1% to about 10% of anhydro-subunit containing oligosaccharides by relative abundance. In some embodiments, said DP3 fraction comprises from about 0.5% to about 10% of anhydro-subunit containing oligosaccharides by relative abundance. In some embodiments, said DP3 fraction comprises from about 5% to about 10% of anhydro-subunit containing oligosaccharides by relative abundance.

In some embodiments, said oligosaccharide preparation comprises from about 2% to about 12% anhydro-subunit containing oligosaccharides by relative abundance. In some embodiments, said oligosaccharide preparation comprises from about 0.5% to about 10% anhydro-subunit containing oligosaccharides by relative abundance. In some embodiments, said oligosaccharide preparation comprises from about 1% to about 10% anhydro-subunit containing oligosaccharides by relative abundance. In some embodiments, said oligosaccharide preparation comprises from about 5% to about 10% anhydro-subunit containing oligosaccharides by relative abundance.

In some embodiments, said DP2 fraction comprises greater than 0.6%, greater than 0.8%, greater than 1.0%, greater than 1.5%, greater than 2%, greater than 3%, greater than 4%, greater than 5%, greater than 6%, greater than 7%, greater than 8%, greater than 9%, greater than 10%, greater than 11%, or greater than 12% anhydro-subunit containing oligosaccharides by relative abundance.

In some embodiments, said DP1 fraction comprises greater than 0.6%, greater than 0.8%, greater than 1.0%, greater than 1.5%, greater than 2%, greater than 3%, greater than 4%, greater than 5%, greater than 6%, greater than 7%, greater than 8%, greater than 9%, greater than 10%, greater than 11%, or greater than 12% anhydro-subunit containing oligosaccharides by relative abundance.

In some embodiments, said DP3 fraction comprises greater than 0.6%, greater than 0.8%, greater than 1.0%, greater than 1.5%, greater than 2%, greater than 3%, greater than 4%, greater than 5%, greater than 6%, greater than 7%, greater than 8%, greater than 9%, greater than 10%, greater than 11%, or greater than 12% anhydro-subunit containing oligosaccharides by relative abundance.

In some embodiments, said oligosaccharide preparation comprises greater than 0.5%, 0.6%, greater than 0.8%, greater than 1.0%, greater than 1.5%, greater than 2%, greater than 3%, greater than 4%, greater than 5%, greater than 6%, greater than 7%, greater than 8%, greater than 9%, greater than 10%, greater than 11%, or greater than 12% anhydro-subunit containing oligosaccharides by relative abundance.

In some embodiments, said oligosaccharide preparation has a DP1 fraction content of from about 1% to about 40% by weight as determined by liquid chromatography.

In some embodiments, said oligosaccharide preparation has a DP2 fraction content of from about 1% to about 35% by weight as determined by liquid chromatography.

In some embodiments, said oligosaccharide preparation has a DP3 fraction content of from about 1% to about 30% by weight as determined by liquid chromatography.

In some embodiments, said oligosaccharide preparation has a DP4 fraction content of from about 0.1% to about 20% by weight as determined by liquid chromatography In some embodiments, said oligosaccharide preparation has a DP5 fraction content of from about 0.1% to about 15% by weight as determined by liquid chromatography.

In some embodiments, a ratio of the DP2 fraction to the DP1 fraction is from about 0.02 to about 0.40 as determined by liquid chromatography.

In some embodiments, a ratio of the DP3 fraction to the DP2 fraction is from about 0.01 to about 0.30 as determined by liquid chromatography.

In some embodiments, an aggregate content of the DP1 and the DP2 fractions in the oligosaccharide preparation is less than 50%, less than 40%, or less than 30% as determined by liquid chromatography.

In some embodiments, said oligosaccharide preparation comprises at least 103, at least 104, at least 105, at least 106 or at least 109 different oligosaccharide species.

In some embodiments, two or more independent oligosaccharides comprise different anhydro-subunits.

In some embodiments, each of said anhydro-subunit containing oligosaccharides comprises one or more anhydro-subunits that are products of thermal dehydration of monosaccharides.

In some embodiments, said oligosaccharide preparation comprises one or more anhydro-subunits selected from anhydro-glucose, anhydro-galactose, anhydro-mannose, anhydro-allose, anhydro-altrose, anhydro-gulose, anhydro-indose, anhydro-talose, anhydro-fructose, anhydro-ribose, anhydro-arabinose, anhydro-rhamnose, anhydro-lyxose, and anhydro-xylose.

In some embodiments, said oligosaccharide preparation comprises one or more anhydro-glucose, anhydro-galactose, anhydro-mannose, or anhydro-fructose subunits.

In some embodiments, said DP1 fraction comprises 1,6-anhydro-β-D-glucofuranose or 1,6-anhydro-β-D-glucopyranose anhydro-subunits. In some embodiments, said DP1 fraction comprises both 1,6-anhydro-β-D-glucofuranose and 1,6-anhydro-β-D-glucopyranose anhydro-subunits.

In some embodiments, a ratio of the 1,6-anhydro-β-D-glucofuranose to the 1,6-anhydro-β-D-glucopyranose is from about 10:1 to 1:10, from about 9:1 to about 1:10, from about 8:1 to about 1:10, from about 7:1 to about 1:10, from about 6:1 to about 1:10, from about 5:1 to about 1:10, from about 4:1 to about 1:10, from about 3:1 to about 1:10, from about 2:1 to about 1:10, from about 10:1 to about 1:9, from about 10:1 to about 1:8, from about 10:1 to about 1:7, from about 10:1 to about 1:6, from about 10:1 to about 1:5, from about 10:1 to about 1:4, from about 10:1 to about 1:3, from about 10:1 to about 1:2, or from about 1:1 to about 3:1 in the oligosaccharide reparation. In some embodiments, a ratio of the 1,6-anhydro-β-D-glucofuranose to the 1,6-anhydro-β-D-glucopyranose is about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, or about 1:10 in the oligosaccharide preparation. In some embodiments, a ratio of the 1,6-anhydro-β-D-glucofuranose to the 1,6-anhydro-β-D-glucopyranose is about 2:1 in the oligosaccharide preparation.

In some embodiments, said DP2 fraction comprises at least 5 species of anhydro-subunit containing oligosaccharides. In some embodiments, said DP2 fraction comprises about 5 to 10 species of anhydro-subunit containing oligosaccharides.

In some embodiments, said oligosaccharide preparation comprises one or more sugar caramelization products. In some embodiments, said sugar caramelization products are selected from a group consisting of: methanol; ethanol; furan; methyl glyoxal; 2-methyl furan; vinyl acetate; glycolaldehyde; acetic acid; acetol; furfural; 2-furanmethanol; 3-furanmethanol; 2-hydroxy cyclopent-2-en-1-one; 5-methyl furfural; 2(5H)-furanone; 2 methyl cyclopentenolone; levoglucosenone; cyclic hydroxyl lactone; 1,4,3,6-dianhydro-α-D-glucopyranose; dianhydro glucopyranose; and 5-hydroxy methyl furfural (5-hmf).

In some embodiments, greater than 50%, 60%, 70%, 80%, 90%, 95%, or 99% of the anhydro-subunit containing oligosaccharides comprise a chain-end anhydro-subunit.

In some embodiments, said oligosaccharide preparation has a weight average molecular weight of from about 300 to about 5000 g/mol as determined by high-performance liquid chromatography (HPLC). In some embodiments, said oligosaccharide preparation has a weight average molecular weight of from about 300 to about 2500 g/mol as determined by HPLC. In some embodiments, said oligosaccharide preparation has a weight average molecular weight of from about 500 to about 2000 g/mol as determined by HPLC. In some embodiments, said oligosaccharide preparation has a weight average molecular weight of from about 500 to about 1500 g/mol as determined by HPLC. In some embodiments, said oligosaccharide preparation has a number average molecular weight of from about 300 to about 5000 g/mol as determined by HPLC. In some embodiments, said oligosaccharide preparation has a number average molecular weight of from about 300 to about 2500 g/mol as determined by HPLC. In some embodiments, said oligosaccharide preparation has a number average molecular weight of from about 500 to about 2000 g/mol as determined by HPLC. In some embodiments, said oligosaccharide preparation has a number average molecular weight of from about 500 to about 1500 g/mol as determined by HPLC.

In some embodiments, said oligosaccharide preparation has a weight average molecular weight of from about 2000 to about 2800 g/mol. In some embodiments, said oligosaccharide preparation has a number average molecular weight of from about 1000 to about 2000 g/mol.

In some embodiments, said relative abundance of oligosaccharides in at least 5, 10, 20, or 30 DP fractions of said oligosaccharide preparation decreases monotonically with its degree of polymerization. In some embodiments, the relative abundance of oligosaccharides in each of the n fractions of said oligosaccharide preparation decreases monotonically with its degree of polymerization. In some embodiments, n is at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100.

In some embodiments, at least one fraction of said oligosaccharide preparation comprises less than 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, or 2% anhydro-subunit containing oligosaccharides by relative abundance. In some embodiments, said oligosaccharide preparation comprises less than 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, or 2% anhydro-subunit containing oligosaccharides by relative abundance. In some embodiments, each fraction of said oligosaccharide preparation comprises less than 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, or 2% anhydro-subunit containing oligosaccharides by relative abundance. In some embodiments, at least one fraction of said oligosaccharide preparation comprises less than 10%, 9%, 8%, 7%, 6%, 5%, 4%, 3%, or 2% anhydro-subunit containing oligosaccharides by relative abundance. In some embodiments, said oligosaccharide preparation comprises less than 10%, 9%, 8%, 7%, 6%, 5%, 4%, 3%, or 2% anhydro-subunit containing oligosaccharides by relative abundance. In some embodiments, each fraction of said oligosaccharide preparation comprises less than 10%, 9%, 8%, 7%, 6%, 5%, 4%, 3%, or 2% anhydro-subunit containing oligosaccharides by relative abundance. In some embodiments, at least one fraction of said oligosaccharide comprises greater than 2%, 3%, 4%, 5%, 6%, 7%, 8%, 9%, 10%, 11%, 12%, 13%, 14%, 15%, 16%, 17%, 18%, 19%, 20%, 30%, 40%, 50%, 60%, 70%, or 80% anhydro-subunit containing oligosaccharides by relative abundance. In some embodiments, said oligosaccharide preparation comprises greater than 2%, 3%, 4%, 5%, 6%, 7%, 8%, 9%, 10%, 11%, 12%, 13%, 14%, 15%, 16%, 17%, 18%, 19%, 20%, 30%, 40%, 50%, 60%, 70%, or 80% anhydro-subunit containing oligosaccharides by relative abundance. In some embodiments, each fraction of said oligosaccharide preparation comprises greater than 2%, 3%, 4%, 5%, 6%, 7%, 8%, 9%, 10%, 11%, 12%, 13%, 14%, 15%, 16%, 17%, 18%, 19%, 20%, 30%, 40%, 50%, 60%, 70%, or 80% anhydro-subunit containing oligosaccharides by relative abundance. In some embodiments, at least one fraction of said oligosaccharide preparation comprises greater than 20%, 21%, 22%, 23%, 24%, or 25% anhydro-subunit containing oligosaccharides by relative abundance. In some embodiments, said oligosaccharide preparation comprises greater than 20%, 21%, 22%, 23%, 24%, or 25% anhydro-subunit containing oligosaccharides by relative abundance. In some embodiments, each fraction of said oligosaccharide preparation comprises greater than 20%, 21%, 22%, 23%, 24%, or 25% anhydro-subunit containing oligosaccharides by relative abundance. In some embodiments, more than 99%, 95%, 90%, 85%, 80%, 75%, 70%, 65%, 60%, 55%, 50%, 45%, 40%, 35%, or 30% of the anhydro-subunit containing oligosaccharides have only one anhydro-subunit.

In some embodiments, said oligosaccharide preparation has a DP1 fraction content from 1 to 40% by relative abundance. In some embodiments, said oligosaccharide preparation has a DP2 fraction content from 1 to 35% by relative abundance. In some embodiments, said oligosaccharide preparation has a DP3 fraction content from 1 to 30% by relative abundance. In some embodiments, said oligosaccharide preparation has a DP4 fraction content from 0.1 to 20% by relative abundance. In some embodiments, said oligosaccharide preparation comprises a DP5 fraction content from 0.1 to 15% by relative abundance. In some embodiments, said oligosaccharide preparation comprises a DP2 fraction and a DP1 fraction, wherein the ratio of said DP2 fraction to said DP1 fraction is 0.02-0.40 by relative abundance. In some embodiments, said oligosaccharide preparation comprises a DP3 fraction and a DP2 fraction, wherein the ratio of said DP3 fraction to said DP2 fraction in said oligosaccharide preparation is 0.01-0.30 by relative abundance. In some embodiments, said oligosaccharide preparation comprises a DP1 fraction and a DP2 fraction, wherein the aggregate content of said DP1 and said DP2 fractions in said oligosaccharide preparation is less than 50, 30, or 10% by relative abundance. In some embodiments, said oligosaccharide preparation comprises at least 25, 50, 75, 100, 103, 104, 105, 106, 109, 110, 120, 150, or 200 different oligosaccharide species.

In some embodiments, at least two independent oligosaccharides of said oligosaccharide preparation comprise different anhydro-subunits. In some embodiments, said oligosaccharide preparation comprises at least one anhydro-subunit that is a product of reversible thermal dehydration of a monosaccharide. In some embodiments, said oligosaccharide preparation comprises at least one anhydro-glucose, anhydro-galactose, anhydro-mannose, anhydro-allose, anhydro-altrose, anhydro-gulose, anhydro-indose, anhydro-talose, anhydro-fructose, anhydro-ribose, anhydro-arabinose, anhydro-rhamnose, anhydro-lyxose, or anhydro-xylose subunit. In some embodiments, said oligosaccharide preparation comprises at least one anhydro-glucose, anhydro-galactose, anhydro-mannose, or anhydro-fructose subunit.

In some embodiments, said oligosaccharide preparation comprises at least one1,6-anhydro-β-D-glucofuranose or 1,6-anhydro-β-D-glucopyranose subunit. In some embodiments, said oligosaccharide preparation comprises at least one 1,6-anhydro-β-D-glucofuranose subunit and at least one 1,6-anhydro-β-D-glucopyranose anhydro-subunit. In some embodiments, a ratio of 1,6-anhydro-β-D-glucofuranose to 1,6-anhydro-β-D-glucopyranose in said oligosaccharide preparation is from about 10:1 to 1:10, 9:1 to 1:10, 8:1 to 1:10, 7:1 to 1:10, 6:1 to 1:10, 5:1 to 1:10, 4:1 to 1:10, 3:1 to 1:10, 2:1 to 1:10, 10:1 to 1:9, 10:1 to 1:8, 10:1 to 1:7, 10:1 to 1:6, 10:1 to 1:5, 10:1 to 1:4, 10:1 to 1:3, 10:1 to 1:2, or 1:1 to 3:1. In some embodiments, a ratio of 1,6-anhydro-β-D-glucofuranose to 1,6-anhydro-β-D-glucopyranose in said oligosaccharide preparation is about 10:1, 9:1, 8:1, 7:1, 6:1, 5:1, 4:1, 3:1, 2:1, 1:1, 1:2, 1:3, 1:4, 1:5, 1:6, 1:7, 1:8, 1:8, 1:9, or 1:10. In some embodiments, a ratio of 1,6-anhydro-β-D-glucofuranose to 1,6-anhydro-β-D-glucopyranose in said oligosaccharide preparation is about 2:1.

In some embodiments, the ratio of 1,6-anhydro-β-D-glucofuranose to 1,6-anhydro-β-D-glucopyranose is about from 10:1 to 1:10, 9:1 to 1:10, 8:1 to 1:10, 7:1 to 1:10, 6:1 to 1:10, 5:1 to 1:10, 4:1 to 1:10, 3:1 to 1:10, 2:1 to 1:10, 10:1 to 1:9, 10:1 to 1:8, 10:1 to 1:7, 10:1 to 1:6, 10:1 to 1:5, 10:1 to 1:4, 10:1 to 1:3, 10:1 to 1:2, or 1:1 to 3:1 in each fraction. In some embodiments, a ratio of 1,6-anhydro-β-D-glucofuranose to 1,6-anhydro-β-D-glucopyranose is about 10:1, 9:1, 8:1, 7:1, 6:1, 5:1, 4:1, 3:1, 2:1, 1:1, 1:2, 1:3, 1:4, 1:5, 1:6, 1:7, 1:8, 1:8, 1:9, or 1:10 in each fraction of said oligosaccharide preparation. In some embodiments, a ratio of 1,6-anhydro-β-D-glucofuranose to 1,6-anhydro-β-D-glucopyranose is about 2:1 in each fraction of said oligosaccharide preparation. In some embodiments, at least 1%, 5%, 10%, 20%, 30%, 40%, 50%, 60%, 70%, 80%, or 90% of said anhydro-subunits in said oligosaccharide preparation are selected from a group consisting of 1,6-anhydro-β-D-glucofuranose and 1,6-anhydro-β-D-glucopyranose.

In some embodiments, said oligosaccharide preparation comprises at least one anhydro-subunit that is a sugar caramelization product. In some embodiments, said sugar caramelization product is selected from a group consisting of: methanol; ethanol; furan; methyl glyoxal; 2-methyl furan; vinyl acetate; glycolaldehyde; acetic acid; acetol; furfural; 2-furanmethanol; 3-furanmethanol; 2-hydroxy cyclopent-2-en-1-one; 5-methyl furfural; 2(5H)-furanone; 2 methyl cyclopentenolone; levoglucosenone; cyclic hydroxyl lactone; 1,4,3,6-dianhydro-α-D-glucopyranose; dianhydro glucopyranose; and 5-hydroxy methyl furfural (5-hmf). In some embodiments, from about 0.1% to 5%, 0.1% to 2%, or 0.1% to 1% of said anhydro-subunits in said oligosaccharide preparation are caramelization products.

In some embodiments, at least 30%, 40%, 50%, 60%, 70%, 80%, 90%, 95%, or 99% of the anhydro-subunit containing oligosaccharides in said oligosaccharide preparation comprise a chain-end anhydro-subunit.

In some embodiments, the weight average molecular weight of said oligosaccharide preparation is from about 300 to 5000 g/mol, 500 to 5000 g/mol, 700 to 5000 g/mol, 500 to 2000 g/mol, 700 to 2000 g/mol, 700 to 1500 g/mol, 300 to 1500 g/mol, 300 to 2000 g/mol, 400 to 1300 g/mol, 400 to 1200 g/mol, 400 to 1100 g/mol, 500 to 1300 g/mol, 500 to 1200 g/mol, 500 to 1100 g/mol, 600 to 1300 g/mol, 600 to 1200 g/mol, or 600 to 1100 g/mol. In some embodiments, the number average molecular weight of said oligosaccharide preparation is from about 300 to 5000 g/mol, 500 to 5000 g/mol, 700 to 5000 g/mol, 500 to 2000 g/mol, 700 to 2000 g/mol, 700 to 1500 g/mol, 300 to 1500 g/mol, 300 to 2000 g/mol, 400 to 1000 g/mol, 400 to 900 g/mol, 400 to 800 g/mol, 500 to 900 g/mol, or 500 to 800 g/mol. In some embodiments, the weight average molecular weight of said oligosaccharide preparation is from about 2000 to 2800 g/mol, 2100 to 2700 g/mol, 2200 to 2600 g/mol, 2300 to 2500 g/mol, or 2320 to 2420 g/mol. In some embodiments, the number average molecular weight of said oligosaccharide preparation is from about 1000 to 2000 g/mol, 1100 to 1900 g/mol, 1200 to 1800 g/mol, 1300 to 1700 g/mol, 1400 to 1600 g/mol, or 1450 to 1550 g/mol.

The present disclosure is based, at least in part, on the discovery that oligosaccharides comprising one or more anhydro-subunit selectively modulate (e.g., promote or inhibit) the growth of microbial species and functions of the gut microflora. Accordingly, the disclosure features, inter alia, methods of reducing the feed conversion ratio (FCR) of an animal by providing a feed comprising a synthetic oligosaccharide feed additive that selectively modulates the level of microbial species already present in the gut microbiome.

Provided herein are methods of promoting the growth of one or more microbial species in the gastrointestinal tract of an animal, comprising: administering a nutritional composition comprising a base nutritional composition and a synthetic oligosaccharide preparation described herein to an animal, wherein the level of one or more microbial species in the gastrointestinal tract of the animal is higher relative to the level of the microbial species in the gastrointestinal tract of an animal administered a nutritional composition lacking the synthetic oligosaccharide preparation or relative to the level of the microbial species in the gastrointestinal tract of the animal prior to administration of the nutritional composition comprising the synthetic oligosaccharide preparation.

In some embodiments, the synthetic oligosaccharide preparation comprises at least n fractions of oligosaccharides each having a distinct degree of polymerization selected from 1 to n (DP1 to DPn fractions), wherein n is an integer greater than 2; wherein each fraction comprises from 1% to 90% anhydro-subunit containing oligosaccharides by relative abundance as measured by mass spectrometry.

In some embodiments, the microbial species is a bacterial species. In other embodiments, the microbial species is an archaea species. In other embodiments, the microbial species is a virus, bacteriophage, or protozoan species.

In some embodiments, the method further comprises obtaining a sample of the gastrointestinal microbiota of the gastrointestinal tract of the animal. In some embodiments, the sample is a biopsy of a gastrointestinal tissue (e.g., a cecal biopsy) or a fecal sample. In some embodiments, the method further comprises detecting the level of the microbial species in the sample.

In some embodiments, the level of 2, 3, 4, 5, or more microbial species in the gastrointestinal tract of the animal are higher relative to the level of the microbial species in the gastrointestinal tract of an animal administered a nutritional composition lacking the synthetic oligosaccharide preparation or relative to the level of the microbial species in the gastrointestinal tract of the animal prior to administration of the nutritional composition comprising the synthetic oligosaccharide preparation. In some embodiments, the method further comprises detecting the level of the 2nd, 3rd, 4th, or 5th microbial species in the sample.

In some embodiments, the microbial species is beneficial to the animal (e.g., beneficial to the health of the animal). In some embodiments, the microbial species belongs to the genus *Bacteroides, Odoribacter, Oscillibacter, Subdoligranulum, Biophila*, or *Barnesiella*. In some embodiments, the microbial species is selected from the group consisting of: *Bacteroides clarus, Bacteroides dorei, Odoribacter splanchinicus*, and *Barnesiella intestinihominis*. In some embodiments, each of the 2nd, 3rd, 4th, or 5th microbial species is a beneficial to the animal (e.g., beneficial to the health of the animal). In some embodiments, at least one of the 2nd, 3rd, 4th, or 5th microbial species belongs to the genus *Bacteroides, Odoribacter, Oscillibacter, Subdoligranulum, Biophila*, or *Barnesiella*. In some embodiments, at least one of the 2nd, 3rd, 4th, or 5th microbial species is selected from the group consisting of: *Bacteroides clarus, Bacteroides dorei, Odoribacter splanchinicus*, and *Barnesiella intestinihominis*.

In some embodiments, the animal has a gastrointestinal microbiota comprising at least 0.1%, 1%, 2%, 3%, 4%, 5%, 6%, 7%, 8%, 9%, or 10% of at least one microbial species that belongs to the genus *Bacteroides, Odoribacter, Oscillibacter, Subdoligranulum, Biophila*, or *Barnesiella*. In some embodiments, the animal has a gastrointestinal microbiota comprising at least 0.1%, 1%, 2%, 3%, 4%, 5%, 6%, 7%, 8%, 9%, or 10% of at least one of *Bacteroides clarus, Bacteroides dorei, Odoribacter splanchinicus*, and *Barnesiella intestinihominis*.

In some embodiments, the nutritional composition comprising the synthetic oligosaccharide preparation is administered to the animal for at least 1, 7, 10, 14, 30, 45, 60, 90, or 120 days. In some embodiments, the nutritional composition comprising the synthetic oligosaccharide preparation is administered to the animal at least once, twice, three, four, or five times a day. In some embodiments, administering comprises providing the nutritional composition to the animal to ingest at will, wherein the animal ingests at least a portion of the nutritional composition in every 24-hour period.

In some embodiments, the animal has a higher body weight relative to the body weight of an animal administered a nutritional composition lacking the synthetic oligosaccharide preparation. In some embodiments, the animal has a higher feed efficiency relative to the feed efficiency of an animal administered a nutritional composition lacking the synthetic oligosaccharide preparation. In some embodiments, the animal has a lower feed conversion ratio relative to the feed conversion ratio of an animal administered a nutritional composition lacking the synthetic oligosaccharide preparation.

In some embodiments, the animal has a higher body weight relative to the body weight of the animal prior to administration of nutritional composition comprising the synthetic oligosaccharide preparation. In some embodiments, the animal has a higher feed efficiency relative to the feed efficiency of the animal prior to administration of nutritional composition comprising the synthetic oligosaccharide preparation. In some embodiments, the animal has a lower feed conversion ratio relative to the feed conversion ratio of the animal prior to administration of nutritional composition comprising the synthetic oligosaccharide preparation.

In some embodiments, the level of the microbial species is determined by DNA sequencing or RNA sequencing. In some embodiments, the level of the microbial species is determined by shotgun DNA sequencing.

In some embodiments, the nutritional composition comprising the synthetic oligosaccharide preparation is administered to an animal. In some embodiments the animal is livestock. In some embodiments the animal is a companion animal. In some embodiments, the animal is a fish (e.g. salmon, tilapia, tropical fish), poultry (e.g. chicken, turkey), seafood (e.g. shrimp), sheep, cow, cattle, buffalo, bison, pig (e.g. nursery pig, grower/finisher pig), cat, dog, rabbit, goat, guinea pig, donkey, camel, horse, pigeon, ferret, gerbil, hamster, mouse, rat, bird, or human. In some embodiments, the animal is poultry. In some embodiments, the animal is a chicken (e.g. broiler, layer, breeder), turkey, duck, or goose. In some embodiments, the animal is a pig (e.g. nursery pig, grower/finisher pig).

In some embodiments, the nutritional composition is an animal feed composition described herein. In some embodiments, the base nutritional composition is base animal feed described herein.

Provided herein are methods of enhancing expression of a microbial protein within the gastrointestinal tract of an animal, comprising: administering a nutritional composition comprising a base nutritional composition and a synthetic oligosaccharide preparation described herein to the animal, wherein the expression one or more microbial protein is higher relative to the expression level in the gastrointestinal tract of an animal administered a nutritional composition lacking the synthetic oligosaccharide preparation or relative to the expression level in the gastrointestinal tract of the animal prior to administration of nutritional composition comprising the synthetic oligosaccharide preparation, and wherein the microbial protein is a hydrolytic enzyme, a protein involved in digestion (e.g. hydrolytic enzymatic digestion), or a protein involved in metabolism.

In some embodiments, the synthetic oligosaccharide preparation comprises at least n fractions of oligosaccharides each having a distinct degree of polymerization selected from 1 to n (DP1 to DPn fractions), wherein n is an integer greater than 2; wherein each fraction comprises from 1% to 90% anhydro-subunit containing oligosaccharides by relative abundance as measured by mass spectrometry.

In some embodiments, the method further comprises obtaining a sample of the gastrointestinal microbiota of the animal. In some embodiments, the sample is a biopsy of a gastrointestinal tissue (e.g., a cecal biopsy) or a fecal sample. In some embodiments, the method further comprises detecting the expression level of the microbial protein in the sample.

In some embodiments, the level of at least 2, 3, 4, or 5 microbial proteins are higher relative to the expression level in the gastrointestinal tract of an animal administered a nutritional composition lacking the synthetic oligosaccharide preparation, and wherein each of the microbial proteins is a hydrolytic enzyme, a protein involved in digestion (e.g. hydrolytic enzymatic digestion), or a protein involved in metabolism. In some embodiments, the level of at least 2, 3, 4, or 5 microbial proteins are higher relative to the expression level in the gastrointestinal tract of the animal prior to administration of the nutritional composition comprising the synthetic oligosaccharide preparation, and wherein each of the microbial proteins is a hydrolytic enzyme, a protein involved in digestion (e.g. hydrolytic enzymatic digestion), or a protein involved in metabolism. In some embodiments, the method further comprises determining the level of the at least the 2nd, 3rd, 4th, or 5th microbial protein in the sample.

In some embodiments, the microbial protein is a carbohydrate active enzyme (CAZymes). In some embodiments, the microbial protein is a sus-like polysaccharide utilization loci (PULs) protein.

In some embodiments, the microbial protein is selected from the group consisting of: GH127 (CAZyme α-L-arabinofuranosidase), susC (outer membrane protein involved in starch binding) and susD (starch binding protein). In some embodiments, the expression level of the microbial protein is determined by analyzing RNA or protein expression.

In some embodiments, the level of one or more microbial species in the gastrointestinal tract of the animal is higher relative to the level of the microbial species in the gastrointestinal tract of an animal administered a nutritional composition lacking the synthetic oligosaccharide preparation. In some embodiments, the level of one or more microbial species in the gastrointestinal tract of the animal is higher relative to the level of the microbial species in the gastrointestinal tract of the animal prior to administration of nutritional composition comprising the synthetic oligosaccharide preparation.

In some embodiments, the level of 2, 3, 4, 5, or more microbial species in the gastrointestinal tract of the animal are higher relative to the level of the microbial species in the gastrointestinal tract of an animal administered a nutritional composition lacking the synthetic oligosaccharide preparation. In some embodiments, the level of 2, 3, 4, 5, or more microbial species in the gastrointestinal tract of the animal are higher relative to the level of the microbial species in the gastrointestinal tract of the animal prior to administration of nutritional composition comprising the synthetic oligosaccharide preparation. In some embodiments, the method further comprises detecting the level of the 2nd, 3rd, 4th, or 5th microbial species in the sample.

In some embodiments, the microbial species is beneficial to the animal (e.g., beneficial to the health of the animal). In some embodiments, the microbial species belongs to the genus *Bacteroides, Odoribacter, Oscillibacter, Subdoligranulum, Biophila*, or *Barnesiella*. In some embodiments, the microbial species is selected from the group consisting of: *Bacteroides clarus, Bacteroides dorei, Odoribacter splanchinicus*, and *Barnesiella intestinihominis*. In some embodiments, each of the 2nd, 3rd, 4th, or 5th microbial species is a beneficial to the animal (e.g., beneficial to the health of the animal). In some embodiments, at least one of the 2nd, 3rd, 4th, or 5th microbial species belongs to the genus *Bacteroides, Odoribacter, Oscillibacter, Subdoligranulum, Biophila*, or *Barnesiella*. In some embodiments, at least one of the 2nd, 3rd, 4th, or 5th microbial species is selected from the group consisting of: *Bacteroides clarus, Bacteroides dorei, Odoribacter splanchinicus*, and *Barnesiella intestinihominis*.

In some embodiments, the animal has a gastrointestinal microbiota comprising at least 0.1%, 1%, 2%, 3%, 4%, 5%, 6%, 7%, 8%, 9%, or 10% of at least one microbial species that belongs to the genus *Bacteroides, Odoribacter, Oscillibacter, Subdoligranulum, Biophila*, or *Barnesiella*. In some embodiments, the animal has a gastrointestinal microbiota comprising at least 0.1%, 1%, 2%, 3%, 4%, 5%, 6%, 7%, 8%, 9%, or 10% of at least one of *Bacteroides clarus, Bacteroides dorei, Odoribacter splanchinicus*, and *Barnesiella intestinihominis*.

In some embodiments, the nutritional composition comprising the synthetic oligosaccharide preparation is administered to the animal for at least 1, 7, 10, 14, 30, 45, 60, 90, or 120 days. In some embodiments, the nutritional composition comprising the synthetic oligosaccharide preparation is administered to the animal at least once, twice, three, four, or five times a day. In some embodiments, administering comprises providing the nutritional composition to the animal to ingest at will, wherein the animal ingests at least a portion of the nutritional composition in every 24-hour period.

In some embodiments, the animal has a higher body weight relative to the body weight of an animal administered a nutritional composition lacking the synthetic oligosaccharide preparation. In some embodiments, the animal has a higher feed efficiency relative to the feed efficiency of an animal administered a nutritional composition lacking the synthetic oligosaccharide preparation. In some embodiments, the animal has a lower feed conversion ratio relative to the feed conversion ratio of an animal administered a nutritional composition lacking the synthetic oligosaccharide preparation.

In some embodiments, the animal has a higher body weight relative to the body weight of the animal prior to administration of nutritional composition comprising the synthetic oligosaccharide preparation. In some embodiments, the animal has a higher feed efficiency relative to the feed efficiency of the animal prior to administration of nutritional composition comprising the synthetic oligosaccharide preparation. In some embodiments, the animal has a lower feed conversion ratio relative to the feed conversion ratio of the animal prior to administration of nutritional composition comprising the synthetic oligosaccharide preparation.

In some embodiments, the level of the microbial species is determined by DNA sequencing or RNA sequencing. In some embodiments, the level of the microbial species is determined by shotgun DNA sequencing.

In some embodiments the animal is livestock. In some embodiments the animal is a companion animal. In some embodiments, the animal is a fish (e.g. salmon, tilapia, tropical fish), poultry (e.g. chicken, turkey), seafood (e.g. shrimp), sheep, cow, cattle, buffalo, bison, pig (e.g. nursery pig, grower/finisher pig), cat, dog, rabbit, goat, guinea pig, donkey, camel, horse, pigeon, ferret, gerbil, hamster, mouse, rat, bird, or human. In some embodiments, the animal is poultry. In some embodiments, the animal is a chicken (e.g. broiler, layer, breeder), turkey, duck, or goose. In some embodiments, the animal is a pig (e.g. nursery pig, grower/finisher pig).

In some embodiments, the nutritional composition is an animal feed composition described herein. In some embodiments, the base nutritional composition is base animal feed described herein.

Provided herein are methods of reducing the feed conversion ratio of an animal, comprising: administering a nutritional composition comprising a base nutritional composition and a synthetic oligosaccharide preparation described herein to the animal, wherein the feed conversion ratio of the animal is lower relative to the feed conversion ratio of an animal administered a nutritional composition lacking the synthetic oligosaccharide preparation or relative to the feed conversion ratio of the animal prior to administration of the nutritional composition comprising the oligosaccharide preparation.

In some embodiments, the synthetic oligosaccharide preparation comprises at least n fractions of oligosaccharides each having a distinct degree of polymerization selected from 1 to n (DP1 to DPn fractions), wherein n is an integer greater than 2; wherein each fraction comprises from 1% to 90% anhydro-subunit containing oligosaccharides by relative abundance as measured by mass spectrometry.

In some embodiments, the animal has a higher body weight relative to the body weight of an animal administered a nutritional composition lacking the synthetic oligosaccharide preparation. In some embodiments, the animal has a higher feed efficiency relative to the feed efficiency of an animal administered a nutritional composition lacking the synthetic oligosaccharide preparation. In some embodiments, the animal has a lower feed conversion ratio relative to the feed conversion ratio of an animal administered a nutritional composition lacking the synthetic oligosaccharide preparation.

In some embodiments, the animal has a higher body weight relative to the body weight of the animal prior to administration of nutritional composition comprising the synthetic oligosaccharide preparation. In some embodiments, the animal has a higher feed efficiency relative to the feed efficiency of the animal prior to administration of nutritional composition comprising the synthetic oligosaccharide preparation. In some embodiments, the animal has a lower feed conversion ratio relative to the feed conversion ratio of the animal prior to administration of nutritional composition comprising the synthetic oligosaccharide preparation.

In some embodiments, the level of one or more microbial species in the gastrointestinal tract of the animal is higher relative to the level of the microbial species in the gastrointestinal tract of an animal administered a nutritional composition lacking the synthetic oligosaccharide preparation or relative to the level of the microbial species in the gastrointestinal tract of the animal prior to administration of the nutritional composition lacking the synthetic oligosaccharide preparation.

In some embodiments, the feed conversion ratio of the animal is at least 75%, 50%, 25%, 15%, 10%, 5%, or 1% less than the feed conversion ratio of an animal administered a nutritional composition lacking the synthetic oligosaccharide. In some embodiments, the feed conversion ratio of the animal is at least 75%, 50%, 25%, 15%, 10%, 5%, or 1% less than the feed conversion ratio of the animal prior to administration of the nutritional composition comprising the synthetic oligosaccharide preparation.

In some embodiments, the feed efficiency of the animal is at least 75%, 50%, 25%, 15%, 10%, 5%, or 1% greater than the feed efficiency of an animal administered the nutritional composition lacking the synthetic oligosaccharide. In some embodiments, the feed efficiency of the animal is at least 75%, 50%, 25%, 15%, 10%, 5%, or 1% greater than the feed efficiency of the animal prior to administration of the nutritional composition comprising the synthetic oligosaccharide preparation.

In some embodiments, the method further comprises obtaining a sample of the gastrointestinal microbiota of the gastrointestinal tract of the animal. In some embodiments, the sample is a biopsy of a gastrointestinal tissue (e.g., a cecal biopsy) or a fecal sample. In some embodiments, the method further comprises detecting the level of the microbial species in the sample.

In some embodiments, the level of 2, 3, 4, 5, or more microbial species in the gastrointestinal tract of the animal are higher relative to the level of the microbial species in the gastrointestinal tract of an animal administered a nutritional composition lacking the synthetic oligosaccharide preparation or relative to the level of the microbial species in the gastrointestinal tract of the animal prior to administration of the nutritional composition comprising the synthetic oligosaccharide preparation. In some embodiments, the method further comprises detecting the level of the 2nd, 3rd, 4th, or 5th microbial species in the sample.

In some embodiments, the microbial species is beneficial to the animal (e.g., beneficial to the health of the animal). In some embodiments, the microbial species belongs to the genus *Bacteroides, Odoribacter, Oscillibacter, Subdoligranulum, Biophila*, or *Barnesiella*. In some embodiments, the microbial species is selected from the group consisting of: *Bacteroides clarus, Bacteroides dorei, Odoribacter splanchinicus*, and *Barnesiella intestinihominis*. In some embodiments, each of the 2nd, 3rd, 4th, or 5th microbial species is a beneficial to the animal (e.g., beneficial to the health of the animal). In some embodiments, at least one of the 2nd, 3rd, 4th, or 5th microbial species belongs to the genus *Bacteroides, Odoribacter, Oscillibacter, Subdoligranulum, Biophila*, or *Barnesiella*. In some embodiments, at least one of the 2nd, 3rd, 4th, or 5th microbial species is selected from the group consisting of: *Bacteroides clarus, Bacteroides dorei, Odoribacter splanchinicus*, and *Barnesiella intestinihominis.*

In some embodiments, the animal has a gastrointestinal microbiota comprising at least 0.1%, 1%, 2%, 3%, 4%, 5%, 6%, 7%, 8%, 9%, or 10% of at least one microbial species that belongs to the genus *Bacteroides, Odoribacter, Oscillibacter, Subdoligranulum, Biophila*, or *Barnesiella*. In some embodiments, the animal has a gastrointestinal microbiota comprising at least 0.1%, 1%, 2%, 3%, 4%, 5%, 6%, 7%, 8%, 9%, or 10% of at least one of *Bacteroides clarus, Bacteroides dorei, Odoribacter splanchinicus*, and *Barnesiella intestinihominis.*

In some embodiments, the nutritional composition comprising the synthetic oligosaccharide preparation is administered to the animal for at least 1, 7, 10, 14, 30, 45, 60, 90, or 120 days. In some embodiments, the nutritional composition comprising the synthetic oligosaccharide preparation is administered to the animal at least once, twice, three, four, or five times a day. In some embodiments, administering comprises providing the nutritional composition to the animal to ingest at will, wherein the animal ingests at least a portion of the nutritional composition in every 24-hour period.

In some embodiments, the level of the microbial species is determined by DNA sequencing or RNA sequencing. In some embodiments, the level of the microbial species is determined by shotgun DNA sequencing.

In some embodiments the animal livestock. In some embodiments the animal is a companion animal. In some embodiments, the animal is a fish (e.g. salmon, tilapia, tropical fish), poultry (e.g. chicken, turkey), seafood (e.g. shrimp), sheep, cow, cattle, buffalo, bison, pig (e.g. nursery pig, grower/finisher pig), cat, dog, rabbit, goat, guinea pig, donkey, camel, horse, pigeon, ferret, gerbil, hamster, mouse, rat, bird, or human. In some embodiments, the animal is poultry. In some embodiments, the animal is a chicken (e.g. broiler, layer, breeder), turkey, duck, or goose. In some embodiments, the animal is a pig (e.g. nursery pig, grower/finisher pig). In some embodiments, the nutritional composition is an animal feed composition. In some embodiments, the base nutritional composition is base animal feed.

Provided herein are methods of increasing the feed efficiency of an animal, comprising: administering a nutritional composition comprising a base nutritional composition and a synthetic oligosaccharide preparation described herein to the animal, wherein the feed efficiency of the animal is higher relative to the feed efficiency of an animal administered a nutritional composition lacking the synthetic oligosaccharide preparation or relative to the feed efficiency of the animal prior to administration of the nutritional composition comprising the synthetic oligosaccharide preparation.

In some embodiments, the synthetic oligosaccharide preparation comprises at least n fractions of oligosaccharides each having a distinct degree of polymerization selected from 1 to n (DP1 to DPn fractions), wherein n is an integer greater than 2; wherein each fraction comprises from 1% to 90% anhydro-subunit containing oligosaccharides by relative abundance as measured by mass spectrometry.

In some embodiments, the level of one or more microbial species in the gastrointestinal tract of the animal is higher relative to the level of the microbial species in the gastrointestinal tract of an animal administered a nutritional composition lacking the synthetic oligosaccharide preparation or relative to the level of the microbial species in the animal prior to administration of the nutritional composition comprising the synthetic oligosaccharide preparation.

In some embodiments, the feed conversion ratio of the animal is at least 75%, 50%, 25%, 15%, 10%, 5%, or 1% less than the feed conversion ratio of an animal administered the nutritional composition lacking the synthetic oligosaccharide. In some embodiments, the feed conversion ratio of the animal is at least 75%, 50%, 25%, 15%, 10%, 5%, or 1% less than the feed conversion ratio of the animal prior to administration of the nutritional composition comprising the synthetic oligosaccharide.

In some embodiments, the feed efficiency of the animal is at least 75%, 50%, 25%, 15%, 10%, 5%, or 1% greater than the feed efficiency of an animal administered the nutritional composition lacking the synthetic oligosaccharide. In some embodiments, the feed efficiency of the animal is at least 75%, 50%, 25%, 15%, 10%, 5%, or 1% greater than the feed efficiency of the animal prior to administration of the nutritional composition comprising the synthetic oligosaccharide.

In some embodiments, the method further comprises obtaining a sample of the gastrointestinal microbiota of the gastrointestinal tract of the animal. In some embodiments, the sample is a biopsy of a gastrointestinal tissue (e.g., a cecal biopsy) or a fecal sample. In some embodiments, the method further comprises detecting the level of the microbial species in the sample.

In some embodiments, the level of 2, 3, 4, 5, or more microbial species in the gastrointestinal tract of the animal are higher relative to the level of the microbial species in the gastrointestinal tract of an animal administered a nutritional composition lacking the synthetic oligosaccharide preparation or relative to the level of the microbial species in the gastrointestinal tract of the animal prior to administration of the nutritional composition comprising the oligosaccharide preparation. In some embodiments, the method further comprises detecting the level of the 2nd, 3rd, 4th, or 5th microbial species in the sample.

In some embodiments, the microbial species is beneficial to the animal (e.g., beneficial to the health of the animal). In some embodiments, the microbial species belongs to the genus *Bacteroides, Odoribacter, Oscillibacter, Subdoligranulum, Biophila*, or *Barnesiella*. In some embodiments, the microbial species is selected from the group consisting of: *Bacteroides clarus, Bacteroides dorei, Odoribacter splanchinicus*, and *Barnesiella intestinihominis*. In some embodiments, each of the 2nd, 3rd, 4th, or 5th microbial species is a beneficial to the animal (e.g., beneficial to the health of the animal). In some embodiments, at least one of the 2nd, 3rd, 4th, or 5th microbial species belongs to the genus *Bacteroides, Odoribacter, Oscillibacter, Subdoligranulum, Biophila*, or *Barnesiella*. In some embodiments, at least one of the 2nd, 3rd, 4th, or 5th microbial species is selected from the group consisting of: *Bacteroides clarus, Bacteroides dorei, Odoribacter splanchinicus*, and *Barnesiella intestinihominis.*

In some embodiments, the animal has a gastrointestinal microbiota comprising at least 0.1%, 1%, 2%, 3%, 4%, 5%, 6%, 7%, 8%, 9%, or 10% of at least one microbial species that belongs to the genus *Bacteroides, Odoribacter, Oscillibacter, Subdoligranulum, Biophila*, or *Barnesiella*. In some embodiments, the animal has a gastrointestinal microbiota comprising at least 0.1%, 1%, 2%, 3%, 4%, 5%, 6%, 7%, 8%, 9%, or 10% of at least one of *Bacteroides clarus, Bacteroides dorei, Odoribacter splanchinicus*, and *Barnesiella intestinihominis*.

In some embodiments, the nutritional composition comprising the synthetic oligosaccharide preparation is administered to the animal for at least 1, 7, 10, 14, 30, 45, 60, 90, or 120 days. In some embodiments, the nutritional composition comprising the synthetic oligosaccharide preparation is administered to the animal at least once, twice, three, four, or five times a day. In some embodiments, administering comprises providing the nutritional composition to the animal to ingest at will, wherein the animal ingests at least a portion of the nutritional composition in every 24-hour period.

In some embodiments, the level of the microbial species is determined by DNA sequencing or RNA sequencing. In some embodiments, the level of the microbial species is determined by shotgun DNA sequencing.

In some embodiments the animal livestock. In some embodiments the animal is a companion animal. In some embodiments, the animal is a fish (e.g. salmon, tilapia, tropical fish), poultry (e.g. chicken, turkey), seafood (e.g. shrimp), sheep, cow, cattle, buffalo, bison, pig (e.g. nursery pig, grower/finisher pig), cat, dog, rabbit, goat, guinea pig, donkey, camel, horse, pigeon, ferret, gerbil, hamster, mouse, rat, bird, or human. In some embodiments, the animal is poultry. In some embodiments, the animal is a chicken (e.g. broiler, layer, breeder), turkey, duck, or goose. In some embodiments, the animal is a pig (e.g. nursery pig, grower/finisher pig). In some embodiments, the nutritional composition is an animal feed composition. In some embodiments, the base nutritional composition is base animal feed.

Provided herein are methods of increasing the body weight of an animal, comprising: administering a nutritional composition comprising a base nutritional composition and a synthetic oligosaccharide preparation described herein to the animal, wherein the body weight of the animal is higher relative to the body weight of an animal administered a nutritional composition lacking the synthetic oligosaccharide preparation or relative to the body weight of the animal prior to administration of the nutritional composition comprising the synthetic oligosaccharide preparation.

In some embodiments, the synthetic oligosaccharide preparation comprises at least n fractions of oligosaccharides each having a distinct degree of polymerization selected from 1 to n (DP1 to DPn fractions), wherein n is an integer greater than 2; wherein each fraction comprises from 1% to 90% anhydro-subunit containing oligosaccharides by relative abundance as measured by mass spectrometry.

In some embodiments, the body weight of the animal is at least 75%, 50%, 25%, 15%, 10%, 5%, or 1% greater than the body weight of the animal administered the nutritional composition lacking the synthetic oligosaccharide. In some embodiments, the body weight of the animal is at least 75%, 50%, 25%, 15%, 10%, 5%, or 1% greater than the body weight of the animal prior to administration of nutritional composition comprising the synthetic oligosaccharide.

In some embodiments, the animal has a higher body weight relative to the body weight of an animal administered a nutritional composition lacking the synthetic oligosaccharide preparation. In some embodiments, the animal has a higher feed efficiency relative to the feed efficiency of an animal administered a nutritional composition lacking the synthetic oligosaccharide preparation. In some embodiments, the animal has a lower feed conversion ratio relative to the feed conversion ratio of an animal administered a nutritional composition lacking the synthetic oligosaccharide preparation.

In some embodiments, the animal has a higher body weight relative to the body weight of the animal prior to administration of the nutritional composition comprising the synthetic oligosaccharide preparation. In some embodiments, the animal has a higher feed efficiency relative to the feed efficiency of the animal prior to administration of the nutritional composition comprising the synthetic oligosaccharide preparation. In some embodiments, the animal has a lower feed conversion ratio relative to the feed conversion ratio of the animal prior to administration of the nutritional composition comprising the synthetic oligosaccharide preparation.

In some embodiments, the level of one or more microbial species in the gastrointestinal tract of the animal is higher relative to the level of the microbial species in the gastrointestinal tract of an animal administered a nutritional composition lacking the synthetic oligosaccharide preparation. In some embodiments, the level of one or more microbial species in the gastrointestinal tract of the animal is higher relative to the level of the microbial species in the gastrointestinal tract of the animal prior to administration of the nutritional composition comprising the synthetic oligosaccharide preparation.

In some embodiments, the feed conversion ratio of the animal is at least 75%, 50%, 25%, 15%, 10%, 5%, or 1% less than the feed conversion ratio of an animal administered the nutritional composition lacking the synthetic oligosaccharide. In some embodiments, the feed conversion ratio of the animal is at least 75%, 50%, 25%, 15%, 10%, 5%, or 1% less than the feed conversion ratio of the animal prior to administration of the nutritional composition comprising the synthetic oligosaccharide.

In some embodiments, the feed efficiency of the animal is at least 75%, 50%, 25%, 15%, 10%, 5%, or 1% greater than the feed efficiency of an animal administered the nutritional composition lacking the synthetic oligosaccharide. In some embodiments, the feed efficiency of the animal is at least 75%, 50%, 25%, 15%, 10%, 5%, or 1% greater than the feed efficiency of the animal prior to administration of the nutritional composition comprising the synthetic oligosaccharide.

In some embodiments, the method further comprises obtaining a sample of the gastrointestinal microbiota of the gastrointestinal tract of the animal. In some embodiments, the sample is a biopsy of a gastrointestinal tissue (e.g., a cecal biopsy) or a fecal sample. In some embodiments, the method further comprises detecting the level of the microbial species in the sample.

In some embodiments, the level of 2, 3, 4, 5, or more microbial species in the gastrointestinal tract of the animal are higher relative to the level of the microbial species in the gastrointestinal tract of an animal administered a nutritional composition lacking the synthetic oligosaccharide preparation. In some embodiments, the level of 2, 3, 4, 5, or more microbial species in the gastrointestinal tract of the animal are higher relative to the level of the microbial species in the gastrointestinal tract of the animal prior to administration of the nutritional composition comprising the synthetic oligosaccharide preparation. In some embodiments, the method further comprises detecting the level of the 2nd, 3rd, 4th, or 5th microbial species in the sample.

In some embodiments, the microbial species is beneficial to the animal (e.g., beneficial to the health of the animal). In some embodiments, the microbial species belongs to the genus *Bacteroides, Odoribacter, Oscillibacter, Subdoligranulum, Biophila*, or *Barnesiella*. In some embodiments, the microbial species is selected from the group consisting of: *Bacteroides clarus, Bacteroides dorei, Odoribacter splanchinicus*, and *Barnesiella intestinihominis*. In some embodiments, each of the 2nd, 3rd, 4th, or 5th microbial species is a beneficial to the animal (e.g., beneficial to the health of the animal). In some embodiments, at least one of the 2nd, 3rd, 4th, or 5th microbial species belongs to the genus *Bacteroides, Odoribacter, Oscillibacter, Subdoligranulum, Biophila*, or *Barnesiella*. In some embodiments, at least one of the 2nd, 3rd, 4th, or 5th microbial species is selected from the group consisting of: *Bacteroides clarus, Bacteroides dorei, Odoribacter splanchinicus*, and *Barnesiella intestinihominis*.

In some embodiments, the animal has a gastrointestinal microbiota comprising at least 0.1%, 1%, 2%, 3%, 4%, 5%, 6%, 7%, 8%, 9%, or 10% of at least one microbial species that belongs to the genus *Bacteroides, Odoribacter, Oscillibacter, Subdoligranulum, Biophila*, or *Barnesiella*. In some embodiments, the animal has a gastrointestinal microbiota comprising at least 0.1%, 1%, 2%, 3%, 4%, 5%, 6%, 7%, 8%, 9%, or 10% of at least one of *Bacteroides clarus, Bacteroides dorei, Odoribacter splanchinicus*, and *Barnesiella intestinihominis.*

In some embodiments, the nutritional composition comprising the synthetic oligosaccharide preparation is administered to the animal for at least 1, 7, 10, 14, 30, 45, 60, 90, or 120 days. In some embodiments, the nutritional composition comprising the synthetic oligosaccharide preparation is administered to the animal at least once, twice, three, four, or five times a day. In some embodiments, administering comprises providing the nutritional composition to the animal to ingest at will, wherein the animal ingests at least a portion of the nutritional composition in every 24-hour period.

In some embodiments, the level of the microbial species is determined by DNA sequencing or RNA sequencing. In some embodiments, the level of the microbial species is determined by shotgun DNA sequencing.

In some embodiments the animal livestock. In some embodiments the animal is a companion animal. In some embodiments, the animal is a fish (e.g. salmon, tilapia, tropical fish), poultry (e.g. chicken, turkey), seafood (e.g. shrimp), sheep, cow, cattle, buffalo, bison, pig (e.g. nursery pig, grower/finisher pig), cat, dog, rabbit, goat, guinea pig, donkey, camel, horse, pigeon, ferret, gerbil, hamster, mouse, rat, bird, or human. In some embodiments, the animal is poultry. In some embodiments, the animal is a chicken (e.g. broiler, layer, breeder), turkey, duck, or goose. In some embodiments, the animal is a pig (e.g. nursery pig, grower/finisher pig). In some embodiments, the nutritional composition is an animal feed composition. In some embodiments, the base nutritional composition is base animal feed.

Provided herein are methods of improving animal health, comprising: administering a nutritional composition comprising a base nutritional composition and a synthetic oligosaccharide preparation described herein to the animal, and wherein the administering results in at least one of a) improving the gastrointestinal microbiota of the animal, b) selectively increasing the level of one or more beneficial bacteria in the gastrointestinal microbiota of the animal, c) improving at least one of weight gain and feed conversion, and d) promoting growth of the animal.

In some embodiments, the synthetic oligosaccharide preparation comprises at least n fractions of oligosaccharides each having a distinct degree of polymerization selected from 1 to n (DP1 to DPn fractions), wherein n is an integer greater than 2; wherein each fraction comprises from 1% to 90% anhydro-subunit containing oligosaccharides by relative abundance as measured by mass spectrometry.

In some embodiments, the animal has a higher body weight relative to the body weight of an animal administered a nutritional composition lacking the synthetic oligosaccharide preparation. In some embodiments, the animal has a higher feed efficiency relative to the feed efficiency of an animal administered a nutritional composition lacking the synthetic oligosaccharide preparation. In some embodiments, the animal has a lower feed conversion ratio relative to the feed conversion ratio of an animal administered a nutritional composition lacking the synthetic oligosaccharide preparation.

In some embodiments, the animal has a higher body weight relative to the body weight of the animal prior to administration of the nutritional composition comprising the synthetic oligosaccharide preparation. In some embodiments, the animal has a higher feed efficiency relative to the feed efficiency of the animal prior to administration of the nutritional composition comprising the synthetic oligosaccharide preparation. In some embodiments, the animal has a lower feed conversion ratio relative to the feed conversion ratio of the animal prior to administration of the nutritional composition comprising the synthetic oligosaccharide preparation.

In some embodiments, the level of one or more microbial species in the gastrointestinal tract of the animal is higher relative to the level of the microbial species in the gastrointestinal tract of an animal administered a nutritional composition lacking the synthetic oligosaccharide preparation. In some embodiments, the level of one or more microbial species in the gastrointestinal tract of the animal is higher relative to the level of the microbial species in the gastrointestinal tract of the animal prior to administration of the nutritional composition comprising the synthetic oligosaccharide preparation.

In some embodiments, the feed conversion ratio of the animal is at least 75%, 50%, 25%, 15%, 10%, 5%, or 1% less than the feed conversion ratio of an animal administered the nutritional composition lacking the synthetic oligosaccharide. In some embodiments, the feed conversion ratio of the animal is at least 75%, 50%, 25%, 15%, 10%, 5%, or 1% less than the feed conversion ratio of the animal prior to administration of the nutritional composition comprising the synthetic oligosaccharide.

In some embodiments, the feed efficiency of the animal is at least 75%, 50%, 25%, 15%, 10%, 5%, or 1% greater than the feed efficiency of an animal administered the nutritional composition lacking the synthetic oligosaccharide.

In some embodiments, the feed efficiency of the animal is at least 75%, 50%, 25%, 15%, 10%, 5%, or 1% greater than the feed efficiency of the animal prior to administration of the nutritional composition comprising the synthetic oligosaccharide.

In some embodiments, the method further comprises obtaining a sample of the gastrointestinal microbiota of the gastrointestinal tract of the animal. In some embodiments, the sample is a biopsy of a gastrointestinal tissue (e.g., a cecal biopsy) or a fecal sample. In some embodiments, the method further comprises detecting the level of the microbial species in the sample.

In some embodiments, the level of 2, 3, 4, 5, or more microbial species in the gastrointestinal tract of the animal are higher relative to the level of the microbial species in the gastrointestinal tract of an animal administered a nutritional composition lacking the synthetic oligosaccharide preparation. In some embodiments, the level of 2, 3, 4, 5, or more microbial species in the gastrointestinal tract of the animal are higher relative to the level of the microbial species in the gastrointestinal tract of the animal prior to administration of the nutritional composition comprising the synthetic oligosaccharide preparation. In some embodiments, the method further comprises detecting the level of the 2nd, 3rd, 4th, or 5th microbial species in the sample.

In some embodiments, the microbial species is beneficial to the animal (e.g., beneficial to the health of the animal). In some embodiments, the microbial species belongs to the genus *Bacteroides, Odoribacter, Oscillibacter, Subdoligranulum, Biophila*, or *Barnesiella*. In some embodiments, the microbial species is selected from the group consisting of: *Bacteroides clarus, Bacteroides dorei, Odoribacter splanchinicus*, and *Barnesiella intestinihominis*. In some embodiments, each of the 2nd, 3rd, 4th, or 5th microbial species is a beneficial to the animal (e.g., beneficial to the health of the animal). In some embodiments, at least one of the 2nd, 3rd, 4th, or 5th microbial species belongs to the genus *Bacteroides, Odoribacter, Oscillibacter, Subdoligranulum, Biophila*, or *Barnesiella*. In some embodiments, at least one of the 2nd, 3rd, 4th, or 5th microbial species is selected from the group consisting of: *Bacteroides clarus, Bacteroides dorei, Odoribacter splanchinicus*, and *Barnesiella intestinihominis*.

In some embodiments, the animal has a gastrointestinal microbiota comprising at least 0.1%, 1%, 2%, 3%, 4%, 5%, 6%, 7%, 8%, 9%, or 10% of at least one microbial species that belongs to the genus *Bacteroides, Odoribacter, Oscillibacter, Subdoligranulum, Biophila*, or *Barnesiella*. In some embodiments, the animal has a gastrointestinal microbiota comprising at least 0.1%, 1%, 2%, 3%, 4%, 5%, 6%, 7%, 8%, 9%, or 10% of at least one of *Bacteroides clarus, Bacteroides dorei, Odoribacter splanchinicus*, and *Barnesiella intestinihominis*.

In some embodiments, the nutritional composition comprising the synthetic oligosaccharide preparation is administered to the animal for at least 1, 7, 10, 14, 30, 45, 60, 90, or 120 days. In some embodiments, the nutritional composition comprising the synthetic oligosaccharide preparation is administered to the animal at least once, twice, three, four, or five times a day. In some embodiments, administering comprises providing the nutritional composition to the animal to ingest at will, wherein the animal ingests at least a portion of the nutritional composition in every 24-hour period.

In some embodiments, the level of the microbial species is determined by DNA sequencing or RNA sequencing. In some embodiments, the level of the microbial species is determined by shotgun DNA sequencing.

In some embodiments the animal is livestock. In some embodiments the animal is a companion animal. In some embodiments, the animal is a fish (e.g. salmon, tilapia, tropical fish), poultry (e.g. chicken, turkey), seafood (e.g. shrimp), sheep, cow, cattle, buffalo, bison, pig (e.g. nursery pig, grower/finisher pig), cat, dog, rabbit, goat, guinea pig, donkey, camel, horse, pigeon, ferret, gerbil, hamster, mouse, rat, bird, or human. In some embodiments, the animal is poultry. In some embodiments, the animal is a chicken (e.g. broiler, layer, breeder), turkey, duck, or goose. In some embodiments, the animal is a pig (e.g. nursery pig, grower/finisher pig).

In some embodiments, the nutritional composition is an animal feed composition described herein. In some embodiments, the base nutritional composition is base animal feed described herein.

Provided herein are methods of inhibiting the growth of a microbial species in the gastrointestinal tract of an animal, comprising: administering a nutritional composition comprising a base nutritional composition and a synthetic oligosaccharide preparation described herein to the animal, and wherein the level of one or more microbial species in the gastrointestinal tract of the animal is lower relative to the level of the microbial species in the gastrointestinal tract of an animal administered a nutritional composition lacking the synthetic oligosaccharide preparation or relative to the level of the microbial species in the gastrointestinal tract of the animal prior to administration of the nutritional composition comprising the synthetic oligosaccharide preparation.

In some embodiments, the synthetic oligosaccharide preparation comprises at least n fractions of oligosaccharides each having a distinct degree of polymerization selected from 1 to n (DP1 to DPn fractions), wherein n is an integer greater than 2; wherein each fraction comprises from 1% to 90% anhydro-subunit containing oligosaccharides by relative abundance as measured by mass spectrometry.

In some embodiments, the microbial species is a bacterial species. In other embodiments, the microbial species is an archaea species. In other embodiments, the microbial species is a virus, bacteriophage, or protozoan species.

In some embodiments, the method comprises obtaining a sample of the gastrointestinal microbiota of the gastrointestinal tract of the animal. In some embodiments, the sample is a biopsy of a gastrointestinal tissue (e.g., a cecal biopsy) or a fecal sample. In some embodiments, the method comprises determining the level of the microbial species in the sample.

In some embodiments, the level of 2, 3, 4, 5, or more microbial species in the gastrointestinal tract of the animal are lower relative to the level of the microbial species in the gastrointestinal tract of an animal administered a nutritional composition lacking the synthetic oligosaccharide preparation. In some embodiments, the level of 2, 3, 4, 5, or more microbial species in the gastrointestinal tract of the animal are lower relative to the level of the microbial species in the gastrointestinal tract of an animal prior to administration of the nutritional composition comprising the synthetic oligosaccharide preparation. In some embodiments, the methods comprise detecting the level of the 2nd, 3rd, 4th, or 5th microbial species in the sample.

In some embodiments, the microbial species is detrimental to the animal. In some embodiments, the microbial species is pathogenic to the animal. In some embodiments, the microbial species is pathogenic to humans but not to animals. In some embodiment, the microbial species is *Helicobacter pullorum*. In some embodiments, the microbial species is pathogenic to humans but not to animals and the microbial species is *Helicobacter pullorum*. In some embodiments, the microbial species belongs to the phylum Proteobacteria. In some embodiments, the microbial species belongs to the genus *Helicobacter, Escherichia, Salmonella, Vibrio*, or *Yersinia*. In some embodiments, the microbial species is selected from the group consisting of: *Helicobacter pullorum, Proteobacteria johnsonii, Escherichia coli, Camplobacter jejuni*, and *Lactobacillus crispatus*.

In some embodiments, each of the 2nd, 3rd, 4th, or 5th microbial species is a detrimental to the animal. In some embodiments, each of the 2nd, 3rd, 4th, or 5th microbial species is pathogenic to the animal. In some of the embodiments, each of the 2nd, 3rd, 4th, or 5th microbial species is pathogenic to humans but not to animals. In some of the embodiments, the microbial species is *Helicobacter pullorum*. In some embodiments, the microbial species is pathogenic to humans but not to animals and the microbial species is *Helicobacter pullorum*. In some embodiments, at least one of the 2nd, 3rd, 4th, or 5th microbial species belongs to the phylum Proteobacteria. In some embodiments, at least one of the 2nd, 3rd, 4th, or 5th microbial species belongs to the genus *Helicobacter, Escherichia, Salmonella, Vibrio*, or *Yersinia*.

In some embodiments, the animal has a gastrointestinal microbiota comprising less than 20%, 15%, 10%, 9%, 8%, 7%, 6%, 5%, 4%, 3%, 2%, 1% or 0.1% *Helicobacter pullorum, Proteobacteria johnsonii, Escherichia coli, Camplobacter jejuni*, and *Lactobacillus crispatus*.

In some embodiments, the nutritional composition comprising the synthetic oligosaccharide preparation is administered to the animal for at least 1, 7, 10, 14, 30, 45, 60, 90, or 120 days.

In some embodiments, the nutritional composition comprising the synthetic oligosaccharide preparation is administered to the animal at least once, twice, three, four, or five times a day. In some embodiments, administering comprises providing the nutritional composition to the animal to ingest at will, wherein the animal ingests at least a portion of the nutritional composition in every 24-hour period.

In some embodiments, the animal has a higher body weight relative to the body weight of an animal administered a nutritional composition lacking the synthetic oligosaccharide preparation. In some embodiments, the animal has a higher feed efficiency relative to the feed efficiency of an animal administered a nutritional composition lacking the synthetic oligosaccharide preparation. In some embodiments, the animal has a lower feed conversion ratio (FCR) relative to the feed conversion ratio of an animal administered a nutritional composition lacking the synthetic oligosaccharide preparation.

In some embodiments, the animal has a higher body weight relative to the body weight of the animal prior to administration of the nutritional composition comprising the synthetic oligosaccharide preparation. In some embodiments, the animal has a higher feed efficiency relative to the feed efficiency of the animal prior to administration of the nutritional composition comprising the synthetic oligosaccharide preparation. In some embodiments, the animal has a lower feed conversion ratio (FCR) relative to the feed conversion ratio of the animal prior to administration of the nutritional composition comprising the synthetic oligosaccharide preparation.

In some embodiments, the level of the microbial species is detected by DNA sequencing or RNA sequencing. In some embodiments, the level of the microbial species is detected by shotgun DNA sequencing.

In some embodiments, the animal is livestock. In some embodiments the animal is a companion animal. In some embodiments, the animal is a fish (e.g. salmon, tilapia, tropical fish), poultry (e.g. chicken, turkey), seafood (e.g. shrimp), sheep, cow, cattle, buffalo, bison, pig (e.g. nursery pig, grower/finisher pig), cat, dog, rabbit, goat, guinea pig, donkey, camel, horse, pigeon, ferret, gerbil, hamster, mouse, rat, bird, or human. In some embodiments, the animal is poultry. In some embodiments, the animal is a chicken (e.g. broiler, layer, breeder), turkey, duck, or goose. In some embodiments, the animal is a pig (e.g. nursery pig, grower/finisher pig).

In some embodiments, the nutritional composition is an animal feed composition described herein. In some embodiments, the base nutritional composition is base animal feed described herein.

Provided herein are methods of increasing survival of an animal, comprising: administering a nutritional composition comprising a base nutritional composition and a synthetic oligosaccharide preparation described herein to the animal.

In some embodiments, the synthetic oligosaccharide preparation comprises at least n fractions of oligosaccharides each having a distinct degree of polymerization selected from 1 to n (DP1 to DPn fractions), wherein n is an integer greater than 2; wherein each fraction comprises from 1% to 90% anhydro-subunit containing oligosaccharides by relative abundance as measured by mass spectrometry.

In some embodiments, the microbial species is a bacterial species. In other embodiments, the microbial species is an archaea species. In other embodiments, the microbial species is a virus, bacteriophage, or protozoan species.

In some embodiments, the animal is exposed to a pathogenic microbial species.

In some embodiments, the animal administered the nutritional composition comprising the synthetic oligosaccharide preparation lives longer relative to an animal administered a nutritional composition lacking the synthetic oligosaccharide preparation.

In some embodiments, the level of one or more microbial species in the gastrointestinal tract of the animal is lower relative to the level of the microbial species in the gastrointestinal tract of an animal administered a nutritional composition lacking the synthetic oligosaccharide preparation or relative to the level of the microbial species in the gastrointestinal tract of the animal prior to administration of the nutritional composition comprising the synthetic oligosaccharide preparation.

In some embodiments, the method comprises obtaining a sample of the gastrointestinal microbiota of the gastrointestinal tract of the animal. In some embodiments, the sample is a biopsy of a gastrointestinal tissue (e.g., a cecal biopsy) or a fecal sample. In some embodiments, the method comprises determining the level of the microbial species in the sample.

In some embodiments, the level of 2, 3, 4, 5, or more microbial species in the gastrointestinal tract of the animal are lower relative to the level of the microbial species in the gastrointestinal tract of an animal administered a nutritional composition lacking the synthetic oligosaccharide preparation. In some embodiments, the level of 2, 3, 4, 5, or more microbial species in the gastrointestinal tract of the animal are lower relative to the level of the microbial species in the gastrointestinal tract of an animal prior to administration of the nutritional composition comprising the synthetic oligosaccharide preparation. In some embodiments, the methods comprise detecting the level of the 2nd, 3rd, 4th, or 5th microbial species in the sample.

In some embodiments, the microbial species is detrimental to the animal. In some embodiments, the microbial species is pathogenic to the animal. In some embodiments, the microbial species is pathogenic to humans but not to animals. In some embodiment, the microbial species is *Helicobacter pullorum*. In some embodiments, the microbial species is pathogenic to humans but not to animals and the microbial species is *Helicobacter pullorum*. In some embodiments, the microbial species belongs to the phylum Proteobacteria. In some embodiments, the microbial species belongs to the genus *Helicobacter, Escherichia, Salmonella, Vibrio*, or *Yersinia*. In some embodiments, the microbial species is selected from the group consisting of: *Helicobacter pullorum, Proteobacteria johnsonii, Escherichia coli, Camplobacter jejuni*, and *Lactobacillus crispatus.*

In some embodiments, each of the 2nd, 3rd, 4th, or 5th microbial species is a detrimental to the animal. In some embodiments, each of the 2nd, 3rd, 4th, or 5th microbial species is pathogenic to the animals. In some of the embodiments, each of the 2nd, 3rd, 4th, or 5th microbial species is pathogenic to humans but not to animals. In some of the embodiments, the microbial species is *Helicobacter pullorum*. In some embodiments, the microbial species is pathogenic to humans but not to animals and the microbial species is *Helicobacter pullorum*. In some embodiments, at least one of the 2nd, 3rd, 4th, or 5th microbial species belongs to the phylum Proteobacteria. In some embodiments, at least one of the 2nd, 3rd, 4th, or 5th microbial species belongs to the genus *Helicobacter, Escherichia, Salmonella, Vibrio*, or *Yersinia.*

In some embodiments, the animal has a gastrointestinal microbiota comprising less than 20%, 15%, 10%, 9%, 8%, 7%, 6%, 5%, 4%, 3%, 2%, 1% or 0.1% *Helicobacter pullorum, Proteobacteria johnsonii, Escherichia coli, Camplobacter jejuni*, and *Lactobacillus crispatus.*

In some embodiments, the nutritional composition comprising the synthetic oligosaccharide preparation is administered to the animal for at least 1, 7, 10, 14, 30, 45, 60, 90, or 120 days.

In some embodiments, the nutritional composition comprising the synthetic oligosaccharide preparation is administered to the animal at least once, twice, three, four, or five times a day. In some embodiments, administering comprises providing the nutritional composition to the animal to ingest at will, wherein the animal ingests at least a portion of the nutritional composition in every 24-hour period.

In some embodiments, the animal has a higher body weight relative to the body weight of an animal administered a nutritional composition lacking the synthetic oligosaccharide preparation. In some embodiments, the animal has a higher feed efficiency relative to the feed efficiency of an animal administered a nutritional composition lacking the synthetic oligosaccharide preparation. In some embodiments, the animal has a lower feed conversion ratio (FCR) relative to the feed conversion ratio of an animal administered a nutritional composition lacking the synthetic oligosaccharide preparation.

In some embodiments, the animal has a higher body weight relative to the body weight of the animal prior to administration of the nutritional composition comprising the synthetic oligosaccharide preparation. In some embodiments, the animal has a higher feed efficiency relative to the feed efficiency of the animal prior to administration of the nutritional composition comprising the synthetic oligosaccharide preparation. In some embodiments, the animal has a lower feed conversion ratio (FCR) relative to the feed conversion ratio of the animal prior to administration of the nutritional composition comprising the synthetic oligosaccharide preparation.

In some embodiments, the level of the microbial species is detected by DNA sequencing or RNA sequencing. In some embodiments, the level of the microbial species is detected by shotgun DNA sequencing.

In some embodiments, the animal is livestock. In some embodiments, the animal is a companion animal. In some embodiments, the animal is a fish (e.g. salmon, tilapia, tropical fish), poultry (e.g. chicken, turkey), seafood (e.g. shrimp), sheep, cow, cattle, buffalo, bison, pig (e.g. nursery pig, grower/finisher pig), cat, dog, rabbit, goat, guinea pig, donkey, camel, horse, pigeon, ferret, gerbil, hamster, mouse, rat, bird, or human. In some embodiments, the animal is poultry. In some embodiments, the animal is a chicken (e.g. broiler, layer, breeder), turkey, duck, or goose. In some embodiments, the animal is a pig (e.g. nursery pig, grower/finisher pig).

In some embodiments, the nutritional composition is an animal feed composition described herein. In some embodiments, the base nutritional composition is base animal feed described herein.

Provided herein are methods of improving animal health, comprising: administering a nutritional composition comprising a base nutritional composition and a synthetic oligosaccharide preparation described herein to the animal, wherein the administering results in at least one of a) improving the gastrointestinal microbiota of the animal, b) selectively decreasing the level of one or more detrimental or pathogenic bacteria in the gastrointestinal microbiota of the animal, c) improving at least one of weight gain and feed conversion ratio, and d) promoting growth of the animal.

In some embodiments, the synthetic oligosaccharide preparation comprises at least n fractions of oligosaccharides each having a distinct degree of polymerization selected from 1 to n (DP1 to DPn fractions), wherein n is an integer greater than 2; wherein each fraction comprises from 1% to 90% anhydro-subunit containing oligosaccharides by relative abundance as measured by mass spectrometry.

In some embodiments, the microbial species is a bacterial species. In other embodiments, the microbial species is an archaea species. In other embodiments, the microbial species is a virus, bacteriophage, or protozoan species.

In some embodiments, the method comprises obtaining a sample of the gastrointestinal microbiota of the gastrointestinal tract of the animal. In some embodiments, the sample is a biopsy of a gastrointestinal tissue (e.g., a cecal biopsy) or a fecal sample. In some embodiments, the method comprises determining the level of the microbial species in the sample.

In some embodiments, the level of 2, 3, 4, 5, or more microbial species in the gastrointestinal tract of the animal are lower relative to the level of the microbial species in the gastrointestinal tract of an animal administered a nutritional composition lacking the synthetic oligosaccharide preparation. In some embodiments, the level of 2, 3, 4, 5, or more microbial species in the gastrointestinal tract of the animal are lower relative to the level of the microbial species in the gastrointestinal tract of an animal prior to administration of the nutritional composition comprising the synthetic oligosaccharide preparation. In some embodiments, the methods comprise detecting the level of the 2nd, 3rd, 4th, or 5th microbial species in the sample.

In some embodiments, the microbial species is detrimental to the animal. In some embodiments, the microbial species is pathogenic to the animal. In some embodiments, the microbial species is pathogenic to humans but not to animals. In some embodiment, the microbial species is *Helicobacter pullorum*. In some embodiments, the microbial species is pathogenic to humans but not to animals and the microbial species is *Helicobacter pullorum*. In some embodiments, the microbial species belongs to the phylum Proteobacteria. In some embodiments, the microbial species belongs to the genus *Helicobacter, Escherichia, Salmonella, Vibrio*, or *Yersinia*. In some embodiments, the microbial species is selected from the group consisting of: *Helico-*

*bacter pullorum, Proteobacteria johnsonii, Escherichia coli, Camplobacter jejuni*, and *Lactobacillus crispatus*.

In some embodiments, each of the 2nd, 3rd, 4th, or 5th microbial species is a detrimental to the animal. In some embodiments, each of the 2nd, 3rd, 4th, or 5th microbial species is pathogenic to the animals. In some of the embodiments, each of the 2nd, 3rd, 4th, or 5th microbial species is pathogenic to humans but not to animals. In some of the embodiments, the microbial species is *Helicobacter pullorum*. In some embodiments, the microbial species is pathogenic to humans but not to animals and the microbial species is *Helicobacter pullorum*. In some embodiments, at least one of the 2nd, 3rd, 4th, or 5th microbial species belongs to the phylum Proteobacteria. In some embodiments, at least one of the 2nd, 3rd, 4th, or 5th microbial species belongs to the genus *Helicobacter, Escherichia, Salmonella, Vibrio*, or *Yersinia*.

In some embodiments, the animal has a gastrointestinal microbiota comprising less than 20%, 15%, 10%, 9%, 8%, 7%, 6%, 5%, 4%, 3%, 2%, 1% or 0.1% *Helicobacter pullorum, Proteobacteria johnsonii, Escherichia coli, Camplobacter jejuni*, and *Lactobacillus crispatus*.

In some embodiments, the nutritional composition comprising the synthetic oligosaccharide preparation is administered to the animal for at least 1, 7, 10, 14, 30, 45, 60, 90, or 120 days.

In some embodiments, the nutritional composition comprising the synthetic oligosaccharide preparation is administered to the animal at least once, twice, three, four, or five times a day. In some embodiments, administering comprises providing the nutritional composition to the animal to ingest at will, wherein the animal ingests at least a portion of the nutritional composition in every 24-hour period.

In some embodiments, the animal has a higher body weight relative to the body weight of an animal administered a nutritional composition lacking the synthetic oligosaccharide preparation. In some embodiments, the animal has a higher feed efficiency relative to the feed efficiency of an animal administered a nutritional composition lacking the synthetic oligosaccharide preparation. In some embodiments, the animal has a lower feed conversion ratio (FCR) relative to the feed conversion ratio of an animal administered a nutritional composition lacking the synthetic oligosaccharide preparation.

In some embodiments, the animal has a higher body weight relative to the body weight of the animal prior to administration of the nutritional composition comprising the synthetic oligosaccharide preparation. In some embodiments, the animal has a higher feed efficiency relative to the feed efficiency of the animal prior to administration of the nutritional composition comprising the synthetic oligosaccharide preparation. In some embodiments, the animal has a lower feed conversion ratio (FCR) relative to the feed conversion ratio of the animal prior to administration of the nutritional composition comprising the synthetic oligosaccharide preparation.

In some embodiments, the level of the microbial species is detected by DNA sequencing or RNA sequencing. In some embodiments, the level of the microbial species is detected by shotgun DNA sequencing.

In some embodiments, the animal is livestock. In some embodiments, the animal is a companion animal. In some embodiments, the animal is a fish (e.g. salmon, tilapia, tropical fish), poultry (e.g. chicken, turkey), seafood (e.g. shrimp), sheep, cow, cattle, buffalo, bison, pig (e.g. nursery pig, grower/finisher pig), cat, dog, rabbit, goat, guinea pig, donkey, camel, horse, pigeon, ferret, gerbil, hamster, mouse, rat, bird, or human. In some embodiments, the animal is poultry. In some embodiments, the animal is a chicken (e.g. broiler, layer, breeder), turkey, duck, or goose. In some embodiments, the animal is a pig (e.g. nursery pig, grower/finisher pig).

In some embodiments, the nutritional composition is an animal feed composition described herein. In some embodiments, the base nutritional composition is base animal feed described herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawing (also "figure" and "FIG." herein), of which:

DETAILED DESCRIPTION

Figure 1:
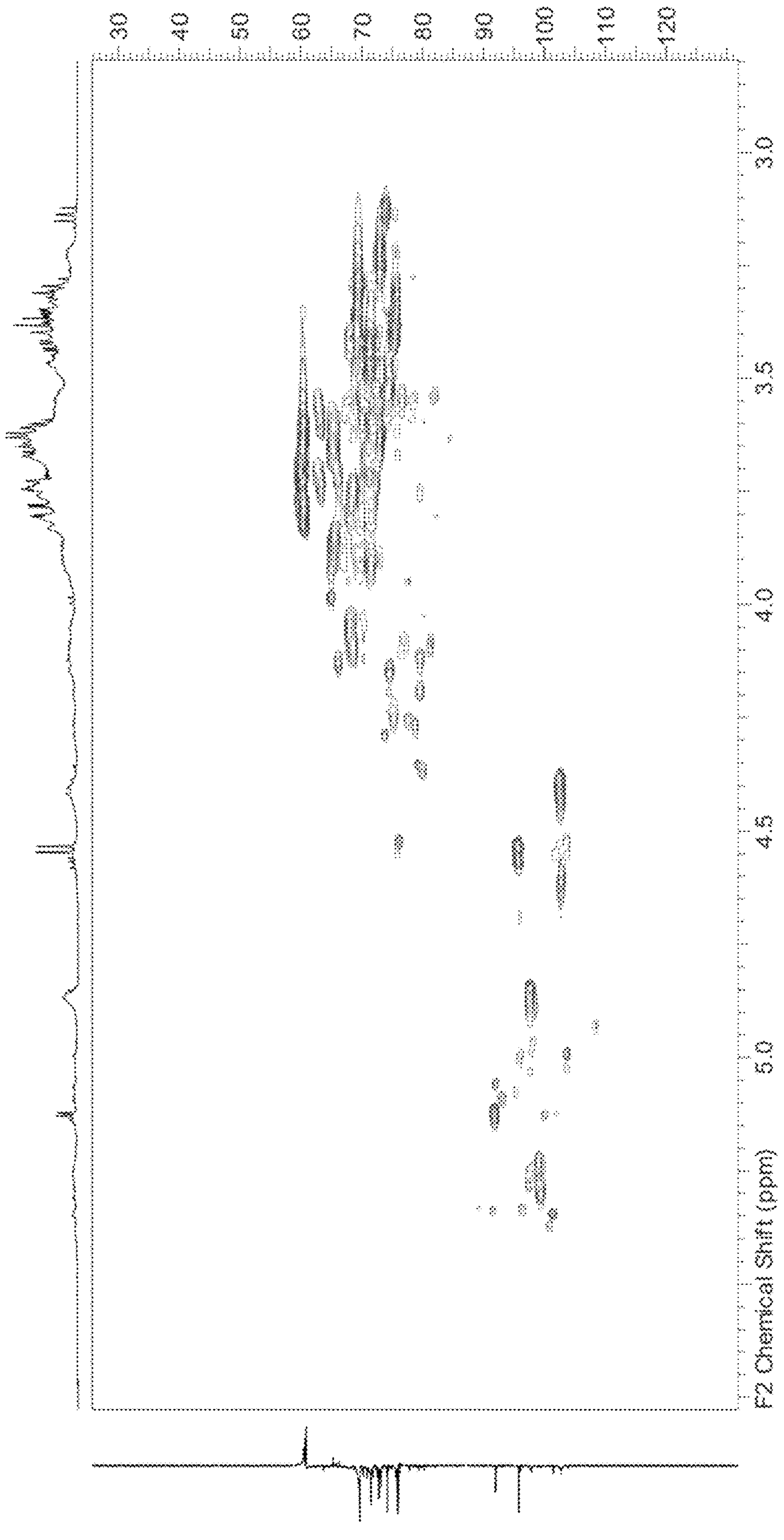
FIG. 1 illustrates part of a $^{1}H$, $^{13}C$-HSQC NMR spectrum of oligosaccharide preparation 9.2.

The following description and examples illustrate embodiments of the present disclosure in detail. It is to be understood that this present disclosure is not limited to the particular embodiments described herein and as such can vary. Those of skill in the art will recognize that there are numerous embodiments and modifications of this present disclosure, which are encompassed within its scope.

All terms are intended to be understood as they would be understood by a person skilled in the art. Unless defined otherwise, all technical and scientific terms used herein have the same meaning as commonly understood by one of ordinary skill in the art to which the disclosure pertains.

The section headings used herein are for organizational purposes only and are not to be construed as limiting the subject matter described.

Although various features of the present disclosure may be described in the context of a single embodiment, the features may also be provided separately or in any suitable combination. Conversely, although the present disclosure may be described herein in the context of separate embodiments for clarity, the present disclosure may also be implemented in a single embodiment.

The following definitions supplement those in the art and are directed to the current application and are not to be imputed to any related or unrelated case, e.g., to any commonly owned patent or application. Although any methods and materials similar or equivalent to those described herein can be used in the practice for testing of the present disclosure, the preferred materials and methods are described herein. Accordingly, the terminology used herein is for the purpose of describing particular embodiments only and is not intended to be limiting.

I. Definitions

The terminology used herein is for the purpose of describing particular cases only and is not intended to be limiting. As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

It is understood that terms such as "comprises," "comprised," "comprising," and the like have the meaning attributed to it in U.S. Patent law; i.e., they mean "includes," "included," "including," and the like and are intended to be inclusive or open ended and does not exclude additional, unrecited elements or method steps; and that terms such as "consisting essentially of" and "consists essentially of" have the meaning ascribed to them in U.S. Patent law; i.e., they allow for elements not explicitly recited, but exclude elements that are found in the prior art or that affect a basic or novel characteristic of the invention.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or B; A or C; B or C; A and B; A and C; B and C; A (alone); B (alone); and C (alone).

When ranges are used herein for physical properties, such as molecular weight, or chemical properties, such as chemical formulae, all combinations and sub-combinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. In some embodiments, the term "about" means within 15%, 10%, 9%, 8%, 7%, 6%, 5%, 4%, 3%, 2%, 1%, 0.5%, 0.1%, or 0.05% of a given value or range.

As used herein the term "administering" includes providing a synthetic oligosaccharide preparation, a nutritional composition, a liquid, or an animal feed composition described herein, to an animal such that the animal can ingest the synthetic oligosaccharide preparation, the nutritional composition, the liquid, or the animal feed composition. In such embodiments, the animal ingests some portion of the synthetic oligosaccharide preparation, the nutritional composition, or the animal feed composition. In some embodiments, the synthetic oligosaccharide preparation, the nutritional composition, the liquid, or the animal feed composition is provided to said animal such that the animal may ingest the synthetic oligosaccharide preparation, the nutritional composition, the liquid, or the animal feed composition at will. In some embodiments, the synthetic oligosaccharide preparation, the nutritional composition, the liquid, or the animal feed composition is administered to said animal as a prescribed diet. In some embodiments, the synthetic oligosaccharide preparation, the nutritional composition, the liquid, or the animal feed composition is administered to said animal via manual feeding, e.g., an oral syringe feeding, a tube feeding, etc. In some embodiments, the synthetic oligosaccharide preparation, the nutritional composition, the liquid, or the animal feed composition is administered to said animal oral, e.g., at will or manually. In some embodiments, the animal ingests some portion of the synthetic oligosaccharide preparation, the nutritional composition, the liquid, or the animal feed composition in every 24-hour period or every other 24-hour period for at least 7 days, 14 days, 21 days, 30 days, 45 days, 60 days, 75 days, 90 days or 120 days. In some embodiments, the oligosaccharide preparation may be dissolved in water or another liquid, and the animal ingests some portion of the oligosaccharide preparation by drinking the liquid. In some embodiments, the oligosaccharide is provided to the animal via its drinking water. In some embodiments, the oligosaccharide preparation, nutritional composition, liquid, or animal feed composition is consumed at will.

As used herein, the term "inclusion level" or "dose" refers to the concentration of an oligosaccharide preparation in a nutritional composition, a liquid, a diet, or an animal feed composition provided to the animal. In some embodiments, the inclusion level is measured as the mass concentration of the oligosaccharide preparation in the final nutritional composition, liquid, diet, or animal feed. For example, the inclusion level may be measured in units of parts per million (ppm) of the oligosaccharide on a dry solids weight basis per the total weight of the final nutritional composition, liquid, diet, or animal feed. In certain embodiments, the dry solids mass of the oligosaccharide preparation is measured as the dry-basis mass of DP1+ species. In other embodiments, the dry solids mass of the oligosaccharide preparation is measured as the dry-basis mass of DP2+ species.

As used herein, the term "specific dose" refers to the quantity of an oligosaccharide preparation consumed by an animal per unit of time and relative to its body mass. In some embodiments, the specific dose may be measured in units of mg of oligosaccharide preparation (on a dry solids-basis) per kg of body weight of the animal per day (i.e., mg/kg/day).

As used herein the term "feed conversion ratio (FCR)," refers to the ratio of feed mass input (for example consumed by the animal) to the animal output, wherein the animal output is the target animal product. For example, the animal output for dairy animals is milk, whereas the animal output for animals raised for meat is body mass.

As used herein, "feed efficiency" refers to the ratio of the animal output to the feed mass input (for example consumed by the animal), wherein the animal output is the target animal product.

As used herein, the term "anhydro-subunit" refers to a product of thermal dehydration of a monosaccharide (or monosaccharide subunit) or a sugar caramelization product. For example, an "anhydro-subunit" can be an anhydro-monosaccharide such as anhydro-glucose. As another example, an "anhydro-subunit" can be linked with one or more regular or anhydro-monosaccharide subunits via glycosidic linkage.

The term "oligosaccharide" refers to a monosaccharide or a compound containing two or more monosaccharide subunits linked by glycosidic bonds. As such, an oligosaccharide includes a regular monosaccharide; an anhydro-monosaccharide; or a compound containing two or more monosaccharide subunits, wherein one or more monosaccharide subunits are optionally, independently replaced by one or more anhydro-subunits. An oligosaccharide can be functionalized. As used herein, the term oligosaccharide encompasses all species of the oligosaccharide, wherein each of the monosaccharide subunit in the oligosaccharide is independently and optionally functionalized and/or replaced with its corresponding anhydro-monosaccharide subunit.

As used herein, the term "oligosaccharide preparation" refers to a preparation that comprises at least one oligosaccharide.

As used herein, the term "gluco-oligosaccharide" refers to a glucose or a compound containing two or more glucose monosaccharide subunits linked by glycosidic bonds. As such, a gluco-oligosaccharide includes a glucose; an anhydro-glucose; or a compound containing two or more glucose monosaccharide subunits linked by glycosidic bonds, wherein one or more of said glucose monosaccharide subunits are each optionally and independently replaced with an anhydro-glucose subunit.

As used herein, the term "galacto-oligosaccharide" refers to a galactose or a compound containing two or more galactose monosaccharide subunits linked by glycosidic bonds. As such, a galacto-oligosaccharide includes a galactose; an anhydro-galactose or a compound containing two or more galactose monosaccharide subunits linked by glycosidic bonds, wherein at least one monosaccharide subunit is optionally replaced with an anhydro-galactose subunit.

As used herein, the term "gluco-galacto-oligosaccharide preparation" refers to a composition that is produced from a complete or incomplete sugar condensation reaction of glucose and galactose. Accordingly, in some embodiments, a gluco-galactose-oligosaccharide preparation comprises gluco-oligosaccharides, galacto-oligosaccharides, compounds containing one or more glucose monosaccharide subunits and one or more galactose monosaccharide subunits linked by glycosidic bonds, or a combination thereof. In some embodiments, a gluco-galactose-oligosaccharide preparation comprises gluco-oligosaccharides and compounds containing one or more glucose monosaccharide subunits and one or more galactose monosaccharide subunits linked by glycosidic bonds. In some embodiments, a gluco-galactose-oligosaccharide preparation comprises galacto-oligosaccharides and compounds containing one or more glucose monosaccharide subunits and one or more galactose monosaccharide subunits linked by glycosidic bonds. In some embodiments, a gluco-galactose-oligosaccharide preparation comprises compounds containing one or more glucose monosaccharide subunits and one or more galactose monosaccharide subunits linked by glycosidic bonds.

As used herein, the term "monosaccharide unit" and "monosaccharide subunit" are used interchangeably. A "monosaccharide subunit" refers to a monosaccharide monomer in an oligosaccharide. For an oligosaccharide having a degree of polymerization of 1, the oligosaccharide can be referred to as a monosaccharide subunit or monosaccharide. For an oligosaccharide having a degree of polymerization of 2 or higher, its monosaccharide subunits are linked via glycosidic bonds.

As used herein, the term "regular monosaccharide" refers to a monosaccharide that does not contain an anhydro-subunit. The term "regular disaccharide" refers to a disaccharide that does not contain an anhydro-subunit. Accordingly, the term "regular subunit" refers to a subunit that is not an anhydro-subunit.

As used herein, the term an "anhydro DPn oligosaccharide," an "anhydro DPn species," or a "DPn anhydro-subunit containing oligosaccharide" refers to an oligosaccharide that has a degree of polymerization of n and comprises one or more anhydro-subunits. As such, an anhydro-glucose is a DP1 anhydro-subunit containing oligosaccharide and a cellotriosan is a DP3 anhydro-subunit containing oligosaccharide.

The term "relative abundance" or "abundance," as used herein, refers to the abundance of a species in terms of how common or rare the species exists. For example, a DP1 fraction comprising 10% anhydro-subunit containing oligosaccharides by relative abundance can refer to a plurality of DP1 oligosaccharides, wherein 10% of the DP1 oligosaccharides are anhydro-monosaccharides. The relative abundance, e.g., for a certain DP fraction of oligosaccharides, can be determined by suitable analytical instrumentations, for example, mass spectrometry and liquid chromatography such as LC-MS/MS, GC-MS, HPLC-MS, and MALDI-MS. In some embodiments, the relative abundance is determined by integrating the area under the peaks of the chromatographs (e.g., LC-MS/MS, GC-MS, and HPLC-MS) that correspond to the fractions of interest. In some embodiments, the relative abundance is determined by the peak intensities (e.g., MALDI-MS). In some embodiments, the relative abundance is determined by a combination of analytical methods such as a weight determination after separation by liquid chromatography.

As used herein, the singular forms "a," "and," and "the" include plural referents unless the context clearly dictates otherwise. Thus, for example, reference to "an agent" includes a plurality of such agents, and reference to "the oligosaccharide" includes reference to one or more oligosaccharides (or to a plurality of oligosaccharides) and equivalents thereof known to those skilled in the art, and so forth.

II. Oligosaccharide Preparation

Disclosed herein are oligosaccharide preparations suitable for use in animal nutritional compositions. In some embodiments, the disclosed oligosaccharide preparation comprises at least n fractions of oligosaccharides each having a distinct degree of polymerization selected from 1 to n (DP1 to DPn fractions), wherein n is an integer greater than or equal to 2. In some embodiments, n is an integer greater than 2. In some embodiments, each of the 1 to n fractions in the oligosaccharide preparation comprises from 1% to 90% anhydro-subunit containing oligosaccharides by relative abundance as measured by mass spectrometry. In some embodiments, the relative abundance of oligosaccharides in each fraction decreases monotonically with its degree of polymerization.

In some embodiments, n is an integer greater than or equal to 3. In some embodiments, n is an integer within a range of 1 to 100, such as 4, 5, 6, 7, 8, 9, 10, 11, 12, 13, 14, 15, 16, 17, 18, 19, 20, 21, 22, 23, 24, 25, 26, 27, 28, 29, 30, 40, or 50. In some embodiments, each of the 1 to n fraction in the oligosaccharide preparation independently comprises from 0.1% to 90% anhydro-subunit containing oligosaccharides by relative abundance as measured by mass spectrometry or by LC-MS/MS or GC-MS. In some embodiments, each of the 1 to n fraction in the oligosaccharide preparation independently comprises from about 0.1% to about 15% anhydro-subunit containing oligosaccharides. In some embodiments, each of the 1 to n fraction in the oligosaccharide preparation independently comprises from about 0.5% to about 15% anhydro-subunit containing oligosaccharides. In some embodiments, the DP1 and DP2 fractions each independently comprises from about 0.1% to about 15% of anhydro-subunit containing oligosaccharides by relative abundance as measured by mass spectrometry such as MALDI-MS or by LC-MS/MS or GC-MS. In some embodiments, the DP1 and DP2 fractions each independently comprises from about 0.5% to about 15% of anhydro-subunit containing oligosaccharides. In some embodiments, the DP1 and DP2 fractions each independently comprises from about 0.1%, 0.2%, 0.3%, 0.4%, 0.5%, 0.8%, 1%, 2% or 3% to about 8%, 9%, 10%, 11%, 12%, 13%, 14%, or 15% of anhydro-subunit containing oligosaccharides by relative abundance as measured by mass spectrometry, LC-MS/MS or GC-MS. In some embodiments, the relative abundance of oligosaccharides in each fraction decreases monotonically with its degree of polymerization.

In some embodiments, the oligosaccharide preparation is a synthetic oligosaccharide preparation. In some embodiments, a synthetic oligosaccharide preparation refers to a plurality of oligosaccharides produced by a process that does not require live organisms. In some embodiments, a synthetic oligosaccharide preparation refers to a plurality of oligosaccharides produced by a process that does not require enzymes. In some embodiments, a synthetic oligosaccharide preparation refers to a plurality of oligosaccharides produced by a chemical process. In certain embodiments, a synthetic oligosaccharide preparation refers to a plurality of oligosaccharides produced by the condensation of sugars.

A. Prebiotic Utility of Oligosaccharides

Disclosed herein are oligosaccharide preparations comprising anhydro-sugar components and/or sugar dehydration product components that exhibit complex functional modulation of a microbial community, such as the animal gut microbiome. The oligosaccharide preparations provide a utility to regulate the utilization of fermentable carbon by microflora and direct metabolic flux to beneficial species, thus providing a microbiome-mediated health or nutritional benefit.

Indigestible carbohydrates can act as prebiotics by providing a fermentable carbon source to a microbial community. For example, diets rich in soluble plant fiber have been identified for their ability to nourish the gut microflora. Additionally, bifidogenic prebiotics support the growth of bifidobacteria (e.g., members of genus *Bifidobacterium*) and lactogenic prebiotics support the growth of *Lactobacillus* species.

Prebiotic fiber may be fermented to beneficial chemical species such as short chain fatty acids (SCFAs). Prebiotic fibers include: resistant starches; cellulose; pectins such as rhamnogalactans, arabinogalactans, arabinans; hemicelluloses such as arabinoxylans, xyloglucans, glucomannans, galactomannans; xylans such as corn cob oligosaccharides; b-glucans such as cereal b-glucans, yeast b-glucans, bacterial b-glucans; polyfructans such as inulin and levan; and gums such as alginate. Inulin is a common bifidogenic prebiotic fiber.

In other cases, prebiotics act by hindering the ability of pathogenic bacteria to engraft and thus infect a host organism via anti-adherence mechanisms such as the competitive binding of cell surface receptor cites. Certain galacto-oligosaccharides provide effective anti-adherence of various enteropathogenic organisms, such as *Escherichia* species.

Prebiotics are typically provided to a host animal by incorporation into the diet, upon which they exhibit a dose-dependent response (at least up to a saturation threshold). For example, providing a higher dose of a bifidogenic prebiotic such as inulin tends to provide a larger increase in the population of *Bifidobacterium* species. Higher doses of inulin correspond to higher production of SCFAs through fermentation. This is because the prebiotic provides a metabolic carbon source and more carbon translates to more fermented product. Similarly, providing a higher dose of an anti-adherence prebiotic provides a likelihood of competitively binding surface receptor sites.

Certain carbohydrate species comprising modified monomeric subunits may affect the manner in which microbial systems utilize other carbohydrates otherwise available to them as a prebiotic source. For example, such carbohydrate species may be a modified carbohydrate species that modulate the microbial starch utilization system (SUS), i.e., proteins responsible for the cell-surface recognition, glycosidic cleavage, and importation of starch metabolites.

Carbohydrate compositions capable of complex modulation of the microbiota of animals have utility as feed additives that improve animal health and nutrition via their impact on the animal microbiome. For example, modulation of butyrate production by the gut microflora confers health benefits to the animal by promoting a healthy gut mucosa, barrier function, and via anti-inflammatory effects. Modulation of propionic acid production affects the metabolic energy extracted from the animal's diet via increased gluconeogenesis. Relevant microbial communities include, for example, ileal, jejunal, and cecal and/or fecal microbiota in poultry, pigs, dogs, cats, horses, or the ruminant microbiota of cattle, cows, sheep, etc. Other microbial communities include the skin microflora, nasal microflora, etc.

Further, disclosed herein are oligosaccharide preparations that are advantageous in that they can be selectively analyzed and quantified in a complex nutritional composition such as complete animal feed due to the presence of anhydro-subunits. It is of commercial utility to assay for the presence and/or concentration of feed additives such as oligosaccharide preparations. Such assay may be performed for the purpose of quality control, to determine whether the additive was blended consistently with the base nutritional composition to provide a final nutritional composition comprising the additive at the intended dose or level of inclusion.

However, the nutritional compositions themselves comprise a large quantity and diversity of carbohydrate structures (e.g., starch, plant fibers and pectins). It is therefore particularly challenging to distinguish small quantities of oligosaccharide-based feed additives from the vast sea of other carbohydrates present as base of the nutritional composition. As such, the herein disclosed oligosaccharide preparation provides a means to distinguish itself from other carbohydrates sources in the nutritional composition through the anhydro-subunits.

B. Degree of Polymerization (DP) Distribution

In some embodiments, the oligosaccharide preparation comprises at least n fractions of oligosaccharides each having a distinct degree of polymerization selected from 1 to n (DP1 to DPn fractions). In some embodiments, the oligosaccharide preparation comprises n fractions of oligosaccharides each having a distinct degree of polymerization selected from 1 to n (DP1 to DPn fractions). For example, in some embodiments, the DP1 fraction comprises one or more monosaccharides and/or one or more anhydro-monosaccharides. As another example, in some embodiments, the DP1 fraction comprises glucose, galactose, fructose, 1,6-anhydro-β-D-glucofuranose, 1,6-anhydro-β-D-glucopyranose, or any combination thereof. As yet another example, in some embodiments, the DP2 fraction comprises one or more regular disaccharides and one or more anhydro-subunit containing disaccharides. In some embodiments, the DP2 fraction comprises lactose.

In some embodiments, n is at least 2, at least 3, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, at least 81, at least 82, at least 83, at least 84, at least 85, at least 86, at least 87, at least 88, at least 89, at least 90, at least 91, at least 92, at least 93, at least 94, at least 95, at least 96, at least 97, at least 98, at least 99, or at least 100. In some embodiments, n is 2, 3, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100. In some embodiments, n is less than 10, less than 11, less than 12, less than 13, less than 14, less than 15, less than 16, less than 17, less than 18, less than 19, less than 20, less than 21, less than 22, less than 23, less than 24, less than 25, less than 26, less than 27, less than 28, less than 29, less than 30, less than 31, less than 32, less than 33, less than 34, less than 35, less than 36, less than 37, less than 38, less than 39, less than 40, less than 41, less than 42, less than 43, less than 44, less than 45, less than 46, less than 47, less than 48, less than 49, less than 50, less than 51, less than 52, less than 53, less than 54, less than 55, less than 56, less than 57, less than 58, less than 59, less than 60, less than 61, less than 62, less than 63, less than 64, less than 65, less than 66, less than 67, less than 68, less than 69, less than 70, less than 71, less than 72, less than 73, less than 74, less than 75, less than 76, less than 77, less than 78, less than 79, less than 80, less than 81, less than 82, less than 83, less than 84, less than 85, less than 86, less than 87, less than 88, less than 89, less than 90, less than 91, less than 92, less than 93, less than 94, less than 95, less than 96, less than 97, less than 98, less than 99, or less than 100. In some embodiments, n is from 2 to 100, from 5 to 90, from 10 to 90, from 10 to 80, from 10 to 70, from 10 to 60, from 10 to 50, from 10 to 40, from 10 to 30, from 15 to 60, from 15 to 50, from 15 to 45, from 15 to 40, from 15 to 35, or from 15 to 30.

Figure 2:
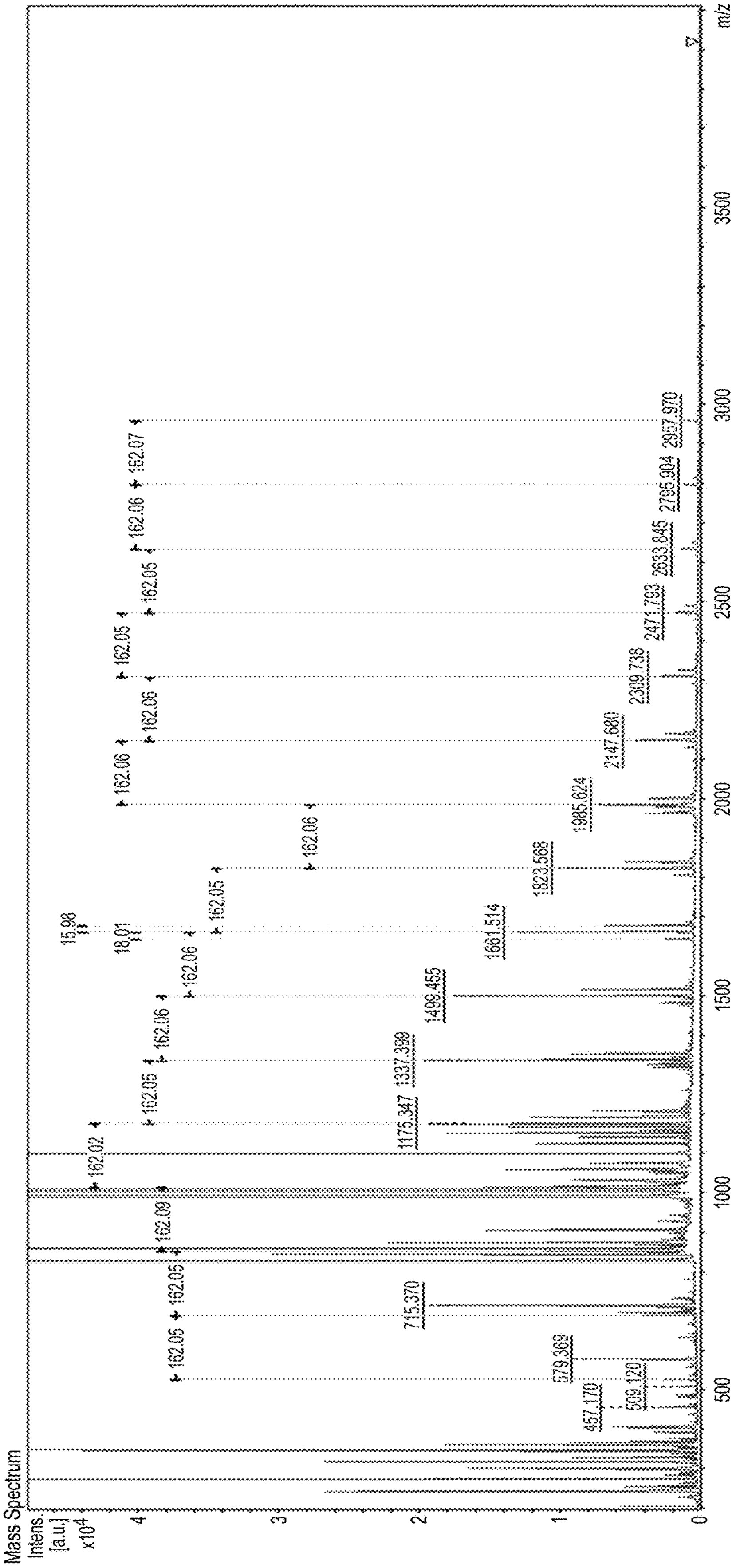
FIG. 2 illustrates a MALDI-MS spectrum of an oligosaccharide preparation from Example 9.7 that demonstrates the presence of anhydro-subunits.

A distribution of the degree of polymerization of the oligosaccharide preparation can be determined by any suitable analytical method and instrumentation, including but not limited to end group method, osmotic pressure (osmometry), ultracentrifugation, viscosity measurements, light scattering method, size exclusion chromatography (SEC), SEC-MALLS, field flow fractionation (FFF), asymmetric flow field flow fractionation (A4F), high-performance liquid chromatography (HPLC), and mass spectrometry (MS). For example, the distribution of the degree of polymerization may be determined and/or detected by mass spectrometry, such as matrix-assisted laser desorption/ionization (MALDI)-MS, liquid chromatography (LC)-MS, or gas chromatography (GC)-MS. For another example, the distribution of the degree of polymerization can be determined and/or detected by SEC, such as gel permeation chromatography (GPC). As yet another example, the distribution of the degree of polymerization can be determined and/or detected by HPLC, FFF, or A4F. In some embodiments, the distribution of the degree of polymerization is determined and/or detected by MALDI-MS. In some embodiments, the distribution of the degree of polymerization is determined and/or detected by GC-MS or LC-MS. In some embodiments, the distribution of the degree of polymerization is determined and/or detected by SEC. In some embodiments, the distribution of the degree of polymerization is determined and/or detected by HPLC. In some embodiments, the distribution of the degree of polymerization is determined and/or detected by a combination of analytical instrumentations such as MALDI-MS and SEC. In some embodiments, the degree of polymerization of the oligosaccharide preparation can be determined based on its molecular weight and molecular weight distribution. For example, FIG. 2 shows a MALDI-MS spectrum that illustrates the degrees of polymerizations of various fractions and the presence of anhydro-subunit containing oligosaccharides (the −18 g/mol MW offset peaks) in all of the observed fractions.

In some embodiments, the relative abundance of oligosaccharides in a majority of the fractions decreases monotonically with its degree of polymerization. In some embodiments, the relative abundance of oligosaccharides of less than 6, less than 5, less than 4, less than 3, or less than 2 fractions of the oligosaccharide preparation do not decrease monotonically with its degree of polymerization.

In some embodiments, the relative abundance of oligosaccharides in at least 5, at least 10, at least 15, at least 20, at least 25, at least 30, at least 35, at least 40, at least 45, or at least 50 DP fractions decreases monotonically with its degree of polymerization. In some embodiments, the relative abundance of oligosaccharides in at least 5, at least 10, at least 15, at least 20, at least 25, at least 30, at least 35, at least 40, at least 45, or at least 50 consecutive DP fractions decreases monotonically with its degree of polymerization. In some embodiments, the relative abundance of oligosaccharides in at least 5, at least 10, at least 20, or at least 30 DP fractions decreases monotonically with its degree of polymerization. In some embodiments, the relative abundance of oligosaccharides in at least 5, at least 10, at least 20, or at least 30 consecutive DP fractions decreases monotonically with its degree of polymerization.

Figure 15:
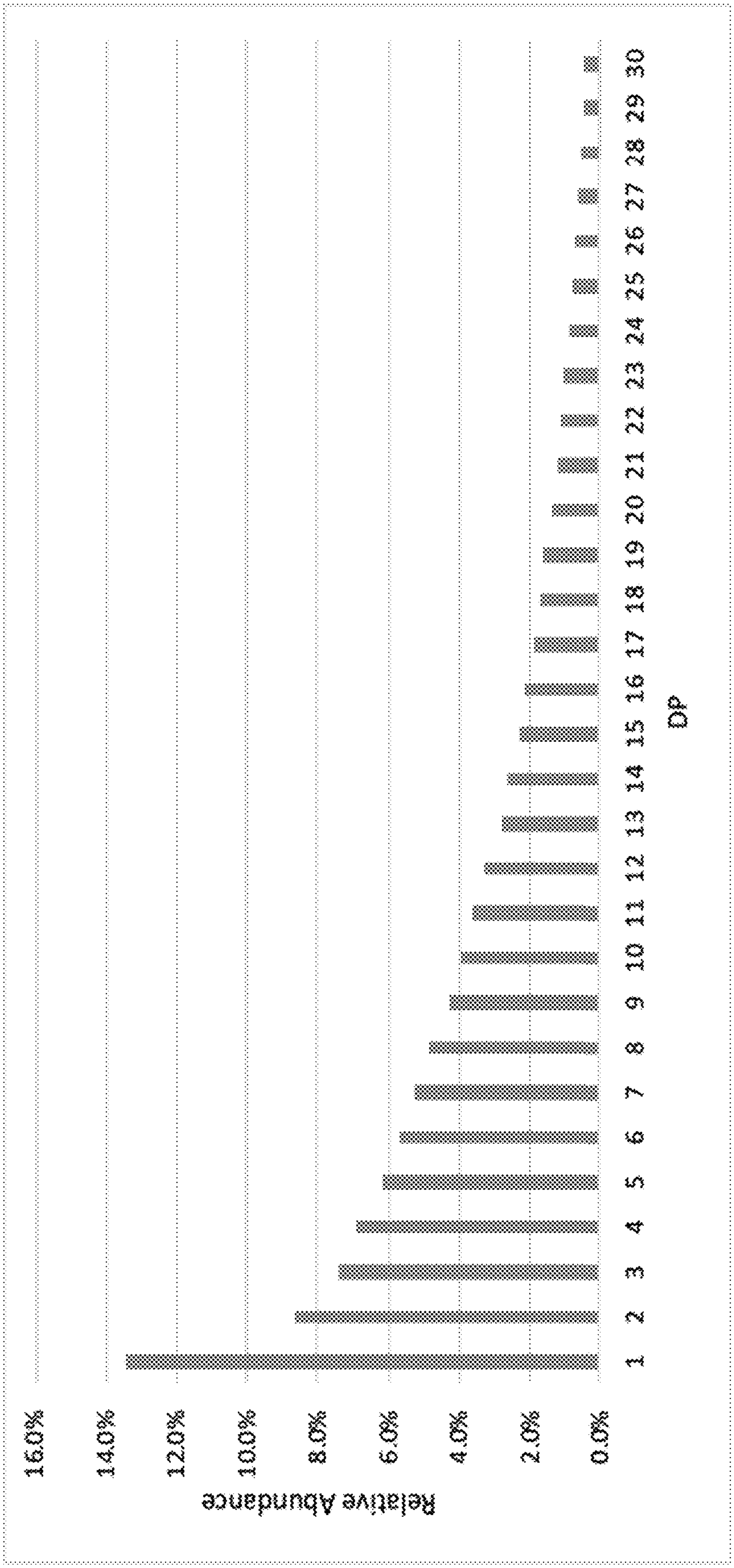
FIG. 15 shows a graph of the relative abundance versus degree of polymerization (DP) of an oligosaccharide of Example 9. The graph shows the oligosaccharide preparation has monotonically decreasing DP distribution.
Figure 16:
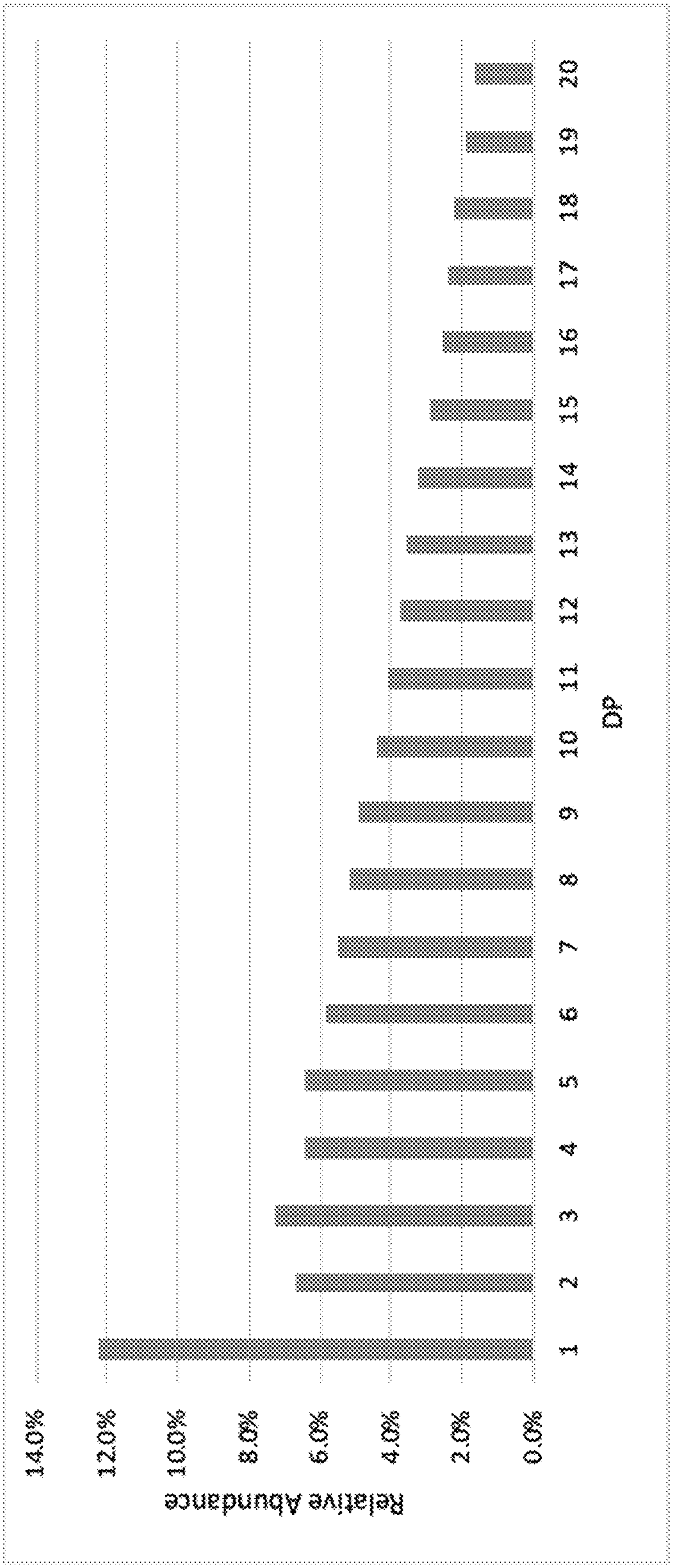
FIG. 16 shows a graph of the relative abundance versus degree of polymerization of an oligosaccharide of Example 9. The graph shows the oligosaccharide preparation has non-monotonically decreasing DP distribution.

In some embodiments, the relative abundance of oligosaccharides in each of the n fractions decreases monotonically with its degree of polymerization. For example, FIG. 15 provides an example of a DP distribution where the relative abundance of oligosaccharides in each of the n fractions decrease monotonically with its DP. For example, in some embodiments, only the relative abundance of oligosaccharides in the DP3 fraction does not decrease monotonically with its degree of polymerization, i.e., the relative abundance of oligosaccharides in the DP3 fraction is lower than the relative abundance of oligosaccharides in the DP4 fraction. In some embodiments, the relative abundance of oligosaccharides in the DP2 fraction is lower than the relative abundance of oligosaccharides in the DP3 fraction. For example, FIG. 16 illustrates a degree of polymerization distribution wherein the relative abundance of oligosaccharides in the DP2 fraction does not decrease monotonically with its degree of polymerization.

In some embodiments, a herein described oligosaccharide preparation has a DP1 fraction content of from about 1% to about 50%, from about 1% to about 40%, from about 1% to about 35%, from about 1% to about 30%, from about 1% to about 25%, from about 1% to about 20%, from about 1% to about 15%, from about 5% to about 50%, from about 5% to about 40%, from about 5% to about 35%, from about 5% to about 30%, from about 5% to about 25%, from about 5% to about 20%, from about 5% to about 15%, from about 10% to about 50%, from about 10% to about 40%, from about 10% to about 35%, from about 10% to about 30%, from about 10% to about 25%, from about 10% to about 20%, or from about 10% to about 15% by weight or by relative abundance. In some embodiments, the oligosaccharide preparation has a DP1 fraction content of from about 10% to about 35%, from about 10% to about 20%, or from about 10% to about 15% by weight or by relative abundance. In some embodiments, the content of the DP1 fraction is determined by MALDI-MS. In some embodiments, the content of the DP1 fraction is determined by HPLC. In some embodiments, the content of the DP1 fraction is determined by LC-MS/MS or GC-MS.

In some embodiments, a herein described oligosaccharide preparation has a DP2 fraction content of from about 1% to about 35%, from about 1% to about 30%, from about 1% to about 25%, from about 1% to about 20%, from about 1% to about 15%, from about 1% to about 10%, from about 5% to about 30%, from about 5% to about 25%, from about 5% to about 20%, from about 5% to about 15%, or from about 5% to about 10% by weight or by relative abundance. In some embodiments, the oligosaccharide preparation has a DP2 fraction content of from about 5% to about 25%, from about 5% to about 20%, from about 5% to about 15%, or from about 5% to about 10% by weight or by relative abundance. In some embodiments, the content of the DP2 fraction is determined by MALDI-MS. In some embodiments, the content of the DP2 fraction is determined by HPLC. In some embodiments, the content of the DP2 fraction is determined by LC-MS/MS or GC-MS.

In some embodiments, a herein described oligosaccharide preparation has a DP3 fraction content of from about 1% to about 30%, from about 1% to about 25%, from about 1% to about 20%, from about 1% to about 15%, from about 1% to about 10%, from about 5% to about 30%, from about 5% to about 25%, from about 5% to about 20%, from about 5% to about 15%, or from about 5% to about 10% by weight or by relative abundance. In some embodiments, the oligosaccharide preparation has a DP3 fraction content of from about 1% to about 15%, from about 1% to about 10%, from about 5% to about 15%, or from about 5% to about 10% by weight or by relative abundance. In some embodiments, the content of the DP3 fraction is determined by MALDI-MS. In some embodiments, the content of the DP3 fraction is determined by HPLC. In some embodiments, the content of the DP3 fraction is determined by LC-MS/MS or GC-MS.

In some embodiments, a herein described oligosaccharide preparation has a DP4 fraction content of from about 0.1% to about 20%, from about 0.1% to about 15%, from about 0.1% to about 10%, from about 0.1% to about 5%, from about 1% to about 20%, from about 1% to about 15%, from about 1% to about 10%, or from about 1% to about 5% by weight or by relative abundance. In some embodiments, the oligosaccharide preparation has a DP4 fraction content of from about 1% to about 15%, from about 1% to about 10%, or from about 1% to about 5% by weight or by relative abundance. In some embodiments, a herein described oligosaccharide preparation has a DP5 fraction content of from about 0.1% to about 15%, from about 0.1% to about 10%, from about 0.1% to about 5%, from about 1% to about 15%, from about 1% to about 10%, or from about 1% to about 5% by weight or by relative abundance. In some embodiments, the oligosaccharide preparation has a DP5 fraction content of from about 1% to about 10% or from about 1% to about 5% by weight or by relative abundance. In some embodiments, the content of the DP4 and/or the DP5 fraction is determined by MALDI-MS. In some embodiments, the content of the DP4 and/or the DP5 fraction is determined by HPLC. In some embodiments, the content of the DP4 and/or the DP5 fraction is determined by LC-MS/MS or GC-MS.

In some embodiments, the ratio of DP2 fraction to DP1 fraction in the oligosaccharide preparation is from about 0.01 to about 0.8, from about 0.02 to about 0.7, from about 0.02 to about 0.6, from about 0.02 to about 0.5, from about 0.02 to about 0.4, from about 0.02 to about 0.3, from about 0.02 to about 0.2, from about 0.1 to about 0.6, from about 0.1 to about 0.5, from about 0.1 to about 0.4, or from about 0.1 to about 0.3 by their weight or relative abundance. In some embodiments, the ratio of DP2 fraction to DP1 fraction in the oligosaccharide preparation is from about 0.02 to about 0.4 by their weight or relative abundance.

In some embodiments, the ratio of DP3 fraction to DP2 fraction in the oligosaccharide preparation is from about 0.01 to about 0.7, from about 0.01 to about 0.6, from about 0.01 to about 0.5, from about 0.01 to about 0.4, from about 0.01 to about 0.3, or from about 0.01 to about 0.2 by their weight or relative abundance. In some embodiments, the ratio of DP3 fraction to DP2 fraction in the oligosaccharide preparation is from about 0.01 to about 0.3 by their weight or relative abundance.

In some embodiments, the aggregate content of DP1 and DP2 fractions in the oligosaccharide preparation is less than 70%, less than 60%, less than 50%, less than 40%, less than 30%, less than 20%, or less than 10% by weight or by relative abundance. In some embodiments, the aggregate content of DP1 and DP2 fractions in the oligosaccharide preparation is less than 50%, less than 30%, or less than 10% by weight or by relative abundance.

In some embodiments, an oligosaccharide preparation described herein has a mean DP value within a range of 2 to 10. In some embodiments, the oligosaccharide preparation has a mean DP value of from about 2 to about 8, from about 2 to about 5, or from about 2 to about 4. In some embodiments, the oligosaccharide preparation has a mean DP value of about 3.5. The mean DP value can be determined by SEC or by elemental analysis.

C. Anhydro-Subunit Level

In some embodiments, each of the n fractions of oligosaccharides independently comprises an anhydro-subunit level. For instance, in some embodiments, the DP1 fraction comprises 10% anhydro-subunit containing oligosaccharides by relative abundance, and the DP2 fraction comprises 15% anhydro-subunit containing oligosaccharides by relative abundance. For another example, in some embodiments, DP1, DP2, and DP3 fraction each comprises 5%, 10%, and 2% anhydro-subunit containing oligosaccharides by relative abundance, respectively. In other embodiments, two or more fractions of oligosaccharides may comprise similar level of anhydro-subunit containing oligosaccharides. For example, in some embodiments, the DP1 and DP3 fraction each comprises about 5% anhydro-subunit containing oligosaccharides by relative abundance.

In some embodiments, each of the 1 to n fractions in a herein described oligosaccharide preparation independently comprises from about 0.1% to 15% of anhydro-subunit containing oligosaccharides by relative abundance as measured by mass spectrometry, LC-MS/MS or GC-MS. In some embodiments, each of the 1 to n fractions in the oligosaccharide preparation independently comprises from about 0.5% to 15% of anhydro-subunit containing oligosaccharides by relative abundance as measured by mass spectrometry, LC-MS/MS or GC-MS. In some embodiments, LC-MS/MS is used to determine the relative abundance for oligosaccharides in the DP1, DP2, and/or DP3 fractions. In some embodiments, GC-MS is used to determine the relative abundance for oligosaccharides in the DP1, DP2, and/or DP3 fractions. In some embodiments, MALDI-MS is used to determine the relative abundance for oligosaccharides in the DP4 fraction or in a higher DP fraction. In some embodiments, the relative abundance of a certain fraction is determined by integrating the area under the peaks of the LC-MS/MS chromatogram that are designated as corresponding to that fraction. In some embodiments, the relative abundance of a certain fraction is determined by integrating the area under the peaks of the GC-MS chromatogram that are designated as corresponding to that fraction.

The level of anhydro-subunits can be determined by any suitable analytical methods, such as nuclear magnetic resonance (NMR) spectroscopy, mass spectrometry, HPLC, FFF, A4F, or any combination thereof. In some embodiments, the level of anhydro-subunits is determined, at least in part, by mass spectrometry such as MALDI-MS. In some embodiments, the level of anhydro-subunits is determined, at least in part, by NMR. In some embodiments, the level of anhydro-subunits containing oligosaccharides is determined, at least in part, by HPLC. In some embodiments, the level of anhydro-subunits containing oligosaccharides is determined by MALDI-MS, as illustrated by the −18 g/mol MW offset peaks in FIG. 2. In some embodiments, the presence and the type of species of anhydro-subunits can be determined and/or detected by NMR, as illustrated by Example 11, FIG. 3, and FIG. 4. In some embodiments, the relative abundance of anhydro-subunit containing oligosaccharides is determined by MALDI-MS. In some embodiments, the relative abundance of anhydro-subunit containing oligosaccharides is determined by LC-MS/MS, as illustrated in FIGS. 26A-26C, 27A-27C, 28A-28C and 29A-29C. In some embodiments, the relative abundance of anhydro-subunit containing oligosaccharides is determined by GC-MS, as illustrated in FIGS. 30A-30B, 31A-31B, 32A-32B and 33A-33B.

In some embodiments, at least one fraction of a herein described oligosaccharide preparation comprises less than 80%, less than 70%, less than 60%, less than 50%, less than 40%, less than 30%, less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1% of anhydro-subunit containing oligosaccharides by relative abundance. In some embodiments, at least one fraction of a herein described oligosaccharide preparation comprises less than 10%, less than 9%, less than 8%, less than 7%, less than 6%, less than 5%, less than 4%, less than 3%, or less than 2% of anhydro-subunit containing oligosaccharides by relative abundance. In other embodiments, at least one fraction of a herein described oligosaccharide preparation comprises greater than 0.5%, greater than 0.8%, greater than 1%, greater than 2%, greater than 3%, greater than 4%, greater than 5%, greater than 6%, greater than 7%, greater than 8%, greater than 9%, greater than 10%, greater than 11%, greater than 12%, greater than 13%, greater than 14%, greater than 15%, greater than 16%, greater than 17%, greater than 18%, greater than 19%, greater than 20%, greater than 30%, greater than 40%, greater than 50%, greater than 60%, greater than 70%, or greater than 80% of anhydro-subunit containing oligosaccharides by relative abundance. In other embodiments, at least one fraction of a herein described oligosaccharide preparation comprises greater than 20%, greater than 21%, greater than 22%, greater than 23%, greater than 24%, greater than 25%, greater than 26%, greater than 27%, greater than 28%, greater than 29%, or greater than 30% of anhydro-subunit containing oligosaccharides by relative abundance. In some embodiments, at least one fraction (such as DP1, DP2, and/or DP3) of the oligosaccharide preparation comprises about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, or about 30% of anhydro-subunit containing oligosaccharides by relative abundance. In some embodiments, at least one fraction (such as DP1, DP2, and/or DP3) of the oligosaccharide preparation comprises about 0.1%, about 0.2%, about 0.3%, about 0.4%, about 0.5%, about 0.6%, about 0.7%, about 0.8%, about 0.9%, about 1%, about 1.5%, about 2%, about 3%, about 4%, about 5%, about 6%, about 7%, about 8%, about 9%, or about 10% of anhydro-subunit containing oligosaccharides by relative abundance. In some embodiments, at least one fraction (such as DP1, DP2, and/or DP3) of the oligosaccharide preparation comprises from about 0.1% to about 90%, from about 0.5% to about 90%, from about 0.5% to about 80%, from about 0.5% to about 70%, from about 0.5% to about 60%, from about 0.5% to about 50%, from about 0.5% to about 40%, from about 0.5% to about 30%, from about 0.5% to about 20%, from about 0.5% to about 10%, from about 0.5% to about 9%, from about 0.5% to about 8%, from about 0.5% to about 7%, from about 0.5% to about 6%, from about 0.5% to about 5%, from about 0.5% to about 4%, from about 0.5% to about 3%, from about 0.5% to about 2%, from about 1% to about 10%, from about 2% to about 9%, from about 2% to about 8%, from about 2% to about 7%, from about 2% to about 6%, from about 2% to about 5%, from about 2% to about 4%, from about 2% to about 3%, or from about 5% to about 10% of anhydro-subunit containing oligosaccharides by relative abundance. In some embodiments, the DP1 and DP2 fractions of the oligosaccharide preparation each independently comprises anhydro-subunit containing oligosaccharides within a range of from about 0.1%, 0.5%, 0.6%, 0.7%, 0.8%, 0.9%, 1%, 1.1%, 1.2%, 1.3%, 1.4%, or 1.5% to about 8%, 9%, 10%, 11%, 12%, or 15% by relative abundance as measured by mass spectrometry, LC-MS/MS, or GC-MS. In some embodiments, the DP1 and DP2 fractions each independently comprises from about 0.5% to about 15% of anhydro-subunit containing oligosaccharides by relative abundance as measured by mass spectrometry or by LC-MS/MS or GC-MS.

In some embodiments, each fraction of a herein described oligosaccharide preparation comprises less than 80%, less than 70%, less than 60%, less than 50%, less than 40%, less than 30%, less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, or less than 2% of anhydro-subunit containing oligosaccharides by relative abundance. In some embodiments, each fraction of a herein described oligosaccharide preparation comprises less than 10%, 9%, 8%, 7%, 6%, 5%, 4%, 3%, or 2% anhydro-subunit containing oligosaccharides by relative abundance. In other embodiments, each fraction of a herein described oligosaccharide preparation comprises greater than 2%, 3%, 4%, 5%, 6%, 7%, 8%, 9%, 10%, 11%, 12%, 13%, 14%, 15%, 16%, 17%, 18%, 19%, 20%, 30%, 40%, 50%, 60%, 70%, or 80% of anhydro-subunit containing oligosaccharides by relative abundance. In other embodiments, each fraction of a herein described oligosaccharide preparation comprises greater than 20%, 21%, 22%, 23%, 24%, 25%, 26%, 27%, 28%, 29%, or 30% anhydro-subunit containing oligosaccharides by relative abundance. In some embodiments, each fraction of a herein described oligosaccharide preparation comprises about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, or about 30% of anhydro-subunit containing oligosaccharides by relative abundance. In some embodiments, each fraction of a herein described oligosaccharide preparation comprises about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, or about 10% of anhydro-subunit containing oligosaccharides by relative abundance. In some embodiments, each fraction of a herein described oligosaccharide preparation comprises from about 0.1% to about 90%, from about 0.1% to about 15%, from about 0.5% to about 90%, from about 0.5% to about 80%, from about 0.5% to about 70%, from about 0.5% to about 60%, from about 0.5% to about 50%, from about 0.5% to about 40%, from about 0.5% to about 30%, from about 0.5% to about 20%, from about 0.5% to about 10%, from about 0.5% to about 9%, from about 0.5% to about 8%, from about 0.5% to about 7%, from about 0.5% to about 6%, from about 0.5% to about 5%, from about 0.5% to about 4%, from about 0.5% to about 3%, from about 0.5% to about 2%, from about 2% to about 9%, from about 2% to about 8%, from about 2% to about 7%, from about 2% to about 6%, from about 2% to about 5%, from about 2% to about 4%, from about 2% to about 3%, or from about 5% to about 10% of anhydro-subunit containing oligosaccharides by relative abundance.

In some embodiments, a herein described oligosaccharide preparation comprises less than 80%, less than 70%, less than 60%, less than 50%, less than 40%, less than 30%, less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1% of anhydro-subunit containing oligosaccharides by relative abundance. In some embodiments, the oligosaccharide preparation comprises less than 10%, 9%, 8%, 7%, 6%, 5%, 4%, 3%, or 2% anhydro-subunit containing oligosaccharides by relative abundance. In other embodiments, the oligosaccharide preparation comprises greater than 0.5%, greater than 0.8%, greater than 1%, greater than 2%, greater than 3%, greater than 4%, greater than 5%, greater than 6%, greater than 7%, greater than 8%, greater than 9%, greater than 10%, greater than 11%, greater than 12%, greater than 13%, greater than 14%, greater than 15%, greater than 16%, greater than 17%, greater than 18%, greater than 19%, greater than 20%, greater than 30%, greater than 40%, greater than 50%, greater than 60%, greater than 70%, or greater than 80% anhydro-subunit containing oligosaccharides by relative abundance. In other embodiments, the oligosaccharide preparation comprises greater than 20%, 21%, 22%, 23%, 24%, 25%, 26%, 27%, 28%, 29%, or 30% anhydro-subunit containing oligosaccharides by relative abundance. In some embodiments, the oligosaccharide preparation comprises about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, or about 30% of anhydro-subunit containing oligosaccharides by relative abundance. In some embodiments, the oligosaccharide preparation comprises about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, or about 10% of anhydro-subunit containing oligosaccharides by relative abundance. In some embodiments, the oligosaccharide preparation comprises from about 0.1% to about 90%, from about 0.1% to about 15%, from about 0.5% to about 90%, from about 0.5% to about 80%, from about 0.5% to about 70%, from about 0.5% to about 60%, from about 0.5% to about 50%, from about 0.5% to about 40%, from about 0.5% to about 30%, from about 0.5% to about 20%, from about 0.5% to about 10%, from about 0.5% to about 9%, from about 0.5% to about 8%, from about 0.5% to about 7%, from about 0.5% to about 6%, from about 0.5% to about 5%, from about 0.5% to about 4%, from about 0.5% to about 3%, from about 0.5% to about 2%, from about 2% to about 9%, from about 2% to about 8%, from about 2% to about 7%, from about 2% to about 6%, from about 2% to about 5%, from about 2% to about 4%, from about 2% to about 3%, or from about 5% to about 10% of anhydro-subunit containing oligosaccharides by relative abundance.

In some embodiments, the DP1 fraction of a herein described oligosaccharide preparation comprises less than 30%, less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1% of anhydro-subunit containing oligosaccharides by relative abundance. In some embodiments, the DP1 fraction of a herein described oligosaccharide preparation comprises greater than 0.1%, greater than 0.5%, greater than 0.8%, greater than 1%, greater than 1.5%, greater than 2%, greater than 3%, greater than 4%, greater than 5%, greater than 6%, greater than 7%, greater than 8%, greater than 9%, greater than 10%, greater than 11%, greater than 12%, greater than 13%, greater than 14%, or greater than 15% of anhydro-subunit containing oligosaccharides by relative abundance. In some embodiments, the DP1 fraction of a herein described oligosaccharide preparation comprises about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% of anhydro-subunit containing oligosaccharides by relative abundance. In some embodiments, the DP1 fraction of a herein described oligosaccharide preparation comprises from about 0.1% to about 15%, from about 0.1% to about 20%, from about 0.5% to about 20%, from 0.5% to about 10%, from about 0.5% to about 15%, from about 1% to about 20%, from about 1% to about 15%, from about 1% to about 10%, from about 2% to about 14%, from about 3% to about 13%, from about 4% to about 12%, from about 5% to about 11%, from about 5% to about 10%, from about 6% to about 9%, or from about 7% to about 8% of anhydro-subunit containing oligosaccharides by relative abundance, or any ranges therebetween. In some embodiments, the DP1 fraction of a herein described oligosaccharide preparation comprises from about 0.5% to about 10% of anhydro-subunit containing oligosaccharides by relative abundance. In some embodiments, the relative abundance of anhydro-subunit containing oligosaccharides is determined by mass spectrometry such as MALDI-MS. In some embodiments, the relative abundance of anhydro-subunit containing oligosaccharides is determined by LC-MS/MS. In some embodiments, the relative abundance of anhydro-subunit containing oligosaccharides is determined by GC-MS.

In some embodiments, the DP2 fraction of a herein described oligosaccharide preparation comprises less than 30%, less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1% of anhydro-subunit containing oligosaccharides by relative abundance. In some embodiments, the DP2 fraction of a herein described oligosaccharide preparation comprises greater than 0.1%, greater than 0.5%, greater than 0.8%, greater than 1%, greater than 1.5%, greater than 2%, greater than 3%, greater than 4%, greater than 5%, greater than 6%, greater than 7%, greater than 8%, greater than 9%, greater than 10%, greater than 11%, greater than 12%, greater than 13%, greater than 14%, or greater than 15% of anhydro-subunit containing oligosaccharides by relative abundance. In some embodiments, the DP2 fraction of a herein described oligosaccharide preparation comprises about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% of anhydro-subunit containing oligosaccharides by relative abundance. In some embodiments, the DP2 fraction of a herein described oligosaccharide preparation comprises from about 0.1% to about 15%, from about 0.1% to about 20%, from about 0.5% to about 20%, from 0.5% to about 10%, from about 0.5% to about 15%, from about 1% to about 20%, from about 1% to about 15%, from about 1% to about 10%, from about 2% to about 14%, from about 3% to about 13%, from about 4% to about 12%, from about 5% to about 11%, from about 0.5% to about 10%, from about 6% to about 9%, or from about 7% to about 8% of anhydro-subunit containing oligosaccharides by relative abundance, or any ranges therebetween. In some embodiments, the DP2 fraction of a herein described oligosaccharide preparation comprises from about 5% to about 10% of anhydro-subunit containing oligosaccharides by relative abundance. In some embodiments, the relative abundance of anhydro-subunit containing oligosaccharides is determined by mass spectrometry such as MALDI-MS. In some embodiments, the relative abundance of anhydro-subunit containing oligosaccharides is determined by LC-MS/MS. In some embodiments, the relative abundance of anhydro-subunit containing oligosaccharides is determined by GC-MS.

In some embodiments, the DP3 fraction of a herein described oligosaccharide preparation comprises less than 30%, less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1% of anhydro-subunit containing oligosaccharides by relative abundance. In some embodiments, the DP3 fraction of a herein described oligosaccharide preparation comprises greater than 0.1%, greater than 0.5%, greater than 0.8%, greater than 1%, greater than 1.5%, greater than 2%, greater than 3%, greater than 4%, greater than 5%, greater than 6%, greater than 7%, greater than 8%, greater than 9%, greater than 10%, greater than 11%, greater than 12%, greater than 13%, greater than 14%, or greater than 15% of anhydro-subunit containing oligosaccharides by relative abundance. In some embodiments, the DP3 fraction of a herein described oligosaccharide preparation comprises about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% of anhydro-subunit containing oligosaccharides by relative abundance. In some embodiments, the DP3 fraction of a herein described oligosaccharide preparation comprises from about 0.1% to about 15%, from about 0.1% to about 20%, from about 0.5% to about 20%, from 0.5% to about 10%, from about 0.5% to about 15%, from about 1% to about 20%, from about 1% to about 15%, from about 1% to about 10%, from about 2% to about 14%, from about 3% to about 13%, from about 4% to about 12%, from about 5% to about 11%, from about 5% to about 10%, from about 6% to about 9%, or from about 7% to about 8% of anhydro-subunit containing oligosaccharides by relative abundance, or any ranges therebetween. In some embodiments, the DP3 fraction of a herein described oligosaccharide preparation comprises from about 0.5% to about 10% of anhydro-subunit containing oligosaccharides by relative abundance. In some embodiments, the relative abundance of anhydro-subunit containing oligosaccharides is determined by mass spectrometry such as MALDI-MS. In some embodiments, the relative abundance of anhydro-subunit containing oligosaccharides is determined by LC-MS/MS. In some embodiments, the relative abundance of anhydro-subunit containing oligosaccharides is determined by GC-MS.

In some embodiments, an anhydro-subunit containing oligosaccharide comprises one or more anhydro-subunits. For instance, a DP1 anhydro-subunit containing oligosaccharide comprises one anhydro-subunit. In some embodiments, a DPn anhydro-subunit containing oligosaccharide may comprise from 1 to n anhydro-subunits. For example, in some embodiments, a DP2 anhydro-subunit containing oligosaccharide comprises one or two anhydro-subunits. In some embodiments, each oligosaccharide in the oligosaccharide preparation independently comprises zero, one, or two anhydro-subunits. In some embodiments, more than 99%, 95%, 90%, 85%, 80%, 75%, 70%, 65%, 60%, 55%, 50%, 45%, 40%, 35%, or 30% of the anhydro-subunit containing oligosaccharides have only one anhydro-subunit. In some embodiments, more than 99%, 95%, 90%, 85%, or 80% of the anhydro-subunit containing oligosaccharides have only one anhydro-subunit.

In some embodiments, one or more oligosaccharides in the oligosaccharide preparation or in each fraction of the oligosaccharide preparation comprise 1, 2, 3, 4, 5, 6, 7, 8, 9, or 10 anhydro-subunits each linked via a glycosidic bond, wherein the glycosidic bonds linking each anhydro-subunit are independently chosen. In some embodiments, one or more oligosaccharides in the oligosaccharide preparation or in each fraction of the oligosaccharide preparation comprise 1, 2, or 3 anhydro-subunits each linked via a glycosidic bond, wherein the glycosidic bond linking each anhydro-subunit are independently chosen. In some embodiments, greater than 50%, 60%, 70%, 80%, 90%, or 99% of oligosaccharides in the oligosaccharide preparation or in each fraction comprise 1, 2, or 3 anhydro-subunits each linked via a glycosidic bond, wherein the glycosidic bond linking each anhydro-subunit are independently chosen. In some embodiments, one or more oligosaccharides in the oligosaccharide preparation or in each fraction comprise 1 anhydro-subunit linked via a glycosidic bond. In some embodiments, greater than 50%, greater than 60%, greater than 70%, greater than 80%, greater than 90%, or greater than 99% of oligosaccharides in the oligosaccharide preparation or in each fraction comprise 1 anhydro-subunit linked via a glycosidic bond.

D. Anhydro-Subunit Species

Figure 23:
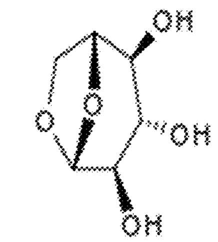
FIG. 23 illustrates two DP1 and one DP2 anhydro-subunit containing oligosaccharides.
Figure 23:
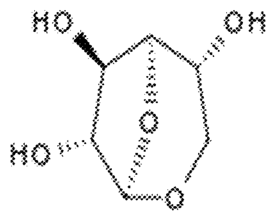
Figure 23:
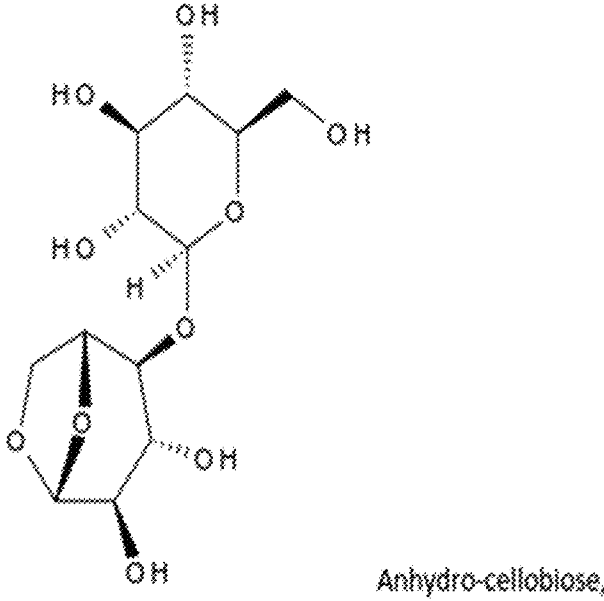
Figure 24:
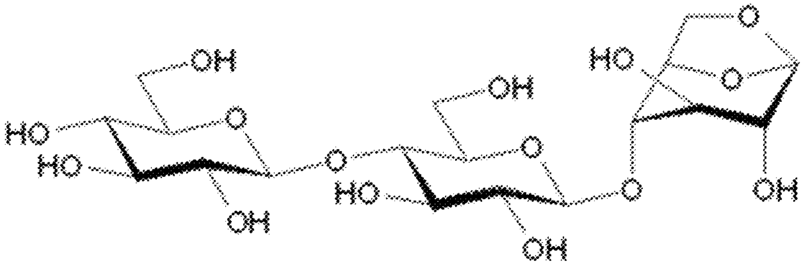
FIG. 24 illustrates an anhydro-subunit containing oligosaccharide (cellotriosan).
Figure 35:
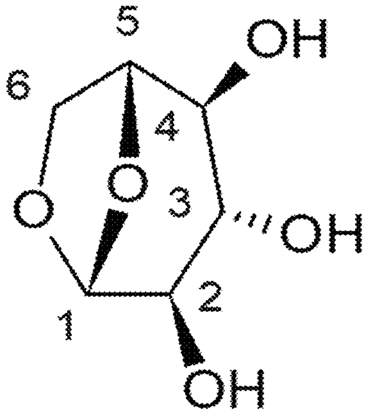
FIG. 35 illustrates the NMR assignments of 1,6-anhydro-beta-D-glucofuranose and 1,6-anhydro-beta-D-glucopyranose.
Figure 35:
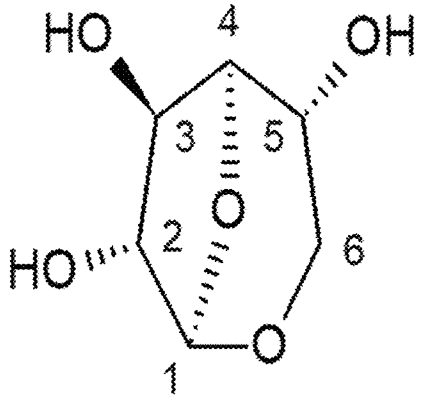

In some embodiments, the oligosaccharide preparation comprises different species of anhydro-subunits. In some embodiments, exemplary anhydro-subunit containing oligosaccharides are illustrated in FIG. 35, FIG. 23, and FIG. 24. In some embodiments, the oligosaccharide preparation comprises one or more anhydro-subunits that are products of thermal dehydration of monosaccharides, i.e., anhydro-monosaccharide subunits. In some embodiments, the oligosaccharide preparation comprises one or more anhydro-subunits that are products of reversible thermal dehydration of monosaccharides.

It is to be understood that an anhydro-monosaccharide (or an anhydro-monosaccharide subunit) refers to one or more species of the thermal dehydration products of the monosaccharide. For example, in some embodiments, an anhydro-glucose refers to 1,6-anhydro-β-D-glucopyranose (levoglucosan) or 1,6-anhydro-β-D-glucofuranose. In some embodiments, a plurality of anhydro-glucose refers to a plurality of 1,6-anhydro-β-D-glucopyranose (levoglucosan), a plurality of 1,6-anhydro-β-D-glucofuranose, a plurality of other thermal dehydration products of glucose, or any combination thereof. Similarly, in some embodiments, a plurality of anhydro-galactose refers to a plurality of any thermal dehydration products of galactose, or any combination thereof.

In some embodiments, an oligosaccharide preparation as described herein comprises one or more anhydro-glucose, anhydro-galactose, anhydro-mannose, anhydro-allose, anhydro-altrose, anhydro-gulose, anhydro-indose, anhydro-talose, anhydro-fructose, anhydro-ribose, anhydro-arabinose, anhydro-rhamnose, anhydro-lyxose, anhydro-xylose, or any combination of these subunits.

In some embodiments, the oligosaccharide preparation comprises one or more anhydro-glucose, anhydro-galactose, anhydro-mannose, or anhydro-fructose subunits. In some embodiments, an oligosaccharide preparation as described herein comprises one or more of: 1,6-anhydro-3-O-β-D-glucopyranosyl-β-D-glucopyranose, 1,6-anhydro-3-O-α-D-glucopyranosyl-β-D-glucopyranose, 1,6-anhydro-2-O-β-D-glucopyranosyl-β-D-glucopyranose, 1,6-anhydro-2-O-α-D-glucopyranosyl-β-D-glucopyranose, 1,6-anhydro-β-D-cellobiose (cellobiosan), 1,6-anhydro-β-D-cellotriose (cellotriosan), 1,6-anhydro-β-D-cellotetraose (cellotetraosan), 1,6-anhydro-β-D-cellopentaose (cellopentaosan), and 1,6-anhydro-β-D-maltose (maltosan).

In some embodiments, the oligosaccharide preparation comprises one or more 1,6-anhydro-β-D-glucofuranose subunits. In some embodiments, the oligosaccharide preparation comprises one or more 1,6-anhydro-β-D-glucopyranose (levoglucosan) subunits. For example, FIG. 35 illustrates two DP1 anhydro-subunit containing oligosaccharides (levoglucosan and 1,6-anhydro-β-D-glucofuranose) and a DP2 anhydro-subunit containing oligosaccharide (anhydro-cellobiose).

The presence and the level of a species of anhydro-subunit may vary based on the feed sugars used to manufacture the oligosaccharide. For instance, in some embodiments, gluco-oligosaccharides comprise anhydro-glucose subunits, galacto-oligosaccharides comprise anhydro-galactose subunits, and gluco-galacto-oligosaccharides comprise anhydro-glucose and anhydro-galactose subunits.

In some embodiments, the oligosaccharide preparation comprises both 1,6-anhydro-β-D-glucofuranose and 1,6-anhydro-β-D-glucopyranose anhydro-subunits. In some embodiments, at least 0.1%, 1%, 5%, 10%, 20%, 30%, 40%, 50%, 60%, 70%, 80%, 90%, or 99% of anhydro-subunits are selected from a group consisting of 1,6-anhydro-β-D-glucofuranose and 1,6-anhydro-β-D-glucopyranose. In some embodiments, at least 1%, 5%, 10%, 20%, 30%, 40%, 50%, 60%, 70%, 80%, or 90% of anhydro-subunits are 1,6-anhydro-β-D-glucofuranose. In some embodiments, at least 1%, 5%, 10%, 20%, 30%, 40%, 50%, or 60% of anhydro-subunits are 1,6-anhydro-β-D-glucopyranose.

In some embodiments, the ratio of 1,6-anhydro-β-D-glucofuranose to 1,6-anhydro-β-D-glucopyranose is from about 10:1 to 1:10, 9:1 to 1:10, 8:1 to 1:10, 7:1 to 1:10, 6:1 to 1:10, 5:1 to 1:10, 4:1 to 1:10, 3:1 to 1:10, 2:1 to 1:10, 10:1 to 1:9, 10:1 to 1:8, 10:1 to 1:7, 10:1 to 1:6, 10:1 to 1:5, 10:1 to 1:4, 10:1 to 1:3, 10:1 to 1:2, or 1:1 to 3:1 in the preparation. In some embodiments, the ratio of 1,6-anhydro-β-D-glucofuranose to 1,6-anhydro-β-D-glucopyranose is about 10:1, 9:1, 8:1, 7:1, 6:1, 5:1, 4:1, 3:1, 2:1, 1:1, 1:2, 1:3, 1:4, 1:5, 1:6, 1:7, 1:8, 1:8, 1:9, or 1:10 in the preparation. In some embodiments, the ratio of 1,6-anhydro-β-D-glucofuranose to 1,6-anhydro-β-D-glucopyranose is about 2:1 in the preparation.

In some embodiments, the ratio of 1,6-anhydro-β-D-glucofuranose to 1,6-anhydro-β-D-glucopyranose is about from 10:1 to 1:10, 9:1 to 1:10, 8:1 to 1:10, 7:1 to 1:10, 6:1 to 1:10, 5:1 to 1:10, 4:1 to 1:10, 3:1 to 1:10, 2:1 to 1:10, 10:1 to 1:9, 10:1 to 1:8, 10:1 to 1:7, 10:1 to 1:6, 10:1 to 1:5, 10:1 to 1:4, 10:1 to 1:3, 10:1 to 1:2, or 1:1 to 3:1 in each fraction. In some embodiments, the ratio of 1,6-anhydro-β-D-glucofuranose to 1,6-anhydro-β-D-glucopyranose is about 10:1, 9:1, 8:1, 7:1, 6:1, 5:1, 4:1, 3:1, 2:1, 1:1, 1:2, 1:3, 1:4, 1:5, 1:6, 1:7, 1:8, 1:8, 1:9, or 1:10 in each fraction. In some embodiments, the ratio of 1,6-anhydro-β-D-glucofuranose to 1,6-anhydro-β-D-glucopyranose is about 2:1 in each fraction.

In some embodiments, the ratio of 1,6-anhydro-β-D-glucofuranose to 1,6-anhydro-β-D-glucopyranose is about from 10:1 to 1:10, 9:1 to 1:10, 8:1 to 1:10, 7:1 to 1:10, 6:1 to 1:10, 5:1 to 1:10, 4:1 to 1:10, 3:1 to 1:10, 2:1 to 1:10, 10:1 to 1:9, 10:1 to 1:8, 10:1 to 1:7, 10:1 to 1:6, 10:1 to 1:5, 10:1 to 1:4, 10:1 to 1:3, 10:1 to 1:2, or 1:1 to 3:1 in at least one fraction. In some embodiments, the ratio of 1,6-anhydro-β-D-glucofuranose to 1,6-anhydro-β-D-glucopyranose is about 10:1, 9:1, 8:1, 7:1, 6:1, 5:1, 4:1, 3:1, 2:1, 1:1, 1:2, 1:3, 1:4, 1:5, 1:6, 1:7, 1:8, 1:8, 1:9, or 1:10 in at least one fraction. In some embodiments, the ratio of 1,6-anhydro-β-D-glucofuranose to 1,6-anhydro-β-D-glucopyranose is about 2:1 in at least one fraction.

In some embodiments, a herein described oligosaccharide preparation comprises anhydro-subunit containing DP2 oligosaccharides. In some embodiments, the oligosaccharide preparation comprises anhydro-lactose, anhydro-sucrose, anhydro-cellobiose, or a combination thereof. In some embodiment, the oligosaccharide preparation comprises from about 2 to 20, 2 to 15, 5 to 20, 5 to 15, or 5 to 10 species of DP2 anhydro-subunit containing oligosaccharides. In some embodiments, an oligosaccharide preparation described herein does not comprise cellobiosan or does not comprise a detectable level of cellobiosan.

In some embodiments, a herein described oligosaccharide preparation comprises one or more anhydro-subunits that are sugar caramelization products. In some embodiments, the oligosaccharide preparation comprises one or more anhydro-subunits are sugar caramelization products selected from the group consisting of: methanol; ethanol; furan; methyl glyoxal; 2-methyl furan; vinyl acetate; glycolaldehyde; acetic acid; acetol; furfural; 2-furanmethanol; 3-furanmethanol; 2-hydroxy cyclopent-2-en-1-one; 5-methyl furfural; 2(5H)-furanone; 2 methyl cyclopentenolone; levoglucosenone; cyclic hydroxyl lactone; 1,4,3,6-dianhydro-α-D-glucopyranose; dianhydro glucopyranose; and 5-hydroxy methyl furfural (5-hmf). In some embodiments, the oligosaccharide preparation comprises 5-hmf anhydro-subunits.

In some embodiments, in the oligosaccharide preparation or in at least one of the DP fractions, the anhydro-subunits that are caramelization products are less abundant than the anhydro-subunits that are products of thermal dehydration of a monosaccharide. In some embodiments, in the oligosaccharide preparation or in at least one of the fractions, the anhydro-subunits that are caramelization products are more abundant than the anhydro-subunits that are products of thermal dehydration of a monosaccharide. In some embodiments, in the oligosaccharide preparation or in at least one of the fractions, anhydro-subunits that are caramelization products and anhydro-subunits that are products of thermal dehydration of a monosaccharide have similar abundance.

In some embodiments, from about 0.01% to about 50%, from about 0.01% to about 40%, from about 0.01% to about 30%, from about 0.01% to about 20%, from about 0.01% to about 10%, from about 0.01% to about 5%, from about 0.01% to about 4%, from about 0.01% to about 3%, from about 0.01% to about 2%, from about 0.01% to about 1%, from about 0.01% to about 0.5%, from about 0.1% to about 50%, from about 0.1% to about 40%, from about 0.1% to about 30%, from about 0.1% to about 20%, from about 0.1% to about 10%, from about 0.1% to about 5%, from about 0.1% to about 4%, from about 0.1% to about 3%, from about 0.1% to about 2%, from about 0.1% to about 1%, or from about 0.1% to about 0.5% of the anhydro-subunits in a herein described oligosaccharide preparation are caramelization products. In some embodiments, from about 0.1% to about 5%, from about 0.1% to about 2%, or from about 0.1% to about 1% of the anhydro-subunits in the oligosaccharide preparation are caramelization products. In some embodiments, less than 50%, less than 40%, less than 30%, less than 25%, less than 20%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1% of the anhydro-subunits in the oligosaccharide preparation are caramelization products.

In some embodiments, from about 0.01% to about 50%, from about 0.01% to about 40%, from about 0.01% to about 30%, from about 0.01% to about 20%, from about 0.01% to about 10%, from about 0.01% to about 5%, from about 0.01% to about 4%, from about 0.01% to about 3%, from about 0.01% to about 2%, from about 0.01% to about 1%, from about 0.01% to about 0.5%, from about 0.1% to about 50%, from about 0.1% to about 40%, from about 0.1% to about 30%, from about 0.1% to about 20%, from about 0.1% to about 10%, from about 0.1% to about 5%, from about 0.1% to about 4%, from about 0.1% to about 3%, from about 0.1% to about 2%, from about 0.1% to about 1%, or from about 0.1% to about 0.5% of the anhydro-subunits in at least one fraction (e.g., DP1, DP2 and/or DP3) of a herein described preparation are caramelization products. In some embodiments, from about 0.1% to about 5%, from about 0.1% to about 2%, or from about 0.1% to about 1% of the anhydro-subunits in at least one fraction (e.g., DP1, DP2 and/or DP3) of the preparation are caramelization products. In some embodiments, less than 50%, 40%, 30%, 25%, 20%, 15%, 14%, 13%, 12%, 11%, 10%, 9%, 8%, 7%, 6%, 5%, 4%, 3%, 2%, or 1% of the anhydro-subunits in at least one fraction of the preparation are caramelization products. In some embodiments, less than 20%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1% of the anhydro-subunits in the DP1, DP2, and/or DP3 fractions of a herein described oligosaccharide preparation are caramelization products.

In some embodiments, from about 0.01% to about 50%, from about 0.01% to about 40%, from about 0.01% to about 30%, from about 0.01% to about 20%, from about 0.01% to about 10%, from about 0.01% to about 5%, from about 0.01% to about 4%, from about 0.01% to about 3%, from about 0.01% to about 2%, from about 0.01% to about 1%, from about 0.01% to about 0.5%, from about 0.1% to about 50%, from about 0.1% to about 40%, from about 0.1% to about 30%, from about 0.1% to about 20%, from about 0.1% to about 10%, from about 0.1% to about 5%, from about 0.1% to about 4%, from about 0.1% to about 3%, from about 0.1% to about 2%, from about 0.1% to about 1%, or from about 0.1% to about 0.5% of the anhydro-subunits in each fraction of a herein described oligosaccharide preparation are caramelization products. In some embodiments, from about 0.1% to about 5%, from about 0.1% to about 2%, or from about 0.1% to about 1% of the anhydro-subunits in each fraction of the preparation are caramelization products. In some embodiments, less than 50%, less than 40%, less than 30%, less than 20%, less than 25%, less than 20%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1% of the anhydro-subunits in each fraction of the preparation are caramelization products.

In some embodiments, each of the oligosaccharides in a herein described oligosaccharide preparation independently and optionally comprises an anhydro-subunit. In some embodiments, two or more independent oligosaccharides comprise the same or different anhydro-subunits. In some embodiments, two or more independent oligosaccharides comprise different anhydro-subunits. For example, in some embodiments, the oligosaccharide preparation comprises a DP1 anhydro-subunit containing oligosaccharide that comprises a 1,6-anhydro-β-D-glucopyranose and a DP2 anhydro-subunit containing oligosaccharide that comprises a 1,6-anhydro-β-D-glucofuranose subunit. In some embodiments, one or more oligosaccharides in the oligosaccharide preparation comprise two or more the same or different anhydro-subunits.

In some embodiments, in any fraction of the oligosaccharide preparation that has a degree of polymerization equal or greater than 2 (i.e., DP2 to DPn fractions), an anhydro-subunit may be linked to one or more regular or anhydro-subunits. In some embodiments, in the DP2 to DPn fractions, at least one anhydro-subunit is linked to one, two, or three other regular or anhydro-subunits. In some embodiments, in the DP2 to DPn fractions, at least one anhydro-subunit is linked to one or two regular subunits. In some embodiments, in the DP2 to DPn fractions, at least one anhydro-subunit is linked to one regular subunit. In some embodiments, in any of the DP2 to DPn fractions, more than 99%, 90%, 80%, 70%, 60%, 50%, 40%, or 30% of anhydro-subunits are linked to one regular subunit. In some embodiments, in each of the DP2 to DPn fraction, more than 99%, 90%, 80%, 70%, 60%, 50%, 40%, or 30% of anhydro-subunits are linked to one regular subunit.

In some embodiments, in any fraction of the oligosaccharide preparation that has a degree of polymerization equal or greater than 2 (i.e., DP2 to DPn fractions), an anhydro-subunit can be located at a chain-end of an oligosaccharide. In some embodiments, in any fraction of the oligosaccharide preparation that has a degree of polymerization equal or greater than 3 (i.e., DP3 to DPn fractions), an anhydro-subunit can be located at a position that is not a chain-end of an oligosaccharide. In some embodiments, in the DP2 to DPn fractions, at least one of the anhydro-subunits is located at the chain-end of an oligosaccharide. In some embodiments, greater than 99%, 95%, 90%, 85%, 80%, 75%, 70%, 65%, 60%, 55%, 50%, 45%, 40%, 35%, or 30% of the anhydro-subunits in the DP2 to DPn fractions are located at the chain-end of the oligosaccharides. In some embodiments, greater than 95%, 90%, 80%, 70%, 60%, 50%, 40%, 30%, 20%, or 10% of the anhydro-subunits in the oligosaccharide preparation are located at the chain-end of the oligosaccharides. In some embodiments, greater than 30%, 40%, 50%, 60%, 70%, 80%, 90%, 95%, or 99% of the anhydro-subunit containing oligosaccharides comprise a chain-end anhydro-subunit. In some embodiments, greater than 80%, 85%, 90%, 91%, 92%, 93%, 94%, 95%, 96%, 97%, 98%, or 99% of the anhydro-subunit containing oligosaccharides comprise a chain-end anhydro-subunit.

E. Glycosidic Linkages

In some embodiments, a herein described oligosaccharide preparation comprises a variety of glycosidic linkages. The type and distribution of the glycosidic linkages can depend on the source and manufacturing method of the oligosaccharide preparation. In some embodiments, the type and distribution of various glycosidic linkages can be determined and/or detected by any suitable methods known in the art such as NMR. For example, in some embodiments, the glycosidic linkages are determined and/or detected by $^{1}$H NMR, $^{13}$C NMR, 2D NMR such as 2D JRES, HSQC, HMBC, DOSY, COSY, ECOSY, TOCSY, NOESY, or ROESY, or any combination thereof. In some embodiments, the glycosidic linkages are determined and/or detected, at least in part, by $^{1}$H NMR. In some embodiments, the glycosidic linkages are determined and/or detected, at least in part, by $^{13}$C NMR. In some embodiments, the glycosidic linkages are determined and/or detected, at least in part, by 2D $^{1}$H, $^{13}$C-HSQC NMR.

In some embodiments, a herein described oligosaccharide preparation comprises one or more α-(1,2) glycosidic linkages, α-(1,3) glycosidic linkages, α-(1,4) glycosidic linkages, α-(1,6) glycosidic linkages, β-(1,2) glycosidic linkages, β-(1,3) glycosidic linkages, β-(1,4) glycosidic linkages, β-(1,6) glycosidic linkages, α-(1,1)-α glycosidic linkages, α-(1,1)-β glycosidic linkages, β-(1,1)-β glycosidic linkages, or any combination thereof.

In some embodiments, the oligosaccharide preparations have a glycosidic bond type distribution of from about 0 to about 60 mol %, from about 5% to about 55 mol %, from about 5% to about 50 mol %, from about 5% to about 45 mol %, from about 5% to about 40 mol %, from about 5% to about 35 mol %, from about 5% to about 30 mol %, from about 5% to about 25 mol %, from about 10% to about 60 mol %, from about 10% to about 55 mol %, from about 10% to about 50 mol %, from about 10% to about 45 mol %, from about 10% to about 40 mol %, from about 10% to about 35 mol %, from about 15% to about 60 mol %, from about 15% to about 55 mol %, from about 15% to about 50 mol %, from about 15% to about 45 mol %, from about 15% to about 40 mol %, from about 15% to about 35 mol %, from about 20% to about 60 mol %, from about 20% to about 55 mol %, from about 20% to about 50 mol %, from about 20% to about 45 mol %, from about 20% to about 40 mol %, from about 20% to about 35 mol %, from about 25% to about 60 mol %, from about 25% to about 55 mol %, from about 25% to about 50 mol %, from about 25% to about 45 mol %, from about 25% to about 40 mol %, or from about 25% to about 35 mol % of α-(1,6) glycosidic linkages.

In some embodiments, the oligosaccharide preparations have a glycosidic bond type distribution of from about 0 to about 50 mol %, from about 0 to about 40 mol %, from about 0 to about 35 mol %, from about 0 to about 30 mol %, from about 0 to about 25 mol %, from about 0 to about 20 mol %, from about 5% to about 40 mol %, from about 5% to about 35 mol %, from about 5% to about 30 mol %, from about 5% to about 25 mol %, from about 5% to about 20 mol %, from about 10% to about 40 mol %, from about 10% to about 35 mol %, from about 10% to about 20 mol %, from about 15% to about 40 mol %, from about 15% to about 35 mol %, from about 15% to about 30 mol %, from about 15% to about 25 mol %, or from about 15% to about 20 mol % of α-(1,3) glycosidic linkages.

In some embodiments, the oligosaccharide preparations have a glycosidic bond type distribution of from about 0 to about 40 mol %, from about 0 to about 35 mol %, from about 0 to about 30 mol %, from about 0 to about 25 mol %, from about 0 to about 20 mol %, from about 0 to about 15 mol %, from about 0 to about 10 mol %, from about 2% to about 30 mol %, from about 2% to about 25 mol %, from about 2% to about 20 mol %, from about 2% to about 15 mol %, from about 2% to about 10 mol %, from about 3% to about 30 mol %, from about 3% to about 25 mol %, from about 3% to about 20 mol %, from about 3% to about 15 mol %, from about 3% to about 10 mol %, from about 5% to about 30 mol %, from about 5% to about 25 mol %, from about 5% to about 20 mol %, from about 5% to about 15 mol %, or from about 5% to about 10 mol % of α-(1,2) glycosidic linkages.

In some embodiments, the oligosaccharide preparations have a glycosidic bond type distribution of from about 0 to about 40 mol %, from about 0 to about 30 mol %, from about 0 to about 25 mol %, from about 0 to about 20 mol %, from about 0 to about 15 mol %, from about 0 to about 10 mol %, or from about 0 to about 5 mol % of α-(1,4) glycosidic linkages. In some embodiments, the oligosaccharide preparations have a glycosidic bond type distribution of less than 40 mol %, less than 30 mol %, less than 20 mol %, less than 15 mol %, less than 10 mol %, less than 9 mol %, less than 8 mol %, less than 7 mol %, less than 6 mol %, less than 5 mol %, less than 4 mol %, less than 3 mol %, or less than 2 mol % of α-(1,4) glycosidic linkages.

In some embodiments, the oligosaccharide preparations have a glycosidic bond type distribution of from about 0 to about 40 mol %, from about 0 to about 35 mol %, from about 0 to about 30 mol %, from about 0 to about 25 mol %, from about 0 to about 20 mol %, from about 0 to about 15 mol %, from about 0 to about 10 mol %, from about 2% to about 30 mol %, from about 2% to about 25 mol %, from about 2% to about 20 mol %, from about 2% to about 15 mol %, from about 2% to about 10 mol %, from about 5% to about 30 mol %, from about 5% to about 25 mol %, from about 5% to about 20 mol %, from about 5% to about 15 mol %, from about 5% to about 10 mol %, from about 8% to about 30 mol %, from about 8% to about 25 mol %, from about 8% to about 20 mol %, from about 8% to about 15 mol %, or from about 10% to about 15 mol % of β-(1,6) glycosidic linkages.

In some embodiments, the oligosaccharide preparations have a glycosidic bond type distribution of from about 0 to about 40 mol %, from about 0 to about 35 mol %, from about 0 to about 30 mol %, from about 0 to about 25 mol %, from about 0 to about 20 mol %, from about 0 to about 15 mol %, from about 0 to about 10 mol %, from about 2% to about 30 mol %, from about 2% to about 25 mol %, from about 2% to about 20 mol %, from about 2% to about 15 mol %, from about 2% to about 10 mol %, from about 3% to about 30 mol %, from about 3% to about 25 mol %, from about 3% to about 20 mol %, from about 3% to about 15 mol %, from about 3% to about 10 mol %, from about 5% to about 30 mol %, from about 5% to about 25 mol %, from about 5% to about 20 mol %, from about 5% to about 15 mol %, or from about 5% to about 10 mol % of β-(1,4) glycosidic linkages.

In some embodiments, the oligosaccharide preparations have a glycosidic bond type distribution of from about 0 to about 40 mol %, from about 0 to about 30 mol %, from about 0 to about 25 mol %, from about 0 to about 20 mol %, from about 0 to about 15 mol %, from about 0 to about 10 mol %, from about 0 to about 5 mol %, from about 1% to about 20 mol %, from about 1% to about 15 mol %, from about 1% to about 10 mol %, from about 1% to about 5 mol %, from about 2% to about 20 mol %, from about 2% to about 15 mol %, from about 2% to about 10 mol %, or from about 2% to about 5 mol % of β-(1,2) glycosidic linkages. In some embodiments, the oligosaccharide preparations have a glycosidic bond type distribution of less than 40 mol %, less than 30 mol %, less than 20 mol %, less than 15 mol %, less than 10 mol %, less than 9 mol %, less than 8 mol %, less than 7 mol %, less than 6 mol %, less than 5 mol %, less than 4 mol %, less than 3 mol %, or less than 2 mol % of β-(1,2) glycosidic linkages.

In some embodiments, the oligosaccharide preparations have a glycosidic bond type distribution of from about 0 to about 40 mol %, from about 0 to about 30 mol %, from about 0 to about 25 mol %, from about 0 to about 20 mol %, from about 0 to about 15 mol %, from about 0 to about 10 mol %, from about 0 to about 5 mol %, from about 1% to about 20 mol %, from about 1% to about 15 mol %, from about 1% to about 10 mol %, from about 1% to about 5 mol %, from about 2% to about 20 mol %, from about 2% to about 15 mol %, from about 2% to about 10 mol %, or from about 2% to about 5 mol % of β-(1,3) glycosidic linkages. In some embodiments, the oligosaccharide preparations have a glycosidic bond type distribution of less than 40 mol %, less than 30 mol %, less than 20 mol %, less than 15 mol %, less than 10 mol %, less than 9 mol %, less than 8 mol %, less than 7 mol %, less than 6 mol %, less than 5 mol %, less than 4 mol %, less than 3 mol %, or less than 2 mol % of β-(1,3) glycosidic linkages.

In some embodiments, the oligosaccharide preparations have a glycosidic bond type distribution that is different from a glycosidic bond type distribution of non-synthetic oligosaccharide preparations. For example, in some embodiments, the oligosaccharide preparations have a glycosidic bond type distribution that is different from that of the base nutritional compositions. In some embodiments, the base nutritional compositions comprise a natural carbohydrate source, such as starch and plant fibers. Some of the natural carbohydrate sources have a high percentage of α-(1,4), α-(1,6), and/or β-(1,6) glycosidic linkages. Accordingly, in some embodiments, the oligosaccharide preparations have a lower percentage of α-(1,4) glycosidic linkages than the base nutritional composition. In some embodiments, the oligosaccharide preparations have a lower percentage of α-(1,6) glycosidic linkages than the base nutritional composition. In other embodiments, the oligosaccharide preparations have a higher percentage of α-(1,6) glycosidic linkages than the base nutritional composition. In some embodiments, the oligosaccharide preparations have a lower percentage of β-(1,6) glycosidic linkages than the base nutritional composition. In some embodiments, the oligosaccharide preparation comprises glycosidic linkages that are not readily digestible or hydrolysable by enzymes.

Specifically, in some embodiments, the α-(1,2), α-(1,3), α-(1,4), α-(1,6), β-(1,2), β-(1,3), β-(1,4), and/or β-(1,6) glycosidic linkages in the glycosidic bond type distribution of a herein described oligosaccharide preparations is at least 50 mol %, at least 40 mol %, at least 30 mol %, at least 20 mol %, at least 15 mol %, at least 10 mol %, at least 5 mol %, at least 2 mol %, or at least 1 mol % lower than that of the base nutritional composition. In some embodiments, the α-(1,2), α-(1,3), α-(1,4), α-(1,6), 0-(1,2), β-(1,3), β-(1,4), and/or β-(1,6) glycosidic linkages in the glycosidic bond type distribution of the oligosaccharide preparations is at least 50 mol %, at least 40 mol %, at least 30 mol %, at least 20 mol %, at least 15 mol %, at least 10 mol %, at least 5 mol %, at least 2 mol %, or at least 1 mol % higher than that of the base nutritional composition.

It should be understood by one of skill in the art that certain types of glycosidic linkages may not be applicable to oligosaccharides comprising certain type of monosaccharides. For example, in some embodiments, the oligosaccharide preparation comprises α-(1,2) glycosidic linkages and α-(1,6) glycosidic linkages. In other embodiments, the oligosaccharide preparation comprises α-(1,2) glycosidic linkages and β-(1,3) glycosidic linkages. In some embodiments, the oligosaccharide preparation comprises α-(1,2) glycosidic linkages, α-(1,3) glycosidic linkages, and β-(1,6) glycosidic linkages. In some embodiments, the oligosaccharide preparation comprises α-(1,2) glycosidic linkages, α-(1,3) glycosidic linkages, α-(1,4) glycosidic linkages, α-(1,6) glycosidic linkages, β-(1,2) glycosidic linkages, β-(1,3) glycosidic linkages, β-(1,4) glycosidic linkages, and β-(1,6) glycosidic linkages F. Molecular Weight The molecular weight and molecular weight distribution of the oligosaccharide preparation may be determined by any suitable analytical means and instrumentation, such as end group method, osmotic pressure (osmometry), ultracentrifugation, viscosity measurements, light scattering method, SEC, SEC-MALLS, FFF, A4F, HPLC, and mass spectrometry. In some embodiments, the molecular weight and molecular weight distribution are determined by mass spectrometry, such as MALDI-MS, LC-MS, or GC-MS. In some embodiments, the molecular weight and molecular weight distribution are determined by size exclusion chromatography (SEC), such as gel permeation chromatography (GPC). In other embodiments, the molecular weight and molecular weight distribution are determined by HPLC. In some embodiments, the molecular weight and molecular weight distribution are determined by MALDI-MS.

In some embodiments, a herein described oligosaccharide preparation has a weight average molecular weight of from about 100 to about 10000 g/mol, from about 200 to about 8000 g/mol, from about 300 to about 5000 g/mol, from about 500 to about 5000 g/mol, from about 700 to about 5000 g/mol, from about 900 to about 5000 g/mol, from about 1100 to about 5000 g/mol, from about 1300 to about 5000 g/mol, from about 1500 to about 5000 g/mol, from about 1700 to about 5000 g/mol, from about 300 to about 4500 g/mol, from about 500 to about 4500 g/mol, from about 700 to about 4500 g/mol, from about 900 to about 4500 g/mol, from about 1100 to about 4500 g/mol, from about 1300 to about 4500 g/mol, from about 1500 to about 4500 g/mol, from about 1700 to about 4500 g/mol, from about 1900 to about 4500 g/mol, from about 300 to about 4000 g/mol, from about 500 to about 4000 g/mol, from about 700 to about 4000 g/mol, from about 900 to about 4000 g/mol, from about 1100 to about 4000 g/mol, from about 1300 to about 4000 g/mol, from about 1500 to about 4000 g/mol, from about 1700 to about 4000 g/mol, from about 1900 to about 4000 g/mol, from about 300 to about 3000 g/mol, from about 500 to about 3000 g/mol, from about 700 to about 3000 g/mol, from about 900 to about 3000 g/mol, from about 1100 to about 3000 g/mol, from about 1300 to about 3000 g/mol, from about 1500 to about 3000 g/mol, from about 1700 to about 3000 g/mol, from about 1900 to about 3000 g/mol, from about 2100 to about 3000 g/mol, from about 300 to about 2500 g/mol, from about 500 to about 2500 g/mol, from about 700 to about 2500 g/mol, from about 900 to about 2500 g/mol, from about 1100 to about 2500 g/mol, from about 1300 to about 2500 g/mol, from about 1500 to about 2500 g/mol, from about 1700 to about 2500 g/mol, from about 1900 to about 2500 g/mol, from about 2100 to about 2500 g/mol, from about 300 to about 1500 g/mol, from about 500 to about 1500 g/mol, from about 700 to about 1500 g/mol, from about 900 to about 1500 g/mol, from about 1100 to about 1500 g/mol, from about 1300 to about 1500 g/mol, from about 2000 to about 2800 g/mol, from about 2100 to about 2700 g/mol, from about 2200 to about 2600 g/mol, from about 2300 to about 2500 g/mol, or from about 2320 to about 2420 g/mol. In some embodiments, the weight average molecular weight of the oligosaccharide preparation is from about 2000 to about 2800 g/mol, from about 2100 to about 2700 g/mol, from about 2200 to about 2600 g/mol, from about 2300 to about 2500 g/mol, or from about 2320 to about 2420 g/mol. In some embodiments, the oligosaccharide preparation has a weight average molecular weight in a range from at least 500 g/mol, 750 g/mol, 1000 g/mol, or 1500 g/mol to at most 1750 g/mol, 2000 g/mol, 2250 g/mol, 2500 g/mol, or 3000 g/mol. In some embodiments, the weight average molecular weight of a herein described oligosaccharide preparation is determined by HPLC according to Example 9.

In some embodiments, a herein described oligosaccharide preparation has a number average molecular weight of from about 100 to about 10000 g/mol, from about 200 to about 8000 g/mol, from about 300 to about 5000 g/mol, from about 500 to about 5000 g/mol, from about 700 to about 5000 g/mol, from about 900 to about 5000 g/mol, from about 1100 to about 5000 g/mol, from about 1300 to about 5000 g/mol, from about 1500 to about 5000 g/mol, from about 1700 to about 5000 g/mol, from about 300 to about 4500 g/mol, from about 500 to about 4500 g/mol, from about 700 to about 4500 g/mol, from about 900 to about 4500 g/mol, from about 1100 to about 4500 g/mol, from about 1300 to about 4500 g/mol, from about 1500 to about 4500 g/mol, from about 1700 to about 4500 g/mol, from about 1900 to about 4500 g/mol, from about 300 to about 4000 g/mol, from about 500 to about 4000 g/mol, from about 700 to about 4000 g/mol, from about 900 to about 4000 g/mol, from about 1100 to about 4000 g/mol, from about 1300 to about 4000 g/mol, from about 1500 to about 4000 g/mol, from about 1700 to about 4000 g/mol, from about 1900 to about 4000 g/mol, from about 300 to about 3000 g/mol, from about 500 to about 3000 g/mol, from about 700 to about 3000 g/mol, from about 900 to about 3000 g/mol, from about 1100 to about 3000 g/mol, from about 1300 to about 3000 g/mol, from about 1500 to about 3000 g/mol, from about 1700 to about 3000 g/mol, from about 1900 to about 3000 g/mol, from about 2100 to about 3000 g/mol, from about 300 to about 2500 g/mol, from about 500 to about 2500 g/mol, from about 700 to about 2500 g/mol, from about 900 to about 2500 g/mol, from about 1100 to about 2500 g/mol, from about 1300 to about 2500 g/mol, from about 1500 to about 2500 g/mol, from about 1700 to about 2500 g/mol, from about 1900 to about 2500 g/mol, from about 2100 to about 2500 g/mol, from about 300 to about 2000 g/mol, from about 500 to about 300 to 2000 g/mol, from about 700 to about 2000 g/mol, from about 900 to about 2000 g/mol, from about 1100 to about 2000 g/mol, from about 300 to about 1500 g/mol, from about 500 to about 1500 g/mol, from about 700 to about 1500 g/mol, from about 900 to about 1500 g/mol, from about 1100 to about 1500 g/mol, from about 1300 to about 1500 g/mol, from about 1000 to about 2000 g/mol, from about 1100 to about 1900 g/mol, from about 1200 to about 1800 g/mol, from about 1300 to about 1700 g/mol, from about 1400 to about 1600 g/mol, or from about 1450 to about 1550 g/mol. In some embodiments, the number average molecular weight of the oligosaccharide preparation is from about 1000 to about 2000 g/mol, from about 1100 to about 1900 g/mol, from about 1200 to about 1800 g/mol, from about 1300 to about 1700 g/mol, 1400 to 1600 g/mol, or 1450-1550 g/mol. In some embodiments, the oligosaccharide preparation has a number average molecular weight in a range from at least 500 g/mol, 750 g/mol, 1000 g/mol, or 1500 g/mol to at most 1750 g/mol, 2000 g/mol, 2250 g/mol, 2500 g/mol, or 3000 g/mol. In some embodiments, the number average molecular weight of a herein described oligosaccharide preparation is determined by HPLC according to Example 9.

G. Types of Oligosaccharides

The species of oligosaccharides present in an oligosaccharide preparation can depend on the type of the one or more feed sugars. For example, in some embodiments, the oligosaccharide preparations comprise a gluco-oligosaccharide when the feed sugars comprise glucose. For example, in some embodiments, the oligosaccharide preparations comprise a galacto-oligosaccharide when the feed sugars comprise galactose. For another example, in some embodiments, the oligosaccharide preparations comprise gluco-galacto-oligosaccharides when the feed sugars comprise galactose and glucose.

In some embodiments, a herein described oligosaccharide preparation comprises one or more species of monosaccharide subunits. In some embodiments, the oligosaccharide preparation comprises oligosaccharides with 1, 2, 3, 4, 5, 6, 7, 8, 9, 10, 11, 12, 13, 14, 15, 16, 17, 18, 19, 20, or more different species of monosaccharides subunits.

In some embodiments, the oligosaccharide preparation comprises oligosaccharides with 1, 2, 3, or 4 different species of monosaccharides subunits. In some embodiments, the oligosaccharide preparation comprises oligosaccharides with 1, 2, or 3 different species of monosaccharides subunits. In some embodiments, the oligosaccharide preparation comprises oligosaccharides with 3 different species of monosaccharides subunits. In some embodiments, the oligosaccharide preparation comprises oligosaccharides with 2 different species of monosaccharides subunits. In some embodiments, the oligosaccharide preparation comprises one species of monosaccharides subunits.

In some embodiments, the oligosaccharide preparation comprises different species of oligosaccharides that each oligosaccharide molecule independently comprises 1, 2, 3, 4, 5, 6, 7, 8, 9, or 10 different species of monosaccharides subunits. In some embodiments, a herein described oligosaccharide preparation comprises $10^2$, $10^3$, $10^4$, $10^5$, or more different species of oligosaccharides.

In some embodiments, some of the oligosaccharides in the preparation comprise one species of monosaccharide subunits and some other oligosaccharides in the same preparation comprise two or more species of monosaccharides subunits. For instance, in some embodiments, when the feed sugars are glucose and galactose, the oligosaccharide preparation can comprise oligosaccharides that comprise only glucose subunits, oligosaccharides that comprise only galactose subunits, oligosaccharides that comprise both glucose and galactose subunits at various ratios, or any combination thereof.

In some embodiments, any or all of the n fractions of the oligosaccharide preparation comprises different species of oligosaccharides subunits that each oligosaccharide independently comprises 1, 2, 3, 4, 5, 6, 7, 8, 9, or 10 different species of monosaccharides subunits. In some embodiments, some of the oligosaccharides in a fraction of the preparation comprise one species of monosaccharide subunits and some other oligosaccharides in the same fraction of the preparation comprise two or more species of monosaccharides subunits.

In some embodiments, a herein described oligosaccharide preparation comprises one or more monosaccharide subunits selected from a group consisting of: triose, tetrose, pentose, hexose, heptose, and any combination thereof, wherein each of the said triose, tetrose, pentose, hexose, or heptose subunit is independently and optionally functionalized and/or replaced with one of its corresponding anhydro-subunits. In some embodiments, the corresponding anhydro-subunit is a product of thermal dehydration of the monosaccharide subunit. In some embodiments, the corresponding anhydro-subunit is a caramelization product of the monosaccharide subunit.

In some embodiments, a herein described oligosaccharide preparation comprises pentose subunits, hexose subunits, or any combination thereof, wherein each of the said pentose or hexose subunit is independently and optionally functionalized and/or replaced with one of its corresponding anhydro-subunits. In some embodiments, the oligosaccharide preparation comprises hexose subunits, wherein each of the said hexose subunits is independently and optionally replaced with one of its corresponding anhydro-subunits.

As used herein, a tetrose refers to a monosaccharide with four carbon atoms, such as erythrose, threose, and erythrulose. As used herein, a pentose refers to a monosaccharide with five carbon atoms, such as arabinose, lyxose, ribose, and xylose. As used herein, a hexose refers to a monosaccharide with six carbon atoms, such as allose, altrose, glucose, mannose, gulose, idose, galactose, talose, psicose, fructose, sorbose, and tagatose. As used herein, a heptose refers to a monosaccharide with seven carbon atoms, such as sedoheptulose and mannoheptulose.

In some embodiments, a herein described oligosaccharide preparation comprises glucose subunit, wherein at least one glucose subunit is optionally replaced with an anhydro-glucose subunit.

In some embodiments, a herein described oligosaccharide preparation comprises galactose subunit, wherein at least one galactose subunit is optionally replaced with anhydro-galactose subunit. In some embodiments, a herein described oligosaccharide preparation comprises galactose and glucose subunits, wherein at least one galactose subunit or at least one glucose subunit is optionally replaced with one of its corresponding anhydro-subunits. In some embodiments, a herein described oligosaccharide preparation comprises fructose and glucose subunits, wherein at least one fructose subunit or at least one glucose subunit is optionally replaced with one of its corresponding anhydro-subunits. In some embodiments, a herein described oligosaccharide preparation comprises mannose and glucose subunit, wherein at least one mannose subunit or at least one glucose subunit is optionally replaced with one of its corresponding anhydro-subunits.

In some embodiments, a herein described oligosaccharide preparation comprises a gluco-galactose-oligosaccharide preparation, a gluco-oligosaccharide preparation, a galacto-oligosaccharide preparation, a fructo-oligosaccharide preparation, a manno-oligosaccharide preparation, an arabino-oligosaccharide preparation, a xylo-oligosaccharide preparation, a gluco-fructo-oligosaccharide preparation, a gluco-manno-oligosaccharide preparation, a gluco-arabino-oligosaccharide preparation, a gluco-xylo-oligosaccharide preparation, a galacto-fructo-oligosaccharide preparation, a galacto-manno-oligosaccharide preparation, a galacto-arabino-oligosaccharide preparation, a galacto-xylo-oligosaccharide preparation, a fructo-manno-oligosaccharide preparation, a fructo-arabino-oligosaccharide preparation, a fructo-xylo-oligosaccharide preparation, a manno-arabino-oligosaccharide preparation, a manno-xylo-oligosaccharide preparation, an arabino-xylo-oligosaccharide preparation, a galacto-arabino-xylo-oligosaccharide preparation, a fructo-galacto-xylo-oligosaccharide preparation, an arabino-fructo-manno-xylo-oligosaccharide preparation, a gluco-fructo-galacto-arabino-oligosaccharide preparation, a fructo-gluco-arabino-manno-xylo oligosaccharide preparation, a gluco-galacto-fructo-manno-arabinoxylo-oligosaccharide preparation, or any combinations thereof; wherein each of the monosaccharide subunit within the preparation is independently and optionally functionalized and/or replaced with one of its corresponding anhydro-subunits.

In certain embodiments, a herein described oligosaccharide preparation comprises more than 99% of glucose subunits by weight. In some embodiments, the oligosaccharide preparation comprises only glucose subunits.

In some embodiments, a herein described oligosaccharide preparation comprises about 45% to 55% of glucose subunits and about 55% to 45% of galactose subunits by weight. In some specific embodiments, the oligosaccharide preparation comprises about 50% glucose and 50% galactose subunits by weight.

In some embodiments, a herein described oligosaccharide preparation comprises about 80% to 95% of glucose subunits and about 20% to 5% of mannose subunits by weight. In some embodiments, the oligosaccharide preparation comprises about 85% to 90% of glucose subunits and about 15% to 10% of mannose subunits by weight.

In some embodiments, a herein described oligosaccharide preparation comprises about 80% to 95% of glucose subunits and about 20% to 5% of galactose subunits by weight. In some embodiments, the oligosaccharide preparation comprises about 85% to 90% of glucose subunits and about 15% to 10% of galactose subunits by weight.

In some embodiments, a herein described oligosaccharide preparation comprises about 80% to 95% of glucose subunits, 0% to 8% of galactose subunits, and 5% to 20% of mannose subunits by weight. In some embodiments, the oligosaccharide preparation comprises about 80% to 90% of glucose subunits, 1% to 5% of galactose subunits, and 10% to 15% of mannose subunits by weight.

In some embodiments, an oligosaccharide preparation described herein comprises from about 1 wt % to about 100 wt %, from about 50 wt % to about 100 wt %, from about 80 wt % to about 98 wt %, or from about 85 wt % to about 95 wt % of glucose subunits, or any ranges therebetween. In some embodiments, galactose subunits are present in an oligosaccharide preparation described herein at an amount of from about 0 wt % to about 90 wt %, from about 1 wt % to about 50 wt %, from about 2 wt % to about 20 wt %, or from about 5 wt % to about 15 wt %, or any ranges therebetween. In some embodiments, mannose subunits are present in an oligosaccharide preparation described herein at an amount of from about 0 wt % to about 90 wt %, from about 1 wt % to about 50 wt %, from about 2 wt % to about 20 wt %, or from about 5 wt % to about 15 wt %, or any ranges therebetween.

In some embodiments, a herein described oligosaccharide preparation has a composition of monosaccharide subunits as shown in Table 28.

TABLE 28

Exemplary Compositions of Oligosaccharide Preparations

| Oligo Composition No. | Glucose and anhydro-glucose subunits (wt %) | Galactose and anhydro-galactose subunits (wt %) | Mannose and anhydro-mannose subunits (wt %) | Fructose and anhydro-fructose subunits (wt %) |
|---|---|---|---|---|
| 1 | 87.5 | 12.5 | 0 | 0 |
| 2 | 100 | 0 | 0 | 0 |
| 3 | 85 | 2.5 | 12.5 | 0 |
| 4 | 87.5 | 0 | 12.5 | 0 |
| 5 | 50 | 50 | 0 | 0 |
| 6 | 75 | 0 | 25 | 0 |
| 7 | 9 | 6 | 0 | 0 |
| 8 | 90 | 0 | 10 | 0 |
| 9 | 95 | 5 | 0 | 0 |
| 10 | 97.5 | 2.5 | 0 | 0 |
| 11 | 85 | 5 | 10 | 0 |
| 12 | 85 | 1.5 | 13.5 | 0 |
| 13 | 80 | 10 | 10 | 0 |
| 14 | 85 | 0 | 15 | 0 |
| 15 | 85 | 15 | 0 | 0 |
| 16 | 87.5 | 0 | 0 | 12.5 |

H. D- Vs. L-Form

In some embodiments, at least one monosaccharide subunit in an oligosaccharide is in L-form.

In some embodiments, at least one monosaccharides subunit in an oligosaccharide is in D-form. In some embodiments, the monosaccharide subunits in a herein described oligosaccharide preparation are in their naturally-abundant form, for example, D-glucose, D-xylose, and L-arabinose.

In some embodiments, a herein described oligosaccharide preparation comprises a mixture of L- and D-forms of monosaccharide subunits. In some embodiments, the ratio of monosaccharide subunits in L- to D- or in D- to L-form is about 1:1, about 1:2, about 1:3, about 1:4, about 1:5, about 1:6, about 1:7, about 1:8, about 1:9, about 1:10, about 1:12, about 1:14, about 1:16, about 1:18, about 1:20, about 1:25, about 1:30, about 1:35, about 1:40, about 1:45, about 1:50, about 1:55, about 1:60, about 1:65, about 1:70, about 1:75, about 1:80, about 1:85, about 1:90, about 1:100 or about 1:150.

I. Functionalized Oligosaccharides

In some embodiments, one or more oligosaccharides in the preparation are independently functionalized. Functionalized oligosaccharides may be produced by, for example, combining one or more sugars with one or more functionalizing compounds in the presence of a catalyst. Methods of producing functionalized oligosaccharides are described in WO 2012/118767, WO 2014/031956, and WO/2016/122887, which are hereby incorporated by reference in their entirety and for their disclosure.

In some embodiments, the functionalizing compound comprises one or more acid groups (e.g., —COOH), hydroxyl groups, or N-containing groups (e.g., —CN, $—NO_2$, and $—N(R_a)_2$, wherein $R_a$ is hydrogen, alkyl, alkenyl, alkynyl, haloalkyl, heteroalkyl, cycloalkyl, aryl, heterocycloalkyl, or heteroaryl groups), S-containing groups (e.g., thiol and sulfates), halides (e.g., —Cl), P-containing groups (e.g., phosphate), or any combination thereof. In some embodiments, the functionalizing compound is linked to at least one monosaccharide subunit via an ether, ester, oxygen-sulfur, amine, or oxygen-phosphorous bond. In some embodiments, one or more functionalizing compounds are linked to a monosaccharide subunit via a single linkage. In some embodiments, at least one functionalizing compound is linked to one or two oligosaccharides via two or more linkages.

It is to be understood that for each oligosaccharide in the oligosaccharide preparation, each of the described embodiments is independent and can be combined as if each and every combination were listed separately; thus, any combination of the embodiments is encompassed by the present disclosure. For instance, the various embodiments can be grouped into several categories that include but are not limited to (i) the presence or absence of anhydro-subunit; (ii) the number and level of anhydro-subunit, (iii) the type of species of anhydro-subunit, (iv) the location of anhydro-subunit, (v) the degree of polymerization, (vi) the molecular weight, (vii) the presence or absence of any functional groups, (viii) the type of the oligosaccharide, (ix) the type of glycosidic linkage, and (x) the L-versus D-form. Accordingly, the described oligosaccharide preparation comprises a plurality of oligosaccharides of different species. In some embodiments, a herein described oligosaccharide preparation comprises at least 10, $10^2$, $10^3$, $10^4$, $10^5$, $10^6$, $10^7$, $10^8$, $10^9$, or $10^{10}$ different oligosaccharide species. In some embodiments, the preparation comprises at least $10^3$, $10^4$, $10^5$, $10^6$, or $10^9$ different oligosaccharide species. In some embodiments, the preparation comprises at least $10^3$ different oligosaccharide species.

III. Methods of Manufacturing Oligosaccharide Preparations

In one aspect, provided herein are methods of manufacturing oligosaccharide preparations. In some embodiments, provided herein are methods of manufacturing oligosaccharide preparations suitable for use in a nutritional composition, such as an animal feed composition, or being fed directly to an animal. In one aspect, provided herein are methods of manufacturing an oligosaccharide preparation comprising heating an aqueous composition comprising one or more feed sugars and a catalyst to a temperature and for a time sufficient to induce polymerization, wherein the catalyst is selected from the group consisting of: (+)-camphor-10-sulfonic acid; 2-pyridinesulfonic acid; 3-pyridinesulfonic acid; 8-hydroxy-5-quinolinesulfonic acid hydrate; α-hydroxy-2-pyridinemethanesulfonic acid; (β)-camphor-10-sulfonic acid; butylphosphonic acid; diphenylphosphinic acid; hexylphosphonic acid; methylphosphonic acid; phenylphosphinic acid; phenylphosphonic acid; tert-butylphosphonic acid; SS)-VAPOL hydrogenphosphate; 6-quinolinesulfonic acid, β-(1-pyridinio)-1-propanesulfonate; 2-(2-pyridinyl)ethanesulfonic acid; β-(2-pyridyl)-5,6-diphenyl-1,2,4-triazine-p,p'-disulfonic acid monosodium salt hydrate; 1,1'-binaphthyl-2,2'-diyl-hydrogenphosphate; bis(4-methoxyphenyl)phosphinic acid; phenyl(3,5-xylyl)phosphinic acid; L-cysteic acid monohydrate; poly(styrene sulfonic acid-co-divinylbenzene); lysine; Ethanedisulfonic acid; Ethanesulfonic acid; Isethionic acid; Homocysteic acid; HEPBS (N-(2-Hydroxyethyl)piperazine-N'-(4-butanesulfonic acid)); HEPES (4-(2-hydroxyethyl)-1-piperazineethanesulfonic acid); 2-Hydroxy-3-morpholinopropanesulfonic acid; 2-(N-morpholino)ethanesulfonic acid; Methanesulfonic acid; Methaniazide; Naphthalene-1-sulfonic acid; Naphthalene-2-sulfonic acid; Perfluorobutanesulfonic acid; 6-sulfoquinovose; Triflic acid; 2-aminoethanesulfonic acid; Benzoic acid; Chloroacetic acid; Trifluoroacetic acid; Caproic acid; Enanthic acid; Caprylic acid; Pelargonic acid; Lauric acid; Pamitic acid; Stearic acid; Arachidic acid; Aspartic acid; Glutamic acid; Serine; Threonine; Glutamine; Cysteine; Glycine; Proline; Alanine; Valine; Isoleucine; Leucine; Methionine; Phenylalanine; Tyrosine; Tryptophan, and wherein the oligosaccharide preparation comprises at least n fractions of oligosaccharides each having a distinct degree of polymerization selected from 1 (DP1 fraction) to n (DPn fraction), wherein n is an integer greater than 2.

In some embodiments, n is an integer greater than or equal to 3. In some embodiments, n is an integer within a range of 1 to 100, such as 4, 5, 6, 7, 8, 9, 10, 11, 12, 13, 14, 15, 16, 17, 18, 19, 20, 21, 22, 23, 24, 25, 26, 27, 28, 29, 30, 40, or 50. In some embodiments, the polymerization of the feed sugars is achieved by a step-growth polymerization. In some embodiments, the polymerization of the feed sugars is achieved by polycondensation.

A. Feed Sugar

In some embodiments, a method of manufacturing oligosaccharide preparations described herein comprises heating one or more types of feed sugars. In some embodiments, the one or more types of feed sugars comprise monosaccharides, disaccharides, trisaccharides, tetrasaccharides, or any mixtures thereof.

In some embodiments, the one or more feed sugars comprise glucose. In some embodiments, the one or more feed sugars comprise glucose and galactose. In some embodiments, the one or more feed sugars comprise glucose, xylose, and galactose. In some embodiments, the one or more feed sugars comprise glucose and mannose. In some embodiments, the one or more feed sugars comprise glucose and fructose. In some embodiments, the one or more feed sugars comprise glucose, fructose, and galactose. In some embodiments, the one or more feed sugars comprise glucose, galactose, and mannose.

In some embodiments, the one or more feed sugars comprise disaccharides such as lactose, sucrose and cellobiose. In some embodiments, the one or more feed sugars comprise trisaccharides, such as maltotriose or raffinose. In certain embodiments, the one or more feed sugar comprises glucose, mannose, galactose, xylose, malto-dextrin, arabinose, or galactose, or any combinations thereof. In certain embodiments, the one or more feed sugars comprise sugar syrup such as corn syrup. In some embodiments, the one or more feed sugars comprise glucose and lactose. In some embodiments, the one or more feed sugars comprise glucose and sucrose.

In some embodiments, the type of feed sugars can impact the resulting manufactured oligosaccharide preparations. For example, in some variations where the one or more feed sugars are all glucose, the resulting oligosaccharide preparations comprise gluco-oligosaccharides preparations. In other embodiments, where the one or more feed sugars are all mannose, the resulting oligosaccharide preparations comprise manno-oligosaccharide preparations. In some embodiments, wherein the one or more feed sugars comprise glucose and galactose, the resulting oligosaccharide preparations comprise gluco-galacto-oligosaccharide preparations. In yet other embodiments, where the one or more feed sugars comprise xylose, glucose and galactose, the resulting oligosaccharide preparations comprise gluco-galacto-xylo-oligosaccharide preparations.

In some embodiments, each of the one or more feed sugars can be independently in its de-hydrate or hydrate form. In some embodiments, the one or more feed sugars comprise glucose, galactose, fructose, mannose, or any combination thereof, and wherein each of the glucose, galactose, fructose, or mannose is independently in its mono-hydrate or de-hydrate form. In some embodiments, the one or more feed sugars comprise a monosaccharide mono-hydrate such as glucose monohydrate. In some embodiments, the one or more feed sugars comprise a saccharide di-hydrate such as trehalose di-hydrate. In some embodiments, the one or more feed sugars comprise at least one sugar in its de-hydrate form and at least one sugar in its hydrate form.

In some embodiments, the one or more feed sugars can be provided as a sugar solution, in which the sugars are combined with water and fed into the reactor. In some embodiments, the sugars can be fed into the reactor in a solid form and combined with water in the reactor. In some embodiments, the one or more feed sugars are combined and mixed before the addition of water. In other embodiments, the one or more feed sugars are combined into water and mixed thereafter.

In some embodiments, the method comprises combining two or more feed sugars with the catalyst to produce an oligosaccharide preparation. In some embodiments, the two or more feed sugars comprise from glucose, galactose, fructose, mannose, lactose, or any combination thereof. In some embodiments, the method comprises combining a mixture of sugars (e.g., monosaccharides, disaccharides, and/or trisaccharides) with the catalyst to produce an oligosaccharide preparation. In other embodiments, the method comprises combining a mixture of sugars and sugar alcohols with the catalyst to produce an oligosaccharide preparation.

In some embodiments, the one or more feed sugars comprise functionalized or modified sugars. Functionalized or modified sugars may comprise amino sugars, sugar acids, sugar alcohols, sugar amides, sugar ethers, or any combination thereof. In some embodiments, amino sugars refer to sugar molecules in which a hydroxyl group is replaced with an amine group. Exemplary amino sugars include, but are not limited to, N-Acetyl-d-glucosamine, mannosamine, neuraminic acid, muramic acid, N-acetyl-neuramin, N-acetyl-muramic, N-acetyl-galactosamine, N-acetyl-mannosa, N-glycolylneuram, acarviosin, D-glucosamine, and D-galactosamine.

In embodiments, sugar acids refer to sugars with a carboxyl group. Exemplary sugar acids include, but are not limited to, aldonic acids (such as glyceric acid, xylonic acid, gluconic acid, and ascorbic acid), ulosonic acids (such as neuraminic acid and ketodeoxyoctulosonic acid), uronic acids (such as glucuronic acid, galacturonic acid, and iduronic acid), and aldaric acids (such as tartaric acid, mucic acid, and saccharic acid).

In some embodiments, sugar alcohols refer to sugar-derived polyols. Exemplary sugar alcohols include, but are not limited to, ethylene glycol, arabitol, glycerol, erythritol, threitol, xylitol, ribitol, mannitol, sorbitol, galactitol, fucitol, iditol, inositol, and volemitol.

In some embodiments, sugar amides refer to sugar molecules that contain a —C(═O)—N— group. In embodiments, sugar ethers refer to sugar molecules that contain an ether bond, such as glucosides.

In some embodiments, the functionalized or modified sugars comprise glucosamine, N-acetylglucosamine, glucuronic acid, galacturonic acid, glucitol, xylitol, mannitol, sorbitol. In some embodiments, the one of more feed sugars comprise deoxysugars, such as fucose, rhamnose, deoxyribose, or fuculose.

In some embodiments, a herein described method of manufacturing oligosaccharide preparation is performed at gram scale. In some embodiments, a herein described method of manufacturing oligosaccharide preparation is performed at kilogram or higher scale. Accordingly, in some embodiments, the method comprises heating an aqueous composition comprising one or more feed sugars at a quantity of more than 0.5, more than 1, more than 2, more than 3, more than 4, more than 5, more than 6, more than 7, more than 9, more than 10, more than 100, or more than 1000 kg. In some embodiments, the method comprises heating an aqueous composition comprising one or more feed sugars at a quantity of no more than 0.5, 1, 2, 3, 4, 5, 6, 7, 9, 10, 100, 1000, or 1500 kg. In some embodiments, the method comprises heating an aqueous composition comprising one or more feed sugars at a quantity of more than 1 kg.

B. Catalyst

In some embodiments, the catalyst provided herein comprises one or more acids. In some embodiments, the catalyst provided herein comprises mineral acid, carboxylic acid; amino acid; sulfonic acid; boronic acid; phosphonic acid; phosphinic acid; sulfuric acid; phosphoric acid; poly(styrene sulfonic acid-co-vinylbenzyl-imidazolium sulfate-co-divinylbenzene); poly(styrene sulfonic acid-co-divinylbenzene); (+)-camphor-10-sulfonic acid; 2-pyridinesulfonic acid; 3-pyridinesulfonic acid; 8-hydroxy-5-quinolinesulfonic acid hydrate; α-hydroxy-2-pyridinemethanesulfonic acid; (β)-camphor-10-sulfonic acid; butylphosphonic acid; diphenylphosphinic acid; hexylphosphonic acid; methylphosphonic acid; phenylphosphinic acid; phenylphosphonic acid; tert-butylphosphonic acid; SS)-VAPOL hydrogenphosphate; 6-quinolinesulfonic acid; β-(1-pyridinio)-1-propanesulfonate; 2-(2-pyridinyl)ethanesulfonic acid; β-(2-pyridyl)-5,6-diphenyl-1,2,4-triazine-p,p'-disulfonic acid monosodium salt hydrate; 1,1'-binaphthyl-2,2'-diyl-hydrogenphosphate; bis(4-methoxyphenyl)phosphinic acid; phenyl(3,5-xylyl)phosphinic acid; L-cysteic acid monohydrate; acetic acid; propionic acid; butanoic acid; glutamic acid; lysine; Ethanedisulfonic acid; Ethanesulfonic acid; Isethionic acid; Homocysteic acid; HEPBS (N-(2-Hydroxyethyl)piperazine-N'-(4-butanesulfonic acid)); HEPES (4-(2-hydroxyethyl)-1-piperazineethanesulfonic acid); 2-Hydroxy-3-morpholinopropanesulfonic acid; 2-(N-morpholino)ethanesulfonic acid; Methanesulfonic acid; Methaniazide; Naphthalene-1-sulfonic acid; Naphthalene-2-sulfonic acid; Perfluorobutanesulfonic acid; 6-sulfoquinovose; Triflic acid; 2-aminoethanesulfonic acid; Benzoic acid; Chloroacetic acid; Trifluoroacetic acid; Caproic acid; Enanthic acid; Caprylic acid; Pelargonic acid; Lauric acid; Pamitic acid; Stearic acid; Arachidic acid; Aspartic acid; Glutamic acid; Serine; Threonine; Glutamine; Cysteine; Glycine; Proline; Alanine; Valine; Isoleucine; Leucine; Methionine; Phenylalanine; Tyrosine; Tryptophan; polymeric acid; carbon-supported acid; or any combination thereof.

In some embodiments, the catalyst provided herein comprises: (+)-camphor-10-sulfonic acid; 2-pyridinesulfonic acid; 3-pyridinesulfonic acid; 8-hydroxy-5-quinolinesulfonic acid hydrate; α-hydroxy-2-pyridinemethanesulfonic acid; (β)-camphor-10-sulfonic acid; butylphosphonic acid; diphenylphosphinic acid; hexylphosphonic acid; methylphosphonic acid; phenylphosphinic acid; phenylphosphonic acid; tert-butylphosphonic acid; SS)-VAPOL hydrogenphosphate; 6-quinolinesulfonic acid, β-(1-pyridinio)-1-propanesulfonate; 2-(2-pyridinyl)ethanesulfonic acid; β-(2-pyridyl)-5,6-diphenyl-1,2,4-triazine-p,p'-disulfonic acid monosodium salt hydrate; 1,1'-binaphthyl-2,2'-diyl-hydrogenphosphate; bis(4-methoxyphenyl)phosphinic acid; phenyl(3,5-xylyl)phosphinic acid; L-cysteic acid monohydrate; poly(styrene sulfonic acid-co-divinylbenzene); lysine; Ethanedisulfonic acid; Ethanesulfonic acid; Isethionic acid; Homocysteic acid; HEPBS (N-(2-Hydroxyethyl)piperazine-N'-(4-butanesulfonic acid)); HEPES (4-(2-hydroxyethyl)-1-piperazineethanesulfonic acid); 2-Hydroxy-3-morpholinopropanesulfonic acid; 2-(N-morpholino)ethanesulfonic acid; Methanesulfonic acid; Methaniazide; Naphthalene-1-sulfonic acid; Naphthalene-2-sulfonic acid; Perfluorobutanesulfonic acid; 6-sulfoquinovose; Triflic acid; 2-aminoethanesulfonic acid; Benzoic acid; Chloroacetic acid; Trifluoroacetic acid; Caproic acid; Enanthic acid; Caprylic acid; Pelargonic acid; Lauric acid; Pamitic acid; Stearic acid; Arachidic acid; Aspartic acid; Glutamic acid; Serine; Threonine; Glutamine; Cysteine; Glycine; Proline; Alanine; Valine; Isoleucine; Leucine; Methionine; Phenylalanine; Tyrosine; Tryptophan; or any combination thereof.

In some embodiments, the catalyst provided herein is (+)-camphor-10-sulfonic acid. In some embodiments, the catalyst provided herein is 2-pyridinesulfonic acid. In some embodiments, the catalyst provided herein is 3-pyridinesulfonic acid. In some embodiments, the catalyst provided herein is 8-hydroxy-5-quinolinesulfonic acid hydrate. In some embodiments, the catalyst provided herein is α-hydroxy-2-pyridinemethanesulfonic acid. In some embodiments, the catalyst provided herein is (β)-camphor-10-sulfonic acid. In some embodiments, the catalyst provided herein is butylphosphonic acid. In some embodiments, the catalyst provided herein is diphenylphosphinic acid. In some embodiments, the catalyst provided herein is hexylphosphonic acid. In some embodiments, the catalyst provided herein is methylphosphonic acid. In some embodiments, the catalyst provided herein is phenylphosphinic acid. In some embodiments, the catalyst provided herein is phenylphosphonic acid. In some embodiments, the catalyst provided herein is tert-butylphosphonic acid. In some embodiments, the catalyst provided herein is SS)-VAPOL hydrogenphosphate. In some embodiments, the catalyst provided herein is 6-quinolinesulfonic acid. In some embodiments, the catalyst provided herein is β-(1-pyridinio)-1-propanesulfonate. In some embodiments, the catalyst provided herein is 2-(2-pyridinyl)ethanesulfonic acid. In some embodiments, the catalyst provided herein is β-(2-pyridyl)-5,6-diphenyl-1,2,4-triazine-p,p'-disulfonic acid monosodium salt hydrate. In some embodiments, the catalyst provided herein is 1,1'-binaphthyl-2,2'-diyl-hydrogenphosphate. In some embodiments, the catalyst provided herein is bis(4-methoxyphenyl) phosphinic acid. In some embodiments, the catalyst provided herein is phenyl(3,5-xylyl)phosphinic acid. In some embodiments, the catalyst provided herein is L-cysteic acid monohydrate. In some embodiments, the catalyst provided herein is poly(styrene sulfonic acid-co-divinylbenzene). In some embodiments, the catalyst provided herein is lysine.

In some embodiments, the catalyst is Ethanedisulfonic acid. In some embodiments, the catalyst is Ethanesulfonic acid. In some embodiments, the catalyst is Isethionic acid. In some embodiments, the catalyst is Homocysteic acid. In some embodiments, the catalyst is HEPBS (N-(2-Hydroxyethyl)piperazine-N'-(4-butanesulfonic acid)). In some embodiments, the catalyst is HEPES (4-(2-hydroxyethyl)-1-piperazineethanesulfonic acid). In some embodiments, the catalyst is 2-Hydroxy-3-morpholinopropanesulfonic acid. In some embodiments, the catalyst is 2-(N-morpholino) ethanesulfonic acid. In some embodiments, the catalyst is Methanesulfonic acid. In embodiments, the catalyst is Naphthalene-1-sulfonic acid. In some embodiments, the catalyst is some embodiments, the catalyst is Methaniazide. In some Naphthalene-2-sulfonic acid. In some embodiments, the catalyst is Perfluorobutanesulfonic acid. In some embodiments, the catalyst is 6-sulfoquinovose. In some embodiments, the catalyst is Triflic acid. In some embodiments, the catalyst is 2-aminoethanesulfonic acid. In some embodiments, the catalyst is Benzoic acid. In some embodiments, the catalyst is Chloroacetic acid. In some embodiments, the catalyst is Trifluoroacetic acid. In some embodiments, the catalyst is Caproic acid. In some embodiments, the catalyst is Enanthic acid. In some embodiments, the catalyst is Caprylic acid. In some embodiments, the catalyst is Pelargonic acid. In some embodiments, the catalyst is Lauric acid. In some embodiments, the catalyst is Pamitic acid. In some embodiments, the catalyst is Stearic acid. In some embodiments, the catalyst is Arachidic acid. In some embodiments, the catalyst is Aspartic acid. In some embodiments, the catalyst is Glutamic acid. In some embodiments, the catalyst is Serine. In some embodiments, the catalyst is Threonine. In some embodiments, the catalyst is Glutamine. In some embodiments, the catalyst is Cysteine. In some embodiments, the catalyst is Glycine. In some embodiments, the catalyst is Proline. In some embodiments, the catalyst is Alanine. In some embodiments, the catalyst is Valine. In some embodiments, the catalyst is Isoleucine. In some embodiments, the catalyst is Leucine. In some embodiments, the catalyst is Methionine. In some embodiments, the catalyst is Phenylalanine. In some embodiments, the catalyst is Tyrosine. In some embodiments, the catalyst is Tryptophan.

In some embodiments, the catalyst provided herein is a polymeric catalyst or a carbon-supported catalyst disclosed in WO 2016122887, which is hereby incorporated by reference in its entirety and for its disclosure.

In some embodiments, the catalyst provided herein is present in an amount of from about 0.01% to about 5%, from about 0.02% to about 4%, from about 0.03% to about 3%, or from about 0.05% to about 2% of the one or more feed sugars by dry weight. In some embodiments, the catalyst provided herein is present in an amount of from about 1% to 2% of the one or more feed sugars by dry weight. In some embodiments, the catalyst provided herein is present in an amount of about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, or about 3.0% of the one or more feed sugars by dry weight.

In some embodiments, the catalyst provided herein is present in an amount of from about 0.01% to about 5%, from about 0.02% to about 4%, from about 0.03% to about 3%, or from about 0.05% to about 2% of the aqueous composition by dry weight. In some embodiments, the catalyst provided herein is present in an amount of from about 1% to 2% of the aqueous composition by dry weight. In some embodiments, the catalyst provided herein is present in an amount of about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, or about 3.0% of the aqueous composition by dry weight.

In some embodiments, the catalyst provided herein is a combination of two or more different catalysts. In some embodiments, the catalyst comprises a recyclable catalyst such as resins and polymeric catalysts and a non-recyclable catalyst. In some embodiments, where the catalyst comprises at least two different catalysts, each of the catalyst is present in an amount provided herein. In other embodiments, where the catalyst comprises at least two different catalysts, the at least two different catalysts are present in aggregate in an amount provided herein.

In some embodiments, the catalyst is added into the aqueous composition in a dry form. In other embodiments, the catalyst is added into the aqueous composition in a wet form such as in an aqueous solution. In some embodiment, the catalyst is combined with the one or more feed sugars before the addition of water. In other embodiments, the catalyst is dissolved into water before its combining with the one or more feed sugars. In some embodiments, the method provided herein comprises producing an aqueous composition by combining the one or more feed sugars in the de-hydrate form and the catalyst in a wet form (e.g., as an aqueous solution).

C. Addition of Water

In some embodiments, the methods of manufacturing the oligosaccharide preparations comprise adding water to form the aqueous composition. In some embodiments, all or part of the water in the aqueous composition is added as free water. In other embodiments, all of the water in the aqueous composition is added as bonded water, for example, in saccharide mono- or di-hydrate. In some embodiments, all of the water in the aqueous composition is added as bonded water in monosaccharide mono-hydrate, such as glucose mono-hydrate. In certain embodiments, all or part of the water in the aqueous composition is added with the catalyst, i.e., via a catalyst solution.

D. Water Content

As the methods of manufacturing the oligosaccharide preparations proceed, water can be produced through reaction. For example, in some embodiments, water is produced (i) with the formation of a glycosidic bond, (ii) with the formation of an anhydro-subunit, or (iii) through other mechanisms or sources. As the sugar condensation and dehydration reactions both involve water, in some embodiments, the water content influences the composition of the oligosaccharide preparation.

Further, in some embodiments, water content influences the viscosity of the aqueous composition, which in turn may affect the effectiveness of mixing of the aqueous composition. For example, in some embodiments, an overly viscous aqueous composition can lead to an undesirable heterogeneous catalyst distribution in the aqueous composition. Moreover, in some embodiments, very low water content may lead to the solidification of the aqueous composition, which prevents effective mixing. On the other hand, in some other embodiments, exceedingly high water content may impede sugar condensation reaction and lower the level of the anhydro-subunits. Accordingly, the present disclosure describes suitable water content for the manufacturing of oligosaccharide preparations.

In some embodiments, a herein described method of manufacturing oligosaccharide preparation comprises forming and/or heating an aqueous composition. In some embodiments, the aqueous composition comprises from about 0% to about 80%, from about 0% to about 70%, from about 0% to about 60%, from about 0% to about 50%, from about 0% to about 40%, from about 0% to about 35%, from about 0% to about 30%, from about 0% to about 25%, from about 0% to about 20%, from about 0% to about 19%, from about 0% to about 18%, from about 0% to about 17%, from about 0% to about 16%, from about 0% to about 15%, from about 0% to about 14%, from about 0% to about 13%, from about 0% to about 12%, from about 0% to about 11%, from about 0% to about 10%, from about 0% to about 9%, from about 0% to about 8%, from about 0% to about 7%, from about 0% to about 6%, from about 0% to about 5%, from about 0% to about 4%, from about 0% to about 3%, from about 0% to about 2%, or from about 0% to about 1% of water by total weight. In some embodiments, the aqueous composition comprises from about 1% to about 20%, from about 1% to about 18%, from about 1% to about 16%, from about 1% to about 14%, from about 1% to about 12%, from about 1% to about 10%, from about 1% to about 8%, from about 1% to about 6%, or from about 1% to about 4% of water by total weight. In some embodiments, the aqueous composition comprises from about 3% to about 16%, from about 3% to about 14%, from about 3% to about 12%, from about 3% to about 10%, from about 3% to about 8%, from about 3% to about 6%, from about 5% to about 16%, from about 5% to about 14%, from about 5% to about 12%, from about 5% to about 10%, from about 7% to about 16%, from about 7% to about 14%, from about 7% to about 12%, from about 7% to about 10%, or from about 8% to about 10% of water by total weight. In some embodiments, the aqueous composition comprises about 1%, about 2%, about 3%, about 4%, about 5%, about 6%, about 7%, about 8%, about 9%, about 10%, about 11%, about 12%, about 13%, about 14%, or about 15% of water by total weight. In some embodiments, the aqueous composition comprises about 9% water by total weight. It should be understood, however, that the amount of water in the aqueous composition can be adjusted based on the reaction conditions and specific catalyst used.

In some embodiments, the water content in the aqueous composition as disclosed above is measured at the beginning of the reaction, for example, before heating the feed sugars. In some embodiments, the water content in the aqueous composition as disclosed above is measured at the end of the polymerization or condensation reaction. In some embodiments, the water content in the aqueous composition as disclosed above is measured as an average water content of the beginning of the reaction and at the end of the reaction.

In certain embodiments, a method described herein can further comprise monitoring the content of water present in the aqueous composition and/or the ratio of water to sugars or catalyst over a period of time. In some embodiments, the method further comprises removing at least a portion of water in the aqueous composition, for example, by distillation. Any method known in the art can be used to remove water from the aqueous composition, including, for example, by vacuum filtration, vacuum distillation, heating, steam, hot air, and/or evaporation.

In some embodiments, herein described oligosaccharide preparations are hygroscopic. Thus, in some embodiments, the hygroscopicity of the feed sugars and the oligosaccharides formed in the polymerization can affect the rate by which the water can be removed from the aqueous composition.

In some embodiments, a herein described method comprises removing at least a portion of water in the aqueous composition such that the water content in the aqueous composition is from about 1% to about 20%, from about 1% to about 18%, from about 1% to about 16%, from about 1% to about 14%, from about 1% to about 12%, from about 1% to about 10%, from about 1% to about 8%, from about 2% to about 16%, from about 2% to about 14%, from about 2% to about 12%, from about 2% to about 10%, from about 2% to about 8%, from about 2% to about 6%, from about 4% to about 16%, from about 4% to about 14%, from about 4% to about 12%, from about 4% to about 10%, from about 4% to about 8%, from about 6% to about 16%, from about 6% to about 12%, from about 6% to about 10%, or from about 6% to about 8% by total weight. In some embodiments, the method comprises removing at least a portion of water in the aqueous composition such that the water content in the aqueous composition is from about 2% to about 10%, from about 2% to about 8%, or from about 4% to about 8% by total weight. In some embodiments, the method comprises removing at least a portion of water in the aqueous composition such that the water content in the aqueous composition is about 2%, about 3%, about 4%, about 5%, about 6%, about 7%, about 8%, about 9%, or about 10% by total weight. In some embodiments, the method comprises removing at least a portion of water in the aqueous composition such that the water content in the aqueous composition is from about 4% to about 8% by total weight. In some embodiments, the method comprises removing at least a portion of water in the aqueous composition such that, at the end of the polymerization and/or condensation reaction, the water content in the aqueous composition is a water content as disclosed above. In some embodiments, the method comprises removing at least a portion of water in the aqueous composition such that, at the beginning of the polymerization and/or condensation reaction, the water content in the aqueous composition is a water content as disclosed above. In some embodiments, the method comprises removing at least a portion of water in the aqueous composition such that, the average water content in the aqueous composition at the beginning and the end of the polymerization and/or condensation reaction is within a range as disclosed above. In some embodiments, the method comprises removing at least a portion of water in the aqueous composition such that, throughout the polymerization and/or condensation reaction, the water content in the aqueous composition remains within a range as disclosed above.

In some embodiments, a herein described method comprises adding at least a portion of water in the aqueous composition such that the water content in the aqueous composition is from about 1% to about 20%, from about 1% to about 18%, from about 1% to about 16%, from about 1% to about 14%, from about 1% to about 12%, from about 1% to about 10%, from about 1% to about 8%, from about 2% to about 16%, from about 2% to about 14%, from about 2% to about 12%, from about 2% to about 10%, from about 2% to about 8%, from about 2% to about 6%, from about 4% to about 16%, from about 4% to about 14%, from about 4% to about 12%, from about 4% to about 10%, from about 4% to about 8%, from about 6% to about 16%, from about 6% to about 12%, from about 6% to about 10%, or from about 6% to about 8% by total weight. In some embodiments, the method comprises adding at least a portion of water in the aqueous composition such that the water content in the aqueous composition is from about 2% to about 10%, from about 2% to about 8%, or from about 4% to about 8% by total weight. In some embodiments, the method comprises adding at least a portion of water in the aqueous composition such that the water content in the aqueous is about 2%, about 3%, about 4%, about 5%, about 6%, about 7%, about 8%, about 9%, or about 10% by total weight. In some embodiments, the method comprises adding at least a portion of water in the aqueous composition such that the water content in the aqueous composition is from about 4% to about 8% by total weight.

In some embodiments, the method comprises adding at least a portion of water in the aqueous composition such that, at the end of the polymerization and/or condensation reaction, the water content in the aqueous composition is a water content as disclosed above. In some embodiments, the method comprises adding at least a portion of water in the aqueous composition such that, at the beginning of the polymerization and/or condensation reaction, the water content in the aqueous composition is a water content as disclosed above. In some embodiments, the method comprises adding at least a portion of water in the aqueous composition such that, the average water content in the aqueous composition at the beginning and the end of the polymerization and/or condensation reaction is within a range as disclosed above. In some embodiments, the method comprises adding at least a portion of water in the aqueous composition such that, throughout the polymerization and/or condensation reaction, the water content in the aqueous composition remains within a range as disclosed above.

In some embodiments, the degrees of polymerization of the oligosaccharides and/or the amount and type of the anhydro-subunits within the oligosaccharide preparation can be regulated by adjusting or controlling the content of water present in the aqueous composition throughout the manufacturing process. For example, in some embodiments, the degrees of polymerization of the oligosaccharides and the amount of the anhydro-subunits are increased by decreasing the water content.

Accordingly, in some embodiments, a herein described method comprises in-process control (IPC) of the water content, which can comprise monitoring water content, maintaining water content, increasing water content, decreasing water content, or any combination thereof. In some embodiments, an IPC process comprises maintaining the water content while the aqueous composition is heated to a temperature described herein. In some embodiments, the method comprises maintaining the water content for the time sufficient to induce polymerization. In some embodiments, the method comprises maintaining the water content within a disclosed range by either adding water or removing water from the aqueous composition, or both. In some embodiments, the method comprises maintaining the water content within a disclosed range by distillation. In some embodiments, the method comprises maintaining the water content within a disclosed range by vacuum distillation. In some embodiments, the method comprises maintaining the water content within a disclosed range by distillation under atmosphere pressure.

In some embodiments, the water content of the aqueous composition is maintained within a range of from about 1% to about 20%, from about 1% to about 18%, from about 1% to about 16%, from about 1% to about 14%, from about 1% to about 12%, from about 1% to about 10%, from about 1% to about 8%, from about 2% to about 16%, from about 2% to about 14%, from about 2% to about 12%, from about 2% to about 10%, from about 2% to about 8%, from about 2% to about 6%, from about 4% to about 16%, from about 4% to about 14%, from about 4% to about 12%, from about 4% to about 10%, from about 4% to about 8%, from about 6% to about 16%, from about 6% to about 12%, from about 6% to about 10%, or from about 6% to about 8% by total weight. In some embodiments, the water content of the aqueous composition is maintained within a range of from about 2% to about 10%, from about 2% to about 8%, or from about 4% to about 8% by total weight. In some embodiments, the water content of the aqueous composition is maintained within a range of from about 2% to about 8% by total weight.

The water content of the aqueous composition can be determined by a variety of analytical methods and instruments. In some embodiments, the water content is determined by an evaporation method (e.g., loss on drying technique), a distillation method, or a chemical reaction method (e.g., Karl Fischer titration). In some embodiments, the water content is determined by an analytical instrument such as a moisture analyzer. In some embodiments, the water content is determined by Karl Fischer titration.

In some embodiments, the water content of the aqueous composition is measured during the reaction and is used to implement in-process control (IPC) of the water content. In certain embodiments, the water content of the reaction is measured by Karl-Fisher titration, IR spectroscopy, NIR spectroscopy, conductivity, viscosity, density, mixing torque, or mixing energy. In some embodiments, the measurement of the water content of the reaction is used to control an apparatus that actively adjusts the water content of the reaction, such as a water addition pump or flow valve.

Figure 34:
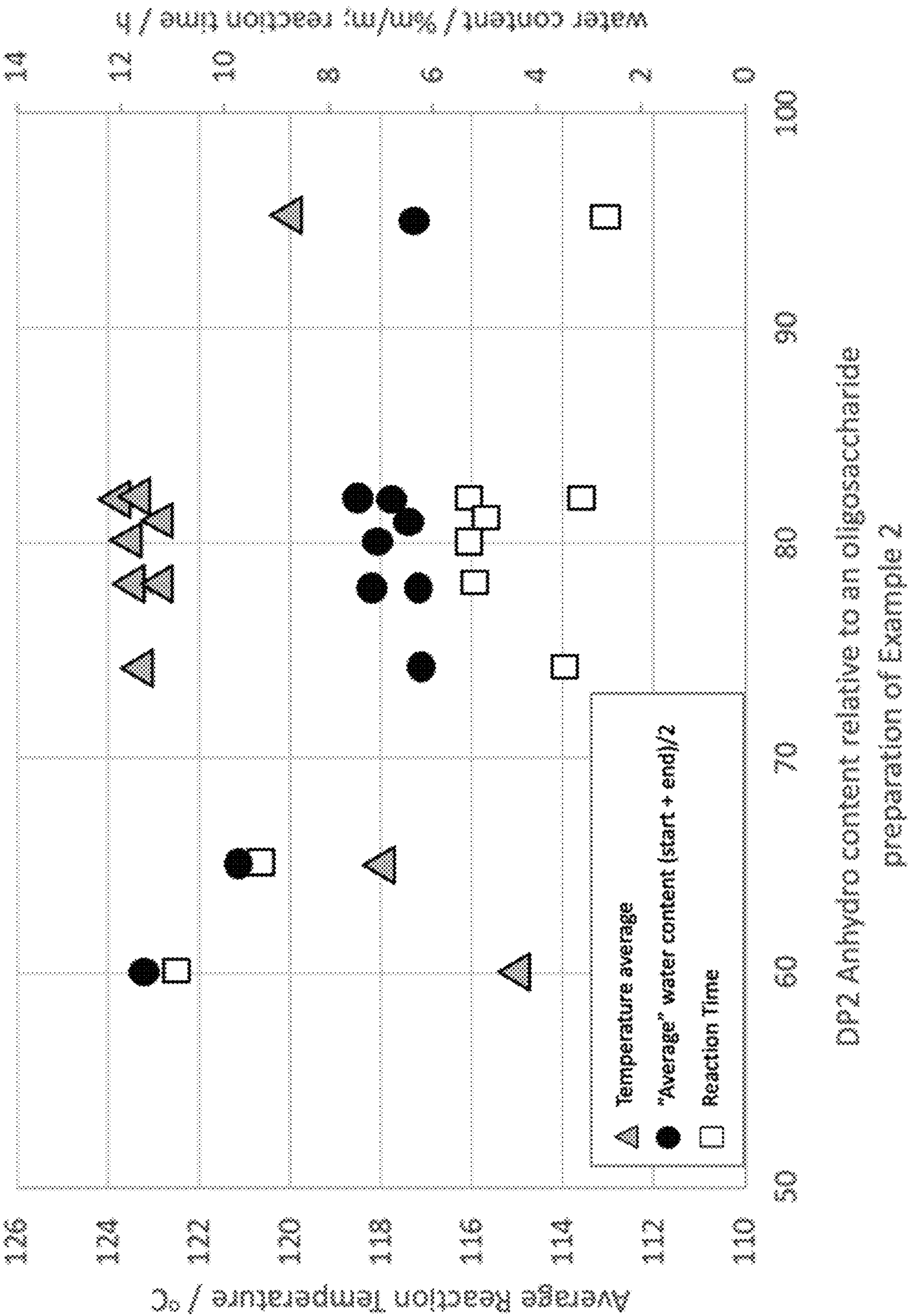
FIG. 34 illustrates the effect of reaction temperature, water content, and reaction time on the content of DP2 anhydro-subunit containing oligosaccharides in the oligosaccharide preparations, as compared to an oligosaccharide preparation according to Example 2.

Without being bound by theory, it is believed that water content during the sugar polymerization and/or condensation reaction can affect the level of the anhydro-subunits in a herein described oligosaccharide preparation. For example, as illustrated in FIG. 34, in some embodiments, a higher water content correlates with a lower level of anhydro-subunits. In some embodiments, a lower reaction temperature can correlate with a lower level of anhydro-subunits content.

E. Temperature

In some embodiments, the degrees of polymerization of the oligosaccharides and/or the amount and type of the anhydro-subunits within the oligosaccharide preparation can be regulated by adjusting the temperature, to which the aqueous composition is heated. In some embodiments, a herein described method of manufacturing an oligosaccharide preparation comprises heating the aqueous composition to a temperature of from about 80° C. to about 250° C., from about 90° C. to about 200° C., from about 100° C. to about 200° C., from about 100° C. to about 180° C., from about 110° C. to about 170° C., from about 120° C. to about 160° C., from about 130° C. to about 150° C., or from about 135° C. to about 145° C. In some embodiments, the method of manufacturing an oligosaccharide preparation comprises heating the aqueous composition to a temperature of from about 100° C. to about 200° C., from about 100° C. to about 180° C., from about 110° C. to about 170° C., from about 120° C. to about 160° C., from about 130° C. to about 150° C., or from about 135° C. to about 145° C. In some embodiments, the method of manufacturing an oligosaccharide preparation comprises heating the aqueous composition to a temperature of from about 135° C. to about 145° C. In other embodiments, the method of manufacturing an oligosaccharide preparation comprises heating the aqueous composition to a temperature of from about 125° C. to about 135° C.

F. Reaction Time

In some embodiments, a herein described method of manufacturing an oligosaccharide preparation comprises heating the aqueous composition for a sufficient time. In some embodiments, the degrees of polymerization of the oligosaccharides manufactured according to the methods described herein can be regulated by the reaction time.

In some embodiments, the sufficient time is prescribed by a number of hours. For example, in some embodiments, the sufficient time is at least 30 minutes, at least 1 hour, at least 2 hours, at least 3 hours, at least 4 hours, at least 5 hours, at least 6 hours, at least 7 hour, at least 8 hours, at least 9 hours, or at least 10 hours. In some embodiments, the sufficient time is from about 1 to about 24 hours, from about 1 to about 16 hours, from about 1 to about 8 hours, from about 1 to about 4 hours, from about 1 to about 3 hours, from about 1 to about 2 hours, from about 2 to about 12 hours, from about 2 to about 10 hours, from about 2 to about 8 hours, from about 2 to about 6 hours, from about 2 to about 4 hours, from about 3 to about 8 hours, from about 3 to about 6 hours, from about 3 to about 5 hours, or from about 3 to about 4 hours.

In some embodiments, the sufficient time is determined by measuring one or more chemical or physical properties of the oligosaccharide preparation, for example, water content, viscosity, molecular weight, anhydro-subunit content, and/or the distribution of degrees of polymerization.

In some embodiments, the molecular weight of the oligosaccharide preparation is monitored during polymerization. In some embodiments, the method comprises heating the aqueous composition for a time sufficient for the aqueous composition to reach a number average molecular weight or weight average molecular weight as described herein. In certain embodiments, the method comprises heating the aqueous composition for a time sufficient for the aqueous composition to reach a number average molecular weight within a range of from about 300 to about 5000 g/mol, from about 500 to about 5000 g/mol, from about 700 to about 5000 g/mol, from about 500 to about 2000 g/mol, from about 700 to about 2000 g/mol, from about 700 to about 1500 g/mol, from about 300 to about 1500 g/mol, from about 300 to about 2000 g/mol, from about 400 to about 1000 g/mol, from about 400 to about 900 g/mol, from about 400 to about 800 g/mol, from about 500 to about 900 g/mol, or from about 500 to about 800 g/mol. In certain embodiments, the method comprises heating the aqueous composition for a time sufficient for the aqueous composition to reach a number average molecular weight of from about 500 to about 2000 g/mol. In certain embodiments, the method comprises heating the aqueous composition for a time sufficient for the aqueous composition to reach a weight average molecular weight within a range of from about 300 to about 5000 g/mol, from about 500 to about 5000 g/mol, from about 700 to about 5000 g/mol, from about 500 to about 2000 g/mol, from about 700 to about 2000 g/mol, from about 700 to about 1500 g/mol, from about 300 to about 1500 g/mol, from about 300 to about 2000 g/mol, from about 400 to about 1300 g/mol, from about 400 to about 1200 g/mol, from about 400 to about 1100 g/mol, from about 500 to about 1300 g/mol, from about 500 to about 1200 g/mol, from about 500 to about 1100 g/mol, from about 600 to about 1300 g/mol, from about 600 to about 1200 g/mol, or from about 600 to about 1100 g/mol. In certain embodiments, the method comprises heating the aqueous composition for a time sufficient for the aqueous composition to reach a weight average molecular weight of from about 700 to about 3000 g/mol.

In some embodiments, the sufficient time is the time required for the aqueous composition to reach reaction equilibrium at the respective reaction temperature. Accordingly, in some embodiments, the method comprises heating the aqueous composition for a time sufficient for the aqueous composition to reach equilibrium. For example, in some embodiments, the equilibrium is determined by measuring the molecular weight, viscosity, or DP distribution of the aqueous composition.

In certain embodiments, the equilibrium is determined by measuring the number average or weight average molecular weight of the aqueous composition. In some embodiments, the equilibrium is determined by the number or weight average molecular weight of the aqueous composition that remains essentially unchanged over time. In some embodiments, the equilibrium is determined by a change of the number or weight average molecular weight of the aqueous composition that is less than certain percentage over a period of time. In some embodiments, the molecular weight of the aqueous composition is measured by HPLC or SEC.

In some embodiments, the equilibrium is determined by a change of the number or weight average molecular weight of the aqueous composition of less than 25%, less than 20%, less than 15%, less than 10%, or less than 5% over a period of time. In some embodiments, the equilibrium is determined by a change of the number or weight average molecular weight of the aqueous composition over a period of 3 hours, 2 hours, 1 hour, 30 minutes, 20 minutes, or 10 minutes. In some embodiments, the equilibrium is determined by a change of the weight average molecular weight of the aqueous composition of less than 15% over the period of 1 hour.

In certain embodiments, the equilibrium is determined by measuring the viscosity of the aqueous composition. In some embodiments, the equilibrium is determined by the viscosity of the aqueous composition that remains essentially unchanged over time. In some embodiments, the equilibrium is determined by a change of the viscosity of the aqueous composition that is less than certain percentage over a period of time. In some embodiments, the viscosity of the aqueous composition is measured by a viscometer or rheometer.

In some embodiments, the equilibrium is determined by a change of the viscosity of the aqueous composition of less than 25%, less than 20%, less than 15%, less than 10%, or less than 5% over a period of time. In some embodiments, the equilibrium is determined by a change of the viscosity of the aqueous composition over a period of 3 hours, 2 hours, 1 hour, 30 minutes, 20 minutes, or 10 minutes. In some embodiments, the equilibrium is determined by a change of the viscosity of the aqueous composition of less than 15% over the period of 1 hour.

In certain embodiments, the equilibrium is determined by measuring the DP distribution of the aqueous composition. In some embodiments, the equilibrium is determined by the DP distribution of the aqueous composition that remains essentially unchanged over time. In some embodiments, a change of the DP distribution of the aqueous composition is determined by calculating a series of Km, wherein $$Km = \frac{[DP_m][H_2O]}{[DP_{m-1}][DP1]},$$

wherein $[H_2O]$ represents the molar water concentration (mol/L), and [DP1], $[DPm-_1]$, and [DPm] represent the molar concentrations of oligosaccharides (mol/L) in the DP1, $DPm-_1$, and DPm fraction, respectively. For example, K2 equals $[DP2][H_2O]/[DP1][DP1]$ according to the above formula. In some embodiments, m is an integer larger than 1 and less than n. In some embodiments, m is an integer larger than 1 and less than or equal to n. In some embodiments, m equals n. In some embodiments, m is 2, 3, 4, 5, 6, 7, 8, 9, or 10.

In some embodiments, the concentration of the oligosaccharides in the DP1, DPm−1, and DPm fractions are determined by SEC, HPLC, FFF, A4F, mass spectrometry, or any other suitable method. In some embodiments, the concentration of the oligosaccharides in the DP1, DPm−1, and DPm fractions are determined by SEC such as GPC. In some embodiments, the concentration of the oligosaccharides in the DP1, DPm−1, and DPm fractions are determined by mass spectrometry such as GC-MS, LC-MS/MS, and MALDI-MS. In some embodiments, the concentration of the oligosaccharides in the DP1, DPm−1, and DPm fractions are determined by HPLC. In some embodiments, the water concentration is determined by an evaporation method (e.g., loss on drying technique), a distillation method, or by a chemical reaction method (e.g., Karl Fischer titration). In some embodiments, the water concentration is determined by any suitable analytical instrument such as a moisture analyzer.

In some embodiments, the method comprises calculating a series of at least 3, at least 4, at least 5, at least 6, at least 7, at least 8, at least 9, at least 10, at least 15, at least 20, at least 30, at least 40, or at least 50 Km numbers. In some embodiments, the method comprises calculating a series of at least 3, at least 4, at least 5, at least 6, at least 7, at least 8, at least 9, at least 10, or at least 15 Km numbers. In some embodiments, the method comprises calculating about 3, 4, 5, 6, 7, 8, 9, 10, or 15 Km numbers. In some embodiments, the method comprises calculating K2 to K4, K2 to K5, K2 to K6, K2 to K7, K2 to K8, K2 to K9, K2 to K10, K2 to K11, K2 to K12, K2 to K13, K2 to K14, K2 to K15, K3 to K5, K3 to K6, K3 to K7, K3 to K8, K3 to K9, K3 to K10, K3 to K11, K3 to K12, K3 to K13, K3 to K14, or K3 to K15. In certain embodiments, the method comprises calculating K2 to K4 or K3 to K5.

In some embodiments, the value of Km depends on the temperature, water concentration, and/or the amount and type of the feed sugars. In some embodiments, Km is from about 0.1 to about 100, from about 0.1 to about 90, from about 0.1 to about 80, from about 0.1 to about 70, from about 0.1 to about 60, from about 0.1 to about 50, from about 0.1 to about 40, from about 0.1 to about 30, from about 0.1 to about 25, from about 0.1 to about 20, or from about 0.1 to about 15. In some embodiments, Km is from about 1 to about 100, from about 1 to about 90, from about 1 to about 80, from about 1 to about 70, from about 1 to about 60, from about 1 to about 50, from about 1 to about 40, from about 1 to about 30, from about 1 to about 25, from about 1 to about 20, from about 1 to about 15, from about 1 to about 10, from about 5 to about 50, from about 5 to about 40, from about 5 to about 30, from about 5 to about 20, from about 5 to about 15, or from about 5 to about 10. In some specific embodiments, Km is from about 1 to about 15 or from about 5 to about 15.

In some embodiments, an average, a standard deviation, and/or a relative standard deviation are determined for the series of Km calculated. As used herein, a relative standard deviation is expressed in percentage, and is obtained by multiplying the standard deviation by 100 and dividing this product by the average.

In some embodiments, the equilibrium is determined by the relative standard deviation of the series of Km of less than 30%, less than 25%, less than 20%, less than 15%, less than 10%, less than 9%, less than 8%, less than 7%, less than 6%, less than 5%, less than 4%, less than 3%, less than 2%, or less than 1%. In some embodiments, the equilibrium is determined by the relative standard deviation of the series of Km of less than 15%, less than 10%, or less than 5%.

G. Post-Reaction Steps

In some embodiments, a herein described method of manufacturing oligosaccharide preparations further comprises one or more additional processing steps after heating the aqueous composition at a temperature and for a sufficient time. In some embodiments, the additional processing steps comprise, for example, separation (such as chromatographic separation), dilution, concentration, drying, filtration, demineralization, extraction, decolorization, or any combination thereof. For example, in some embodiments, the method comprises a dilution step and a decolorization step. In some embodiments, the method comprises a filtration step and a drying step.

In some embodiments, the method comprises a dilution step, where water is added into the oligosaccharide preparation to make a syrup of oligosaccharide preparation. In some embodiments, the concentration of oligosaccharide preparation in the syrup is from about 5% to about 80%, from about 10% to about 70%, from about 10% to about 60%, from about 10% to about 50%, from about 10% to about 40%, from about 10% to about 30%, or from about 15% to about 25%. In other embodiments, the method does not comprise a dilution step, but rather, the oligosaccharide preparation is allowed to solidify. In some embodiments, the method comprises a filtration step. In some embodiments, the method comprises recycling the catalyst by filtration.

In some embodiments, the method described herein further comprises a decolorization step. In some embodiments, the oligosaccharide preparation may undergo a decolorization step using any method known in the art, including, for example, treatment with an absorbent, activated carbon, chromatography (e.g., using ion exchange resin), hydrogenation, and/or filtration (e.g., microfiltration).

In some embodiments, the oligosaccharide preparation is contacted with a material to remove salts, minerals, and/or other ionic species. In certain embodiments, the oligosaccharide preparation is flowed through an anionic/cationic exchange column pair. In one embodiment, the anionic exchange column contains a weak base exchange resin in a hydroxide form and the cationic exchange column contains a strong acid exchange resin in a protonated form.

In some embodiments, the method comprises a concentration step. In some embodiments, the centration step produces an oligosaccharide preparation with increased concentration. For example, in some embodiments, the concentration step comprises evaporation (e.g., vacuum evaporation), drying (e.g., freeze-drying and spray drying) or any combination thereof.

In some embodiments, the method comprises an isolation step, wherein at least a portion of the oligosaccharide preparation is separated. In some embodiments, the isolation step comprises crystallization, precipitation, filtration (e.g., vacuum filtration), and centrifugation, or any combination thereof.

In some embodiments, the method comprises a separation step. In some embodiments, the separation step comprises separating at least a portion of the oligosaccharide preparation from at least a portion of the catalyst, from at least a portion of the unreacted feed sugars, or from both. In some embodiments, the separation step comprises filtration, chromatography, differential solubility, precipitation, extraction, or centrifugation.

H. Reactors

The methods described herein can comprise the use of one or more reactors suitable for sugar condensation, considering the reaction temperature, pH, pressure, and other factors. In some embodiments, the one or more suitable reactors comprise a fed-batch stirred reactor, a batch stirred reactor, a continuous flow stirred reactor, a continuous plug-flow column reactor, an attrition reactor, or a reactor with stirring induced by an electromagnetic field. In some embodiments, the one or more suitable reactors comprise a reactor described in Ryu, S. K., and Lee, J. M., Bioconversion of waste cellulose by using an attrition bioreactor, Biotechnol. Bioeng. 25: 53-65(1983); Gusakov, A. V., and Sinitsyn, A. P., Kinetics of the enzymatic hydrolysis of cellulose: 1. A mathematical model for a batch reactor process, Enz. Microb. TechnoL, 7: 346-352 (1985); Gusakov, A. V., Sinitsyn, A. P., Davydkin, I. Y., Davydkin, V. Y., Protas, O. V., Enhancement of enzymatic cellulose hydrolysis using a novel type of bioreactor with intensive stirring induced by electromagnetic field, Appl. Biochem. Biotechnol., 56: 141-153(1996); or Fernanda de Castilhos Corazza, Flavio Faria de Moraes, Gisella Maria Zanin and Ivo Neitzel, Optimal control in fed-batch reactor for the cellobiose hydrolysis, Acta Scientiarum. Technology, 25: 33-38 (2003).

In some embodiments, the one or more suitable reactors comprise fluidized bed, upflow blanket, immobilized, or extruder type reactors for hydrolysis and/or fermentation. In some embodiments, the one or more suitable reactors comprise an open reactor, a closed reactor, or both. In some embodiments, where the method comprises a continuous process, the one or more suitable reactors can include a continuous mixer such as a screw mixer.

Process

In some embodiments, a herein described method of manufacturing oligosaccharide preparations comprises a batch process, a continuous process, or both. In some embodiments, the method of manufacturing the oligosaccharide preparation comprises a batch process. For example, in some embodiments of the batch process, manufacturing of subsequent batches of the oligosaccharide preparation does not start until the completion of the current batch. In some embodiments, during the batch process, all or a substantial amount of oligosaccharide preparation is removed from the reactor. In some embodiments, during the batch process, all the feed sugars and the catalyst are combined in a reactor before the aqueous composition is heated to the described temperature or before the polymerization is induced. In some embodiments, during the batch process, the feed sugars are added before, after, or simultaneous with the addition of the catalyst.

In some embodiments, the batch process is a fed-batch process, wherein all the feed sugars are not added into the reactor at the same time. In some embodiments of the fed-batch process, at least a portion of the feed sugars are added into the reactor during polymerization or after the aqueous composition is heated to the described temperature. In some embodiments of the fed-batch process, at least 10%, 20%, 30%, 40%, 50%, or 60% by weight of the feed sugars are added into the reactor during polymerization or after the aqueous composition is heated to the described temperature.

In some embodiments, the method of manufacturing the oligosaccharide preparation comprises a continuous process. For example, in some embodiments of the continuous process, the contents of the reactor continuously flow through the reactor. In some embodiments, the combination of the feed sugars with the catalyst and the removal of at least a portion of the oligosaccharide preparation are performed concurrently.

In some embodiments, the method of manufacturing the oligosaccharide preparation comprises a single-pot or multi-pot process. For example, in some embodiments of the single-pot process, the polymerization is performed in a single reactor. For another example, in some embodiments of the multi-pot process, the polymerization is performed in more than one reactor. In some embodiments of the multi-pot process, the method comprises 2, 3, or more reactors. In some embodiments of the multi-pot process, the method comprises a combination step, where the polymerization products from two or more reactors are combined.

I. Process

In some embodiments, the method of manufacturing the oligosaccharide preparation comprises a batch process, a continuous process, or both. In some embodiments, the method of manufacturing the oligosaccharide preparation comprises a batch process. For example, in some embodiments of the batch process, manufacturing of subsequent batches of the oligosaccharide preparation does not start until the completion of the current batch. In some embodiments, during the batch process, all or a substantial amount of oligosaccharide preparation is removed from the reactor. In some embodiments, during the batch process, all the feed sugars and the catalyst are combined in a reactor before the aqueous composition is heated to the described temperature or before the polymerization is induced. In some embodiments, during the batch process, the feed sugars are added before, after, or simultaneous with the addition of the catalyst.

In some embodiments, the batch process is a fed-batch process, wherein all the feed sugars are not added into the reactor at the same time. In some embodiments of the fed-batch process, at least a portion of the feed sugars are added into the reactor during polymerization or after the aqueous composition is heated to the described temperature. In some embodiments of the fed-batch process, at least 10%, 20%, 30%, 40%, 50%, or 60% by weight of the feed sugars are added into the reactor during polymerization or after the aqueous composition is heated to the described temperature.

In some embodiments, the method of manufacturing the oligosaccharide preparation comprises a continuous process. For example, in some embodiments of the continuous process, the contents of the reactor continuously flow through the reactor. In some embodiments, the combination of the feed sugars with the catalyst and the removal of at least a portion of the oligosaccharide preparation are performed concurrently.

In some embodiments, the method of manufacturing the oligosaccharide preparation comprises a single-pot or multi-pot process. For example, in some embodiments of the single-pot process, the polymerization is performed in a single reactor. For another example, in some embodiments of the multi-pot process, the polymerization is performed in more than one reactor. In some embodiments of the multi-pot process, the method comprises 2, 3, or more reactors. In some embodiments of the multi-pot process, the method comprises a combination step, where the polymerization products from two or more reactors are combined.

IV. Nutritional Compositions Comprising Oligosaccharide Preparations

Provided herein are nutritional compositions comprising an oligosaccharide preparation. In certain embodiments, provided herein are nutritional compositions comprising a described oligosaccharide preparation, wherein the presence and/or concentration of the oligosaccharide preparation within the nutritional compositions may be selectively determined and/or detected. Oligosaccharide preparations, which exhibit complex functional modulation of a microbial community, may be important components of nutritional compositions. Thus, the presence and/or concentration of an oligosaccharide preparation within nutritional compositions may be one of the factors that need to be measured in the quality control and manufacturing process of the nutritional compositions. Accordingly, the provided nutritional compositions are advantageous in terms of quality control and manufacturing purposes as the presence and/or concentration of the oligosaccharide preparation may be selectively determined and/or detected. For example, in some embodiments, the presence and concentration of the oligosaccharide preparation may be determined and/or detected by measuring a signal associated with the anhydro-subunit containing oligosaccharides.

In some embodiments, the nutritional composition is an animal feed composition. In some embodiments, the nutritional composition comprises a base nutritional composition.

A. Base Nutritional Compositions

In some embodiments, the base nutritional composition comprises a carbohydrate source that is different from the oligosaccharide preparation. For example, in some embodiments, the base nutritional composition comprises a naturally occurring carbohydrate source such as starch and plant fibers. In some embodiments, the base nutritional composition comprises starch. In some embodiments, the base nutritional composition comprises plant fibers.

In some embodiments, the base nutritional composition comprises one or more carbohydrate sources that are derived from: seeds, roots, tubers, corn, tapioca, arrowroot, wheat, rice, potatoes, sweet potato, sago, beans (e.g., favas, lentils, mung beans, peas, and chickpeas.), maize, cassava, or other starchy foods (e.g., acorns, arrowroot, arracacha, bananas, barley, breadfruit, buckwheat, *canna*, colacasia, katakuri, kudzu, malanga, millet, oats, oca, polynesian arrowroot, sorghum, rye, taro, chestnuts, water chestnuts, and yams).

In some embodiments, the base nutritional composition comprises one or more carbohydrate sources that are derived from: legumes (e.g., peas, soybeans, lupins, green beans, and other beans), oats, rye, chia, barley, fruits (e.g., figs, avocados, plums, prunes, berries, bananas, apple skin, quinces, and pears), vegetables (e.g., broccoli, carrots, cauliflower, zucchini, celery, nopal, and Jerusalem artichokes), root tubers, root vegetables (e.g., sweet potatoes and onions), psyllium seed husks, seeds (e.g., flax seeds), nuts (e.g., almonds), whole grain foods, wheat, corn bran, lignans, or any combination thereof. In some embodiments, the base nutritional composition comprises one or more plant fibers derived from wheat bran, sugar beet pulp, fuzzy cottonseeds, soy hulls, or any combination thereof.

In some embodiments, the base nutritional composition comprises less than 500 ppm, less than 400 ppm, less than 300 ppm, less than 200 ppm, less than 100 ppm, less than 50 ppm, less than 10 ppm, less than 5 ppm, or less than 1 ppm anhydro-subunits or anhydro-subunit containing oligosaccharides. In some embodiments, the base nutritional composition comprises less than 50 ppm, less than 10 ppm, less than 5 ppm, or less than 1 ppm anhydro-subunits or anhydro-subunit containing oligosaccharides. In some embodiments, the base nutritional composition is essentially free of anhydro-subunits.

In some embodiments, the base nutritional composition lacks a detectable level of anhydro-subunits. Depending on the methods of detecting or determination, an anhydro-subunit level below a certain threshold can be undetectable. For example, in some embodiments, a detectable level of anhydro-subunit can refer to at least 1000 ppm, at least 500 ppm, at least 400 ppm, at least 300 ppm, at least 200 ppm, at least 100 ppm, at least 50 ppm, at least 10 ppm, at least 5 ppm, or at least 1 ppm of anhydro-subunit or anhydro-subunit containing oligosaccharides in the base nutritional composition.

In some embodiments, the base nutritional composition comprises a plurality of oligosaccharides. In some embodiments, the base nutritional composition comprises a glycosidic bond type distribution that is different from the oligosaccharide preparation. For example, in some embodiments, the base nutritional composition comprises a higher percentage of α-(1,4) glycosidic linkages than the oligosaccharide preparation. In some embodiments, the glycosidic linkages such as the α-(1,4) glycosidic linkages in the base nutritional compositions are digestible by one or more enzymes. In some embodiments, the glycosidic linkages in the base nutritional composition are more readily digestible and/or hydrolysable than the glycosidic linkages in the oligosaccharide preparation.

In some embodiments, the level of α-(1,2) glycosidic linkage, α-(1,3) glycosidic linkage, α-(1,6) glycosidic linkage, β-(1,2) glycosidic linkage, β-(1,3) glycosidic linkage, β-(1,4) glycosidic linkage, or β-(1,6) glycosidic linkage in the base nutritional composition is at least 2%, at least 3%, at least 4%, at least 5%, at least 6%, at least 7%, at least 8%, at least 9%, at least 10%, at least 11%, at least 12%, at least 13%, at least 14%, or at least 15% lower than the level of the respective glycosidic linkage in the oligosaccharide preparation. In some embodiments, the level of α-(1,2) glycosidic linkage, α-(1,3) glycosidic linkage, α-(1,6) glycosidic linkage, β-(1,2) glycosidic linkage, β-(1,3) glycosidic linkage, β-(1,4) glycosidic linkage, or β-(1,6) glycosidic linkage in the base nutritional composition is at least 10% lower than the level of the respective glycosidic linkage in the oligosaccharide preparation.

In some embodiments, the level of α-(1,4) glycosidic linkage in the base nutritional composition is at least 50%, at least 40%, at least 35%, at least 30%, at least 25%, at least 20%, at least 15%, at least 10%, at least 5%, or at least 2% higher than the level of α-(1,4) glycosidic linkage in the oligosaccharide preparation. In some embodiments, the level of α-(1,4) glycosidic linkage in the base nutritional composition is at least 10% higher than the level of α-(1,4) glycosidic linkage in the oligosaccharide preparation.

B. Animal Feed Composition

Depending on the type and age of an animal, a nutritional composition can comprise the oligosaccharide preparation and the base nutritional composition at different ratio. For example, the oligosaccharide preparation may be combined with the base nutritional composition at various ratios suitable for the type and age of an animal. In some embodiments, the oligosaccharide preparation is present in the nutritional composition at a concentration of from about 1 to about 10000 ppm, from about 1 to about 5000 ppm, from about 1 to about 3000 ppm, from about 1 to about 2000 ppm, from about 1 to about 1500 ppm, from about 1 to about 1000 ppm, from about 1 to about 500 ppm, from about 1 to about 250 ppm, from about 1 to about 100 ppm, from about 10 to about 5000 ppm, from about 10 to about 3000 ppm, from about 10 to about 2000 ppm, from about 10 to about 1500 ppm, from about 10 to about 1000 ppm, from about 10 to about 500 ppm, from about 10 to about 250 ppm, from about 10 to about 100 ppm, from about 50 to about 5000 ppm, from about 50 to about 3000 ppm, from about 50 to about 2000 ppm, from about 50 to about 1500 ppm, from about 50 to about 1000 ppm, from about 50 to about 500 ppm, from about 50 to about 250 ppm, from about 50 to about 100 ppm, from about 100 to about 5000 ppm, from about 100 to about 3000 ppm, from about 100 to about 2000 ppm, from about 100 to about 1500 ppm, from about 100 to about 1000 ppm, from about 100 to about 500 ppm, from about 100 to about 400 ppm, from about 100 to about 300 ppm, from about 100 to about 200 ppm, from about 200 to about 5000 ppm, from about 200 to about 3000 ppm, from about 200 to about 2500 ppm, from about 200 to about 2000 ppm, from about 200 to about 1500 ppm, from about 200 to about 1000 ppm, from about 200 to about 500 ppm, from about 500 to about 5000 ppm, from about 500 to about 3000 ppm, from about 500 to about 2500 ppm, from about 500 to about 2000 ppm, from about 500 to about 1500 ppm, or from about 500 to about 1000 ppm. In some embodiments, the oligosaccharide preparation is present in the nutritional composition at a concentration of from about 1 to about 5000 ppm, from about 1 to about 1000 ppm, from about 1 to about 500 ppm, from about 10 to about 5000 ppm, from about 10 to about 2000 ppm, from about 10 to about 1000 ppm, from about 10 to about 500 ppm, from about 10 to about 250 ppm, from about 10 to about 100 ppm, from about 50 to about 5000 ppm, from about 50 to about 2000 ppm, from about 50 to about 1000 ppm, from about 50 to about 500 ppm, from about 50 to about 250 ppm, or from about 50 to about 100 ppm. In some embodiments, the oligosaccharide preparation is present in the nutritional composition at a concentration of from about 1 to about 5000 ppm, from about 10 to about 1000 ppm, from about 10 to about 500 ppm, or from about 50 to about 500 ppm.

In some embodiments, the oligosaccharide preparation is present in the nutritional composition at a concentration of greater than 10 ppm, greater than 50 ppm, greater than 100 ppm, greater than 200 ppm, greater than 300 ppm, greater than 400 ppm, greater than 500 ppm, greater than 600 ppm, greater than 1000 ppm, or greater than 2000 ppm. In some embodiments, the oligosaccharide preparation is present in the nutritional composition at a concentration of greater than 10 ppm, greater than 50 ppm, greater than 100 ppm, greater than 200 ppm, or greater than 500 ppm.

In some embodiments, depending on the type and age of an animal, the nutritional composition can further comprise proteins, minerals (such as copper, calcium, and zinc), salts, essential amino acids, vitamins, and/or antibiotics.

Also provided herein is a method of administering a nutritional composition comprising a base nutritional composition and the disclosed oligosaccharide preparation to an animal. In some embodiments, the animal is selected from cattle (e.g., beef cattle and dairy cattle), swine, aquatic animal, and poultry. In some embodiments, the animal is swine, such as sows, piglets, and hogs. In other embodiments, the animal is poultry such as chicken, duck, turkey, goose, quail, and hen. In embodiments, the poultry is a broiler, a breeder, or a layer. In some embodiments, the animal is an aquatic animal such salmon, catfish, bass, eel, tilapia, flounder, shrimp, and crab. In some embodiments, the nutritional composition is administered to an animal in a dry form, a liquid form, a paste, or a combination thereof. In some embodiments, the form of administration, the feeding rate, and the feeding schedule can vary depending on the type and age of the animal.

C. Methods of Producing Nutritional Compositions

Provided herein are methods of manufacturing a nutritional composition comprising: combining an oligosaccharide preparation with a base nutritional composition. In some embodiments, the oligosaccharide preparation comprises anhydro-subunit containing oligosaccharides. In some embodiments, the oligosaccharide preparation comprises a glycosidic bond type distribution that is different from that of the base nutritional composition.

In some embodiments, the oligosaccharide preparation is a synthetic oligosaccharide preparation. In some embodiments, the synthetic oligosaccharide preparation comprises at least n fractions of oligosaccharides each having a distinct degree of polymerization selected from 1 to n (DP1 to DPn fractions). In some embodiments, n is an integer greater than or equal to 2. In some embodiments, n is an integer greater than 2. In some embodiments, n is an integer greater than or equal to 3. In some embodiments, n is an integer within a range of 1 to 100, such as 4, 5, 6, 7, 8, 9, 10, 11, 12, 13, 14, 15, 16, 17, 18, 19, 20, 21, 22, 23, 24, 25, 26, 27, 28, 29, 30, 40, or 50. In some embodiments, each of the DP1 to DPn fraction comprises from 0.1% to 90% anhydro-subunit containing oligosaccharides by relative abundance as measured by mass spectrometry. In some embodiments, the DP1 and DP2 fractions of the oligosaccharide preparation each independently comprises from about 0.1% to about 15% or from about 0.5% to about 10% of anhydro-subunit containing oligosaccharides by relative abundance as measured by mass spectrometry. In some embodiments, the DP1 and DP2 fractions of the oligosaccharide preparation each independently comprises anhydro-subunit containing oligosaccharides within a range of from about 0.1%, 0.5%, 0.6%, 0.7%, 0.8%, 0.9%, 1%, 1.1%, 1.2%, 1.3%, 1.4%, or 1.5% to about 8%, 9%, 10%, 11%, 12%, 15% or 20% by relative abundance as measured by mass spectrometry. In some embodiments, the relative abundance of oligosaccharides in each of the n fractions decreases monotonically with its degree of polymerization. In some embodiments, the relative abundance of oligosaccharides in at least 5, 10, 20, or 30 DP fractions decreases monotonically with its degree of polymerization.

In some embodiments, the method of manufacturing a nutritional composition comprises mixing the oligosaccharide preparation with the base nutritional composition. For example, in some embodiments, the mixing may be performed by an industrial blender and/or mixer such as drum blender, double cone blender, ribbon blender, V blender, shear mixer, and paddle mixer.

In some embodiments, the method of manufacturing a nutritional composition further comprises a herein described quality control step. In some embodiments, the herein described quality control step comprises determining a level of a signal in a sample of the nutritional composition and calculating a concentration of the oligosaccharide preparation in the nutritional composition based on the level of the signal. In some embodiments, the herein described quality control step comprises detecting a signal in a sample of the nutritional composition through analytical instrumentation, and accepting or rejecting a batch of the nutritional composition based on the presence or absence of the signal. In some embodiments, the herein described quality control step comprises detecting, through analytical instrumentation, the presence or absence of a first signal in a first sample of the nutritional composition, and a second signal in a second sample of the nutritional composition, and comparing the first signal and the second signal. In some embodiments, the signal, the first signal, and/or the second signal is/are (i) indicative of one or more anhydro-subunit containing oligosaccharides, (ii) associated with a degree of polymerization (DP) distribution of oligosaccharides, or (iii) associated with α-(1,2) glycosidic linkage, α-(1,3) glycosidic linkage, α-(1,6) glycosidic linkage, β-(1,2) glycosidic linkage, β-(1,3) glycosidic linkage, β-(1,4) glycosidic linkage, or β-(1,6) glycosidic linkage of oligosaccharides.

Additionally, in some embodiments, the method of manufacturing a nutritional composition comprises, after performing the quality control step, further mixing the oligosaccharide preparation with the base nutritional composition, adjusting the level of the oligosaccharide preparation, or a combination thereof. In some embodiments, adjusting the level of the oligosaccharide preparation comprises adding additional oligosaccharide preparation into the nutritional composition or removing a portion of the oligosaccharide preparation from the nutritional composition. In some embodiments, adjusting the level of the oligosaccharide preparation comprises adding additional base nutritional composition into the nutritional composition or removing a portion of the base nutritional composition from the nutritional composition. In some particular embodiments, adjusting the level of the oligosaccharide preparation comprises adding additional oligosaccharide preparation into the nutritional composition.

D. Animal Feed Pre-Mix

In some embodiments, the nutritional composition comprises an animal feed pre-mix comprising a described oligosaccharide preparation.

In some embodiments, the animal feed pre-mix comprises a carrier material, which may be combined with the oligosaccharide preparation to produce the animal feed pre-mix. In some embodiments, the carrier material may be any material in dry or liquid form that is suitable to be combined with the oligosaccharide preparation in the nutritional composition. In some embodiments, the carrier material comprises dried distiller's grains, clay, vermiculite, diatamacious earth, hulls such as ground rice hulls and ground oat hulls, silica such as feed grade silica gel and feed grade fumed silica, corn such as corn gluten feed, corn gluten meal, and milled corn, or any combinations thereof. In some embodiments, the carrier material is milled corn. In other embodiments, the carrier material is ground rice hulls or ground oat hulls.

In some embodiments, the animal feed pre-mix is produced by combining a carrier material with the oligosaccharide preparation, both in a dry form. In some embodiments, the animal feed pre-mix is produced by combining a carrier material with the oligosaccharide preparation; one of the two is in a dry form. In some embodiments, the animal feed pre-mix is produced by combining a carrier material with the oligosaccharide preparation, both in a liquid form. For example, in some embodiments, an oligosaccharide preparation in a liquid form refers to the oligosaccharide in a solution, e.g., an aqueous solution of the oligosaccharides such as syrup.

In some embodiments, the animal feed pre-mix is produced by combining a carrier material with a syrup comprising the oligosaccharide preparation. In some embodiments, the concentration of the oligosaccharide preparation in the syrup is at least 40%, at least 45%, at least 50%, at least 55%, at least 60%, at least 65%, at least 70%, at least 75%, or at least 80% by weight. In some embodiments, the concentration of the oligosaccharide preparation in the syrup is about from 40% to 80%, 50% to 75%, or 60% to 70% by weight.

In some embodiments, the animal feed pre-mix is in a powder (e.g., flowable powder), a slush, a slurry, a pellets form, or a liquid form. In some embodiments, the animal feed pre-mix has a moisture content of less than 40%, 30%, 20%, 15%, 10%, or 5% by weight. In some embodiments, the animal feed pre-mix has a moisture content of less than 10% or 5% by weight. In some embodiments, the animal feed pre-mix has a moisture content of higher than 5%, 10%, 15%, 20%, 25%, or 30% by weight. In further embodiments, the moisture content of the animal feed pre-mix is adjusted to any of the described ranges. For example, in some embodiments, the animal feed pre-mix is dried to increase its moisture content to a described range.

In some embodiments, depending on a specific application, the animal feed pre-mix comprises various levels of the oligosaccharide preparation. In some embodiments, the animal feed pre-mix comprises at least 1%, 5%, 10%, 15%, 20%, 25%, 30%, 40%, 50%, 60%, 70%, 80%, 90%, 95%, or 99% the oligosaccharide preparation by dry weight. In some embodiments, the animal feed pre-mix comprises at most 50%, 60%, 70%, 80%, 90%, 95%, or 99% the oligosaccharide preparation by dry weight.

In some embodiments, the animal feed pre-mix or the carrier material further comprises other animal nutrition such as minerals, fats, and proteins. In some embodiments, the carrier material or the animal feed pre-mix comprises copper, zinc, or both. In some embodiments, the carrier material or the animal feed pre-mix comprises an ionophore or other coccidiostat. In some embodiments, the carrier material or the animal feed pre-mix comprises an antibiotic. In some embodiments, the carrier material comprises a carbohydrate source. In some embodiments, the carbohydrate source in the carrier material does not comprise anhydro-subunits. In some embodiments, the carbohydrate source in the carrier material comprises a glycosidic bond type distribution that is different from the glycosidic bond type distribution of the oligosaccharide preparation.

Accordingly, in some embodiments, the method of manufacturing a nutritional composition comprises combining the animal feed pre-mix with the base nutritional composition.

V. Methods of Providing Oligosaccharide Preparations to Animals

In some embodiments, the methods described herein include providing oligosaccharide preparations to animals. In certain variations, animals are treated by being fed or provided an oligosaccharide preparation. In some embodiments, the animals are provided an oligosaccharide preparation at an intended specific dose. A specific dose may be quantified, for example, as the mass of oligosaccharide preparation consumed by the animal per unit of time (e.g., grams per day), or as the mass of oligosaccharide preparation consumed by the animal per unit of time per unit animal body mass (e.g., mg of oligosaccharide per kg of body mass per day). In certain embodiments, the specific dose of an oligosaccharide preparation is 1, 5, 10, 15, 20, 25, 30, 40, 50, 60, 70, 80, 90, 100, 110, 120, 130, 140, 150, 160, 170, 180, 190, 200, 225, 250, 275, 300, 350, 400, 450, 500, 1000, 1500, 2000, 3000, 4000, 5000, or 10000 mg/kg/day. In some embodiments, the mass of the oligosaccharide preparation is measured as the DP1+ content on a dry solids basis. In some embodiments, the mass of the oligosaccharide preparation is measured as the DP2+ content on a dry solids basis.

In some embodiments, animals are provided oligosaccharide preparations by oral administration via nutritional compositions. In some embodiments, the nutritional composition is formulated to contain an oligosaccharide preparation at a fixed concentration or level of inclusion. The oligosaccharide concentration or level of inclusion in the nutritional composition can be quantified by, for example, the mass fraction of the oligosaccharide preparation per total mass of the final feed or nutritional composition. In some embodiments, the concentration or level of inclusion is measured in parts per million (ppm) of oligosaccharide on a dry solids basis per final nutritional composition on an as-is basis. In some embodiments, the concentration of the oligosaccharide preparation is measured as the mass fraction of DP1+ species on a dry solids basis. In some embodiments, the concentration of the oligosaccharide preparation is measured as the mass fraction of DP2+ species on a dry solids basis.

One of ordinary skill in the art would know various methods and techniques for determining the concentration of the oligosaccharide preparation in the nutritional composition or final feed to achieve an intended specific dose. For example, average daily feed intake as a functional of age is established for different species of broiler chickens and might be used by a nutritionist or veterinarian to determine a desired level of inclusion in final feed.

In some embodiments, animals are provided oligosaccharide preparations by oral administration via consumed liquids. In some embodiments, the oligosaccharide preparations are provided via drinking water. In some embodiments, the concentration of the oligosaccharide preparation in the drinking water is selected to provide an intended specific dose of oligosaccharide preparation to the animal.

VI. Selectively Modulating Growth of Gastrointestinal Microbes

A. Selectively Promoting the Growth of Beneficial Gastrointestinal Microbes

In some embodiments, the methods described herein include selectively enhancing or promoting the growth of one or more microbial (e.g., bacterial) species in the gastrointestinal tract of an animal and in some embodiments quantifying the level of the one or more microbial (e.g., bacterial) species. In some embodiments, the make-up of the gastrointestinal microbiota of an animal is shifted by the oligosaccharide preparation toward that of a healthy state. In some embodiments, the microbial (e.g., bacterial) species is beneficial to the animal (e.g., beneficial to the health).

In some embodiments, the microbial species is an archaea species. In some embodiments, the microbial species is bacteria, virus, bacteriophage, parasite, fungi or protozoan species. In some embodiments, the microbial species is a bacterial species.

Bacteria disclosed herein include, but are not limited to, organisms classified as genera *Bacteroides, Odoribacter, Oscillibacter, Subdoligranulum, Biophila, Barnesiella*, or *Ruminococcus*. Exemplary bacteria also include, but are not limited to, organisms classified as genera *Enterococcus, Lactobacillus, Propionibacterium, Bifidobacterium*, or *Streptococcus*.

Microbial species include, but are not limited to, *Bacteroides clarus, Bacteroides dorei, Odoribacter splanchinicus*, and *Barnesiella intestinihominis*.

In some embodiments, the animal has a gastrointestinal microbiota comprising at least 0.1%, 1%, 2%, 3%, 4%, 5%, 6%, 7%, 8%, 9%, 10%, 15%, 20%, 25%, 30%, 35%, 40%, 45%, or 50% of at least one microbial species classified as genera *Bacteroides, Odoribacter, Oscillibacter, Subdoligranulum, Biophila, Barnesiella*, or *Ruminococcus* (e.g., as measured in a gastrointestinal sample as disclosed herein). In some embodiments, the animal has a gastrointestinal microbiota comprising at least 0.1%, 1%, 2%, 3%, 4%, 5%, 6%, 7%, 8%, 9%, 10%, 15%, 20%, 25%, 30%, 35%, 40%, 45%, or 50% of at least one microbial species classified as genera *Enterococcus, Lactobacillus, Propionibacterium, Bifidobacterium*, or *Streptococcus* (e.g., as measured in a gastrointestinal sample as disclosed herein).

In some embodiments, the animal has a gastrointestinal microbiota comprising at least 0.1%, 1%, 2%, 3%, 4%, 5%, 6%, 7%, 8%, 9%, 10%, 15%, 20%, 25%, 30%, 35%, 40%, 45%, or 50% of at least one of *Bacteroides clarus, Bacteroides dorei, Odoribacter splanchinicus*, or *Barnesiella intestinihominis* (e.g., as measured in a gastrointestinal sample as disclosed herein).

In some embodiments, the animal has a gastrointestinal microbiota comprising at least 0.1%, 1%, 2%, 3%, 4%, 5%, 6%, 7%, 8%, 9%, 10%, 15%, 20%, 25%, 30%, 40%, or 50% of a combination of one or more microbial species classified as genera *Bacteroides, Odoribacter, Oscillibacter, Subdoligranulum, Biophila, Barnesiella*, or *Ruminococcus* (e.g., as measured in a gastrointestinal sample as disclosed herein). In some embodiments, the animal has a gastrointestinal microbiota comprising at least 0.1%, 1%, 2%, 3%, 4%, 5%, 6%, 7%, 8%, 9%, 10%, 15%, 20%, 25%, 30%, 40%, or 50% of a combination of one or more microbial species classified as genera *Enterococcus, Lactobacillus, Propionibacterium,*

*Bifidobacterium*, or *Streptococcus* (e.g., as measured in a gastrointestinal sample as disclosed herein).

In some embodiments, the animal has a gastrointestinal microbiota comprising at least 0.1%, 1%, 2%, 3%, 4%, 5%, 6%, 7%, 8%, 9%, 10%, 15%, 20%, 25%, 30%, 40%, or 50% of a combination of one or more of *Bacteroides clarus, Bacteroides dorei, Odoribacter splanchinicus*, or *Barnesiella intestinihominis* (e.g., as measured in a gastrointestinal sample as disclosed herein).

B. Selectively Inhibiting Growth of Pathogenic Gastrointestinal Microbes

In certain embodiments, the methods described herein include selectively reducing or inhibiting the growth of one or more microbial (e.g., bacterial) species in the gastrointestinal tract of an animal and in some embodiments quantifying the level of the one or more microbial (e.g., bacterial) species. In some embodiments, the microbial (e.g., bacterial) species is detrimental to the animal (e.g., detrimental to the health of the animal). In some embodiments, the microbial (e.g., bacterial) species is pathogenic to the animal. In some embodiments, the microbial (e.g., bacterial) species is pathogenic to humans but not to animals. In some embodiments, the make-up of the gastrointestinal microbiota of an animal is shifted by the oligosaccharide preparation toward that of a healthy state.

In some embodiments, the microbial species is an archaea species. In some embodiments, the microbial species is bacteria, virus, bacteriophage, parasite, fungi or protozoan species. In some embodiments, the microbial species is a bacterial species.

Bacteria disclosed herein include, but are not limited to, bacteria of the phylum Proteobacteria. Bacteria also include, but are not limited to, organisms classified as genera *Helicobacter, Escherichia, Salmonella, Vibrio*, or *Yersinia*. Exemplary bacteria also include, but are not limited to, organisms classified as genera *Treponema, Streptococcus, Staphylococcus, Shigella, Rickettsia, Orientia, Pseudomonas, Neisseria, Mycoplasma, Mycobacterium, Listeria, Leptospira, Legionella, Klebsiella, Haemophilus, Francisella, Ehrlichia, Enterococcus, Coxiella, Corynebacterium, Clostridium, Chlamydia, Chlamydophila, Campylobacter, Burkholderia, Brucella, Borrelia, Bordetella, Bifidobacterium*, and *Bacillus*. Microbial species include, but are not limited to, *Helicobacter pullorum, Proteobacteria johnsonii, Escherichia coli, Campylobacter jejuni*, and *Lactobacillus crispatus*. Microbial species also include, but are not limited to, *Aeromonas hydrophila, Campylobacter fetus, Plesiomonas shigelloides, Bacillus cereus, Campylobacter jejuni, Clostridium botulinum, Clostridium difficile, Clostridium perfringens*, enteroaggregative *Escherichia coli*, enterohemorrhagic *Escherichia coli*, enteroinvasive *Escherichia coli*, enterotoxigenic *Escherichia coli, Helicobacter pylori, Klebsiellia pneumonia, Lysteria monocytogenes, Plesiomonas shigelloides, Salmonella* spp., *Salmonella typhi, Salmonella paratyphi, Shigella* spp., *Staphylococcus* spp., *Staphylococcus aureus*, vancomycin-resistant *enterococcus* spp., *Vibrio* spp., *Vibrio cholerae, Vibrio parahaemolyticus, Vibrio vulnificus*, and *Yersinia enterocolitica*. In some embodiments, the bacterium is singe or multi drug resistant.

In some embodiments, the animal has a gastrointestinal microbiota comprising less than 50%, 40%, 30%, 20%, 15%, 10%, 9%, 8%, 7%, 6%, 5%, 4%, 3%, 2%, 1% or 0.1% bacteria classified as genera *Helicobacter, Proteobacteria, Escherichia, Campylobacter*, or *Lactobacillus* (e.g., as measured in a gastrointestinal sample as disclosed herein). In some embodiments, the combination of bacteria classified as genera *Helicobacter, Proteobacteria, Escherichia, Campylobacter*, or *Lactobacillus* is less than 50%, 40%, 30%, 20%, 15%, 10%, 9%, 8%, 7%, 6%, 5%, 4%, 3%, 2%, 1% or 0.1% of the gastrointestinal microbiota of the animal (e.g., as measured in a gastrointestinal sample as disclosed herein).

In some embodiments, the animal has a gastrointestinal microbiota comprising less than 50%, 40%, 30%, 20%, 15%, 10%, 9%, 8%, 7%, 6%, 5%, 4%, 3%, 2%, 1% or 0.1% *Helicobacter pullorum, Proteobacteria johnsonii, Escherichia coli, Campylobacter jejuni*, or *Lactobacillus crispatus* (e.g., as measured in a gastrointestinal sample as disclosed herein). In some embodiments, the combination of *Helicobacter pullorum, Proteobacteria johnsonii, Escherichia coli, Campylobacter jejuni*, or *Lactobacillus crispatus* is less than 50%, 40%, 30%, 20%, 15%, 10%, 9%, 8%, 7%, 6%, 5%, 4%, 3%, 2%, 1% or 0.1% of the gastrointestinal microbiota of the animal (e.g., as measured in a gastrointestinal sample as disclosed herein).

C. Sampling and Detecting Gastrointestinal Microbes

In certain embodiments, the methods described herein include detecting or quantifying one or more microbial (e.g., bacterial) species in the gastrointestinal microbiota of an animal. In certain embodiments, the microbial (e.g., bacterial) species is detected or quantified in a gastrointestinal microbiota sample from an animal. Gastrointestinal microbiota samples can be obtained from an animal in any standard form which reflects the microbial contents of the gastrointestinal tract of the animal. Gastrointestinal microbiota samples include gastrointestinal tissue samples obtained e.g., by endoscopic biopsy. Gastrointestinal tissues include, e.g., oral tissue, esophagus, stomach, intestine, ileum, cecum, colon or rectum. Samples also feces, saliva, and gastrointestinal ascites. Methods of obtaining gastrointestinal microbiota samples are standard and known to the skilled artisan.

In some embodiments, the sample is a single sample from a single animal. In some embodiments, the sample is a combination of multiple samples from a single animal. In some embodiments, microbes (e.g., bacteria (e.g., total bacteria)) are purified from the sample prior to analysis. In some embodiments, microbes (e.g., bacteria) from a single sample are purified. In some embodiments, microbes (e.g., bacteria) from multiple samples from a single animal are purified and subsequently combined prior to analysis.

In some embodiments, total DNA or total RNA is isolated from the sample. Genomic DNA can be extracted from samples using standard methods known to the skilled artisan and including commercially available kits, such as the Mo Bio Powersoil®-htp 96 Well Soil DNA Isolation Kit (Mo Bio Laboratories, Carlsbad, CA), the Mo Bio Powersoil® DNA Isolation Kit (Mo Bio Laboratories, Carlsbad, CA), or the QIAamp DNA Stool Mini Kit (QIAGEN, Valencia, CA) according to the manufacturer's instructions. RNA can be extracted from samples using standard assays known to the skilled artisan including commercially available kits, such as the RNeasy PowerMicrobiome Kit (QIAGEN, Valencia, CA) and RiboPure Microbial RNA Purification Kit (Life Technologies, Carlsbad, CA). Another method for isolation of microbial (e.g., bacterial) RNA may involve enrichment of mRNA in purified samples of microbial RNA through removal of tRNA. Alternatively, RNA may be converted to cDNA, which can be used to generate sequencing libraries using standard methods such as the Nextera XT Sample Preparation Kit (Illumina, San Diego, CA).

Identification and determination of the relative abundance of a microbial (bacterial) species in a sample may be determined by standard molecular biology methods known to the skilled artisan, including e.g., genetic analysis (e.g.

DNA sequencing (e.g., full genome sequencing, whole genome shotgun sequencing (WSG)), RNA sequencing, PCR, quantitative PCR (qPCR)), serology and antigen analysis, microscopy, metabolite identification, gram staining, flow cytometry, immunological techniques, and culture based methods such as counting colony forming units.

In some embodiments, identification and relative abundance of a microbial (e.g., bacterial) species is determined by whole genome shot gun sequencing (WGS), wherein extracted DNA is fragmented into pieces of various lengths (from 300 to about 40,000 nucleotides) and directly sequenced without amplification. Sequence data can be generated using any sequencing technology including for example, but not limited to Sanger, Illumina, 454 Life Sciences, Ion Torrent, ABI, Pacific Biosciences, and/or Oxford Nanopore.

Sequencing libraries for microbial whole-genome sequencing (WGS) may be prepared from microbial (e.g., bacterial) genomic DNA. For genomic DNA that has been isolated from an animal sample, the DNA may optionally be enriched for microbial DNA using commercially available kits, for example, the NEBNext Microbiome DNA Enrichment Kit (New England Biolabs, Ipswich, MA) or other enrichment kit. Sequencing libraries may be prepared from the genomic DNA using commercially available kits as well, such as the Nextera Mate-Pair Sample Preparation Kit, TruSeq DNA PCR-Free or TruSeq Nano DNA, or the Nextera XT Sample Preparation Kit (Illumina, San Diego, CA) according to the manufacturer's instructions.

Alternatively, libraries can be prepared using other kits compatible with the Illumina sequencing platform, such as the NEBNext DNA Library Construction Kit (New England Biolabs, Ipswich, MA). Libraries may then be sequenced using standard sequencing technology including, but not limited to, a MiSeq, HiSeq or NextSeq sequencer (Illumina, San Diego, CA).

Alternatively, a whole genome shotgun fragment library prepared using standard methods in the art may be used. For example, the shotgun fragment library could be constructed using the GS FLX Titanium Rapid Library Preparation Kit (454 Life Sciences, Branford, CT), amplified using a GS FLX Titanium emPCR Kit (454 Life Sciences, Branford, CT), and sequenced following standard 454 pyrosequencing protocols on a 454 sequencer (454 Life Sciences, Branford, CT).

Nucleic acid sequences can be analyzed to define taxonomic assignments using sequence similarity and phylogenetic placement methods or a combination of the two strategies. A similar approach can be used to annotate protein names, protein function, transcription factor names, and any other classification schema for nucleic acid sequences. Sequence similarity based methods include BLAST, BLASTx, tBLASTn, tBLASTx, RDP-classifier, DNAclust, RapSearch2, DIAMOND, USEARCH, and various implementations of these algorithms such as QIIME or Mothur. These methods map a sequence read to a reference database and select the best match. Common databases include KEGG, MetaCyc, NCBI non-redundant database, Greengenes, RDP, and Silva for taxonomic assignments. For functional assignments, reads are mapped to various functional databases such as COG, KEGG, BioCyc, MetaCyc, and the Carbohydrate-Active Enzymes (CAZy) database. Microbial clades are assigned using software including MetaPhlAn.

In some embodiments, the microbial constituents are identified by characterizing the DNA sequence of microbial 16S small subunit ribosomal RNA gene (16S rRNA gene). 16S rRNA gene is approximately 1,500 nucleotides in length, and in general is highly conserved across organisms, but contain specific variable and hypervariable regions (V1-V9) that harbor sufficient nucleotide diversity to differentiate species- and strain-level taxa of most organisms. These regions in bacteria are defined by nucleotides 69-99, 137-242, 433-497, 576-682, 822-879, 986-1043, 1117-1173, 1243-1294 and 1435-1465 respectively using numbering based on the *E. coli* system of nomenclature.

Composition of a microbial community can be deduced by sequencing full 16S rRNA gene, or at least one of the VI, V2, V3, V4, V5, V6, V7, V8, and V9 regions of this gene or by sequencing of any combination of variable regions from this gene (e.g. V1-3 or V3-5). In one embodiment, the VI, V2, and V3 regions are used to characterize a microbiota. In another embodiment, the V3, V4, and V5 regions are used to characterize a microbiota. In another embodiment, the V4 region is used to characterize a microbiota.

Sequences that are at least 97% identical to each other are grouped into Operational Taxonomic Units (OTUs). OTUs that contain sequences with 97% similarity correspond to approximately species level taxa. At least one representative sequence from each OTU is chosen and is used to obtain a taxonomic assignment for an OTU by comparison to a reference database of highly curated 16S rRNA gene sequences (such as Greengenes or SILVA databases). Relationship between OTUs in a microbial community could be deduces by constructing a phylogenetic tree from representative sequences from each OTU. Using known techniques, in order to determine the full 16S sequence or the sequence of any variable region of the 16S sequence, genomic DNA is extracted from a microbial sample, the 16S rRNA (full region or specific variable regions) amplified using polymerase chain reaction (PCR), the PCR products are cleaned, and nucleotide sequences delineated to determine the genetic composition of 16S rRNA gene or a variable region of the gene. If full 16S sequencing is performed, the sequencing method used may be, but is not limited to, Sanger sequencing. If one or more variable regions is used, such as the V4 region, the sequencing can be, but is not limited to being performed using the Sanger method or using a next-generation sequencing method, such as an Illumina method. Primers designed to anneal to conserved regions of 16S rRNA genes (e.g., the 515F and 805R primers for amplification of the V4 region) could contain unique barcode sequences to allow characterizing multiple microbial communities simultaneously.

In addition to the 16S rRNA gene, a selected set of genes that are known to be marker genes for a given species or taxonomic group is analyzed to assess the composition of a microbial community. These genes are alternatively assayed using a PCR-based screening strategy. For example, various strains of pathogenic *Escherichia coli* are distinguished using genes that encode heat-labile (LTI, LTIIa, and LTIIb) and heat-stable (STI and STII) toxins, verotoxin types 1, 2, and 2e (VT1, VT2, and VT2e, respectively), cytotoxic necrotizing factors (CNF1 and CNF2), attaching and effacing mechanisms (eaeA), enteroaggregative mechanisms (Eagg), and enteroinvasive mechanisms (Einv).

The optimal genes to utilize to determine the taxonomic composition of a microbial community by use of marker genes are familiar to one with ordinary skill in the art of sequence based taxonomic identification.

In some embodiments, the identity of the microbial composition is characterized by identifying nucleotide markers or genes, in particular highly conserved genes (e.g., "housekeeping" genes), or a combination thereof. Using defined methods, DNA extracted from a microbial sample will have specific genomic regions amplified using PCR and sequenced to determine the nucleotide sequence of the amplified products.

D. Microbial Gene Transcription

In certain embodiments, the methods described herein include promoting expression of one or more microbial (e.g., bacterial) protein in the gastrointestinal tract of an animal. In some embodiments, the microbial protein is a bacterial protein. In certain embodiments the microbial (e.g., bacterial) protein is a hydrolytic enzyme, a protein involved in digestion (e.g. hydrolytic enzymatic digestion), or a protein involved in metabolism. Microbial proteins include, but are not limited to, a carbohydrate active enzyme (CAZymes), a sus-like polysaccharide utilization loci (PULs) protein, GH127 (CAZyme α-L-arabinofuranosidase), susC (outer membrane protein involved in starch binding) and susD (starch binding protein).

Microbial (e.g., bacterial) proteins described herein can be detected and quantified using standard molecular biology techniques. For example, the level of expression on a microbial protein can be detected in a gastrointestinal sample of an animal by RNA (e.g. RNA sequencing, shotgun sequencing, quantitative PCR) or protein expression (e.g. ELISA, western blot, other immunological techniques).

VII. Methods of Enhancing Animal Performance

A. Feed Conversion Ratio

In some embodiments, the methods described herein include reducing the feed conversion ratio of an animal. In some embodiments, an animal administered a synthetic oligosaccharide preparation, a nutritional composition, an animal feed pre-mix, or an animal feed composition as described herein has a lower feed conversion ratio compared to an animal provided a diet that does not include the synthetic oligosaccharide preparation. As used herein the term "feed conversion ratio (FCR)," refers to the ratio of feed mass input (for example consumed by the animal) to the animal output, wherein the animal output is the target animal product. For example, the animal output for dairy animals is milk, whereas the animal output for animals raised for meat is body mass.

In some embodiments, the animal is raised for meat, and the target animal output is body mass. Thus, in some embodiments, the FCR refers to the ratio of the weight of feed consumed compared to the final body weight of the animal prior to processing. In some embodiments, the FCR refers to the ratio of the weight of feed consumed compared to the final body weight gain of the animal prior to processing. It should be understood that FCR may be measured for an animal or population of animals over different time periods. For example, in some embodiments, the FCR is an FCR over the entire lifetime of the animal. In other embodiments, the FCR is a daily FCR, or a weekly FCR, or a cumulative FCR measured up until a particular moment in time (for example, a particular day).

A person of skill in the art would recognize that the performance target minimum FCR (optimal FCR) may be different for different types of animals and may be different for different breeds of one type animal (for example, different breeds of broiler chickens, or different breeds of swine). The performance target minimum FCR may also be different depending on age of the animal (for example, chickens or swine in a grower phase compared to a finisher phase), or the sex of the animal. It should be clear that the optimal FCR may be different depending on any combination of these factors.

Performance target minimum generally refers to the lowest feed efficiency observed for a given animal and breed under ideal growing conditions, ideal animal health, and ideal dietary nutrition. It is well known to one skilled in the art that under common growing conditions, an animal may not achieve the performance target minimum FCR. An animal may not achieve its performance target minimum FCR due to a variety of health, nutrition, environmental, and/or community influences. An animal may not achieve its performance target minimum FCR when raised in a challenged environment, which may include, for example, environmental pathogenic stress, excessive environmental temperature (heat stress), excessive environmental humidity, crowding, or other social interaction effects, such as difficulty accessing feed or drinking water. In some embodiments, an animal may not achieve its performance target minimum FCR due to disease or environmental pathogenic stress. In other embodiments, an animal may not achieve its performance target minimum FCR due to excessive environmental temperature (heat stress), or excessive environmental humidity. In yet other embodiments, an animal may not achieve its performance target minimum FCR due to crowding, or other social interaction effects, such as difficulty accessing feed or drinking water.

In some embodiments, an animal provided a diet which does not include the synthetic oligosaccharide preparation described herein has an FCR that is at least 1%, 2%, 3%, 4%, 5%, 6%, 7%, 8%, 9%, or 10% higher than the performance target minimum FCR. In certain embodiments, an animal provided a diet which does not include a synthetic oligosaccharide preparation described herein has an FCR that is 1% to 10% higher than the performance target minimum, 2% to 10% higher than the performance target minimum, or 5% to 10% higher than the performance target minimum.

In some embodiments, an animal provided a nutritional composition comprising a synthetic oligosaccharide preparation, a nutritional composition, an animal feed pre-mix, or an animal feed composition as described herein has an FCR that is closer to the performance target minimum compared to an animal provided a diet that does not include the synthetic oligosaccharide preparation. In particular embodiments, the animal provided a synthetic oligosaccharide preparation, nutritional composition, animal feed pre-mix, or animal feed composition as described herein has an FCR that is between 0 to 10% higher than the performance target minimum, between 0 to 5% higher than the performance target minimum, or between 0 to 2% higher than the performance target minimum.

In some embodiments, an animal provided a synthetic oligosaccharide preparation, a nutritional composition, animal feed pre-mix, or animal feed composition as described herein has a lower feed conversion ratio compared to an animal provided a diet that does not include the synthetic oligosaccharide preparation. For example, in certain embodiments, the animal provided a diet comprising the synthetic oligosaccharide preparation consumes less food but has the same animal output as compared to an animal provided a diet that does not include the synthetic oligosaccharide preparation. In other embodiments, the animal provided a diet comprising the synthetic oligosaccharide preparation consumes the same amount of food but has a higher animal output as compared to an animal provided a diet that does not include the synthetic oligosaccharide preparation.

In yet other embodiments, the animal provided a diet comprising the synthetic oligosaccharide preparation consumes less food and has a higher animal output as compared to an animal provided a diet that does not include the synthetic oligosaccharide preparation.

In some embodiments, the FCR of an animal provided a synthetic oligosaccharide preparation, nutritional composition, animal feed pre-mix, or animal feed composition as described herein is reduced at least 1%, at least 2%, at least 4%, at least 6%, at least 8%, at least 10%, at least 12%, between 1 to 10%, between 4 to 10%, between 1 to 8%, between 4 to 8%, between 1 to 6%, or between 4 to 6% as compared to an animal provided a diet that does not include the synthetic oligosaccharide preparation. In some embodiments, the animal is poultry. In certain embodiments, the FCR of the poultry is reduced over 0 to 14 days of age, over 15 to 28 days of age, over 29 to 35 days of age, over 35 days, over 42 days, over 6 weeks, over 6.5 weeks, over 0 to 35 days of age, over 0 to 42 days of age, over 0 to 6 weeks of age, over 0 to 6.5 weeks of age, over 15 to 35 days of age, over 36 to 42 days of age, over 15 to 39 days of age, or over 40 to 46 days of age.

In one embodiment, the FCR over 35 days for poultry provided a synthetic oligosaccharide preparation, nutritional composition, animal feed pre-mix, or animal feed composition as described herein is reduced by between 4 to 6% as compared to poultry provided a diet that does not include the synthetic oligosaccharide preparation. For example, in a certain embodiment, the FCR over 35 days for poultry provided a nutritional composition describing a synthetic oligosaccharide preparation, nutritional composition, animal feed pre-mix, or animal feed composition as described herein is 1.53, the FCR over 35 days for poultry provided a diet without the synthetic oligosaccharide preparation is 1.61, and the FCR of the poultry provided the nutritional composition comprising a oligosaccharide preparation, nutritional composition, animal feed pre-mix, or animal feed composition is reduced about 5% compared to the poultry provided a diet without the synthetic oligosaccharide preparation. In some embodiments, the FCR over 42 days, over 6 weeks, or over 6.5 weeks days for poultry provided a synthetic oligosaccharide preparation, nutritional composition, animal feed pre-mix, or animal feed composition as described herein is reduced by between 4 to 6% as compared to poultry provided a diet that does not include the synthetic oligosaccharide preparation.

In some embodiments, an animal population provided a synthetic oligosaccharide preparation, nutritional preparation, animal feed pre-mix, or animal feed composition as described herein has a lower FCR compared to an animal population provided a diet that does not include the synthetic oligosaccharide preparation, wherein the FCR is corrected for mortality in the animal population.

In certain embodiments, an animal provided a synthetic oligosaccharide preparation, animal feed pre-mix, or animal feed composition has a lower FCR than an animal provided a diet that does not include the synthetic oligosaccharide preparation, but which does include one or more antibiotics, one or more ionophores, soluble corn fiber, modified wheat starch, or yeast mannan, or any combinations thereof.

It is known to one skilled in the art, that when determining FCR, the FCR may be adjusted for mortality to reduce noise due to small number statistics. Methods for adjusting FCR for mortality are well known to one skilled in the art.

In some embodiments that may be combined with any of the foregoing embodiments, the poultry is an individual poultry, while in other embodiments the poultry is a poultry population.

In some embodiments, the animal is poultry, and the animal feed composition is poultry feed, wherein the synthetic oligosaccharide preparation, poultry nutritional composition, poultry feed pre-mix, or poultry feed composition feed reduces feed conversion ratio (FCR) by up to about 10%, or about 5%, or between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, when fed to poultry as compared to poultry fed a feed composition without the synthetic oligosaccharide preparation.

In certain embodiments, the poultry suffers from a disease or a disorder, or is raised in a challenged environment, wherein the synthetic oligosaccharide preparation, poultry nutritional composition, poultry feed pre-mix, or poultry feed composition feed reduces feed conversion ratio (FCR) by up to about 30%, about 25%, about 20%, about 15%, about 10%, or about 5%, or between 1% and 30%, between 5% and 30%, between 10% and 30%, between 5% and 20%, between 10% and 20%, between 1% and 20%, between 1% and 15%, between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, when fed to poultry as compared to poultry fed a feed composition without the synthetic oligosaccharide preparation.

In some embodiments, the animal is swine, and the animal feed composition is swine feed, wherein the synthetic oligosaccharide preparation, swine nutritional composition, swine feed pre-mix, or swine feed composition reduces feed conversion ratio (FCR) by up to about 15%, about 10%, or about 5%, or between 1% and 15%, between 2% and 15%, between 3% and 15%, between 4% and 15%, between 5% and 15%, between 10% and 15%, between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, when fed to swine as compared to swine fed a feed composition without the synthetic oligosaccharide preparation.

In certain embodiments, the swine suffers from a disease or a disorder, or is raised in a challenged environment, wherein the synthetic oligosaccharide preparation, swine nutritional composition, swine feed pre-mix, or swine feed composition reduces feed conversion ratio (FCR) by up to about 40%, about 35% about 30%, about 25%, about 20%, about 15%, about 10%, or about 5%, or between 1% and 40%, between 5% and 40%, between 10% and 40%, between 15% and 40%, between 20% and 40%, between 25% and 40%, between 30% and 40%, between 1% and 30%, between 5% and 30%, between 10% and 30%, between 5% and 20%, between 10% and 20%, between 1% and 20%, between 1% and 15%, between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, when fed to swine as compared to swine fed a feed composition without the synthetic oligosaccharide preparation.

B. Body Weight

In some embodiments, a subject animal that is fed a synthetic oligosaccharide preparation, nutritional composition, animal feed pre-mix, or animal feed composition described herein may experience an increase in weight gain, compared to a control animal that is not fed the oligosaccharide preparation, nutritional composition, animal feed pre-mix, or animal feed composition. In certain embodiments, both the subject animal and the control animal consume the same quantity of feed on a weight basis, but the subject animal provided the synthetic oligosaccharide preparation, nutritional composition, animal feed pre-mix, or animal feed composition experiences an increase in weight gain compared to the control animal that is fed a diet that does not include the synthetic oligosaccharide preparation.

The weight gain of an animal may be determined by any suitable methods known in the art. For example, to determine weight gain of an animal that is subjected to a feeding regimen of the synthetic oligosaccharide preparation, nutritional composition, animal feed pre-mix, or animal feed composition, one of skill in the art can measure the mass of an animal prior to the feeding regimen, measure the mass of the animal after the animal is fed the synthetic oligosaccharide preparation, nutritional composition, animal feed pre-mix, or animal feed composition, and determine the difference between those two measurements.

In some embodiments, the weight gain may be an average daily weight gain (also referred to as average daily gain (ADG)), an average weekly weight gain (AWG), or a final body weight gain (BWG).

C. Average Daily Weight Gain

In some embodiments, providing an animal with a synthetic oligosaccharide preparation, nutritional composition, animal feed pre-mix, or animal feed composition results in an increased average daily weight gain than an animal provided feed without the synthetic oligosaccharide preparation. In some embodiments, providing an animal population with a synthetic oligosaccharide preparation, nutritional composition, animal feed pre-mix, or animal feed composition results in an increased average daily weight gain than an animal population provided feed without the synthetic oligosaccharide preparation.

In one embodiment, the average daily weight gain for an animal is the weight gained each day by an individual animal, averaged over a given period of time. In some embodiments, the average daily weight gain for an animal population is the average daily weight gain for each individual animal, averaged over the population; wherein the average daily weight gain is the weight gained each day by the individual animal, averaged over a given period of time. In yet other embodiments, the average daily weight gain for an animal population is the total weight gained by the population each day, divided by the number of individual animals in the population, averaged over a given period of time.

It should be understood that the daily weight gain or average daily weight gain may be further averaged, for example to provide an average daily weight gain across animal populations.

In certain embodiments, the animal is poultry, and the poultry provided a synthetic oligosaccharide preparation, nutritional composition, animal feed pre-mix, or animal feed composition has an average daily weight gain of at least 20 grams per day, at least 30 grams per day, at least 40 grams per day, at least 50 grams per day, at least 60 grams per day, at least 70 grams per day, at least 80 grams per day, at least 90 grams per day, between 20 to 100 grams per day, between 20 to 80 grams per day, between 30 to 50 grams per day, between 40 to 60 grams per day, between 50 to 70 grams per day, or between 70 to 90 grams per day. In one embodiment, the animal is poultry, and the poultry provided a synthetic oligosaccharide preparation, nutritional composition, animal feed pre-mix, or animal feed composition has an average daily weight gain of at least 50 grams per day. In certain embodiments, the poultry provided a synthetic oligosaccharide preparation, nutritional composition, animal feed pre-mix, or animal feed composition has an average daily weight gain of at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than the average daily weight gain of poultry provided a diet that does not include the synthetic oligosaccharide preparation.

In certain embodiments, the animal is poultry, and the poultry is between 0 to 14 days of age, and the average daily weight gain is at least 30 grams, at least 40 grams, or at least 50 grams per day.

In other embodiments, the animal is poultry, the poultry is between 14 to 28 days of age, and the average daily weight gain is at least 70 grams, at least 80 grams, or at least 90 grams per day.

In still other embodiments, the animal is poultry, the poultry is between 29 to 35 days of age, and the average daily weight gain is at least 50 grams, at least 60 grams, or at least 70 grams per day.

In some embodiments that may be combined with the foregoing, the animal is poultry, and the animal feed composition is poultry feed, wherein the synthetic oligosaccharide preparation, poultry nutritional composition, poultry feed pre-mix, or poultry feed composition increases average daily gain in poultry by up to about 10%, or about 5%, or between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, when fed to the poultry as compared to poultry fed a feed composition without the synthetic oligosaccharide preparation.

In certain embodiments, the poultry suffers from a disease or a disorder, or is raised in a challenged environment, wherein the synthetic oligosaccharide preparation, poultry nutritional composition, poultry feed pre-mix, or poultry feed composition increases average daily gain in poultry by up to about 30%, about 25%, about 20%, about 15%, about 10%, or about 5%, or between 1% and 30%, between 5% and 30%, between 10% and 30%, between 5% and 20%, between 10% and 20%, between 1% and 20%, between 1% and 15%, between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, when fed to the poultry as compared to poultry fed a feed composition without the synthetic oligosaccharide preparation.

In some embodiments that may be combined with the foregoing, the animal is swine, and the animal feed composition is swine feed, wherein the synthetic oligosaccharide preparation, swine nutritional preparation, swine feed pre-mix, or swine feed composition increases average daily gain in swine by up to about 15%, about 10%, or about 5%, or between 1% and 15%, between 2% and 15%, between 3% and 15%, between 4% and 15%, between 5% and 15%, between 10% and 15%, between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, when fed to swine as compared to swine fed a feed composition without the synthetic oligosaccharide preparation.

In certain embodiments, the swine suffers from a disease or a disorder, or is raised in a challenged environment, wherein the oligosaccharide preparation, swine nutritional composition, swine feed pre-mix, or swine feed composition increases average daily gain in swine by up to about 40%, about 35% about 30%, about 25%, about 20%, about 15%, about 10%, or about 5%, or between 1% and 40%, between 5% and 40%, between 10% and 40%, between 15% and 40%, between 20% and 40%, between 25% and 40%, between 30% and 40%, between 1% and 30%, between 5% and 30%, between 10% and 30%, between 5% and 20%, between 10% and 20%, between 1% and 20%, between 1% and 15%, between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, when fed to swine as compared to swine fed a feed composition without the synthetic oligosaccharide preparation.

In certain embodiments, the animal is swine, and the swine provided a synthetic oligosaccharide preparation, swine nutritional preparation, swine feed pre-mix, or swine feed composition has an average daily weight gain of at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than the average daily weight gain of swine provided a diet that does not include the synthetic oligosaccharide preparation.

D. Average Weekly Weight Gain

In some embodiments, providing an animal with a synthetic oligosaccharide preparation, nutritional composition, animal feed pre-mix, or animal feed composition results in an increased average weekly weight gain than an animal provided feed without the synthetic oligosaccharide preparation. In some embodiments, providing an animal population with a synthetic oligosaccharide preparation, nutritional composition, animal feed pre-mix, or animal feed composition results in an increased average weekly weight gain than an animal population provided feed without the synthetic oligosaccharide preparation.

In one embodiment, the average weekly weight gain for an animal is the weight gained each week by an individual animal, averaged over a given period of time. In some embodiments, the average weekly weight gain for an animal population is the average weekly weight gain for each individual animal, averaged over the population; wherein the average weekly weight gain is the weight gained each week by the individual animal, averaged over a given period of time. In yet other embodiments, the average weekly weight gain for an animal population is the total weight gained by the population each week, divided by the number of individual animals in the population, averaged over a given period of time. It should be understood that the average weekly weight gain may be further averaged, for example to provide an average weekly weight gain across animal populations.

In certain embodiments, the animal is poultry, and poultry provided a synthetic oligosaccharide preparation, nutritional composition, animal feed pre-mix, or animal feed composition has an average weekly weight gain of at least 100 grams per week, at least 200 grams per week, at least 300 grams per week, at least 400 grams per week, at least 500 grams per week, at least 600 grams per week, at least 700 grams per week, at least 800 grams per week, between 100 to 800 grams per week, between 100 to 400 grams per week, between 300 to 600 grams per week, between 500 to 800 grams per week, or between 350 to 550 grams per week. In one embodiment, poultry provided a synthetic oligosaccharide preparation, nutritional composition, animal feed pre-mix, or animal feed composition has an average weekly weight gain of at least 400 grams per week. In certain embodiments, poultry provided a synthetic oligosaccharide preparation, nutritional composition, animal feed pre-mix, or animal feed composition has an average weekly weight gain of at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than the average weekly weight gain of poultry provided a diet that does not include the oligosaccharide preparation.

In certain embodiments, the animal is swine, and swine provided a synthetic oligosaccharide preparation, swine nutritional composition, swine feed pre-mix, or swine feed composition has an average weekly weight gain of at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than the average weekly weight gain of swine provided a diet that does not include the synthetic oligosaccharide preparation.

E. Final Body Weight Gain

In some embodiments, providing an animal with a synthetic oligosaccharide preparation, nutritional composition, animal feed pre-mix, or animal feed composition results in an increased final body weight gain than an animal provided feed without the synthetic oligosaccharide preparation. In some embodiments, providing an animal population with a synthetic oligosaccharide preparation, nutritional composition, animal feed pre-mix, or animal feed composition results in an increased average final body weight gain than an animal population provided feed without the synthetic oligosaccharide preparation.

In some embodiments, providing an animal or animal population with a synthetic oligosaccharide preparation, nutritional composition, animal feed pre-mix, or animal feed composition results in a final body weight gain or average final body weight gain that is closer to the performance target maximum than an animal or animal population that is provided feed without the synthetic oligosaccharide preparation. The performance target maximum generally refers to the highest practical body weight gain observed for a given type of animal and breed under ideal growing conditions, ideal animal health, and ideal dietary nutrition.

In one embodiment, the final body weight gain is the quantity of weight an individual animal gains over a period of time. For example, in one embodiment, the total body weight gain is the quantity of weight an individual animal gains from 0 days of age until the final weight taken prior to processing of the animal, or the final weight taken on the day of processing of the animal. For example, in one embodiment, the day 0 to 28 total body weight gain for an animal is the quantity of weight an individual animal gains from 0 days of age until 28 days of age.

In another embodiment, the average total body weight gain is the quantity of weight an individual animal gains over a period of time, averaged across an animal population. For example, in one embodiment, the average total body weight gain is the quantity of weight an individual animal gains from 0 days of age until the final weight taken prior to processing of the animal, or the final weight taken on the day of processing of the animal, averaged across the animal population. In yet another embodiment, the average total body weight gain is the quantity of weight an animal population gains over a period of time, divided by the number of individual animals in the population. For example, in one embodiment, the average total body weight gain is the quantity of weight an animal population gains from 0 days of age until the final weight taken prior to processing of the animal population, or the final weight taken on the day of processing of the animal, divided by the number of individual animals in the population.

It should be understood that the values for total body weight gain and average total body weight gain can be further averaged. For example, the average total body weight gain for different populations of the same type of animal may be averaged to obtain an average total body weight gain across populations.

In certain embodiments, the animal is poultry, and poultry provided a synthetic oligosaccharide preparation, nutritional composition, animal feed pre-mix, or animal feed composition has a final body weight gain of at least 3 kg, at least 2.5 kg, at least 2 kg, at least 1.5 kg, at least 1 kg, between 1 to 3 kg, or between 1.5 to 2.5 kg. In one embodiment, poultry provided a synthetic oligosaccharide preparation, animal feed pre-mix, or animal feed composition has a final body weight gain of at least 2 kg. In certain embodiments, poultry provided a synthetic oligosaccharide preparation, animal feed pre-mix, or animal feed composition has a final body weight gain of at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than the final body weight gain of poultry provided a diet that does not include the synthetic oligosaccharide preparation. In certain embodiments, poultry provided a synthetic oligosaccharide preparation, animal feed pre-mix, or animal feed composition has a final body weight gain of at least 0.01 kg, at least 0.02 kg, at least 0.03 kg, at least 0.04 kg, at least 0.05 kg, at least 0.06 kg, at least 0.07 kg, at least 0.08 kg, at least 0.09 kg, at least 0.1 kg, between 0.01 to 0.1 kg, between 0.03 to 0.07 kg, or between 0.04 to 0.06 kg greater than the final body weight gain of poultry provided a diet that does not include the synthetic oligosaccharide preparation.

In certain embodiments, the animal is poultry, and poultry provided a synthetic oligosaccharide preparation, nutritional composition, animal feed pre-mix, or animal feed composition has an average final body weight gain of at least 3 kg, at least 2.5 kg, at least 2 kg, at least 1.5 kg, at least 1 kg, between 1 to 3 kg, or between 1.5 to 2.5 kg. In one embodiment, poultry provided a synthetic oligosaccharide preparation, nutritional composition, animal feed pre-mix, or animal feed composition has an average final body weight gain of at least 2 kg. In certain embodiments, poultry provided a synthetic oligosaccharide preparation, nutritional composition, animal feed pre-mix, or animal feed composition has an average final body weight gain of at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than the average final body weight gain of poultry provided a diet that does not include the synthetic oligosaccharide preparation. In certain embodiments, poultry provided a synthetic oligosaccharide preparation, nutritional composition, animal feed pre-mix, or animal feed composition has an average final body weight gain of at least 0.01 kg, at least 0.02 kg, at least 0.03 kg, at least 0.04 kg, at least 0.05 kg, at least 0.06 kg, at least 0.07 kg, at least 0.08 kg, at least 0.09 kg, at least 0.1 kg, between 0.01 to 0.1 kg, between 0.03 to 0.07 kg, or between 0.04 to 0.06 kg greater than the average final body weight gain of poultry provided a diet that does not include the synthetic oligosaccharide preparation.

In some embodiments, the animal is poultry, and the poultry is between 0 to 14 days of age, between 15 to 28 days of age, between 29 to 35 days of age, between 0 to 42 days of age, between 0 to 6 weeks of age, or between 0 to 6.5 weeks of age. In some embodiments, the starter phase is 0 to 14 days of age, the grower phase is 15 to 28 days of age, and the finisher phase is 29 to 35 days of age. In other embodiments, the starter phase is 0 to 14 days of age, the grower phase is 15 to 35 days of age, and the finisher phase is 36 to 42 days of age. In yet other embodiments, the starter phase is 0 to 14 days of age, the grower phase is 15 to 39 days of age, and the finisher phase is 40 to 46 days of age. It should be understood that the length of the starter phase, growing phase, and finisher phase for poultry may change depending on the intended use of the poultry, or the poultry product. For example, in some embodiments the length of the starter phase, grower phase, and finisher phase may be different if the intended use of the poultry is as a broiler chicken, compared to processing for tray-pack chicken meat.

In some embodiments that may be combined with any of the foregoing embodiments, the poultry is an individual poultry, while in other embodiments the poultry is a poultry population.

In certain embodiments, swine provided a synthetic oligosaccharide preparation, swine nutritional composition, swine feed pre-mix, or swine feed composition has a final body weight gain of at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than the final body weight gain of swine provided a diet that does not include the synthetic oligosaccharide preparation.

In certain embodiments, swine provided a synthetic oligosaccharide preparation, swine nutritional composition, swine feed pre-mix, or swine feed composition has an average final body weight gain of at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than the average final body weight gain of swine provided a diet that does not include the synthetic oligosaccharide preparation.

In some embodiments that may be combined with any of the foregoing embodiments, the swine is an individual swine, while in other embodiments the swine is a swine population.

F. Yield of Animal Product

In certain embodiments, providing an animal with a synthetic oligosaccharide preparations, nutritional composition, animal feed pre-mix, or animal feed composition as described herein results in an increased yield of animal product, as compared to an animal provided feed that does not include the synthetic oligosaccharide preparation. In some embodiments, the animal provided a synthetic oligosaccharide preparation, nutritional composition, animal feed pre-mix, or animal feed composition yields at least 1%, at least 2%, at least 3%, at least 4%, at least 5%, at least 6%, at least 7%, at least 8%, at least 9%, at least 10%, between 1 to 10%, between 4 to 10%, between 6 to 10%, or between 2 to 8% more animal product compared to an animal provided feed that does not include the synthetic oligosaccharide preparation. For example, in some embodiments, the animal product is the meat of the animal, and an animal provided a synthetic oligosaccharide preparation as described herein yields a greater quantity of meat compared to an animal that is not provided the oligosaccharide preparation.

In some embodiments, providing an animal population the synthetic oligosaccharide preparation, nutritional composition, animal feed pre-mix, or animal feed composition results in an increased average yield of animal product, as compared to an animal population provided feed that does not include the synthetic oligosaccharide preparation. In some embodiments, the average animal product yield is the quantity of animal product yielded from each individual animal, averaged across the animal population.

In some embodiments, the animal product is the meat of an animal (e.g., that may be sold to consumers, processed to produce a food product, or consumed by a human). In certain embodiments, the animal is poultry, and the animal product is a poultry eviscerated carcass, leg meat from a poultry eviscerated carcass, breast meat from a poultry eviscerated carcass, drumstick meat from a poultry eviscerated carcass, fat from a poultry eviscerated carcass, breast meat from a poultry deboned carcass, or leg meat from a poultry deboned carcass. In other embodiments, the animal is poultry, and the animal product is white meat, breast meat filets, and breast meat tenders. In another embodiment, the animal is poultry and the product is tray-pack chicken meat. In yet another embodiment, the animal is poultry and the product is whole bird without giblets (WOG).

In some embodiments, the yield of animal product is the yield obtained from an individual animal. In some embodiments, the average yield of animal product is the yield obtained from each individual animal in an animal population, averaged across the population. In yet another embodiment, the average yield of animal product is the total yield of animal product yielded from an animal population, divided by the number of individual animals in the animal population.

In some embodiments, the animal is poultry, the yield of leg meat from a poultry eviscerated carcass is at least 6%, at least 8%, at least 10%, at least 12%, between 6 to 12%, between 8 to 12%, between 10 to 18%, between 12 to 16%, or between 12 to 14% of live weight for poultry provided a synthetic oligosaccharide preparation, nutritional composition, animal feed pre-mix, or animal feed composition. In certain embodiments, the yield of leg meat from a poultry eviscerated carcass from poultry provided a synthetic oligosaccharide preparation, nutritional composition, animal feed pre-mix, or animal feed composition as described herein is at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than for poultry provided a diet that does not include the synthetic oligosaccharide preparation.

In some embodiments, the animal is poultry, and the average yield of leg meat from a poultry eviscerated carcass is at least 6%, at least 8%, at least 10%, at least 12%, between 6 to 12%, between 8 to 12%, between 10 to 18%, between 12 to 16%, or between 12 to 14% of live weight for poultry provided a synthetic oligosaccharide preparations, nutritional composition, animal feed pre-mix, or animal feed composition. In certain embodiments, the average yield of leg meat from a poultry eviscerated carcass from poultry provided a synthetic oligosaccharide preparation, nutritional composition, animal feed pre-mix, or animal feed composition as described herein is at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than for poultry provided a diet that does not include the synthetic oligosaccharide preparation.

In some embodiments, the animal is poultry, and the yield of breast meat from a poultry eviscerated carcass is at least 10%, at least 12%, at least 15%, at least 16%, at least 18%, at least 20%, at least 22%, at least 24%, at least 28%, between 10 to 18%, between 12 to 16%, between 18 to 29%, between 20 to 27%, or between 20 to 25% of live weight for poultry provided a synthetic oligosaccharide preparations, nutritional composition, animal feed pre-mix, or animal feed composition. In certain embodiments, the yield of breast meat from a poultry eviscerated carcass from poultry provided a synthetic oligosaccharide preparation, nutritional composition, animal feed pre-mix, or animal feed composition as described herein is at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than for poultry provided a diet that does not include the synthetic oligosaccharide preparation.

In some embodiments, the animal is poultry, and the average yield of breast meat from a poultry eviscerated carcass is at least 10%, at least 12%, at least 15%, at least 16%, at least 18%, at least 20%, at least 22%, at least 24%, at least 28%, between 10 to 18%, between 12 to 16%, between 18 to 29%, between 20 to 27%, or between 20 to 25% of live weight for poultry provided a synthetic oligosaccharide preparations, nutritional composition, animal feed pre-mix, or animal feed composition. In certain embodiments, the average yield of breast meat from a poultry eviscerated carcass from poultry provided a synthetic oligosaccharide preparation, nutritional composition, animal feed pre-mix, or animal feed composition as described herein is at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than for poultry provided a diet that does not include the synthetic oligosaccharide preparation.

In some embodiments, the animal is poultry, and the yield of drumstick meat from a poultry eviscerated carcass is at least 5%, at least 7%, at least 8%, at least 9%, at least 10%, at least 11%, at least 12%, between 5 to 14%, between 7 to 10%, between 7 to 15%, between 9 to 13%, or between 9 to 11% of live weight for poultry provided a synthetic oligosaccharide preparation, nutritional composition, animal feed pre-mix, or animal feed composition. In certain embodiments, the yield of drumstick meat from a poultry eviscerated carcass from poultry provided a synthetic oligosaccharide preparation, nutritional composition, animal feed pre-mix, or animal feed composition as described herein is at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than for poultry provided a diet that does not include the synthetic oligosaccharide preparation.

In some embodiments, the animal is poultry, and the average yield of drumstick meat from a poultry eviscerated carcass is at least 5%, at least 7%, at least 8%, at least 9%, at least 10%, at least 11%, at least 12%, between 5 to 14%, between 7 to 10%, between 7 to 15%, between 9 to 13%, or between 9 to 11% of live weight for poultry provided a synthetic oligosaccharide preparation, nutritional composition, animal feed pre-mix, or animal feed composition. In certain embodiments, the average yield of drumstick meat from a poultry eviscerated carcass from poultry provided a synthetic oligosaccharide preparation, nutritional composition, animal feed pre-mix, or animal feed composition as described herein is at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than for poultry provided a diet that does not include the synthetic oligosaccharide preparation.

In some embodiments, the animal is poultry, and the yield of breast meat from a poultry deboned carcass is at least 14%, at least 16%, at least 18%, at least 20%, at least 22%, at least 24%, between 14 to 16%, between 18 to 30%, between 20 to 28%, or between 20 to 26% of live weight for poultry provided a synthetic oligosaccharide preparation, nutritional composition, animal feed pre-mix, or animal feed composition. In certain embodiments, the yield of breast meat from a poultry deboned carcass from poultry provided an oligosaccharide preparation, animal feed pre-mix, or animal feed composition as described herein is at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than for poultry provided a diet that does not include the synthetic oligosaccharide preparation.

In some embodiments, the animal is poultry, and the average yield of breast meat from a poultry deboned carcass is at least 14%, at least 16%, at least 18%, at least 20%, at least 22%, at least 24%, between 14 to 16%, between 18 to 30%, between 20 to 28%, or between 20 to 26% of live weight for poultry provided a synthetic oligosaccharide preparations, nutritional composition, animal feed pre-mix, or animal feed composition. In certain embodiments, the average yield of breast meat from a poultry deboned carcass from poultry provided a synthetic oligosaccharide preparation, nutritional composition, animal feed pre-mix, or animal feed composition as described herein is at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than for poultry provided a diet that does not include the synthetic oligosaccharide preparation.

In some embodiments, the animal is poultry, and the yield of leg meat from a poultry deboned carcass is at least 6%, at least 8%, at least 10%, at least 12%, at least 14%, at least 16%, at least 18%, between 6 to 18%, between 8 to 16%, between 12 to 21%, between 14 to 19%, or between 14 to 17% of live weight for poultry provided a synthetic oligosaccharide preparations, nutritional composition, animal feed pre-mix, or animal feed composition. In certain embodiments, the yield of leg meat from a poultry deboned carcass from poultry provided a synthetic oligosaccharide preparation, nutritional composition, animal feed pre-mix, or animal feed composition as described herein is at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than for poultry provided a diet that does not include the synthetic oligosaccharide preparation.

In some embodiments, the animal is poultry, and the average yield of leg meat from a poultry deboned carcass is at least 6%, at least 8%, at least 10%, at least 12%, at least 14%, at least 16%, at least 18%, between 6 to 18%, between 8 to 16%, between 12 to 21%, between 14 to 19%, or between 14 to 17% of live weight for poultry provided a synthetic oligosaccharide preparation, nutritional composition, animal feed pre-mix, or animal feed composition. In certain embodiments, the average yield of leg meat from a poultry deboned carcass from poultry provided an oligosaccharide preparation, animal feed pre-mix, or animal feed composition as described herein is at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than for poultry provided a diet that does not include the synthetic oligosaccharide preparation.

In some embodiments, the animal is poultry, and the yield of fat from a poultry eviscerated carcass is at least 0.1%, at least 0.2%, at least 0.3%, at least 0.4%, at least 0.5%, at least 0.6%, at least 0.7%, at least 0.8%, at least 0.9%, at least 1%, at least 1.2%, at least 1.4%, at least 1.6%, between 0.1 to 2%, between 0.2 to 1%, between 0.5 to 2%, or between 0.3 to 0.7% of live weight for poultry provided a synthetic oligosaccharide preparation, nutritional composition, animal feed pre-mix, or animal feed composition. In certain embodiments, the yield of fat from a poultry eviscerated carcass from poultry provided a synthetic oligosaccharide preparation, nutritional composition, animal feed pre-mix, or animal feed composition as described herein is at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than for poultry provided a diet that does not include the synthetic oligosaccharide preparation.

In some embodiments, the animal is poultry, and the average yield of fat from a poultry eviscerated carcass is at least 0.1%, at least 0.2%, at least 0.3%, at least 0.4%, at least 0.5%, at least 0.6%, at least 0.7%, at least 0.8%, at least 0.9%, at least 1%, at least 1.2%, at least 1.4%, at least 1.6%, between 0.1 to 2%, between 0.2 to 1%, between 0.5 to 2%, or between 0.3 to 0.7% of live weight for poultry provided a synthetic oligosaccharide preparations, nutritional composition, animal feed pre-mix, or animal feed composition. In certain embodiments, the average yield of fat from a poultry eviscerated carcass from poultry provided a synthetic oligosaccharide preparation, nutritional composition, animal feed pre-mix, or animal feed composition as described herein is at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than for poultry provided a diet that does not include the synthetic oligosaccharide preparation.

In some embodiments, the animal is poultry, and the yield of a poultry eviscerated carcass is at least 50%, at least 55%, at least 60%, at least 65%, at least 70%, at least 75%, at least 80%, at least 85%, at least 90%, between 50 to 95%, between 60 to 85%, or between 65 to 75% of live weight for poultry provided a synthetic oligosaccharide preparations, nutritional composition, animal feed pre-mix, or animal feed composition. In certain embodiments, the yield of a poultry eviscerated carcass from poultry provided a synthetic oligosaccharide preparation, nutritional composition, animal feed pre-mix, or animal feed composition as described herein is at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than for poultry provided a diet that does not include the synthetic oligosaccharide preparation.

In some embodiments, the animal is poultry, and the average yield of a poultry eviscerated carcass is at least 50%, at least 55%, at least 60%, at least 65%, at least 70%, at least 75%, at least 80%, at least 85%, at least 90%, between 50 to 95%, between 60 to 85%, or between 65 to 75% of live weight for poultry provided a synthetic oligosaccharide preparations, nutritional composition, animal feed pre-mix, or animal feed composition. In certain embodiments, the average yield of a poultry eviscerated carcass from poultry provided a synthetic oligosaccharide preparation, nutritional composition, animal feed pre-mix, or animal feed composition as described herein is at least 1%, at least 2%, at least 3%, at least 4%, at least 5%, at least 6%, at least 8%, at least 9%, at least 10%, at least 11%, at least 12%, between 1 to 10%, between 2 to 8%, or between 3 to 5% greater than for poultry provided a diet that does not include the synthetic oligosaccharide preparation.

Methods for deboning a poultry carcass are well known to one skilled in the art of poultry processing. It should be understood that meat yielded from poultry may be measured, for example, as the ratio of the mass of recovered meat to the final weight of the bird prior to processing. In some embodiments, the animal is poultry, and the poultry is at least 35 days old, at least 42 days old, at least 6 weeks old, at least 6.5 weeks old before the poultry is processed to produce a poultry eviscerated carcass, poultry deboned carcass, white meat, breast meat filets, and breast meat tenders, tray-pack chicken meat, whole bird without giblets (WOG), or meat as described above.

In other embodiments, the animal is poultry, and the animal product is eggs. In some embodiments, the animal is swine, and the swine product is the meat of swine (e.g., that may be sold to consumers, processed to produce a food product, or consumed by a human). In some embodiments, the yield of swine product is the yield obtained from an individual swine. In some embodiments, the average yield of swine product is the yield obtained from each individual swine in a swine population, averaged across the population. In yet another embodiment, the average yield of swine product is the total yield of swine product yielded from swine population, divided by the number of individual swine in the swine population.

In certain embodiments, an animal or animal population provided a synthetic oligosaccharide preparation, nutritional composition, animal feed pre-mix, or animal feed composition has a higher average daily weight gain, higher average weekly weight gain, higher final body weight gain, higher average final body weight gain, or increased average yield of animal product, or any combinations thereof, than an animal or animal population provided a diet that does not include the synthetic oligosaccharide preparation, but which does include one or more antibiotics, one or more ionophores, soluble corn fiber, modified wheat starch, or yeast mannan, or any combinations thereof.

A person of skill in the art would recognize that the maximum theoretical weight gain may be different for different types of animals and may be different for different breeds of the same type of animal (for example, different types of broiler chickens, or different types of swine).

A person of skill in the art would recognize that the maximum theoretical weight gain may be different for different types of animals and may be different for different breeds of the same type of animal (for example, different types of broiler chickens, or different types of swine).

In some embodiments, the animal is poultry. In some embodiments that may be combined with any of the foregoing embodiments, the poultry is an individual poultry, while in other embodiments the poultry is a poultry population. In other embodiments, the animal is swine. In some embodiments that may be combined with any of the foregoing embodiments, the swine is an individual swine, while in other embodiments the swine is a swine population.

G. Feed Intake

In certain embodiments, providing an animal with a synthetic oligosaccharide preparation nutritional composition, animal feed pre-mix, or animal feed composition as described herein results in an increased average daily feed intake, as compared to an animal provided feed that does not include the synthetic oligosaccharide preparation.

Average daily feed intake (ADFI) refers to the average mass of feed consumed by an animal over a specified period of time. In certain embodiments, the average daily feed intake is measured by dispensing a known mass of feed to a group of a fixed number of animals, allowing the animals in the group to consume the dispensed feed freely (ad libidum) for a specified number of days, weighing the mass of unconsumed feed at the end of the period, and calculating the average daily feed intake (ADFI) as the difference between the dispensed feed mass minus the residual feed mass, divided by the number of animals in the group, and divided by the number of days in the period. In other embodiments, the average daily feed intake may be corrected for any animals that die or are culled from the group, using methods that are known to one skilled in the art.

In some embodiments, the animal is poultry, and the animal feed composition is poultry feed, wherein the synthetic oligosaccharide preparation, poultry feed pre-mix, or poultry feed composition feed increases average daily feed intake by up to about 10%, or about 5%, or between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, when fed to poultry as compared to poultry fed a feed composition without the synthetic oligosaccharide preparation.

In certain embodiments, the poultry suffers from a disease or is raised in a challenged environment, wherein the synthetic oligosaccharide preparation, poultry nutritional composition, poultry feed pre-mix, or poultry feed composition increases average daily feed intake by up to about 30%, about 25%, about 20%, about 15%, about 10%, or about 5%, or between 1% and 30%, between 5% and 30%, between 10% and 30%, between 5% and 20%, between 10% and 20%, between 1% and 20%, between 1% and 15%, between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, when fed to poultry as compared to poultry fed a feed composition without the synthetic oligosaccharide preparation.

In some embodiments that may be combined with the foregoing, the animal is swine, and the animal feed composition is swine feed, wherein the oligosaccharide preparation, swine nutritional composition, swine feed pre-mix, or swine feed composition increases average daily feed intake by up to about 15%, about 10%, or about 5%, or between 1% and 15%, between 2% and 15%, between 3% and 15%, between 4% and 15%, between 5% and 15%, between 10% and 15%, between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, when fed to swine as compared to swine fed a feed composition without the synthetic oligosaccharide preparation.

In certain embodiments, the swine suffers from a disease or is raised in a challenged environment, wherein the synthetic oligosaccharide preparation, swine nutritional composition, swine feed pre-mix, or swine feed composition increases average daily feed intake by up to about 40%, about 35% about 30%, about 25%, about 20%, about 15%, about 10%, or about 5%, or between 1% and 40%, between 5% and 40%, between 10% and 40%, between 15% and 40%, between 20% and 40%, between 25% and 40%, between 30% and 40%, between 1% and 30%, between 5% and 30%, between 10% and 30%, between 5% and 20%, between 10% and 20%, between 1% and 20%, between 1% and 15%, between 1% and 10%, between 2% and 10%, between 3% and 10%, between 4% and 10%, between 5% and 10%, between 2% and 5%, between 2% and 6%, between 2% and 7%, between 2% and 8%, between 2% and 9%, or between 1% and 5%, when fed to swine as compared to swine fed a feed composition without the synthetic oligosaccharide preparation.

The methods of enhancing growth of an animal or animal population described herein include providing an oligosaccharide preparation, animal feed pre-mix, or animal feed to the animal or animal population. The oligosaccharide preparation, animal feed pre-mix, or animal feed may be provided in any suitable form, to any suitable type of animal, using any suitable feeding schedule to enhance the growth of the animal or animal population.

VIII. Animals

The synthetic oligosaccharide preparation, nutritional composition, animal feed pre-mix, or the animal feed composition may be provided to any suitable animal. In some embodiments, the animal is monogastric. It is generally understood that a monogastric animal has a single-chambered stomach. In other embodiments, the animal is a ruminant. It is generally understood that a ruminant has a multi-chambered stomach. In some embodiments, the animal is a ruminant in the pre-ruminant phase.

Examples of such ruminants in the pre-ruminant phase include nursery calves.

In some embodiments, the animal is livestock. In some embodiments, the animal is a companion animal. In some embodiments, the animal is poultry. Examples of poultry include chicken, duck, turkey, goose, quail, or Cornish game hen. In one variation, the animal is a chicken. In some embodiments, the poultry is a layer hen, a broiler chicken, or a turkey. In other embodiments, the animal is a mammal, including, for example, a cow, a pig, a goat, a sheep, a deer, a bison, a rabbit, an alpaca, a llama, a mule, a horse, a reindeer, a water buffalo, a yak, a guinea pig, a rat, a mouse, an alpaca, a dog, a cat, or a human. In one variation, the animal is a cow. In another variation, the animal is a pig.

The animal feed composition may also be used in aquaculture. In some embodiments, the animal is an aquatic animal. Examples of aquatic animals may include a trout, a salmon, a bass, a tilapia, a shrimp, an oyster, a mussel, a clam, a lobster, or a crayfish. In one variation, the animal is a fish.

In some embodiments, the animal is a fish (e.g. salmon, tilapia, tropical fish), poultry (e.g. chicken, turkey), seafood (e.g. shrimp), sheep, cow, cattle, buffalo, bison, pig (e.g. nursery pig, grower/finisher pig), cat, dog, rabbit, goat, guinea pig, donkey, camel, horse, pigeon, ferret, gerbil, hamster, mouse, rat, bird, or human.

IX. Administration

In some embodiments, administration comprises providing a synthetic oligosaccharide preparation, a nutritional composition, or an animal feed composition described herein, to an animal such that the animal may ingest the synthetic oligosaccharide preparation, the nutritional composition, or the animal feed composition at will. In such embodiments, the animal ingests some portion of the synthetic oligosaccharide preparation, the nutritional composition, or the animal feed composition.

The synthetic oligosaccharide preparation, nutritional composition, animal feed pre-mix, or animal feed composition may be provided to the animal on any appropriate schedule. In some embodiments, the animal is provided the synthetic oligosaccharide preparation, nutritional composition, animal feed pre-mix, or animal feed composition on a daily basis, on a weekly basis, on a monthly basis, on an every other day basis, for at least three days out of every week, or for at least seven days out of every month. In some embodiments, the animal is provided the oligosaccharide preparation, animal feed pre-mix, or animal feed composition during certain diet phases.

For example, some animals are provided a starter diet between 0 to 14 days of age. In other embodiments, an animal is provided a grower diet between 15 to 28 days of age, between 15 to 35 days of age, or between 15 to 39 days of age. In still other embodiments, an animal is provided a finisher diet between 29 to 35 days of age, between 36 to 42 days of age, or between 40 to 46 days of age.

In certain embodiments, the synthetic oligosaccharide preparation, nutritional composition, animal feed pre-mix, or animal feed composition is provided to the animal during the starter diet phase, the grower diet phase, or the finisher diet phase, or any combinations thereof.

In certain embodiments, the animal is poultry, and the poultry is provided a starter diet between 0 to 15 days of age, a grower diet between 16 to 28 days of age, and a finisher diet between 29 to 35 days of age. In other embodiments, the animal is poultry, and the poultry is provided a starter diet between 0 to 14 days of age, a grower diet between 15 to 35 days of age, and a finisher diet between 36 to 42 days of age. In still other embodiments, the animal is poultry, and the poultry is provided a starter diet between 0 to 14 days of age, a grower diet between 15 to 39 days of age, and a finisher diet between 20 to 46 days of age.

In some embodiments, the synthetic oligosaccharide preparation, nutritional composition, animal feed pre-mix, or animal feed composition is provided to the poultry during the starter diet phase, the grower diet phase, or the finisher diet phase, or any combinations thereof.

The oligosaccharide preparations described herein may be fed to individual animals or an animal population. For example, in one variation where the animal is poultry, the oligosaccharide preparations may be fed to an individual poultry or a poultry population.

The synthetic oligosaccharide preparation, nutritional composition, animal feed pre-mix, or the animal feed composition may be provided to an animal in any appropriate form, including, for example, in solid form, in liquid form, or a combination thereof. In certain embodiments, the oligosaccharide preparation or the animal feed composition is a liquid, such as a syrup or a solution.

In other embodiments, the oligosaccharide preparation, animal feed pre-mix, or the animal feed composition is a solid, such as pellets or powder. In yet other embodiments, the oligosaccharide preparation, animal feed pre-mix, or the animal feed composition may be fed to the animal in both liquid and solid components, such as in a mash.

EXAMPLES

Example 1

Synthesis of a Gluco-Galacto-Oligosaccharide Preparation

Synthesis of a gluco-galacto-oligosaccharide preparation was performed in a three-liter reaction vessel using catalyst loadings, reaction times, and reaction temperatures that were selected to enable suitable production at the kg scale.

D-glucose monohydrate (825.16 g), D-lactose monohydrate (263.48 g) and 2-pyridinesulfonic acid (1.0079 g, Sigma-Aldrich, St. Louis, US) were added to a three-liter, three-neck round bottom flask with a center 29/42 ground glass joint and two 24/40 side ground glass joints. A 133 mm Teflon stirring blade was affixed to a glass stir shaft using PTFE tape. The stir rod was secured through the center point using a Teflon bearing adapter and attached to an overhead high-torque mechanical mixer via flexible coupler. The flask was secured inside a hemispherical electric heating mantle operated by a temperature control unit via a J-type wand thermocouple inserted through a rubber septum in one of the side ports. The tip of the thermocouple was adjusted to reside within the reaction mixture with several mm clearance above the mixing element. A secondary temperature probe connected to an auxiliary temperature monitor was also inserted and secured by the same means. The second side port of the flask was equipped with a reflux condenser cooled by a water-glycol mixture maintained below 4° C. by a recirculating bath chiller.

The reaction mixture was gradually heated to 130° C. with continuous mixing with a stir rate of 80-100 rpm. When the reaction mixture reached 120° C., the reflux condenser was re-positioned into a distillation configuration, with the distillated collected in a 250 mL round bottom flask placed in an ice bath. The mixture was maintained at 130° C. with continuous mixing for 6 hours, after which the thermocouple box was powered off. The distillation apparatus was removed and 390 g of 60° C. distilled water was gradually added into the three-neck flask. The resulting mixture was left to stir at 40 RPM for 10 hours. Approximately 1,250 g of a viscous, light-amber material was collected and measured by refractive index to have a concentration of 71.6 Brix.

The final water content of the reactor product was measured by Karl Fisher titration for a representative aliquot of the reactor contents drawn at the end of the reaction. At a reaction temperature of 130° C., the water content of the reaction product was determined to be 5.8 wt % water on an as-is basis.

Example 2

Synthesis of a Gluco-Oligosaccharide Preparation

Synthesis of a gluco-oligosaccharide preparation was performed in a three-liter reaction vessel using catalyst loadings, reaction times, and reaction temperatures that were selected to enable suitable production at the kg scale.

D-glucose monohydrate (1,150 g) was added to a three-liter, three-neck round bottom flask with one center 29/42 ground glass joint and two side 24/40 ground glass joints. A 133 mm Teflon stirring blade was affixed to glass stir shaft using PTFE tape. The stir rod was secured through the center port of the flask using a Teflon bearing adapter and attached to an overhead high-torque mechanical mixer via flex coupling. The flask was secured inside a hemispherical electric heating mantle operated by a temperature control unit via a J-type wand thermocouple inserted through a rubber septum in one of the side ports. The tip of the thermocouple was adjusted to reside within the reaction mixture with several mm clearance above the mixing element. A secondary temperature probe connected to an auxiliary temperature monitor was also inserted and secured by the same means. The second side port of the flask was equipped with a reflux condenser cooled by a water-glycol mixture maintained below 4 C by a recirculating bath chiller.

The reaction mixture was gradually heated to 130° C. with continuous mixing with a stir rate of 80-100 rpm. When the reaction temperature increased to between 120° C. and 130° C., (+)-Camphor-10-sulfonic acid (1.16 g, Sigma-Aldrich, St. Louis) was added to the three-neck flask and the apparatus was switched from a reflux condenser to a distillation configuration with a round bottom collection flask placed in an ice bath. This setup was maintained for 1 and a half hours, after which the thermocouple box was powered off, the distillation apparatus was removed, and 390 g of 23 degrees C. distilled water was gradually added into the three-neck flask. The resulting mixture was left to stir at 40 rpm for 10 hours until the moment of collection. Approximately 1300 g of a viscous, dark-amber material was collected and measured to have a concentration of 72.6 brix.

Example 3

Synthesis of a Gluco-Galacto-Manno-Oligosaccharide Preparation

Synthesis of a gluco-galacto-manno-oligosaccharide preparation was performed in a three-liter reaction vessel using catalyst loadings, reaction times, and reaction temperatures that were selected to enable suitable production at the kg scale.

The gluco-galacto-manno-oligosaccharide was prepared as two separate components synthesized in separate reaction vessels that were independently collected. Each synthesis used different starting reactants but followed the same procedure and methods to completion. The final gluco-galacto-manno-oligosaccharide was a homogeneous syrup formed from the mixing of both synthesis products.

For the synthesis of the first component, 990.54 g of glucose monohydrate, 105.58 g of lactose monohydrate and 1.00 g of 2-pyridinesulfonic acid were added to a three-liter, three-neck round bottom flask with one center 29/42 ground joint flanked by two 24/40 ground joints. A 133 mm Teflon stirring blade was affixed to a 440 mm glass stir shaft using PTFE tape. The stir rod was secured through the center point using a Teflon bearing adapter and attached to an overhead high-torque mechanical mixer via flexible coupler. The flask was placed inside a hemispherical electric heating mantle operated by a temperature control unit via a J-type wand thermocouple inserted through a rubber septum in one of the side ports. The tip of the thermocouple was adjusted to reside within the reaction mixture with several mm clearance above the mixing element. A secondary temperature probe connected to an auxiliary temperature monitor was also inserted and secured by the same means. The second side port of the flask was equipped with a reflux condenser cooled by a water-glycol mixture maintained below 4° C. by a recirculating bath chiller.

The reaction mixture was gradually heated to 130° C. with continuous mixing with a stir rate of 80-100 rpm. Once a temperature control box reading between 120 C and 130° C. was observed, the apparatus was switched from a reflux condenser to a distillation configuration with a round bottom collection flask placed in an ice bath. This setup was maintained for approximately 6 hours and 10 minutes, after which the heating mantle was powered off, the distillation apparatus was removed, and 390 g of 60° C. distilled water was gradually added into the three-neck flask. The resulting mixture was left to stir at 40 rpm for 10 hours until the moment of collection. Approximately 1250 g of a viscous, light-amber material was collected and measured by refractive index to have a concentration of 73.1 Brix.

For the synthesis of the second component, 825.04 g of glucose monohydrate, 251.16 g of pure mannose from wood, 25.10 g distilled water, and 1.00 g of 2-pyridinesulfonic acid were added to a three-liter, three-neck round bottom flask with one center 29/42 ground joint flanked by two 24/40 ground joints. The remainder of the second component's synthesis followed the same procedure and methods as those of the first, until the moment of collection. Approximately 1250 g of a viscous, dark-amber material was collected and measured to have a concentration of 72.3 brix.

The entirety of the first and second components were transferred into a suitably sized HDPE container and mixed thoroughly by hand until homogenous. The final syrup mixture was approximately 2.5 kg, dark-amber in color, viscous and was measured to have a concentration of approximately 72 brix.

Example 4

Synthesis of a Gluco-Manno-Oligosaccharide Preparation

Synthesis of a gluco-oligosaccharide preparation was performed in a three-liter reaction vessel using catalyst loadings, reaction times, and reaction temperatures that were selected to enable suitable production at the kg scale.

A gluco-manno-oligosaccharide was prepared as two separate components synthesized in separate reaction vessels that were independently collected. Each synthesis used different starting reactants but followed the same procedure and methods to completion. The final gluco-manno-oligosaccharide was a homogeneous syrup formed from the mixing of both synthesis products.

For the synthesis of the first component, 1264.80 g of glucose monohydrate was added to a three-liter, three-neck round bottom flask with one center 29/42 ground joint flanked by two 24/40 ground joints. A 133 mm Teflon stirring blade was affixed to a 440 mm glass stir shaft using PTFE tape. The stir rod was secured through the center point using a Teflon bearing adapter and attached to an overhead high-torque mechanical mixer via flexible coupler. The flask was placed inside a hemispherical electric heating mantle operated by a temperature control unit via a J-type wand thermocouple inserted through a rubber septum in one of the side ports. The tip of the thermocouple was adjusted to reside within the reaction mixture with several mm clearance above the mixing element. A secondary temperature probe connected to an auxiliary temperature monitor was also inserted and secured by the same means. The second side port of the flask was equipped with a reflux condenser cooled by a water-glycol mixture maintained below 4° C. by a recirculating bath chiller.

The reaction mixture was gradually heated to 130° C. with continuous mixing with a stir rate of 80-100 rpm. Once a temperature control box reading between 120° C. and 130° C. was observed, 1.15 g of (+)-camphor-10-sulfonic acid was added to the three-neck flask and the apparatus was switched from a reflux condenser to a distillation configuration with a round bottom collection flask placed in an ice bath. This setup was maintained for approximately 1 hour, after which the thermocouple box was powered off, the distillation apparatus was removed, and 390 g of 23° C. distilled water was gradually added into the three-neck flask. The resulting mixture was left to stir at 40 rpm for 10 hours until the moment of collection. Approximately 1350 g of a viscous, light-amber material was collected and measured to have a concentration of 71.8 brix.

For the synthesis of the second component, 949.00 g of glucose monohydrate, 288.00 g of pure mannose from wood, 27.94 g distilled water, and 1.15 g of 2-pyridinesulfonic acid were added to a three-liter, three-neck round bottom flask with one center 29/42 ground joint flanked by two 24/40 ground joints. The remainder of the second component's synthesis followed the same procedure and methods as those of the first until the moment of collection, except (+)-camphor-10-sulfonic acid was not added as the reflux condenser was switched to a distillation configuration and the resulting setup was maintained for approximately 6 hours. Approximately 1350 g of a viscous, dark-amber material was collected and measured to have a concentration of 72.0 brix.

The entirety of the first and second components were transferred into a suitably sized HDPE container and mixed thoroughly by hand until homogenous. The final syrup mixture was approximately 2.7 kg, dark-amber in color, viscous and was measured by refractive index to have a concentration of approximately 72 Brix.

Example 5

Synthesis of a Gluco-Manno-Oligosaccharide Preparation

Kilogram scale production of the oligosaccharide preparation was performed in a three-liter reaction vessel using catalyst loadings, reaction times, and reaction temperatures found to be suitable for production at the 1 kg scale.

A gluco-manno-oligosaccharide was prepared as two separate components synthesized in separate reaction vessels that were independently collected. Each synthesis used different starting reactants but followed the same procedure and methods to completion. The final gluco-manno-oligosaccharide was a homogeneous syrup formed from the mixing of both synthesis products.

For the synthesis of the first component, 1261.00 g of glucose monohydrate and 1.15 g of 2-pyridinesulfonic acid were added to a three-liter, three-neck round bottom flask with one center 29/42 ground joint flanked by two 24/40 ground joints. A 133 mm Teflon stirring blade was affixed to a 440 mm glass stir shaft using PTFE tape. The stir rod was secured through the center point using a Teflon bearing adapter and attached to an overhead high-torque mechanical mixer via flexible coupler. The flask was secured inside a hemispherical electric heating mantle operated by a temperature control unit via a J-type wand thermocouple inserted through a rubber septum in one of the side ports.

The tip of the thermocouple was adjusted to reside within the reaction mixture with several mm clearance above the mixing element. A secondary temperature probe connected to an auxiliary temperature monitor was also inserted and secured by the same means. The second side port of the flask was equipped with a reflux condenser cooled by a water-glycol mixture maintained below 4° C. by a recirculating bath chiller.

The reaction mixture was gradually heated to 130° C. with continuous mixing with a stir rate of 80-100 rpm. Once a temperature control box reading between 120° C. and 130° C. was observed, the apparatus was switched from a reflux condenser to a distillation configuration with a round bottom collection flask placed in an ice bath. This setup was maintained for approximately 6 hours, after which the thermocouple box was powered off, the distillation apparatus was removed, and 390 g of 23° C. distilled water was gradually added into the three-neck flask. The resulting mixture was left to stir at 40 rpm for 10 hours until the moment of collection. Approximately 1250 g of a viscous, light-amber material was collected and measured to have a concentration of 73.5 brix.

For the synthesis of the second component, 949.00 g of glucose monohydrate, 288.00 g of pure mannose from wood, 28.94 g distilled water, and 1.15 g of 2-pyridinesulfonic acid were added to a three-liter, three-neck round bottom flask with one center 29/42 ground joint flanked by two 24/40 ground joints. The remainder of the second component's synthesis followed the same procedure and methods as those of the first until the moment of collection. Approximately 1250 g of a viscous, dark-amber material was collected and measured to have a concentration of 73.3 brix.

The entirety of the first and second components were transferred into a suitably sized HDPE container and mixed thoroughly by hand until homogenous. The final syrup mixture was approximately 2.5 kg, dark-amber in color, viscous and was measured to have a concentration of approximately 73 brix.

Example 6

Synthesis of a Gluco-Galacto-Oligosaccharide Preparation

Kilogram scale production of the oligosaccharide preparation was performed in a three-liter reaction vessel using catalyst loadings, reaction times, and reaction temperatures found to be suitable for production at the 1 kg scale.

A 3 L three-neck flask was equipped with an overhead mixer connected via a 10 mm diameter glass stir-shaft to a 14 cm crescent-shaped mixing element. The mixing element was positioned with approximately 5 mm clearance from the walls of the flask. The flask was heated via a hemispherical electric heating mantle powered by a temperature control unit connected to a wand-type thermocouple probe inserted into the reaction flask. The thermocouple probe was placed to provide 5-10 mm clearance above the mixing element. The flask was charged with 576 grams of food-grade dextrose monohydrate and 577 grams of food-grade D-galactose monohydrate and heated to approximately 115° C. to obtain a molten sugar syrup. Once the syrup was obtained, the flask was fitted with a jacketed reflux condenser cooled to 4° C. by circulating chilled glycol/water and the temperature. 31 grams of Dowex Marathon C (moisture content 0.48 g $H_2O$/g resin) were added to the mixture to form a stirred suspension. The condenser was repositioned into distillation configuration and the suspension was heated to 145° C.

A mixing rate of approximately 80 RPM and a temperature of 145° C. was maintained for 3.8 hours, after which the set point on the temperature control unit was reduced to 80° C. and 119 mL of 60° C. deionized water was gradually added to the flask to obtain a dark amber syrup containing residual Dowex resin. The resulting suspension was further diluted to 60 Brix, cooled to room temperature and vacuum filtered through a 0.45 micron filter to remove the resin. 1,200 grams of light-amber syrup at 60 Brix concentration was obtained.

Example 7

Synthesis of a Gluco-Oligosaccharide Preparation

Kilogram scale production of the oligosaccharide preparation was performed in a three-liter reaction vessel using catalyst loadings, reaction times, and reaction temperatures found to be suitable for production at the 1 kg scale.

A 3 L three-neck flask was equipped with an overhead mixer connected via a 10 mm diameter glass stir-shaft to a 14 cm crescent-shaped mixing element. The mixing element was positioned with approximately 5 mm clearance from the walls of the flask. The flask was heated via a hemispherical electric heating mantle powered by a temperature control unit connected to a wand-type thermocouple probe inserted into the reaction flask. The thermocouple probe was placed to provide 5-10 mm clearance above the mixing element. The flask was gradually charged with 1,148 grams of food-grade dextrose monohydrate and heated to approximately 115° C. to obtain a molten sugar syrup. Once the syrup was obtained, the flask was fitted with a jacketed distillation condenser cooled to 4° C. by circulating chilled glycol/water. The reaction temperature was gradually increased to 145° C. Once the temperature was obtained and stable, 31 grams of Dowex Marathon C (moisture content 0.48 g $H_2O$/g resin) was added to the mixture and a mixing rate of approximately 80 RPM and a temperature of 145° C. was maintained for 3.8 hours.

After 3.8 hours, the set point on the temperature control unit was reduced to 80° C. and 119 mL of 60° C. deionized water was gradually added to the flask to obtain a dark amber syrup containing residual Dowex resin. The resulting suspension was further diluted to 60 Brix, cooled to room temperature and vacuum filtered through a 0.45 micron filter to remove the resin. 1,113 grams of dark-amber gluco-oligosaccharide syrup at 60 Brix concentration was obtained.

Example 8

Single-Pot Syntheses of Oligosaccharide Preparations

A single pot (single component) synthesis of the oligosaccharide from Example 3 was demonstrated at 300 gram scale in a one-liter reaction vessel using catalyst loadings, reaction times, and reaction temperatures found to be suitable for the single pot reaction.

30 g of food-grade D-glucose monohydrate from corn, 37.50 g of food grade D-mannose from wood, 15.60 g of food-grade D-lactose monohydrate, 3.96 g of distilled water and 0.270 g of 2-pyridinesulfonic acid (Sigma-Aldrich, St. Louis) were added to a one-liter, three-neck round bottom flask with one center 29/42 ground joint flanked by two 24/40 ground joints. A Teflon stirring blade was affixed to a 220 mm glass stir shaft using PTFE tape. The stir rod was secured through the center point using a Teflon bearing adapter and attached to an overhead high-torque mechanical mixer via flexible coupler. The flask was secured inside a hemispherical electric heating mantle operated by a temperature control unit via a J-type wand thermocouple inserted through a rubber septum in one of the side ports. The tip of the thermocouple was adjusted to reside within the reaction mixture with several mm clearance above the mixing element. A secondary temperature probe connected to an auxiliary temperature monitor was also inserted and secured by the same means. The second side port of the flask was equipped with a reflux condenser cooled by a water-glycol mixture maintained below 4° C. by a recirculating bath chiller.

The reaction mixture was gradually heated to 130° C. with continuous mixing with a stir rate of 80-100 rpm. Once a temperature control box reading between 120° C. and 130° C. was observed, the apparatus was switched from a reflux condenser to a distillation configuration with a round bottom collection flask placed in an ice bath. The mixture was maintained at 130° C. with continuous stirring for approximately 5 hours and 40 minutes, after which the heating mantle and distillation apparatus was removed. Approximately 40 g of 23° C. distilled water was gradually added into the three-neck flask. The resulting mixture was left to stir at 40 rpm for 10 hours until the moment of collection.

Approximately 389 g of a viscous, dark-amber material was collected and measured to have a concentration of 67.0 brix. Consistency with the oligosaccharide preparation from Example 3 was confirmed by SEC chromatography and 2D HSQC NMR spectroscopy.

Example 9

Characterization of Oligosaccharide Preparations

The methods and procedures from Examples 1-8 were used to prepare replicate batches and blends of the oligosaccharides of Examples 1-7. In preparing the various batches of Examples 9.1-9.7, both multi-pot (multi-component) and single-pot variants of the respective synthetic schemes were employed. The resulting materials were analyzed by HPLC Size Exclusion Chromatography (SEC) to characterize the molecular weight distribution, LC-MS/MS analysis to quantify the DP2 anhydro-sugar content, and 2D $^{1}H$, $^{13}C$-HSQC NMR to fingerprint the molecular structure of the corresponding oligosaccharide preparations. Materials were prepared as follows:

Example 9.1: eleven batches of the oligosaccharide preparation from Example 1 were prepared and blended into four separate lots to produce oligosaccharide 9.1.

Example 9.2: seven batches of the oligosaccharide preparation from Example 2 were prepared and blended into two separate lots to produce oligosaccharide 9.2.

Example 9.3: twelve batches of the oligosaccharide preparation from Example 3 were prepared and blended into five separate lots to produce oligosaccharide 9.3.

Example 9.4: four batches of the oligosaccharide preparation from Example 4 were prepared and blended into a single lot to produce oligosaccharide 9.4.

Example 9.5: four batches of the oligosaccharide preparation from Example 5 were prepared and blended into a single lot to produce oligosaccharide 9.5.

Example 9.6: two batches of the oligosaccharide preparation from Example 6 were prepared and blended into a single lot to produce oligosaccharide 9.6.

Example 9.7: two batches of the oligosaccharide preparation from Example 7 were prepared and blended into a single lot to produce oligosaccharide 9.7.

Further structural variants of oligosaccharide preparations of Examples 1-7 were synthesized at 300 gram scale using the methods of Examples 1-7 but varying the starting sugar compositions, acid, acid loading, time, and reaction temperature. Oligosaccharide preparations were synthesized as follows:

Example 9.8: 300 grams of sucrose, 3 grams of phosphoric acid, and 27 grams of water were reacted at 125° C. for about one hour to obtain a dark brown oligosaccharide syrup that was then diluted to 60 Brix with distilled water.

Example 9.9: 270 grams of glucose, 30 grams of sucrose, 0.3 grams of phenylphosphonic acid, and 27 grams of water were reacted at 130° C. for between one to four hours to obtain a dark brown oligosaccharide syrup that was then diluted to 60 Brix with distilled water.

Example 9.10: 225 grams of glucose, 75 grams of lactose, 3 grams of butylphosphonic acid and 27 grams of water were reacted at 130° C. for between one to four hours to obtain a dark amber oligosaccharide syrup that was then diluted to 60 Brix with distilled water.

Example 9.11: 225 grams of glucose, 75 grams of lactose, 3 grams of phenylphosphonic acid and 27 grams of water were reacted at 130° C. for between one to five hours to obtain a dark amber oligosaccharide syrup that was then diluted to 60 Brix with distilled water.

Example 9.12: 270 grams of glucose, 30 grams of lactose, 3 grams of phenylphosphinic acid and 27 grams of water were reacted at 130° C. for between three to five hours to obtain a dark brown oligosaccharide syrup that was then diluted to 60 Brix with distilled water.

Example 9.13: 300 grams of glucose, 3 grams of phenylphosphinic acid, and 27 grams of water were reacted at 130° C. for one to three hours to obtain a dark amber oligosaccharide syrup that was then diluted to 60 Brix with distilled water.

Example 9.14: 300 grams of glucose, 2 grams of propionic acid, and 27 grams of water were reacted at 130° C. for one to four hours to obtain an amber oligosaccharide syrup that was then diluted to 60 Brix with distilled water.

Example 9.15: 300 grams of glucose, 0.15 grams of 8-hydroxy-5-quinolinesulfonic acid hydrate, and 27 grams of water were reacted at 130° C. for two to four hours to obtain an amber oligosaccharide syrup that was then diluted to 60 Brix with distilled water.

In the above reactions, all masses refer to the pure component masses, and the total mass of reactant water was inclusive of any carry-along water provided by the moisture content and/or water of hydration of the reactant sugars.

Characterization of Oligosaccharide Preparations:

The resulting materials were analyzed by HPLC Size Exclusion Chromatography (SEC) to characterize the molecular weight distribution, LC-MS/MS analysis to quantify the DP2 anhydrosugar content, and 2D $^{1}H$, $^{13}C$-HSQC NMR to fingerprint the molecular structure of the corresponding oligosaccharide preparations.

Polymer Molecular Weight determined by HPLC:

The number average molecular weight (MWn) and weight-average molecular weight (MWw) of the oligosaccharide preparations of Examples 9.1-9.7 were determined by HPLC. SEC analysis was performed on an Agilent 1100 series HPLC with refractive index detection using an Agilent PL aquagel-OH 20 column at 40° C. with distilled water at 0.45 mL/min as the mobile phase. Retention-time to MW calibration was performed using standard solutions with known molecular weight and standard methods from the art were used to determine the various distribution properties from the SEC chromatogram. The MWn and MWw of oligosaccharide preparations with multiple lots are shown below in Table 1.

TABLE 1

MWn and MWw of Oligosaccharide Preparations

| Oligosaccharide Preparation | MWn (g/mol) | MWw (g/mol) |
|---|---|---|
| 9.1 | 719 ± 11 | 1,063 ± 23 |
| 9.2 | 808 ± 30 | 1,336 ± 122 |
| 9.3 | 757 ± 15 | 1,186 ± 49 |
| 9.4 | 761 | 1,196 |
| 9.5 | 755 | 1,177 |
| 9.6 | 505 | 709 |
| 9.7 | 762 ± 12 | 1,154 ± 14 |

Anhydro-DP2 Content Analysis by GC-MS:

The anhydro DP2 content of oligosaccharide preparations was determined by LC-MS/MS using a Capcell Pak NH2 (Shiseido; 250×4. 6 mm, 5 μm) column at a flowrate of 1 mL/min under isocratic conditions of water/acetonitrile 35/65. Prior to MS the flow was split 1:4 and a makeup flow of 50 μL 0.05% NH4OH was added to enhance ionization. For MS detection ESI probe was used in negative mode and MRM method allowed targeted analysis.

The anhydro DP2 contents of the oligosaccharide preparations was first determined relative to that of the oligosaccharide preparation of Example 9.7 as a reference composition. The absolute anhydro DP2 content of the reference oligosaccharide preparation of Example 9.7 was then determined by HPLC-MS/MS to be about 10% and the anhydro DP2 contents of the oligosaccharide preparations of Examples 9.1 to 9.6 were then obtained by calculation. The relative and absolute DP2 contents were determined as described in Table 2.

TABLE 2

Anhydro DP2 content for oligosaccharide preparations with multiple lots

| Oligosaccharide Preparation | Relative Anhydro DP2 Content % Relative to Ex 9.7 | Anhydro DP2 Content (g AHDP2/g total DP2) |
|---|---|---|
| 9.1 | 53% | 5.3% |
| 9.2 | 14% | 1.4% |
| 9.3 | 57% | 5.7% |
| 9.4 | 53% | 5.3% |
| 9.5 | 33% | 3.3% |
| 9.6 | 50% | 5.0% |
| 9.7 | 100% | 10.0% |

Molecular Fingerprint by 2D $^1$H, $^{13}$C-HSOC NMR:

The molecular structures of the oligosaccharide preparations of Example 9 were characterized by 2D $^1$H, $^{13}$C-HSQC NMR spectroscopy. Samples were prepared by drying 125 mg (dry solids basis) of the oligosaccharide preparation at 40° C. and re-dissolving in $D_2O$ containing 0.1% acetone. NMR spectra were acquired at 300K on either a Bruker Avance NMR spectrometer operating at a proton frequency of 400 MHz or on a Bruker Avance III NMR spectrometer operating at a proton frequency of 600 MHz equipped with a cryogenically cooled 5 mm TCI probe. FIG. 1 provides an illustrative 2D $^1$H, $^{13}$C HSQC NMR spectrum of the oligosaccharide preparation of oligosaccharide preparation 9.7.

The anomeric region of the $^1$H, $^{13}$C-HSQC spectrum, F2 ($\delta^1$H)=4.2-6.0 ppm and F1($\delta^{13}$C)=90-120 ppm, was used to fingerprint the linkage distribution of the oligosaccharide preparations. Each peak in the anomeric region was integrated and its relative abundance was determined relative to that of the total anomeric region. 2D $^1$H, $^{13}$C HSQC fingerprinting was performed on the four lots of the oligosaccharide preparation 9.1.

TABLE 3

Relative Abundances of F2 and F1 Peaks of Oligosaccharide Preparation 9.1

| F2 (ppm) | F1 (ppm) | AUC (Average ± SEM) |
|---|---|---|
| 5.43 | 92.42 | 0.4% ± 0.3% |
| 5.44 | 102.07 | 0.4% ± 0.1% |
| 5.43 | 90.05 | 0.5% ± 0.2% |
| 5.40 | 100.22 | 1.6% ± 0.4% |
| 5.37 | 98.33 | 0.7% ± 0.4% |
| 5.35 | 99.70 | 2.7% ± 0.6% |
| 5.33 | 96.53 | 0.3% ± 0.2% |
| 5.24 | 100.86 | 0.5% ± 0.2% |
| 5.22 | 92.71 | 20.2% ± 3.9% |
| 5.21 | 102.45 | 0.5% ± 0.4% |
| 5.18 | 93.86 | 0.9% ± 0.4% |
| 5.17 | 96.01 | 0.4% ± 0.1% |
| 5.09 | 96.88 | 0.6% ± 0.3% |
| 5.03 | 108.49 | 0.4% ± 0.2% |
| 5.02 | 109.16 | 0.4% ± 0.4% |
| 4.98 | 99.19 | 0.6% ± 0.3% |
| 4.95 | 98.51 | 30.6% ± 4.1% |
| 4.86 | 98.53 | 0.7% ± 0.5% |
| 4.79 | 96.84 | 0.6% ± 0.3% |
| 4.71 | 103.48 | 2.5% ± 0.7% |
| 4.64 | 103.56 | 0.8% ± 0.4% |
| 4.63 | 102.49 | 0.7% ± 0.5% |
| 4.62 | 104.56 | 1.4% ± 0.4% |
| 4.57 | 97.07 | 1.6% ± 0.3% |
| 4.50 | 103.30 | 25.9% ± 2.2% |
| 4.45 | 103.56 | 2.4% ± 1.3% |

Example 10

Determination of the Anhydro Sugar Subunits of an Oligosaccharide Preparation The relative abundance of anhydro sugar subunits in the oligosaccharide preparations of Example 9 was determined by MALDI-MS on a Bruker Ultraflex instrument. Samples were dissolved in water to a concentration of 10 mg/ml, from which 5 μl were mixed with matrix solution (30 mg/ml DHB in 80% ethanol and water in a ratio 1:10). Plates were prepared by applying 1 μl of the analyte solution to the target plate and dried at ambient air. In some cases, samples were re-crystalized by applying 1 μl ethanol prior to MS analysis.

Figure 25A:
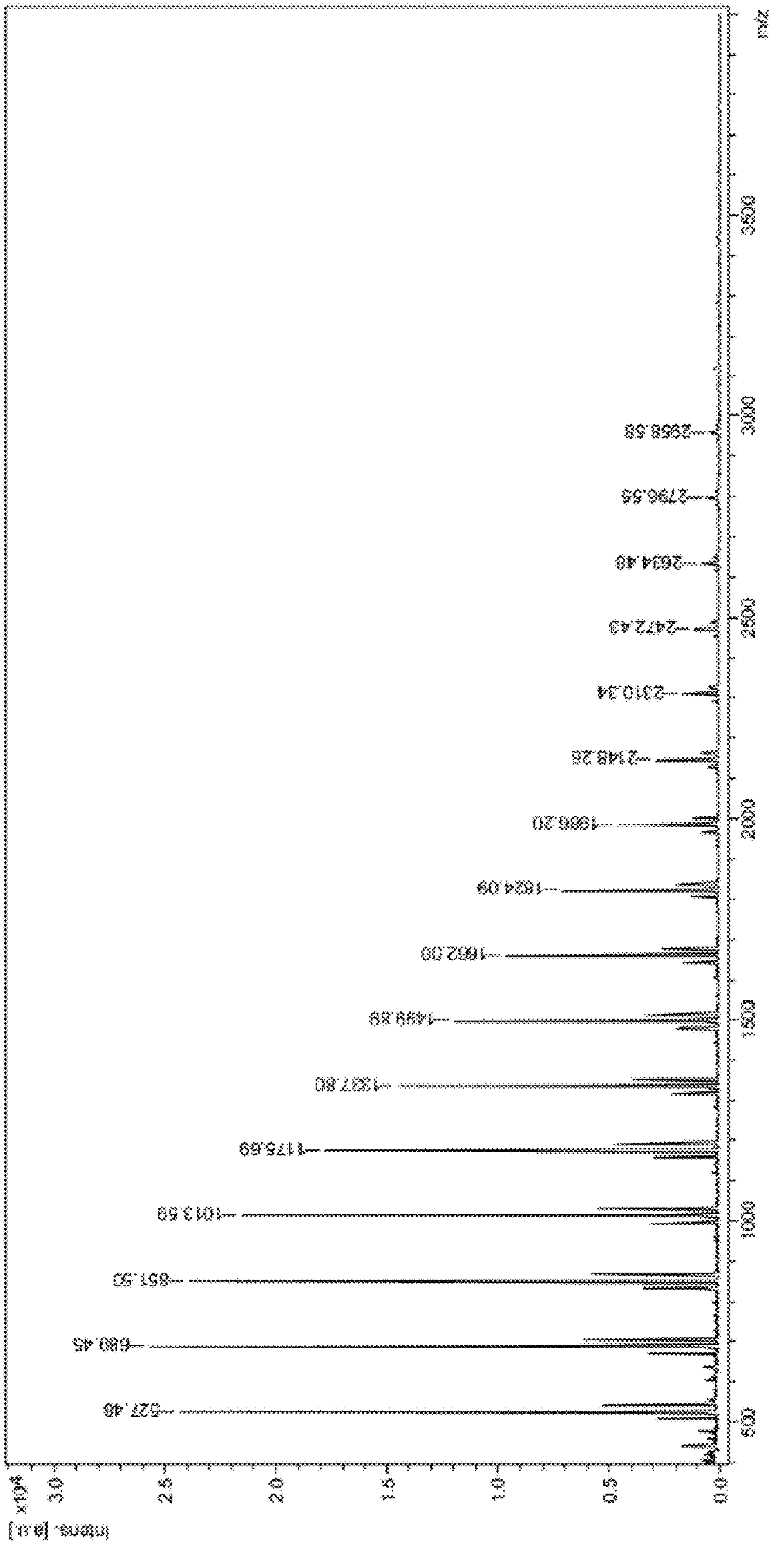
FIG. 25A illustrate a MALDI-MS spectrum of an oligosaccharide preparation from Example 2 that demonstrates the presence of anhydro-subunits.
Figure 25B:
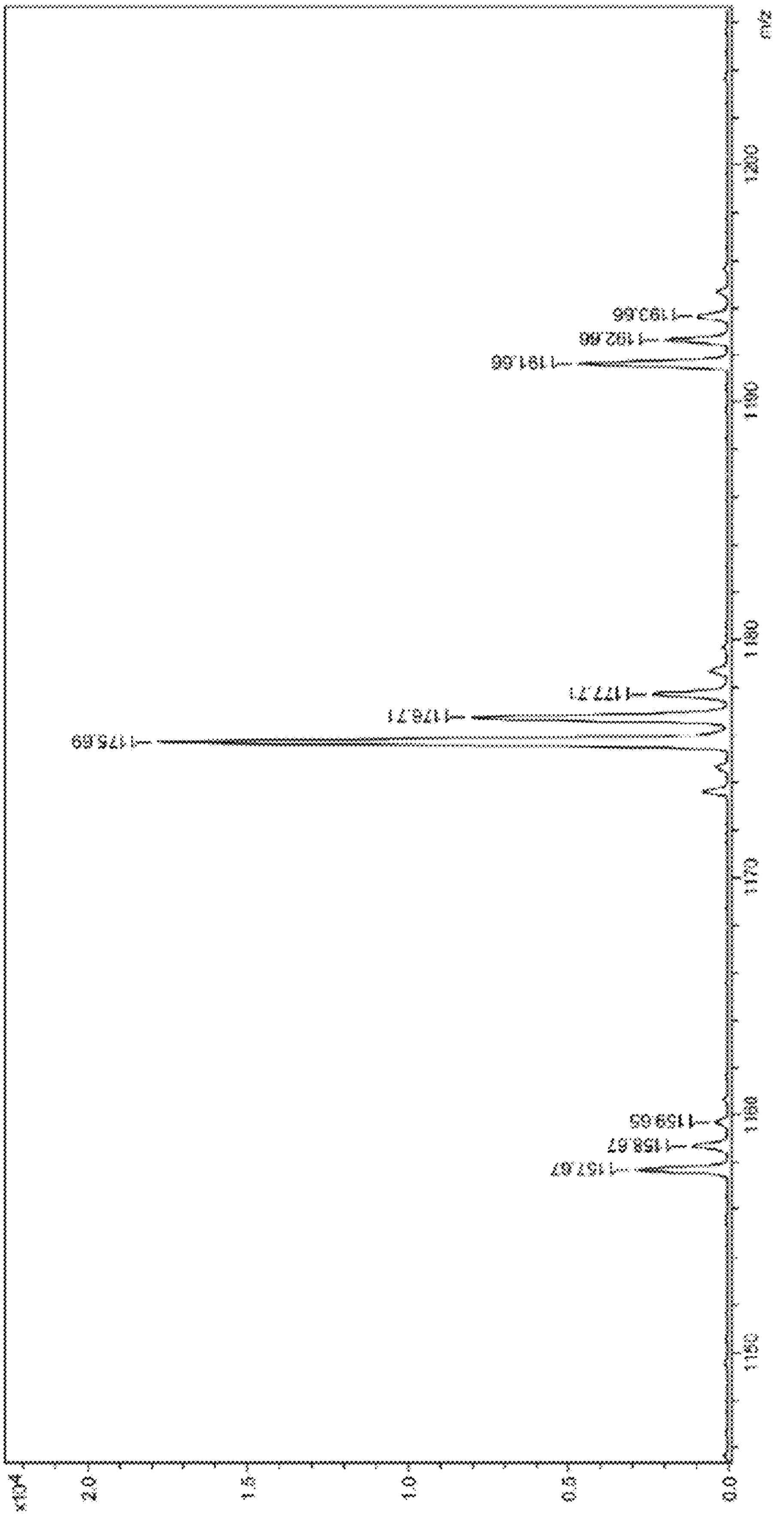
FIG. 25B illustrates a MALDI-MS spectrum of an oligosaccharide preparation from Example 2 that demonstrates the presence of anhydro-subunits.
Figures 26A, 26B, 26C:
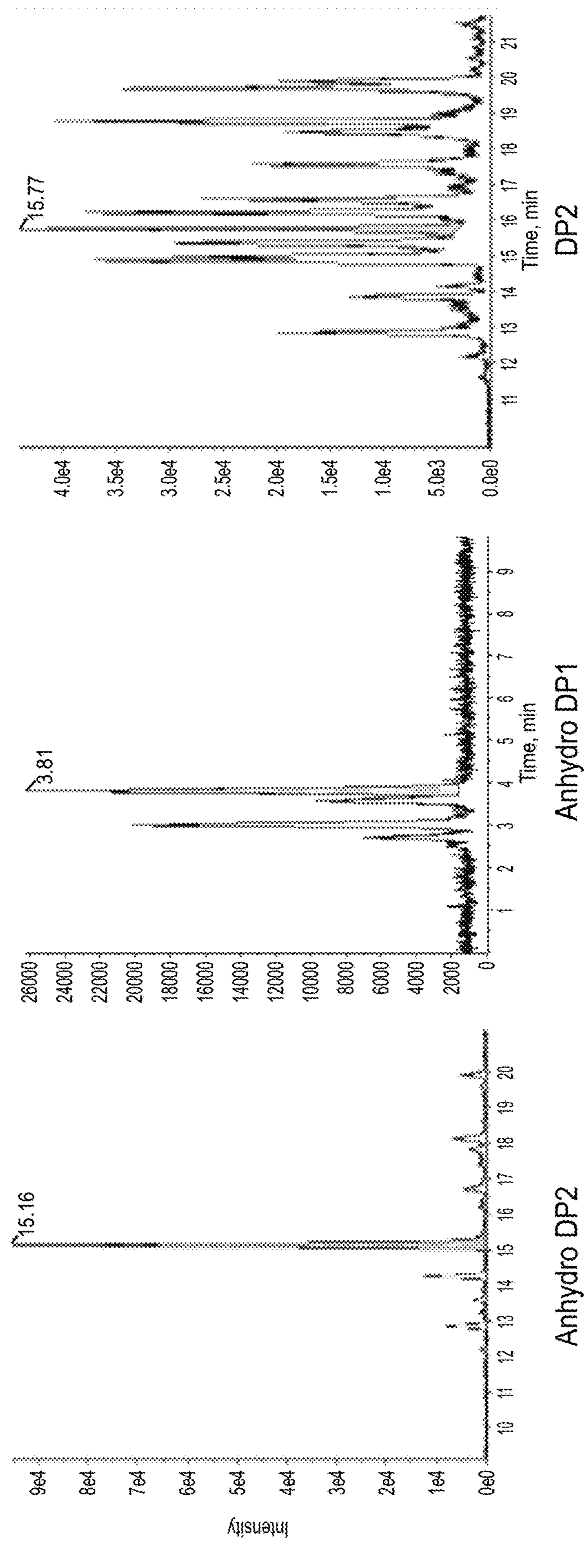
FIG. 26A illustrates LC-MS/MS detection of the anhydro DP2, anhydro DP1, and DP2 species of an oligosaccharide preparation of Example 1.
FIG. 26B illustrates LC-MS/MS detection of the anhydro DP2, anhydro DP1, and DP2 species of an oligosaccharide preparation of Example 1.
FIG. 26C illustrates LC-MS/MS detection of the anhydro DP2, anhydro DP1, and DP2 species of an oligosaccharide preparation of Example 1.
Figure 27C:
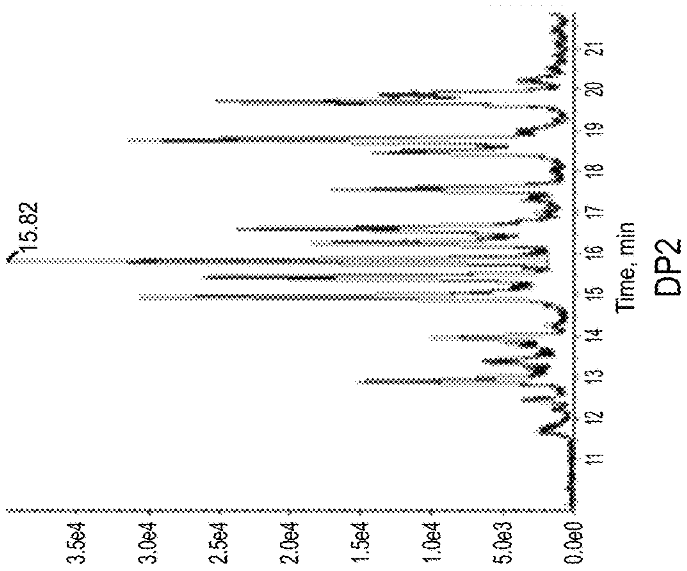
FIG. 27C illustrates LC-MS/MS detection of the anhydro DP2, anhydro DP1, and DP2 species of an oligosaccharide preparation of Example 3.
Figure 27B:
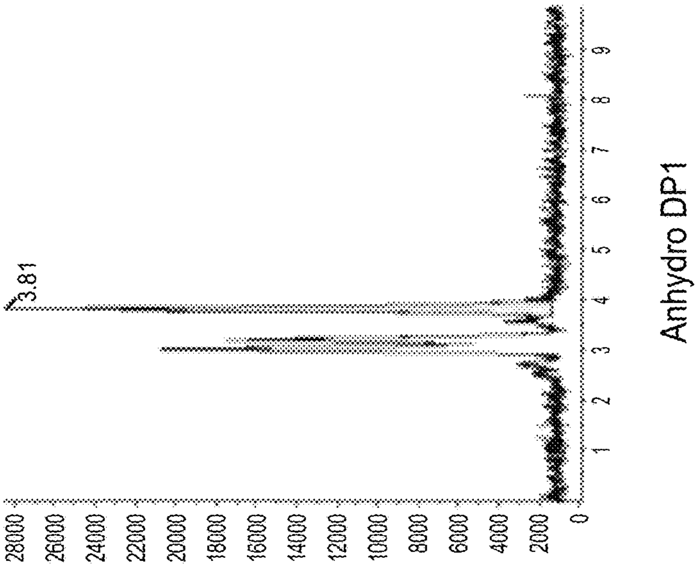
FIG. 27B illustrates LC-MS/MS detection of the anhydro DP2, anhydro DP1, and DP2 species of an oligosaccharide preparation of Example 3.
Figure 27A:
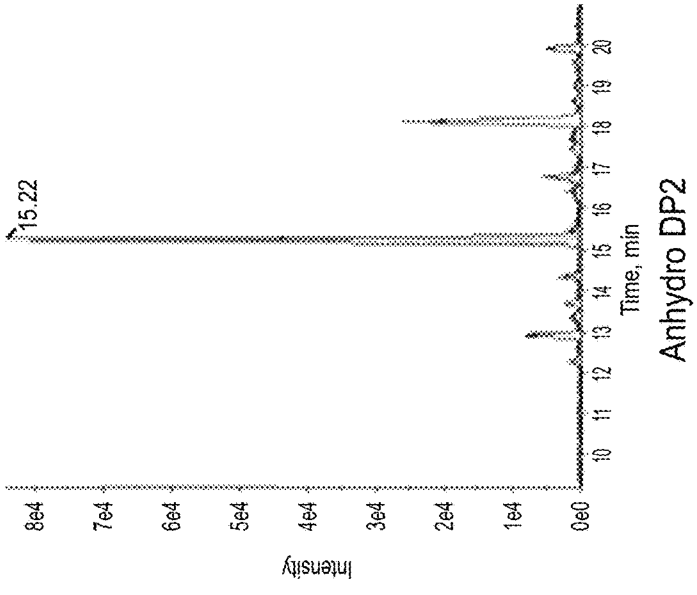
FIG. 27A illustrates LC-MS/MS detection of the anhydro DP2, anhydro DP1, and DP2 species of an oligosaccharide preparation of Example 3.
Figure 28A:
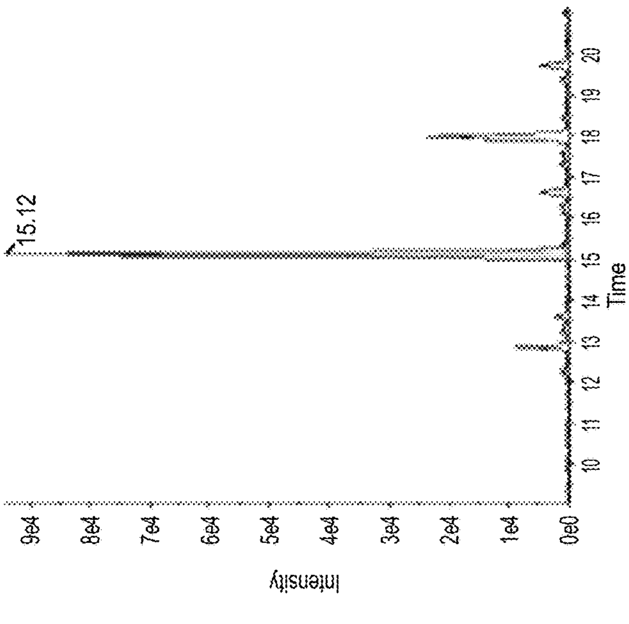
FIG. 28A illustrate LC-MS/MS detection of the anhydro DP2, anhydro DP1, and DP2 species of an oligosaccharide preparation of Example 4.
Figure 28B:
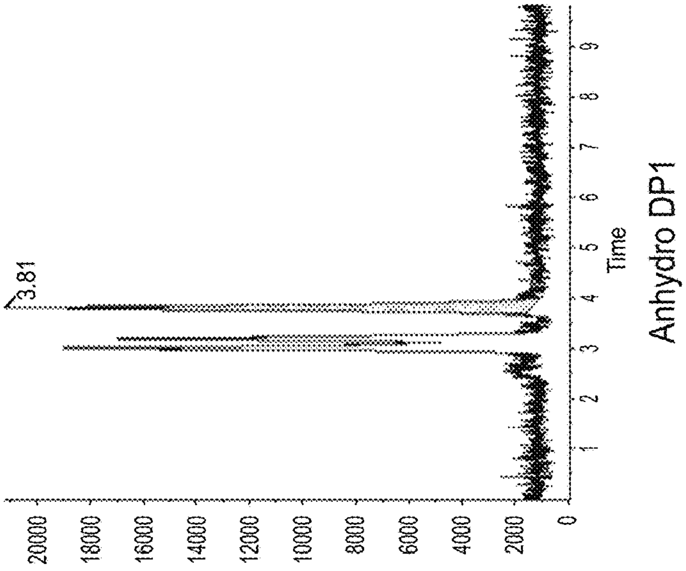
FIG. 28B illustrate LC-MS/MS detection of the anhydro DP2, anhydro DP1, and DP2 species of an oligosaccharide preparation of Example 4.
Figure 28C:
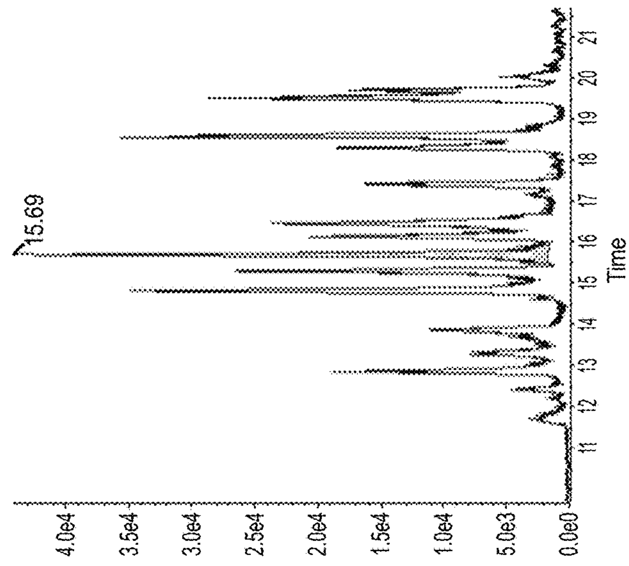
FIG. 28C illustrate LC-MS/MS detection of the anhydro DP2, anhydro DP1, and DP2 species of an oligosaccharide preparation of Example 4.
Figure 29C:
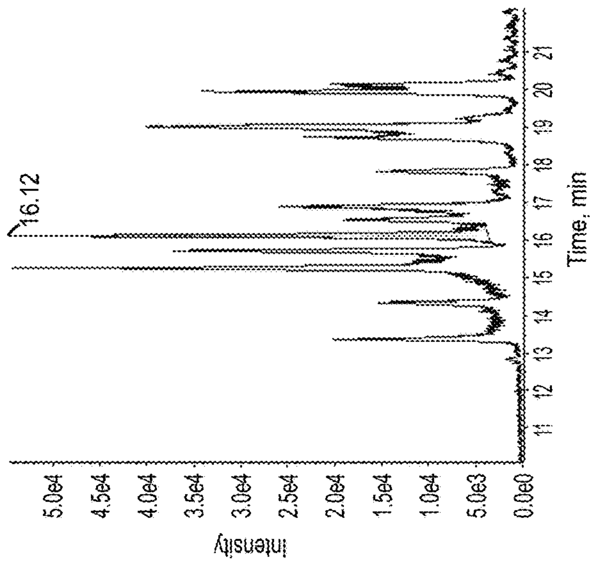
FIG. 29C illustrate LC-MS/MS detection of the anhydro DP2, anhydro DP1, and DP2 species of an oligosaccharide preparation of Example 7.
Figure 29B:
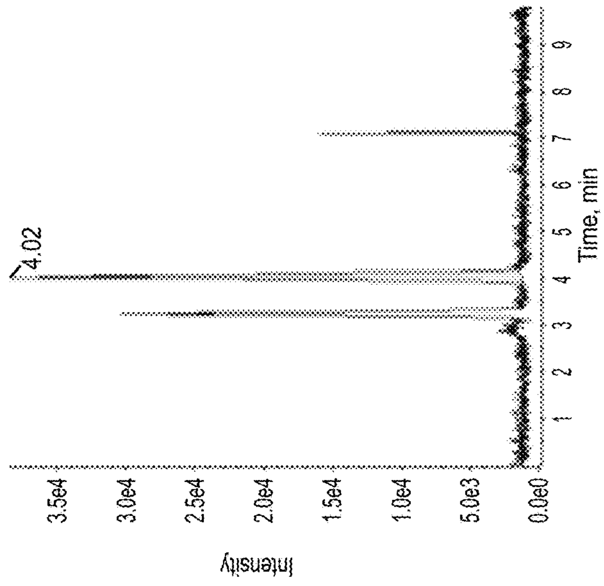
FIG. 29B illustrate LC-MS/MS detection of the anhydro DP2, anhydro DP1, and DP2 species of an oligosaccharide preparation of Example 7.
Figure 29A:
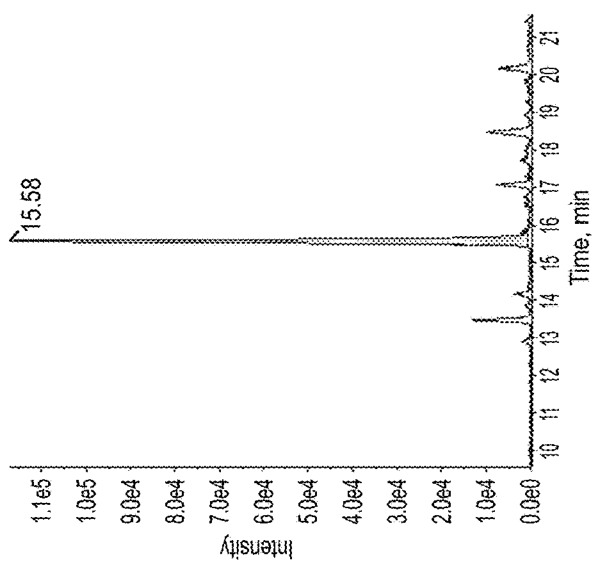
FIG. 29A illustrate LC-MS/MS detection of the anhydro DP2, anhydro DP1, and DP2 species of an oligosaccharide preparation of Example 7.
Figure 30A:
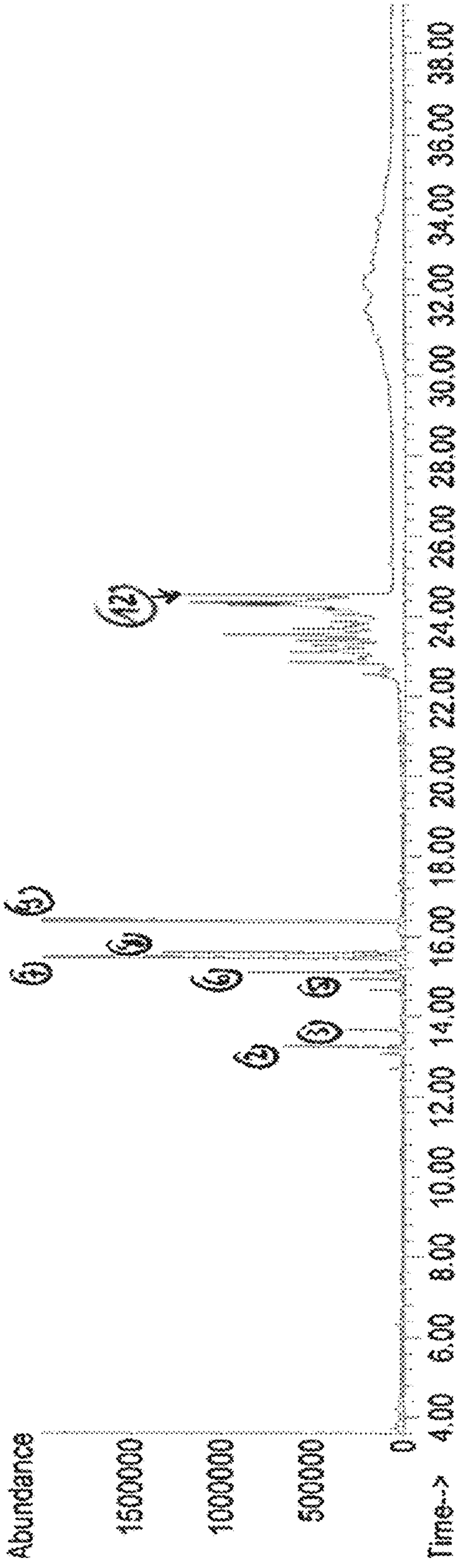
FIG. 30A illustrates GC-MS spectrum detection of the DP1, anhydro DP1, DP2 and anhydro DP2 fractions of an oligosaccharide preparation of Example 1.
Figure 30B:
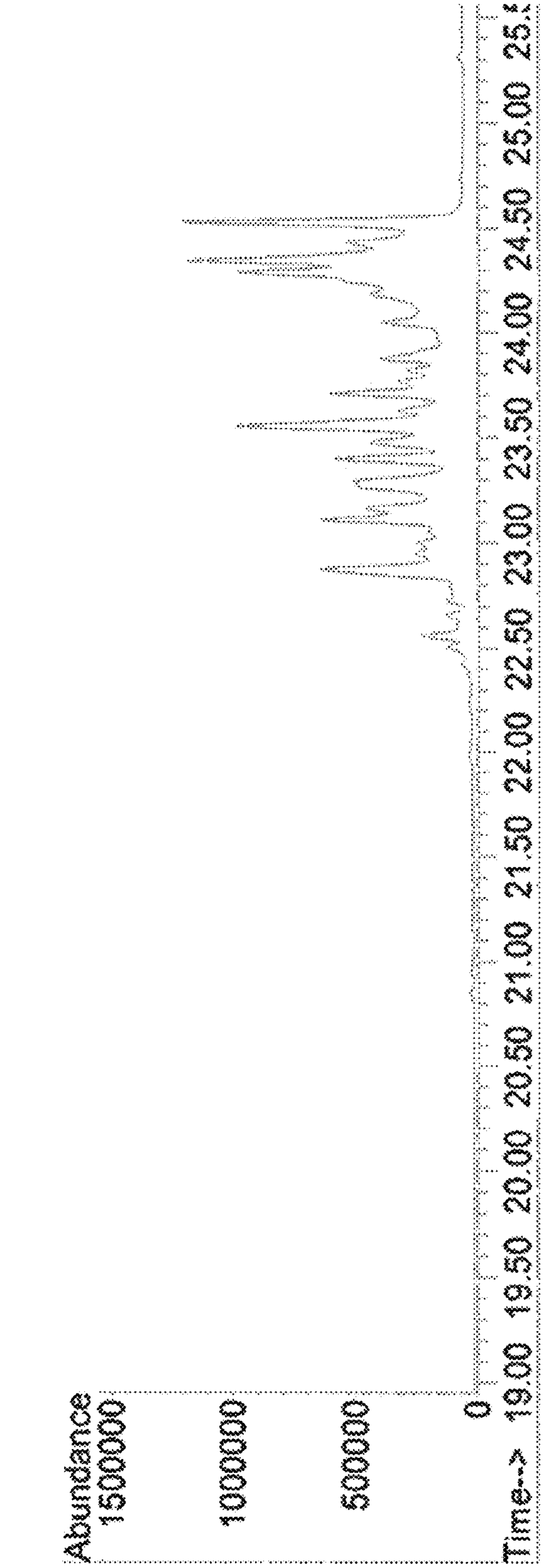
FIG. 30B illustrates an enlargement of the DP2 and anhydro DP 2 fractions as shown in FIG. 30A.
Figure 31A:
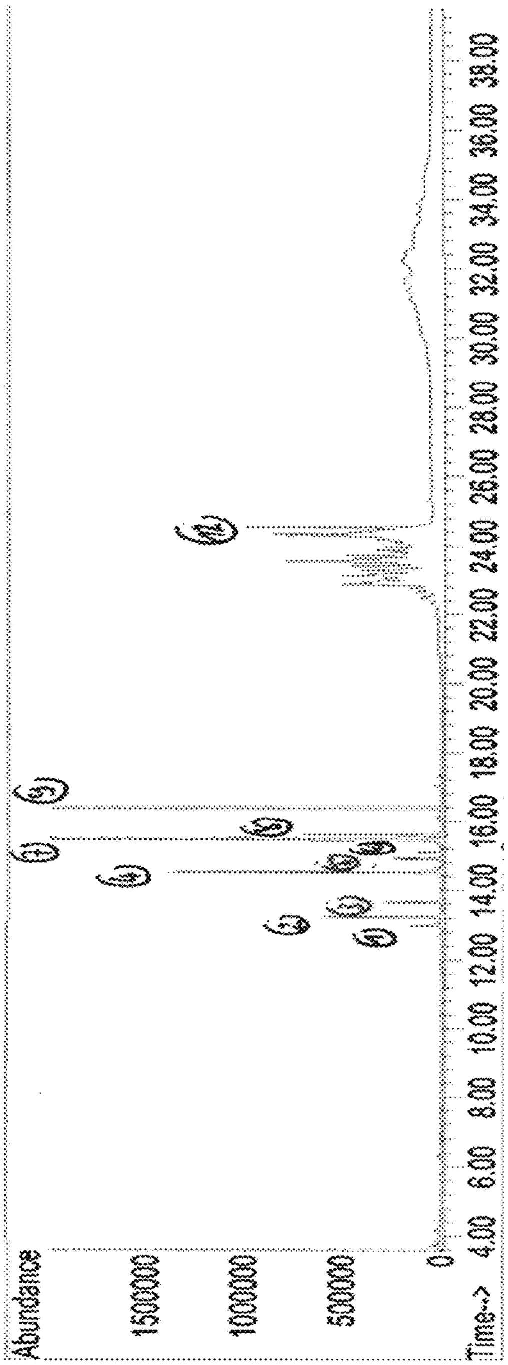
FIG. 31A illustrates GC-MS spectrum detection of the DP1, anhydro DP1, DP2 and anhydro DP2 fractions of an oligosaccharide preparation of Example 3.
Figure 31B:
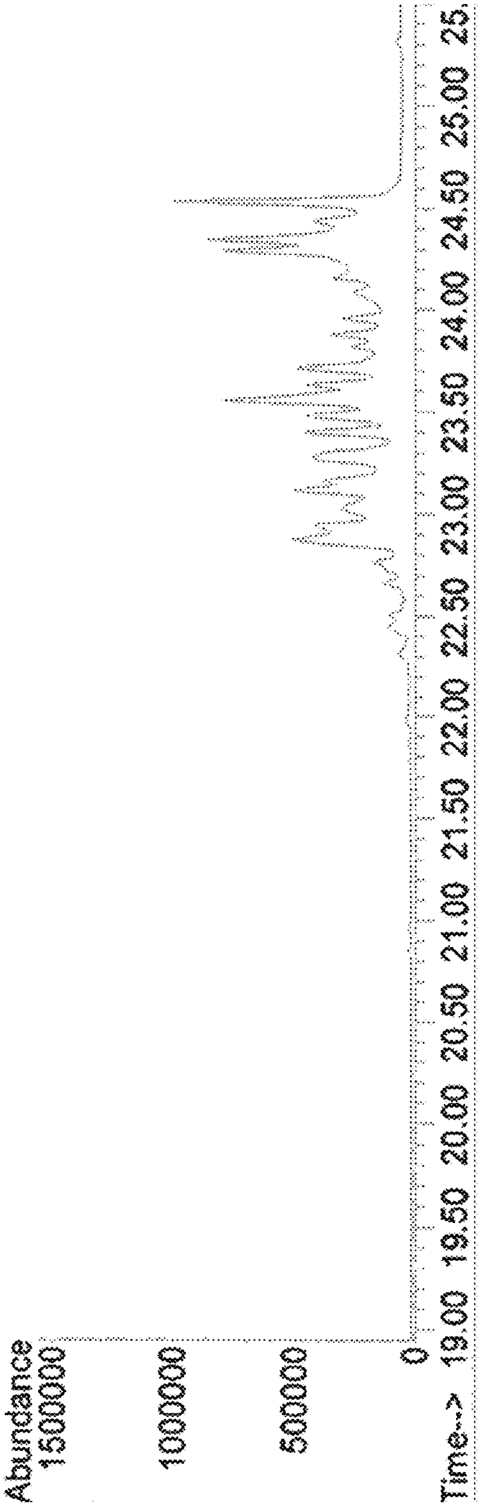
FIG. 31B illustrates an enlargement of the DP2 and anhydro DP 2 fractions as shown in FIG. 31A.
Figure 32A:
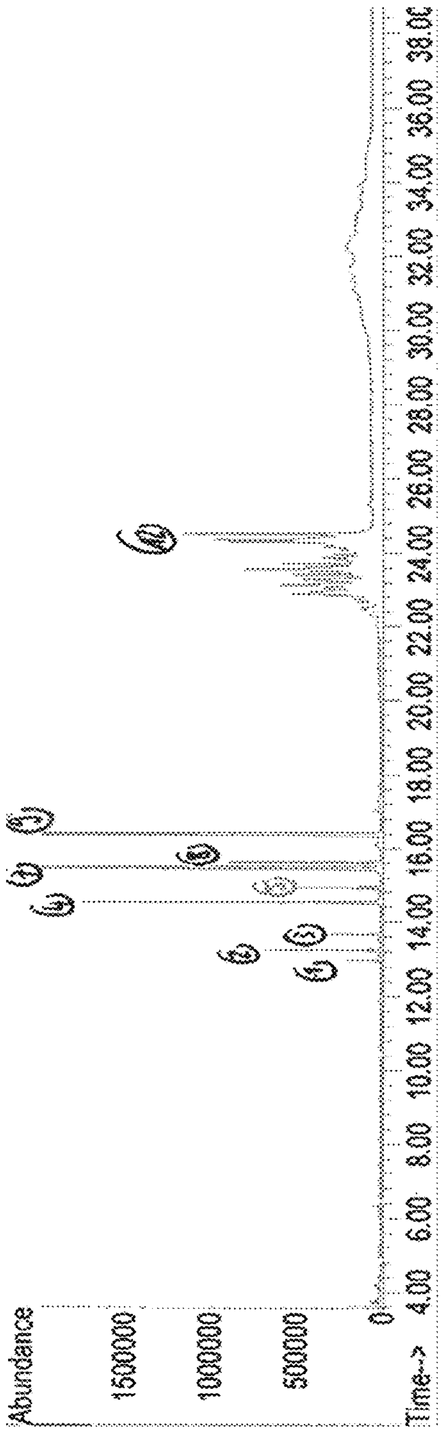
FIG. 32A illustrates GC-MS spectrum detection of the DP1, anhydro DP1, DP2 and anhydro DP2 fractions of an oligosaccharide preparation of Example 4.
Figure 32B:
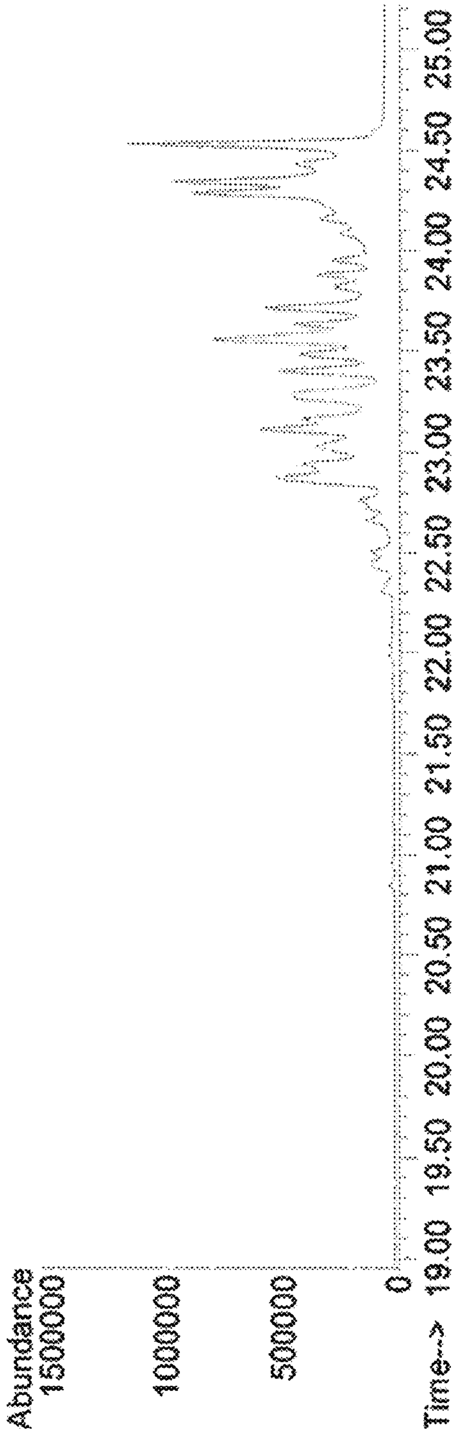
FIG. 32B illustrates an enlargement of the DP2 and anhydro DP 2 fractions as shown in FIG. 32A.
Figure 33A:
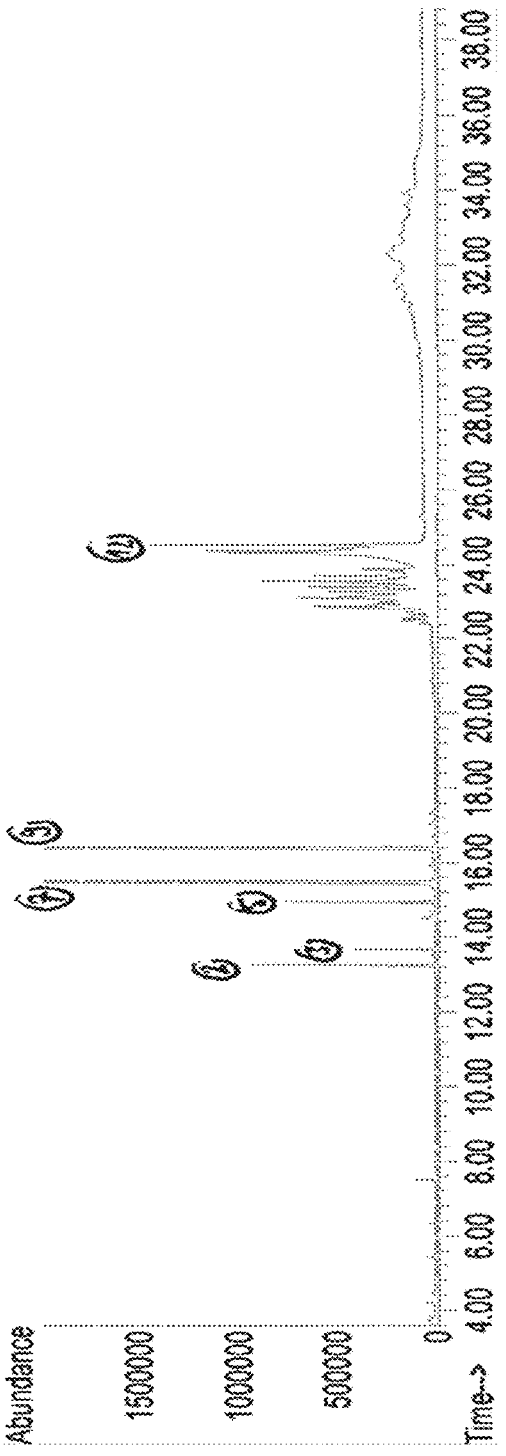
FIG. 33A illustrates GC-MS spectrum detection of the DP1, anhydro DP1, DP2 and anhydro DP2 fractions of an oligosaccharide preparation of Example 7.
Figure 33B:
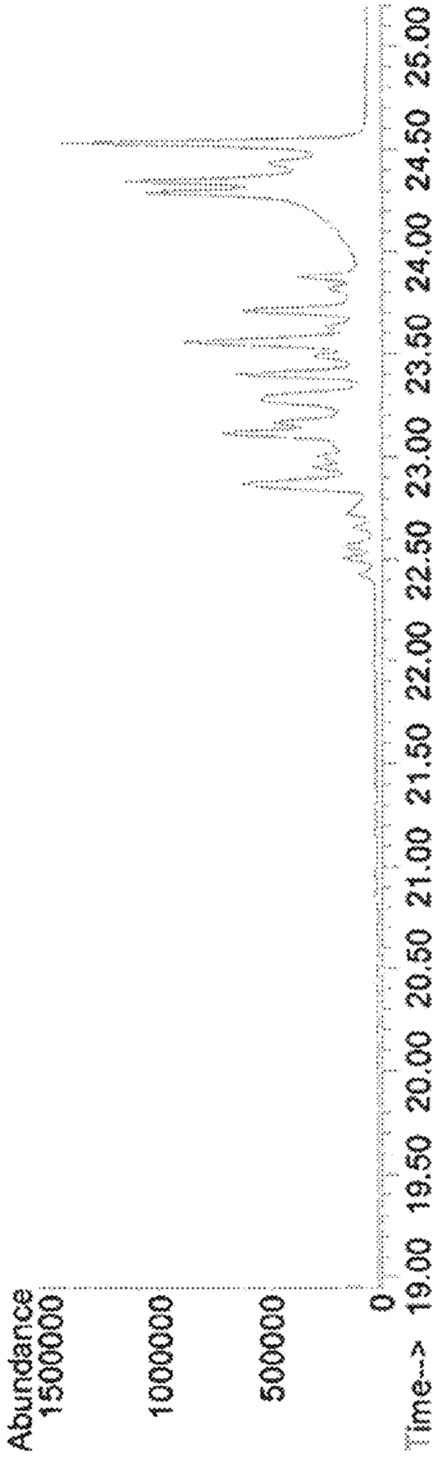
FIG. 33B illustrates an enlargement of the DP2 and anhydro DP 2 fractions as shown in FIG. 33A.

FIG. 2 provides an illustrative MALDI spectrum of an oligosaccharide preparation from Example 9. Anhydro-sugar subunits are clearly observed as offset peaks shifted by −18 g/mol relative to its respective principal DP parent. Offset peaks are observed at all values of DP, indicating that anhydrosugar subunits are detected at all oligosaccharide sizes. The relative intensity of the anhydro subunit peak was determined to be about 10% of the total peak intensity for each DP, from which the total anhydro subunit relative abundance was determined to be about 10%. FIG. 25A and FIG. 25B illustrate MALDI spectra of an oligosaccharide preparation from Example 2. Anhydro-sugar subunits are observed at every DP level with a relative intensity in the range of 5-10%.

Example 11

Characterization of the Anhydro Sub-Units of an Oligosaccharide Preparation

The anhydrosugar subunits of the oligosaccharide preparations of Example 9 were characterized using a combination of LC-MS, GC-MS, LC-MS/MS, and NMR methods.

Figure 3:
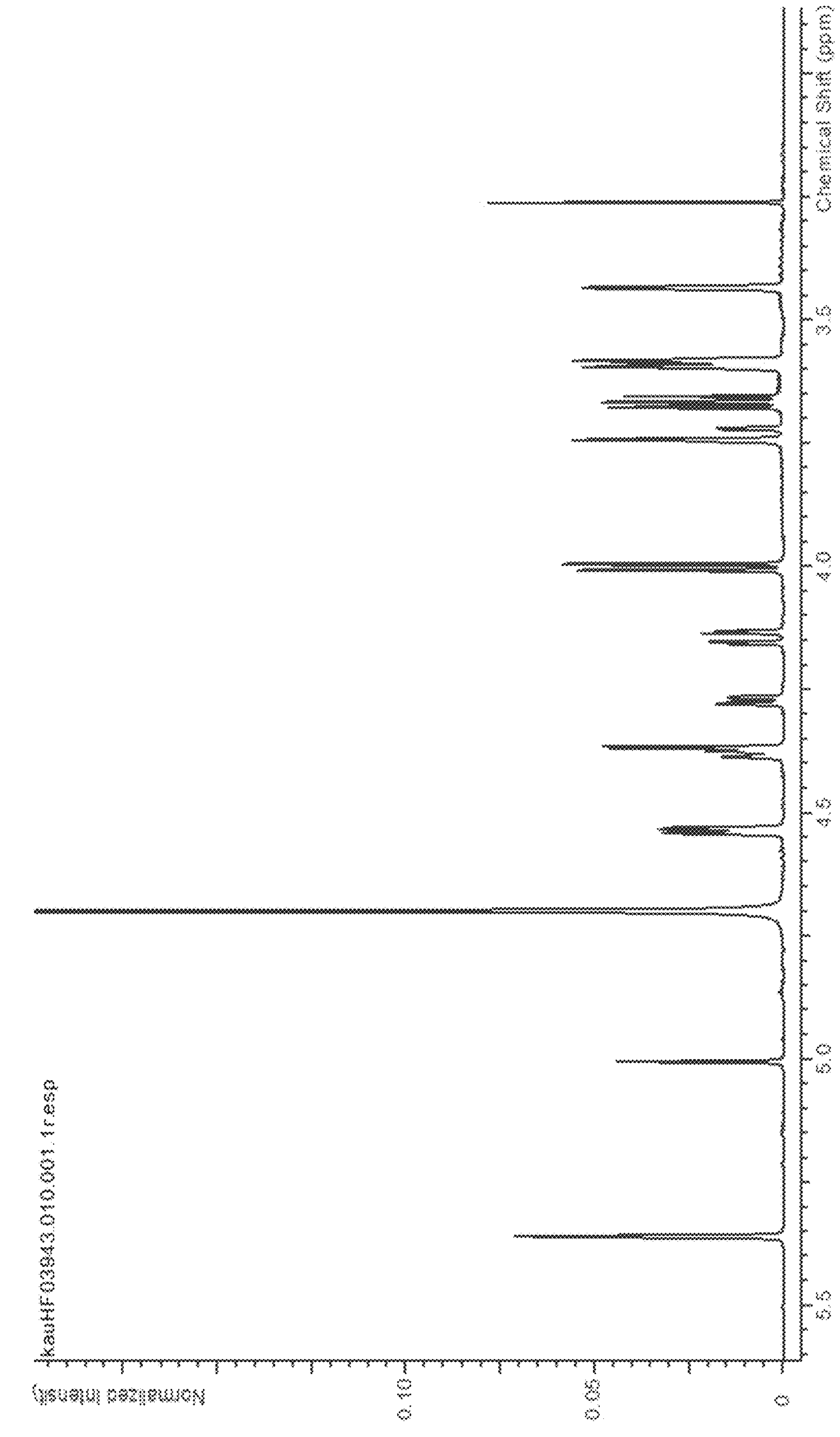
FIG. 3 illustrates a 1D $^{1}H$ NMR spectrum of the anhydro-DP1 component of an oligosaccharide preparation of Example 9.
Figure 4:
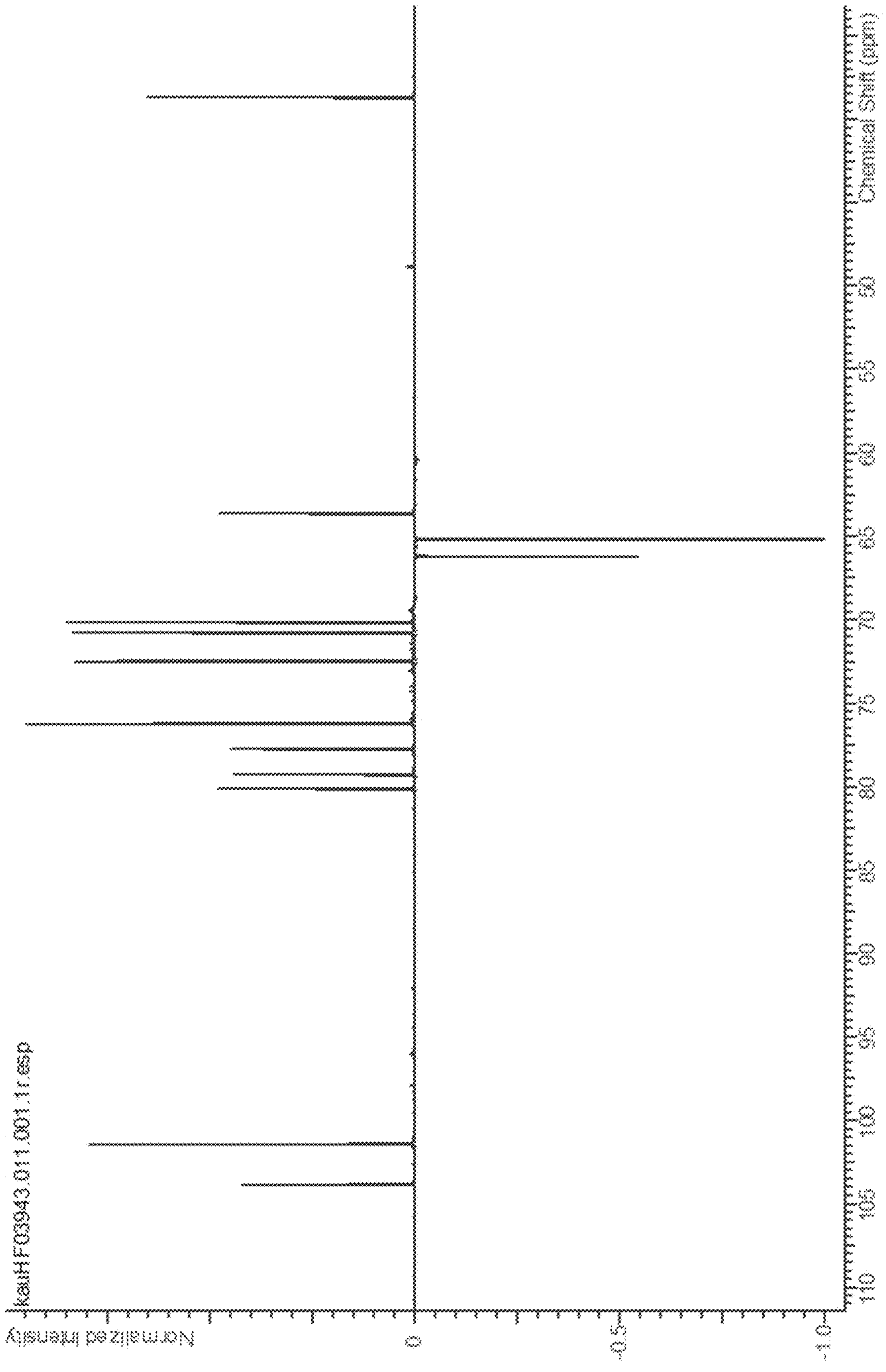
FIG. 4 illustrates a 1D APT $^{13}C$-NMR spectrum of an anhydro-DP1 component of an oligosaccharide preparation of Example 9.

Characterization of Anhydro-DP1 Components:

The anhydro DP1 component of an oligosaccharide preparation from Example 9 was isolated by preparative liquid chromatography. The isolated anhydro-DP1 component was prepared for NMR by dissolving it in 0.75 mL of D2O. FIG. 3 provides an illustrative 1D $^{1}$H-NMR spectrum of an anhydro DP1 fraction isolated from an oligosaccharide of Example 9 and FIG. 4 provides an illustrative APT $^{13}$C-NMR spectrum of the same isolated anhydro DP1 fraction.

Using the following peak assignments in Table 4, the ratio of 1,6-anhydro-beta-D-glucofuranose to 1,6-Anhydro-beta-D-glucopyranose was determined by NMR to be 2:1.

TABLE 4

NMR Peak Assignments

| | 1,6-anhydro-beta-D-glucofuranose | | 1,6-Anhydro-beta-D-glucopyranose | |
|---|---|---|---|---|
| # | $^{1}$H (ppm) | $^{13}$C (ppm) | $^{1}$H (ppm) | $^{13}$C (ppm) |
| 1 | 5.33 | 101.9 | 5.01 | 104.4 |
| 2 | 3.40 | 70.6 | 4.37 | 79.8 |
| 3 | 3.56 (ov)[a] | 73.0 | 4.27 | 78.3 |
| 4 | 3.56 (ov)[a] | 71.3 | 4.38 | 80.6 |
| 5 | 4.50 | 76.7 | 3.74 | 64.1 |
| 6 | 3.97, 3.64 | 65.7 | 4.14, 3.72 | 66.7 |

[a]Ov indicates overlapped signal

Characterization of the Anhydro-DP2 Components

The anhydrosugar subunits of the oligosaccharide preparations of Example 9 were characterized using a combination of LC-MS, GC-MS, LC-MS/MS, and NMR methods. The anhydro DP2 content of the oligosaccharide preparations of Example 9 were determined by GC-MS and LC-MS/MS analysis. Gas chromatography was performed using a 30 m×0.25 mm fused silica column containing HP-5MS stationary phase, with 21.57 psi constant pressure Helium as the carrier gas. Aliquots were pre-derivatized by acetylation by dissolving 20 mg of sample in 0.5 mL pyridine with 0.5 mL acetic anhydride for 30 minutes at 60° C. 1 uL samples were injected at 300° C. with an oven temperature program starting at 70° C. and ramping by 10° C. per minute to 315° C. Detection was performed on an Agilent 5975C MSD with an electron energy of 70 eV.

Figure 5:
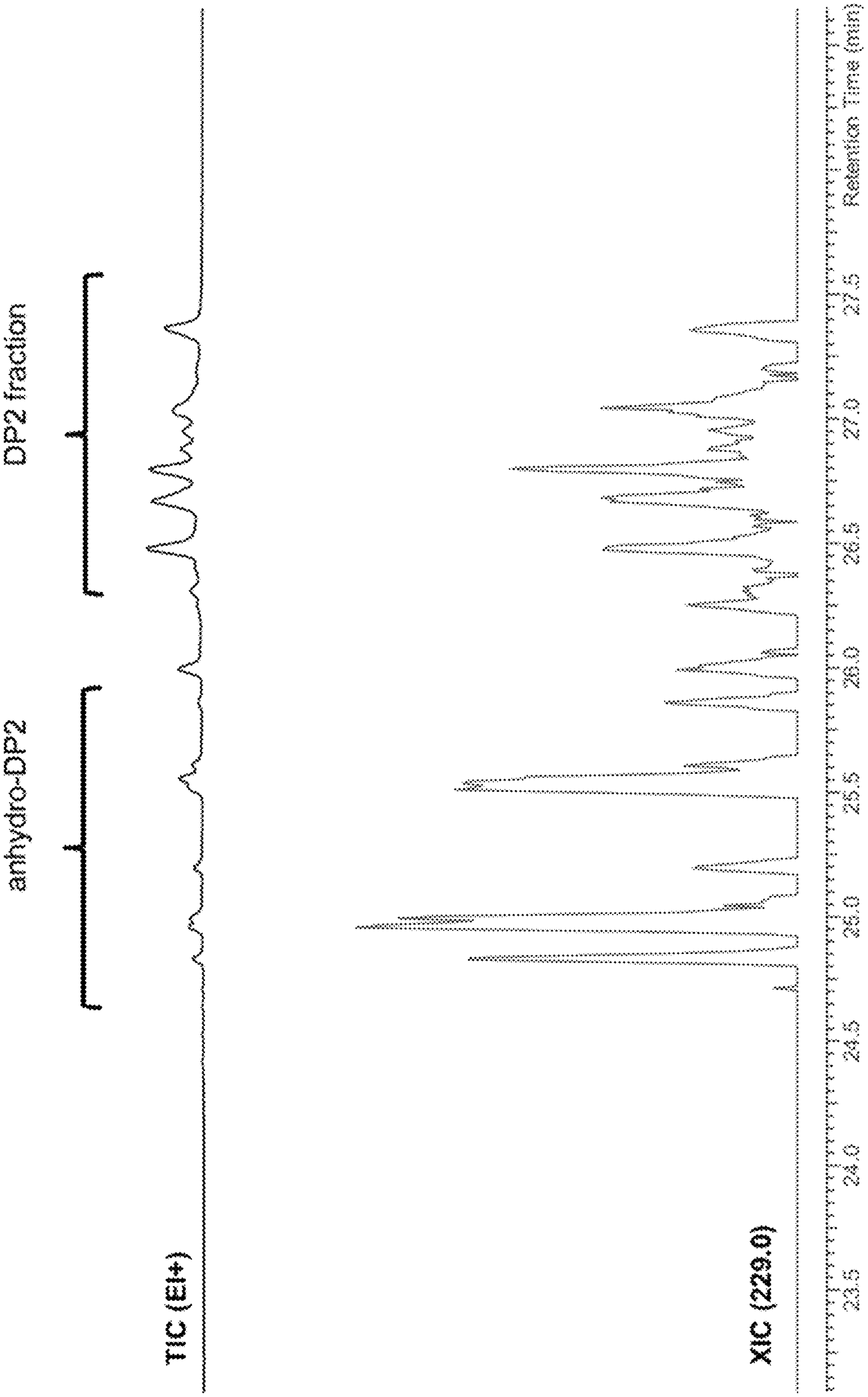
FIG. 5 illustrates the GC-MS chromatogram (TIC and XIC (m/z 229) plots) showing the DP2 and anhydro-DP2 components of oligosaccharide preparation 2.9 following derivatization.

FIG. 5 illustrates an enlargement of the GC-MS chromatogram for the oligosaccharide preparation 9.7. The TIC and XIC (m/z 229) plots demonstrate that the DP2 and anhydro-DP2 components are clearly resolved. FIGS. 30A-30B, 31A-31B, 32A-32B, and 33A-33B illustrate the presence of the DP1, anhydro DP1, DP2 and anhydro DP2 fractions as detected by GC-MS in an oligosaccharide preparation of Example 1, Example 3, Example 4, and Example 7, respectively. As shown in FIGS. 30A-30B, 31A-31B, 32A-32B, and 33A-33B, anhydro DP1 and DP1 fractions have a retention time of from about 12-17 minutes, and anhydro DP2 and DP2 fractions have a retention time of about from 22-25 minutes.

Figure 36:
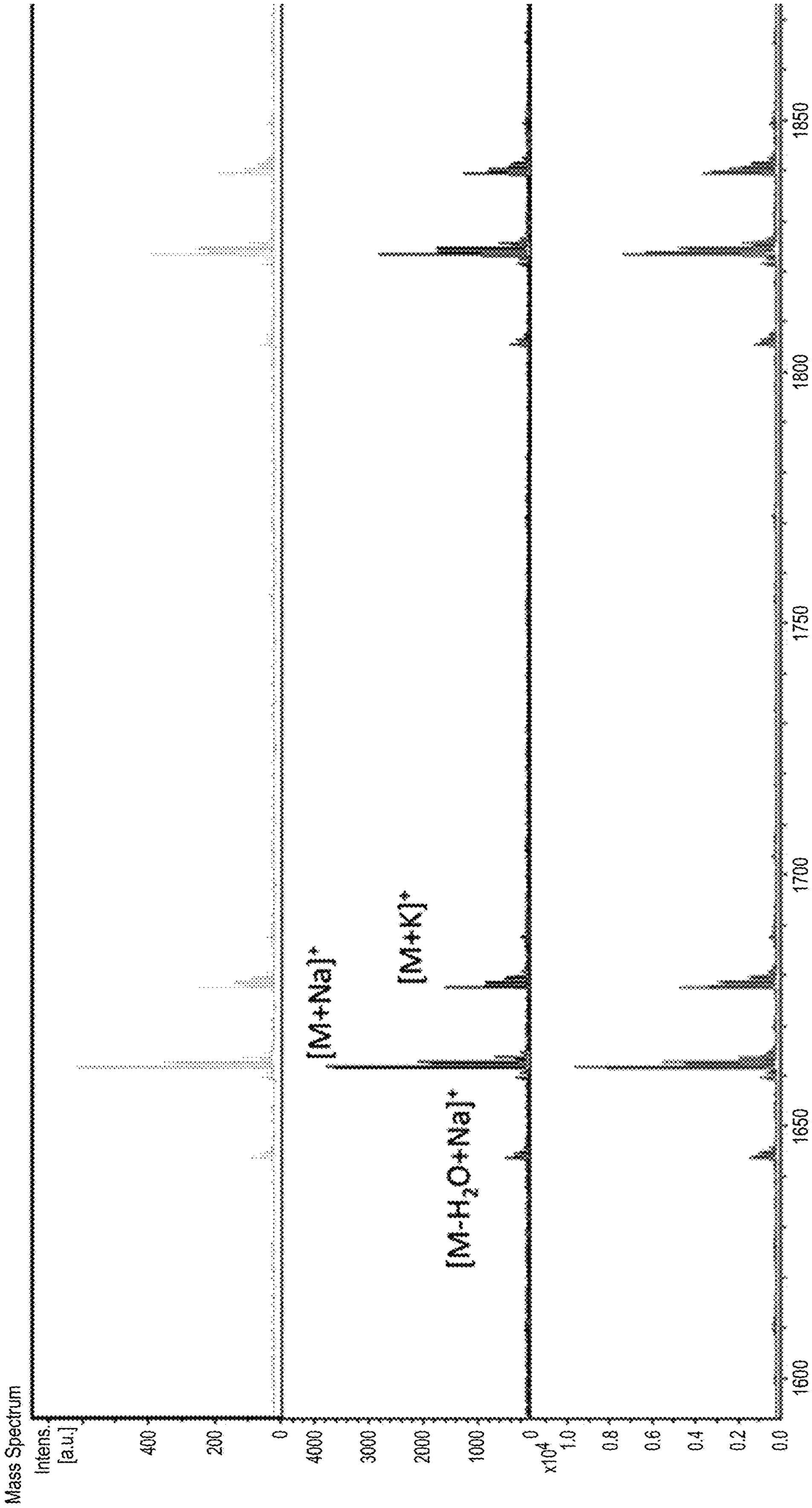
FIG. 36 illustrates MALDI-MS spectra comparing the oligosaccharide preparation from Example 9 at different laser energies.

FIG. 36 illustrates MALDI-MS spectra comparing the oligosaccharide preparation from Example 9 at different laser energies. Relative abundancy of signals was nearly unchanged, demonstrating that no loss of water is introduced by the laser ionization. Hence, proving the presence of anhydro-sugar subunits in the oligosaccharide preparation.

Example 12

Observation of Caramelization Subunits in an Oligosaccharide Preparation

Figure 6:
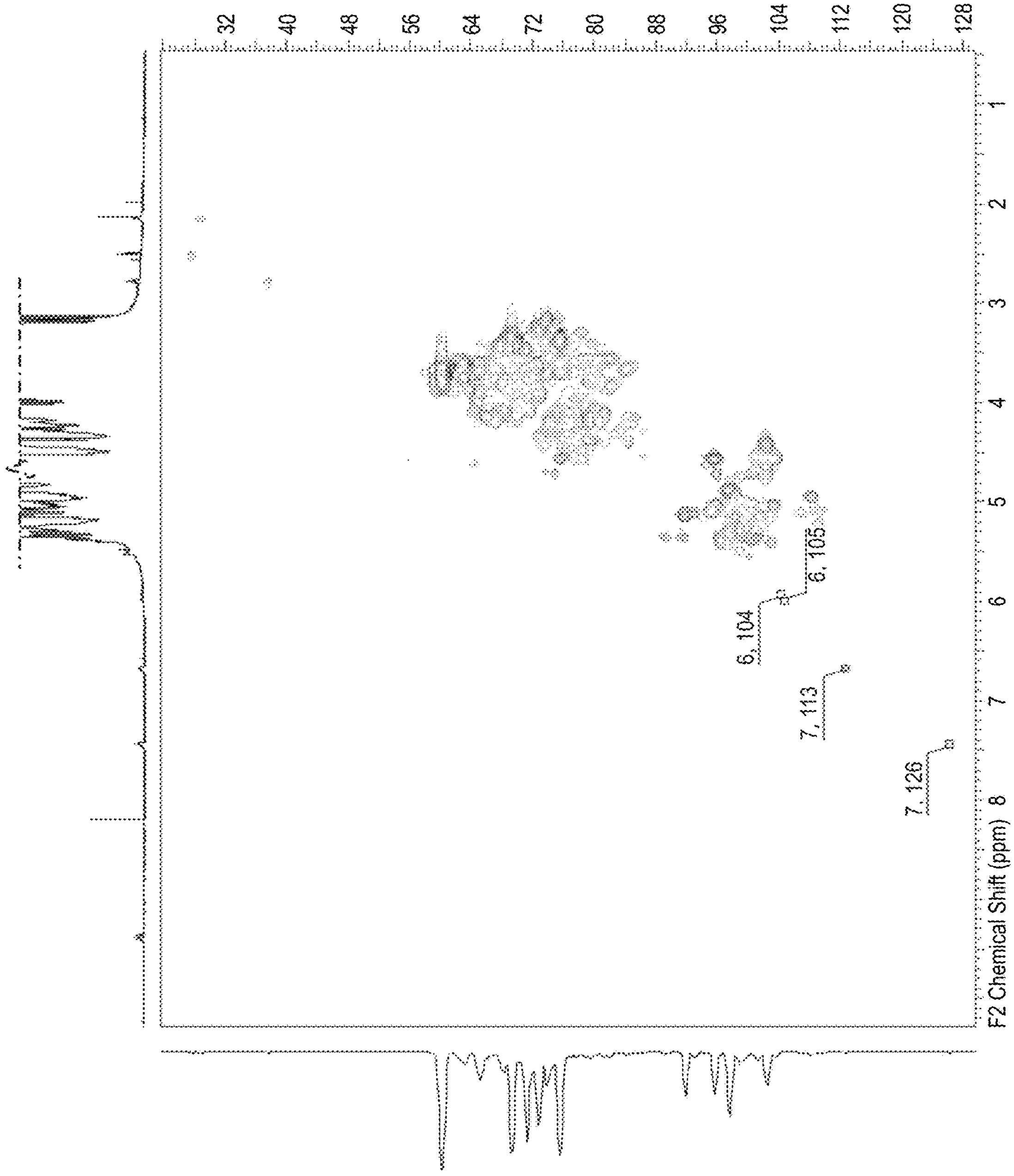
FIG. 6 illustrates a $^{1}H$, $^{13}C$-HSQC spectrum of an oligosaccharide preparation with a caramelization anhydro-subunit.

An oligosaccharide preparation comprising a 5-hydroxymethylfurfural caramelization subunit was demonstrated by a combination of HPLC analysis and 2D $^{1}$H, $^{13}$C HSQC NMR. A 50 mg aliquot of an oligosaccharide preparation from Example 9 was dissolved in 0.8 mL $D_2O$. The resulting 2D $^{1}$H, $^{13}$C HSQC spectrum was analyzed for the presence of a glycosidic linkage between 5-hmf and the anomeric carbon of glucose, with the following peak assignments: $^{1}$H NMR: □□=9.39 ppm (CHO,m), 7.44 ppm (Ar—H,m), 6.68 ppm (Ar—H, m), 4.60 ppm (CH2,m); and $^{13}$C NMR: □□□□180.0, 150.6, 126.2, 112.7, 159.9, 64.5. The absence of free 5-hmf was confirmed by HPLC using an Agilent 1100 HPLC system equipped with a 3000 mm Bio-Rad Aminex 87H using 25 mM aqueous sulfuric acid at 0.65 mL/min isocratic elution and UV detection. 5-hmf was quantified against an authentic sample. No 5-hmf peak was observed in the oligosaccharide preparation of Example 9, but was observed following low-temperature acid hydrolysis of the oligosaccharide preparation under conditions not expected to produce free 5-hmf in the hydrolysate. FIG. 6 provides an illustrative 2D HSQC spectrum of an oligosaccharide preparation that incorporates a caramelization subunit.

Example 13

Comparative Example

Figure 7:
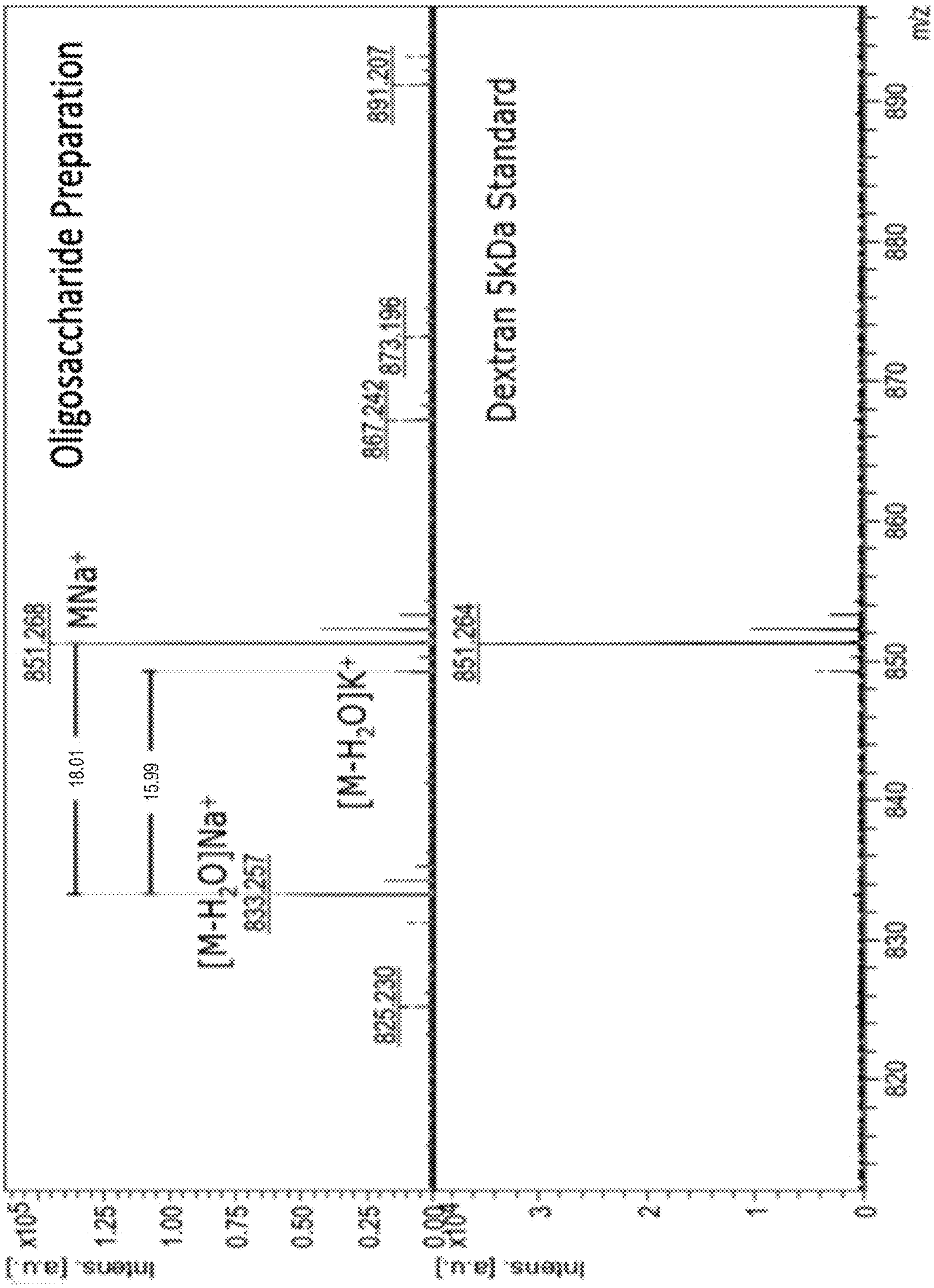
FIG. 7 illustrates a part of a MALDI-MS spectrum comparing an oligosaccharide preparation of Example 9 at different laser energies.

A commercial 5 kDa dextran was analyzed by MALDI-MS for the presence of anhydrosugar subunits. FIG. 7 shows the clear presence of the offset peak shifted—18 g/mol from the principal DP peak (Na+ adduct at 851.268 g/mol). By contrast the dextran sample was found to be essentially free of anhydro sugar subunits.

Example 14

Quantification of the Anhydro DP Component by LC-MS/MS

Figure 8A:
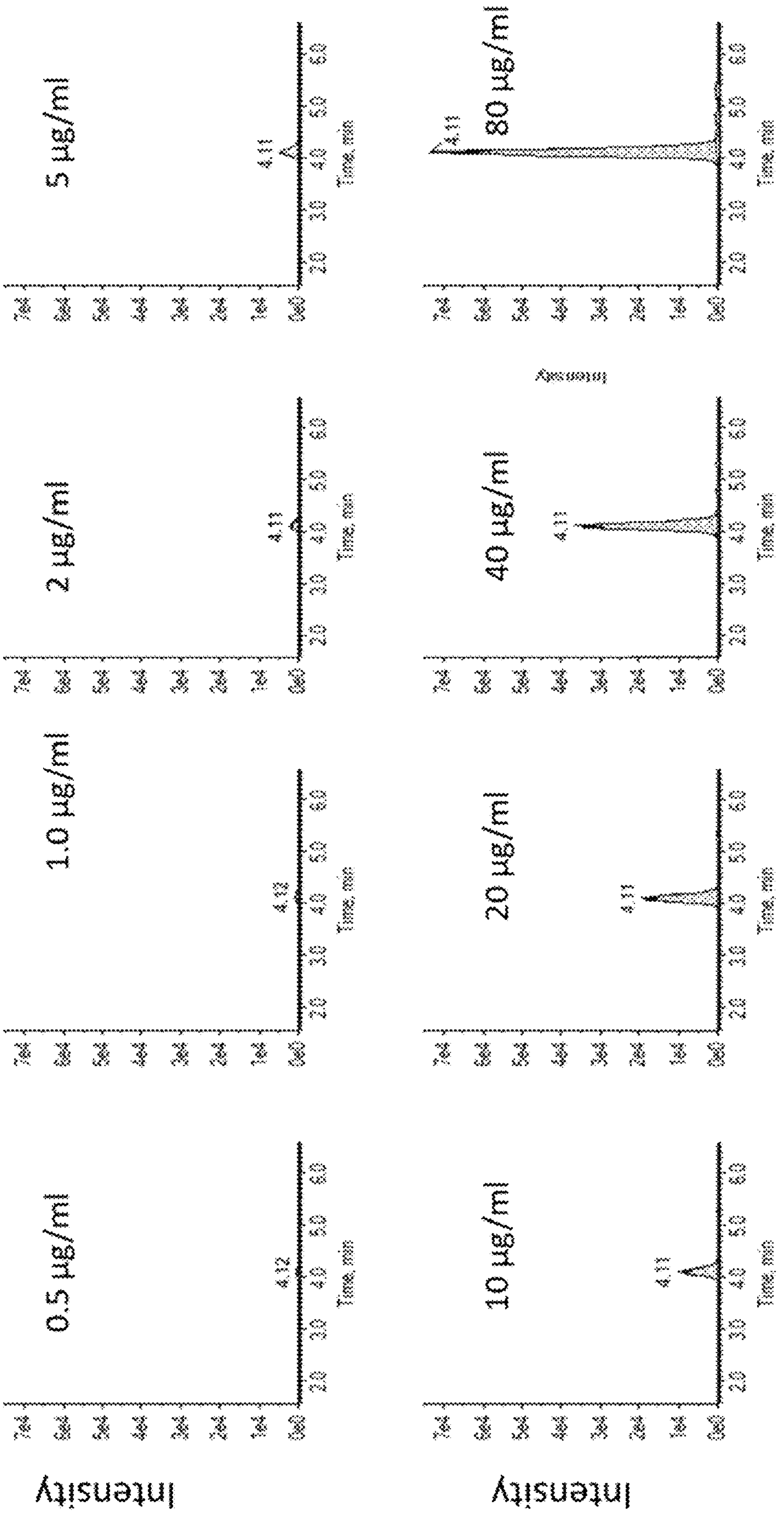
FIG. 8A illustrates LC-MS/MS detection of the anhydro DP2 species at concentration of 1-80 □g/mL of an oligosaccharide preparation in water.
Figure 8B:
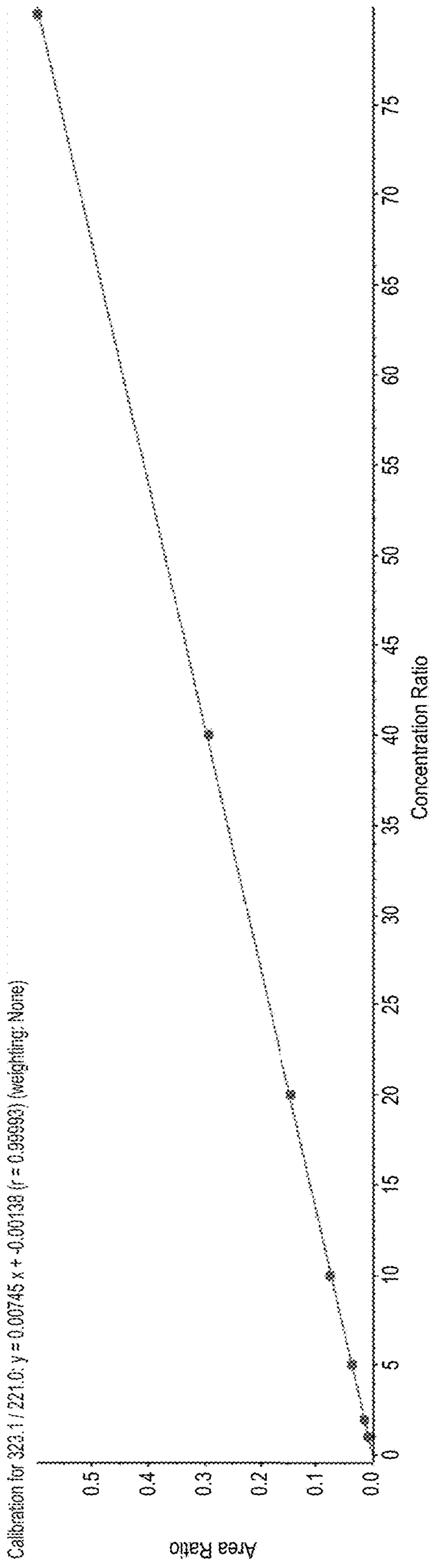
FIG. 8B shows a linear calibration curve resulting from the LC-MS/MS detection of FIG. 8A.

The DP2 fraction of oligosaccharide preparations was isolated by liquid chromatography. Samples were dissolved in water and separated using a Capcell Pak NH2 (Shiseido; 250×4. 6 mm, 5 μm) column at a flowrate of 1 mL/min under isocratic conditions of water/acetonitrile 35/65. In some cases, following chromatographic separation, 50 μL 0.05% NH4OH was added to enhance ionization. The anhydro DP2 content was determined by MS/MS detection. For MS detection ESI probe was used in negative mode and MRM method allowed targeted analysis. FIG. 8A illustrates detection an oligosaccharide preparation from Example 9 over a concentration range of 1-80 □g/mL in water, with a linear calibration curve (shown in FIG. 8B) from the area under the LC-MS/MS chromatogram to concentration.

FIGS. 26A-26C, 27A-27C, 28A-28C, and 29A-29C illustrate the presence of the anhydro DP2, anhydro DP1, and DP2 species detected by LC-MS/MS in an oligosaccharide preparation of Example 1, Example 3, Example 4, and Example 7, respectively.

Example 15

Preparation of Feed Comprising Oligosaccharide Preparations

Poultry and swine diets were prepared to demonstrate the incorporation of oligosaccharide preparations into the diet. Control feeds exhibiting a variety of ingredient compositions and corresponding treated feeds obtained by augmenting the respective control feeds with the oligosaccharide preparations of Example 9 were prepared as follows:

Example Feed 15.1: Control Feed 15.1 (CTR) was prepared using 62% corn meal and 32% soybean meal. Treated Feed 15.1 (TRT) was prepared by augmenting the control feed 15.1 (CTR) with 500 mg/kg of an oligosaccharide preparation from Example 9. For the treated diet, the oligosaccharide preparation was provided in a powder form by drying the oligosaccharide onto ground rice hulls as a carrier and adding the powder to the mixer using a micro-ingredient balance prior to pelleting.

Example Feed 15.2: Control Feed 15.2 (CTR) was prepared using 62% corn meal, 3% soybean concentrate, and 26% soybean meal. Treated Feed 15.2 (TRT) was prepared by augmenting the control feed 15.2 (CTR) with 500 mg/kg of an oligosaccharide preparation from Example 9. For the treated diet, the oligosaccharide preparation was provided in a powder form by drying the oligosaccharide onto ground rice hulls as a carrier and adding the powder to the mixer using a micro-ingredient balance prior to pelleting.

Example Feed 15.3: Control Feed 15.3 (CTR) was prepared using 52% corn meal, 6% corn starch, 5% soybean concentrate, 26% soybean meal, and a titanium oxide microtracer. Treated Feed 15.3 (TRT) was prepared by augmenting the control feed 15.3 (CTR) with 500 mg/kg of an oligosaccharide preparation. For the treated diet, the oligosaccharide preparation was provided in a powder form by drying the oligosaccharide onto ground rice hulls as a carrier and adding the powder to the mixer using a micro-ingredient balance prior to pelleting.

Example Feed 15.4: Control Feed 15.4 (CTR) was prepared using 55% corn meal and 39% soybean meal. Treated Feed 15.4 (TRT) was prepared by augmenting the control feed 15.4 (CTR) with 1,000 mg/kg of an oligosaccharide preparation. For the treated diet, the oligosaccharide preparation was provided in a powder form by drying the oligosaccharide onto ground rice hulls as a carrier and adding the powder to the mixer using a micro-ingredient balance prior to pelleting.

Example Feed 15.5: Control Feed 15.5 (CTR) was prepared using 62% corn meal, 3% soybean concentrate, and 26% soybean meal. Treated Feed 15.5 (TRT) was prepared by augmenting the control feed 15.5 (CTR) with 500 mg/kg of an oligosaccharide preparation from Example 9. For the treated diet, the oligosaccharide preparation was provided in a powder form and adding the powder to the mixer using a micro-ingredient balance prior to pelleting.

Example Feed 15.6: Control Feed 15.6 (CTR) was a commercial U.S. corn-soy starter poultry feed. Treated Feed 15.6 (TRT) was a commercial U.S. corn-soy starter poultry feed containing 500 ppm of an oligosaccharide preparation. For the treated diet, the oligosaccharide preparation was provided in a powder form and adding the powder to the mixer using a micro-ingredient balance prior to pelleting.

Example Feed 15.7: Control Feed 15.7 (CTR) was a research corn-soy poultry feed with the following diet composition: corn meal 62.39%, soybean meal 31.80%, calcium carbonate 0.15%, bicalcic-phosphate 2.2%, sodium chloride 0.15%, DL-Methionine 0.15%, L-Lysine 0.10%, Soya Oil 2.00%, vitamin-mineral premix 1.00%, and coccidiostat 0.06%. Treated Feed 15.7 (TRT) was obtained by supplementing the control feed 15.7 (CTR) with 1000 ppm of the oligosaccharide preparation of Example 9.1. For the treated diet, the oligosaccharide preparation was provided as 60% syrup in water and was applied by spraying the syrup onto the feed post pelleting.

Example Feed 15.8: Control Feed 15.8 (CTR) was a research corn-soy poultry feed with the following composition: wheat meal 48.45%, soybean meal 32.00%, rye 12%, calcium carbonate 0.20%, bicalcic phosphate 2.00%, sodium chloride 0.20%, DL-methionine 0.15%, soya oil 4.00%, vitamin-mineral premix 1.00%. Treated Feed 15.7 (TRT) was obtained by supplementing the control feed 15.7 (CTR) with 1000 ppm of the oligosaccharide preparation of Example 9.3. For the treated diet, the oligosaccharide preparation was provided as 60% syrup in water and was applied by spraying the syrup onto the feed post pelleting.

As would be understood by one skilled in the art, the 15.1-15.6 also contained industry standard levels of fat, vitamins, minerals, amino acids, other micronutrients and feed enzymes. In some cases the feeds contained a cocciodiostat, but were free in all cases of antibiotic growth promoters. The feeds were provided as either mash, pelletized, or crumbled diets, according to standard practices.

Example 16

Extraction of Feed Samples

Diets prepared according to the procedures of Example 15 were processed by extraction. Feed samples were ground with a mill. Five grams of the resulting milled feed were weighted into a 50 mL volumetric flask and hot water (approx. 80° C.) was added. After shaking, the mixture was incubated in an ultrasonic water bath at 80° C. for 30 minutes. After cooling, the solution was centrifuged for 20 min at 3000×g and the supernatant was filtered through a 1.2 m filter followed by a 0.45 m filter (and in some cases by a 0.22 m filter). The resulting filtered solutions were evaporated to dryness with a rotary evaporator.

In some cases, the extraction was performed using 50 wt % ethanol in water as an alternative extraction solvent. In some cases, the filtration step was performed using a 5,000 Dalton molecular-weight cutoff membrane filter.

Example 17

Enzymatic Processing of Feed Extracts

The feed extracts of Example 16 were subjected to one or more enzymatic hydrolysis steps to digest oligosaccharides naturally present in the feed. A mixture of α-Amylase and amyloglycosidases were used to digest α(1,4) linkages of gluco-oligosaccharides and starch. Invertase and α-galactosidase were used to remove sucrose, raffinose, and other common fiber saccharides.

Enzyme solutions were prepared as follows: Amyloglucosidase (*A. niger*) 36000 U/g solution at 800 U/mL in ammonium acetate buffer (ammonium acetate 0.2 M pH 5 containing 0.5 mM MgCl2 and 200 mM $CaCl_2$)), α-Amylase (Porcine Pancreas) 100000 U/g Megazyme: solution at 800 U/mL in ammonium acetate, Invertase from Backer's yeast (*S. cerevisiae*) 300 U/mg Sigma: solution at 600 U/mL in ammonium acetate buffer, α-Galactosidase from *A. niger* Megazyme 1000 U/mL.

The dry feed extracts of Example 16 were re-suspended in 10 mL ammonium acetate buffer. 50 μl of α-amylase (4 U/mL final), 50 μl of amyloglucosidase (4 U/mL final), 50 μl of invertase (3 U/mL final) were added. 20 μl α-galactosidase (2 U/mL final) was added optionally. The solution was incubated for 4 hours at 60° C. The digested extract was then filtered through an ultrafiltration filter (Vivaspin Turbo 4, 5000 MWCO, Sartorius) before being evaporated to dryness on a nitrogen evaporation system. In variations of the enzymatic digestion, one or more of the above enzymes were used in combinations and the digestion period was varied between 4 hours to overnight digestion. The enzyme concentrations were varied up to twice the above loadings, and the full enzymatic digestion procedure was repeated multiple times in sequence on the same feed.

TABLE 5

List of Feed Samples for Extraction and Digestion

| | Matrix | Extraction solvent | Filtration | Enzyme digestion |
|---|---|---|---|---|
| 1 | Blank feed | Water | 0.22 μM | — |
| 2 | Anhydro-Oligomers feed 1000 mg/kg | Water | 0.22 μM | — |
| 3 | Blank Feed | ethanol/water 50/50 | 0.22 μM | — |
| 4 | Anhydro-Oligomers feed 1000 mg/kg | ethanol/water 50/50 | 0.22 μM | — |
| 5 | Anhydro-Oligomers | Water | 0.22 μM | a + b (4 h 60° C.) |
| 6 | Blank feed | Water | 0.22 μM | a + b (4 h 60° C.) |
| 7 | Anhydro-Oligomers feed 1000 mg/kg | Water | 0.22 μM | a + b (4 h 60° C.) |
| 10 | Blank feed | ethanol/water 50/50 | 0.22 μM | — |
| 11 | Anhydro-Oligomers feed 1000 mg/kg | ethanol/water 50/50 | 0.22 μM | — |
| 12 | Anhydro-Oligomers feed 1000 mg/kg | Water | 0.45 μM | a + b (4 h 60° C.) |
| 13 | Anhydro-Oligomers feed 1000 mg/kg | Water | 0.22 μM | a + b (4 h 60° C.) |
| 14 | Blank starter feed A | Water | 0.45 μM | a + b (4 h 60° C.) |
| 15 | Anhydro-Oligomers starter feed B 2000 mg/kg | Water | 0.45 μM | a + b (4 h 60° C.) |
| 16 | Blank feed | Water | 0.45 μM | a + b + c (4 h 60° C.) |
| 17 | Anhydro-Oligomers feed 1000 mg/kg | Water | 0.45 μM | a + b + c (4 h 60° C.) |
| 18 | Rice spelt/Anhydro-Oligomers | Water | 0.45 μM | — |
| 19 | Rice spelt/Anhydro-Oligomers | ethanol/water 50/50 | 0.45 μM | — |
| 20 | Blank feed | Water | 0.45 μM | a + b + c (4 h 60° C.) |
| 21 | Anhydro-Oligomers feed 1000 mg/kg | Water | 0.45 μM | a + b + c (4 h 60° C.) |
| 22 | Grower feed C (blank) | Water | 0.45 μM | |
| 23 | Grower feed D (Anhydro-Oligomers 2000 mg/kg) | Water | 0.45 μM | |
| 24 | Pre starter feed A (blank) | Water | 0.45 μM | |
| 25 | Pre starter feed D (Anhydro-Oligomers 1000 mg/kg) | Water | 0.45 μM | |
| 26 | Grower feed C (blank) | Water | 0.45 μM | a + b + c + d (4 h 60° C.) |
| 27 | Grower feed D (Anhydro-Oligomers 2000 mg/kg) | Water | 0.45 μM | a + b + c + d (4 h 60° C.) |
| 28 | Pre starter feed A (blank) | Water | 0.45 μM | a + b + c + d (4 h 60° C.) |
| 29 | Pre starter feed D (Anhydro-Oligomers 1000 mg/kg) | Water | 0.45 μM | a + b + c + d (4 h 60° C.) |
| 30 | Maize | Water | 0.45 μM | — |
| 31 | Wheat | Water | 0.45 μM | — |
| 32 | Soy | Water | 0.45 μM | — |
| 33 | Maize | Water | 0.45 μM | a + b + c + d (4 h 60° C.) |
| 34 | Wheat | Water | 0.45 μM | a + b + c + d (4 h 60° C.) |
| 35 | Soy | Water | 0.45 μM | a + b + c + d (4 h 60° C.) |
| 41 | Blank Feed | Water | 0.45 μM | |
| 42 | Anhydro-Oligomers feed 1000 mg/kg | Water | 0.45 μM | |
| 43 | Blank feed | Water | ultra 5000 MWCO | a + b + c X2 (overnight 60° C.) |
| 44 | Anhydro-Oligomers feed 1000 mg/kg | Water | ultra 5000 MWCO | a + b + c X2 (overnight 60° C.) |

Anhydro-Oligomers refer to anhydro-subunit containing oligosaccharides.

Blank feeds refer to nutritional compositions without added anhydro-oligomers.

Enzyme a = Amyloglucosidase (*A. niger*) 36000 U/g Megazyme

Enzyme b = α-Amylase (Porcine Pancreas) 100000 U/g Megazyme

Enzyme c = Invertase from Baker's yeast (*S. cerevisiae*) 300 U/mg Sigma

Enzyme d = α-Galactosidase from *A. niger* 620 U/mg Megazyme

Example 18

Detection of Oligosaccharide Preparations in Feed

The Control and Treated diets according to Example 15 were assayed to detect the absence or presence of oligosaccharide preparations. After diet manufacture, 1 kg samples were drawn from the final feed. The extractable solids content of the feed was obtained by water extraction using the procedure of Example 16. The resulting extracts were analyzed for the presence of anhydro-DP species by LC-MS/MS according to the procedure of Example 14.

Figure 9:
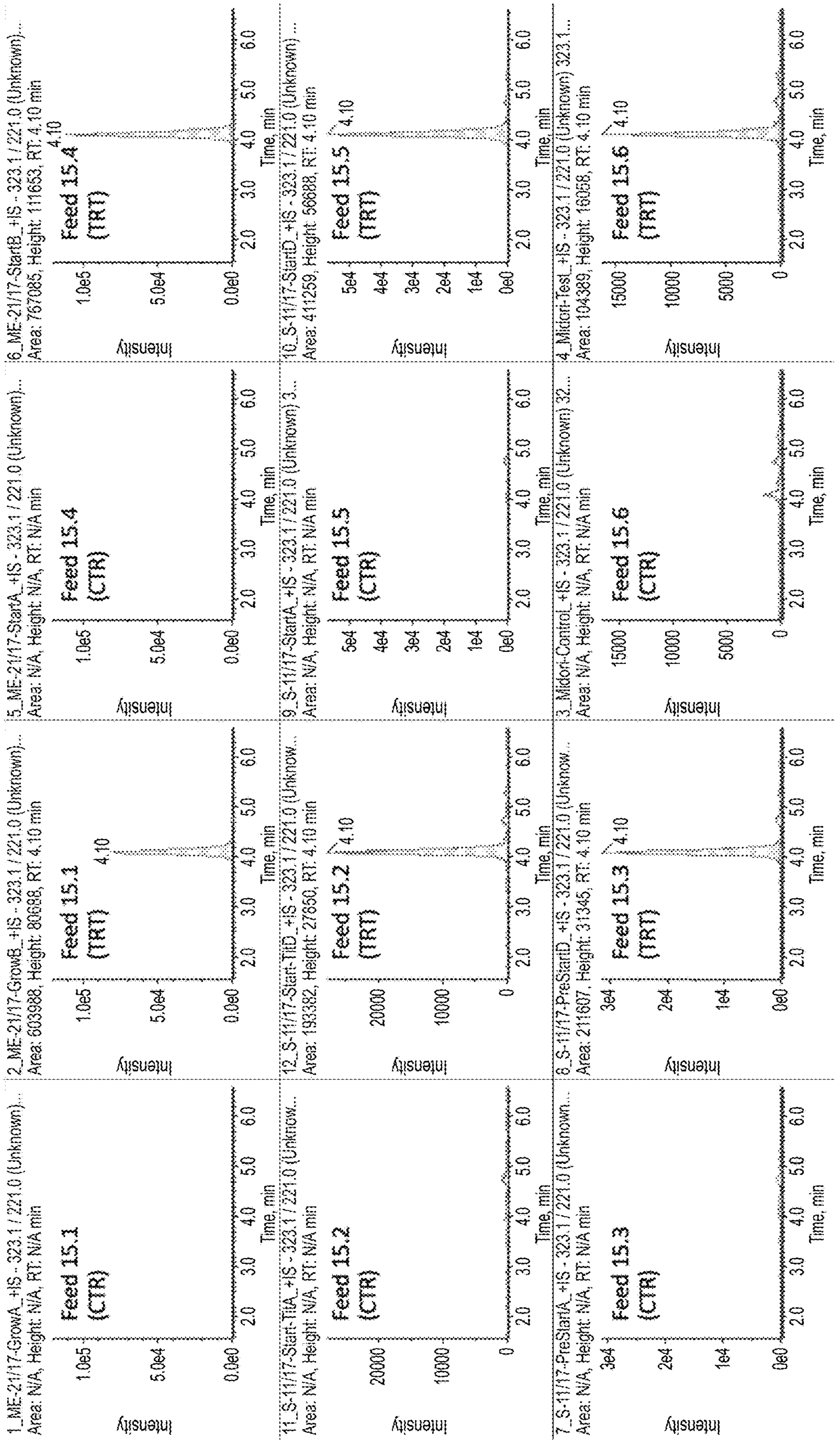
FIG. 9 illustrates the quantification of the anhdro-DP2 content of various control and treated diet compositions.

FIG. 9 shows the absence of anhydro-DP2 species in the control feeds of Examples 15.1(CTR)-15.6(CTR) versus the presence of anhydro-DP2 species in the treated feeds of Examples 15.1(TRT)-15.6(TRT). Integration of the resulting LC-MS/MS chromatograms was used to determine the presence of the oligosaccharide preparations of Example 9 in the final feed. Specifically, feeds were determined to contain the respective oligosaccharide preparation if the area under the anhydro-DP2 peak exceeded the limit of detection (or any other suitable threshold established in the method).

Example 19

Quantification of Oligosaccharide Preparations in Feed

The Control and Treated diets according to Example 15 were assayed to determine the concentration of oligosaccharide preparations in the final feed. After diet manufacture, 1 kg samples were drawn from the final feed. The extractable solids content of the feed was obtained by water extraction using the procedure of Example 16. The resulting extracts were analyzed for the presence of anhydro-DP species by LC-MS/MS according to the procedure of Example 14 and the area of the anhydro-DP2 peak was compared against a standard calibration curve to determine the concentration of the oligosaccharide preparation in the feed (Table 6).

TABLE 6

Concentration of Oligosaccharide Preparation in Feed

| Feed | Oligosaccharide Content (ppm) in Control Feed | Oligosaccharide Content (ppm) in Treated Feed |
|---|---|---|
| Example 15.1 | Not detected | 1642 |
| Example 15.2 | Not detected | 953 |
| Example 15.3 | Not detected | 1912 |
| Example 15.4 | Not detected | 549 |
| Example 15.5 | Not detected | 406 |
| Example 15.6 | Trace | 401 |

Example 20

NMR Characterization of Anhydro-Subunit Containing Gluco-Oligosaccharides

Gluco-oligosaccharide preparations comprising anhydro-subunits were characterized by i) the degree of polymerization and ii) the glycosidic linkage distribution of the glucose units.

The relative molar abundances of □(1,1)□, □(1,1)□, □(1,1)□, □(1,2), □(1,2), □(1,3), □(1,3), □(1,4), □□(1,4), □(1,6), and □(1,6) linkages were identified by NMR spectroscopy. $^1$H NMR chemical shifts for the anomeric protons were determined as follows: the region d=4.5-5.5 ppm was considered, with the resonances of C-2 to C-6 covalently bound clustered at ~d 3.2 and 3.9 ppm. Due to coupling with the H-atom at C-2, the anomeric proton appears as a doublet and the axial position appears at higher field than the equatorial position. The sugar conformation was elucidated from the coupling constant of neighboring protons: equatorial-equatorial, equatorial-axial (small coupling constants) or axial-axial (larger coupling constants).

Elucidation of glycosidic linkages was also performed by $^{13}$C NMR. Primary, secondary, tertiary, and quaternary carbons were distinguished by proton off-resonance decoupling or polarization transfer. Carbons attached to methoxy groups resonate at a lower field than corresponding carbon atoms with free hydroxy groups and ring carbon atoms with axial hydroxy groups generally absorb at higher field than corresponding carbons with equatorial hydroxy groups. Thus, following these guidelines, and comparing with reported chemical shifts for both $^1$H and $^{13}$C of analogous sugars in literature most of the signals were assigned.

For the determination of the linkage distribution, J-RES and $^1$H, $^{13}$C-HSQC were used. For some samples, the HSQC method showed a superior performance. For each analysis, approximately 50 mg of freeze-dried product were dissolved in D2O and transferred to a 5 mm NMR tube. Any residual catalyst or solids were removed by filtration. NMR experiments were performed on a Bruker Avance III NMR spectrometer operating at 600 MHz proton corresponding to 150 MHz carbon Larmor frequency. The instrument was equipped with a cryogenically cooled 5 mm TCI probe. All experiments are carried out at 298 K. $^1$H NMR spectra were recorded and calibrated in deuterated water (4.75 ppm). $^{13}$C NMR spectra are calibrated with acetone (30.9 ppm). Data were acquired using TopSpin 3.5 and processed with ACD/Labs running on a personal computer.

Figure 10:
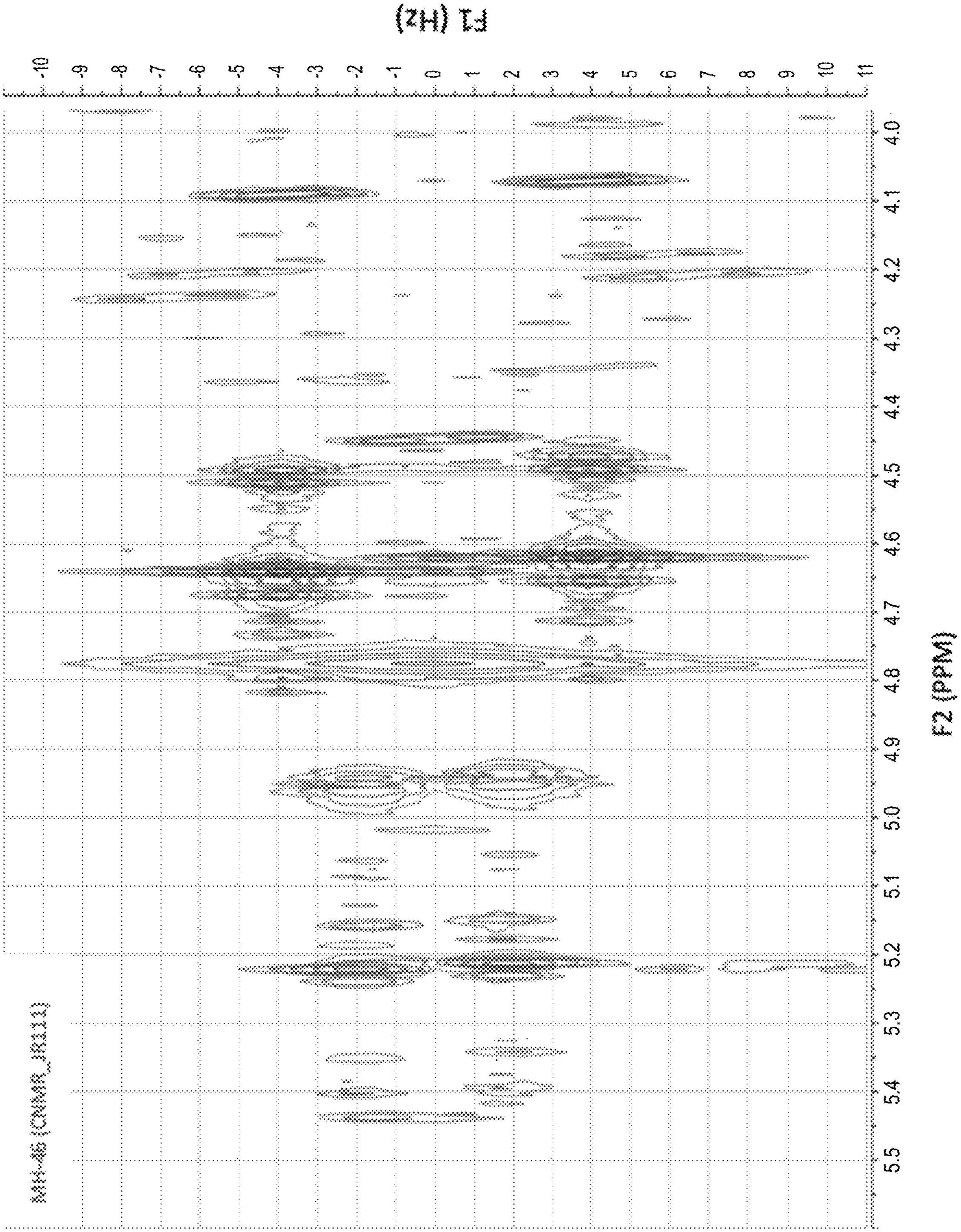
FIG. 10 illustrates a 2D-$^1$H JRES NMR spectrum of an anhydro-subunit containing gluco-oligosaccharides sample.

FIG. 10 provides a representative 2D-1H JRES NMR spectrum of an anhydro-subunit containing gluco-oligosaccharide sample with solvent pre-saturation. Assignments of the different glycosidic linkages were made according to Table 7.

TABLE 7

Relative Molar Abundance for Glycosidic Linkages in an Anhydro-subunit Containing Gluco-oligosaccharides Sample (2D-1H JRES NMR Method)

| Linkage | Relative Molar Abundance Tested in Lab I | Relative Molar Abundance Tested in Lab II |
|---|---|---|
| α(1, 2) | 10.1% | 9.2% |
| α(1, 4) | 2.0% | 17.0% |
| α(1, 3) | 4.5% | 1.3% |
| α(1, 6) | 28.9% | 33.6% |
| β(1, 2) | 5.7% | 6.5% |
| β(1, 3) | 13.3% | 6.3% |
| β(1, 4) | 17.9% | 10.7% |
| β(1, 6) | 18.9% | 14.5% |

As shown in Table 7, for some samples, discrepancies were observed between experiments performed by different labs using different instruments for the 2D-$^1$H JRES NMR analysis.

Figure 11:
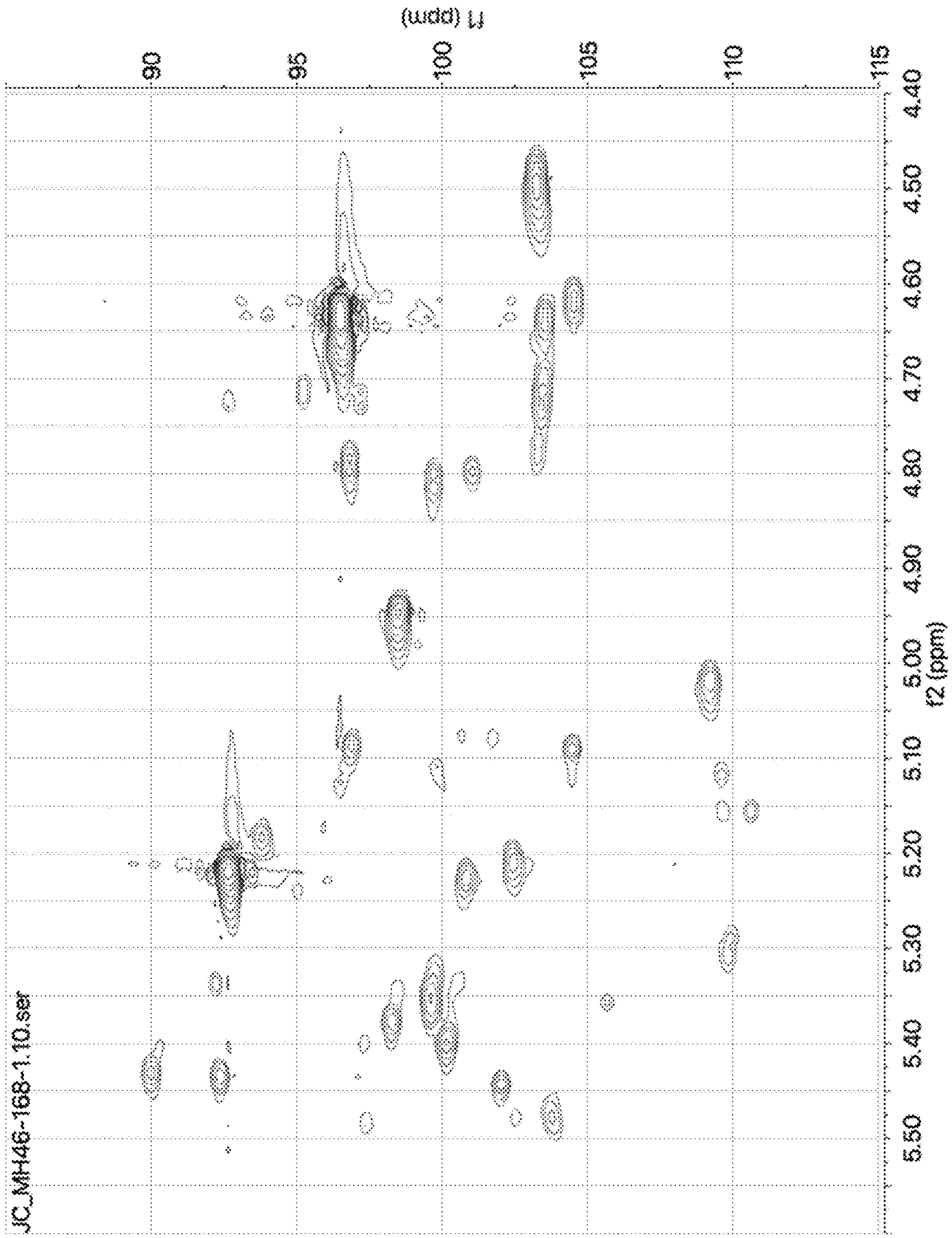
FIG. 11 is a representative $^1$H, $^{13}$C-HSQC NMR spectrum of an anhydro-subunit containing gluco-oligosaccharides sample with relevant resonances and assignments used for linkage distribution.

FIG. 11 provides a representative $^1$H, $^{13}$C-HSQC NMR spectrum of an anhydro-subunit containing gluco-oligosaccharides sample with relevant resonances and assignments used for linkage distribution. By contrast the determination by $^1$H, $^{13}$C-HSQC NMR was found to be consistent between two different labs and instruments, as shown in Table 8.

TABLE 8

| Relative Molar Abundance for Glycosidic Linkages in Four Anhydro-subunit Containing Gluco-oligosaccharides Samples ($^1$H, $^{13}$C- HSQC NMR Method) | | | | | | | | |
|---|---|---|---|---|---|---|---|---|
| | Sample 1 | | Sample 2 | | Sample 3 | | Sample 4 | |
| Linkage | Lab I | Lab II | Lab I | Lab II | Lab I | Lab II | Lab I | Lab II |
| α(1, 2) | 9.2% | 9.2% | 9.0% | 9.5% | 9.1% | 9.9% | 9.1% | — |
| α(1, 4) | 1.4% | 1.3% | 1.2% | 1.3% | 1.3% | 1.3% | 0.0% | — |
| α(1, 3) | 17.7% | 17.0% | 17% | 17.7% | 17.5% | 16.7% | 21.9% | — |
| α(1, 6) | 33.9% | 33.6% | 33.6% | 30.9% | 36.0% | 31.6% | 34.4% | — |
| β(1, 2) | 5.7% | 6.5% | 5.7% | 7.6% | 5.2% | 7.6% | 5.2% | — |
| β(1, 3) | 4.1% | 6.3% | 4.2% | 6.2% | 4.4% | 6.1% | 5.6% | — |
| β(1, 4) | 8.5% | 10.7% | 8.9% | 10.7% | 7.6% | 10.7% | 8.3% | — |
| β(1, 6) | 12.3% | 14.5% | 12.6% | 11.6% | 11.7% | 11.6% | 11.0% | — |

Figure 12:
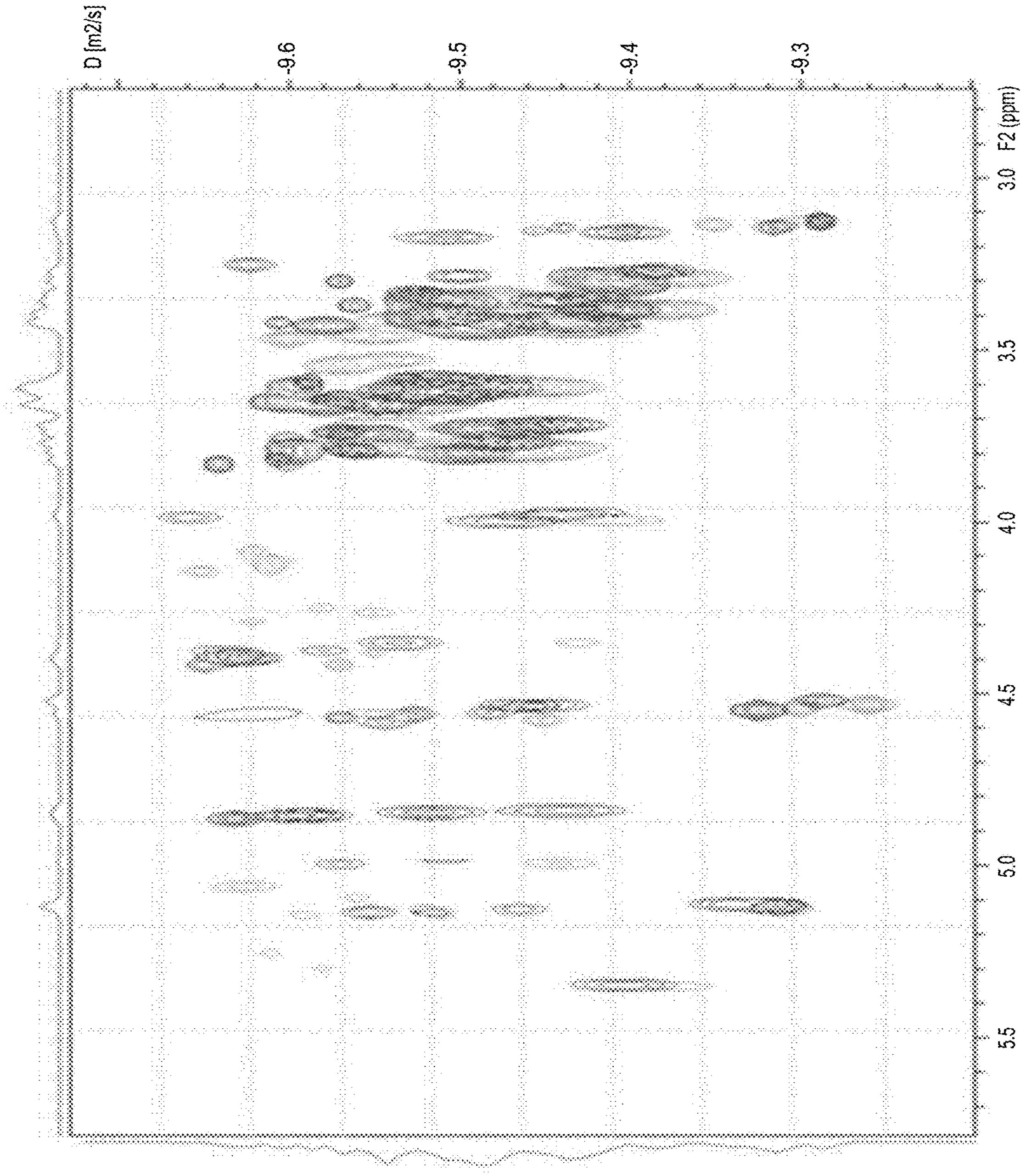
FIG. 12 illustrates an overlay of $^1$H DOSY spectra of three anhydro-subunit containing oligosaccharides.
Figure 13:
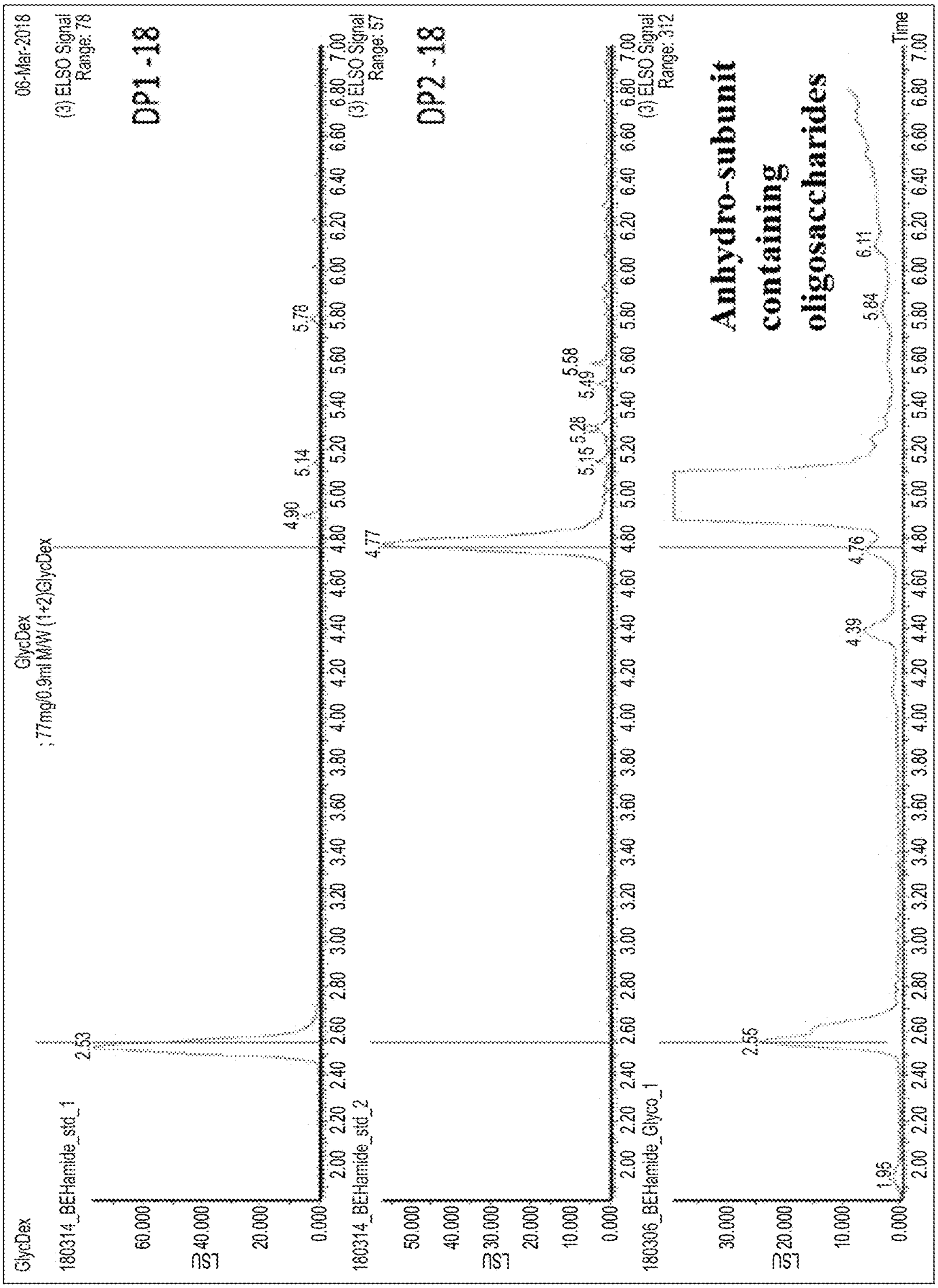
FIG. 13 illustrates a comparison of 1,6-Anhydro-β-D-glucose (DP1-18), 1,6-Anhydro-β-D-celobiose (DP2-18), and an anhydro-subunit containing oligosaccharides sample.
Figure 14:
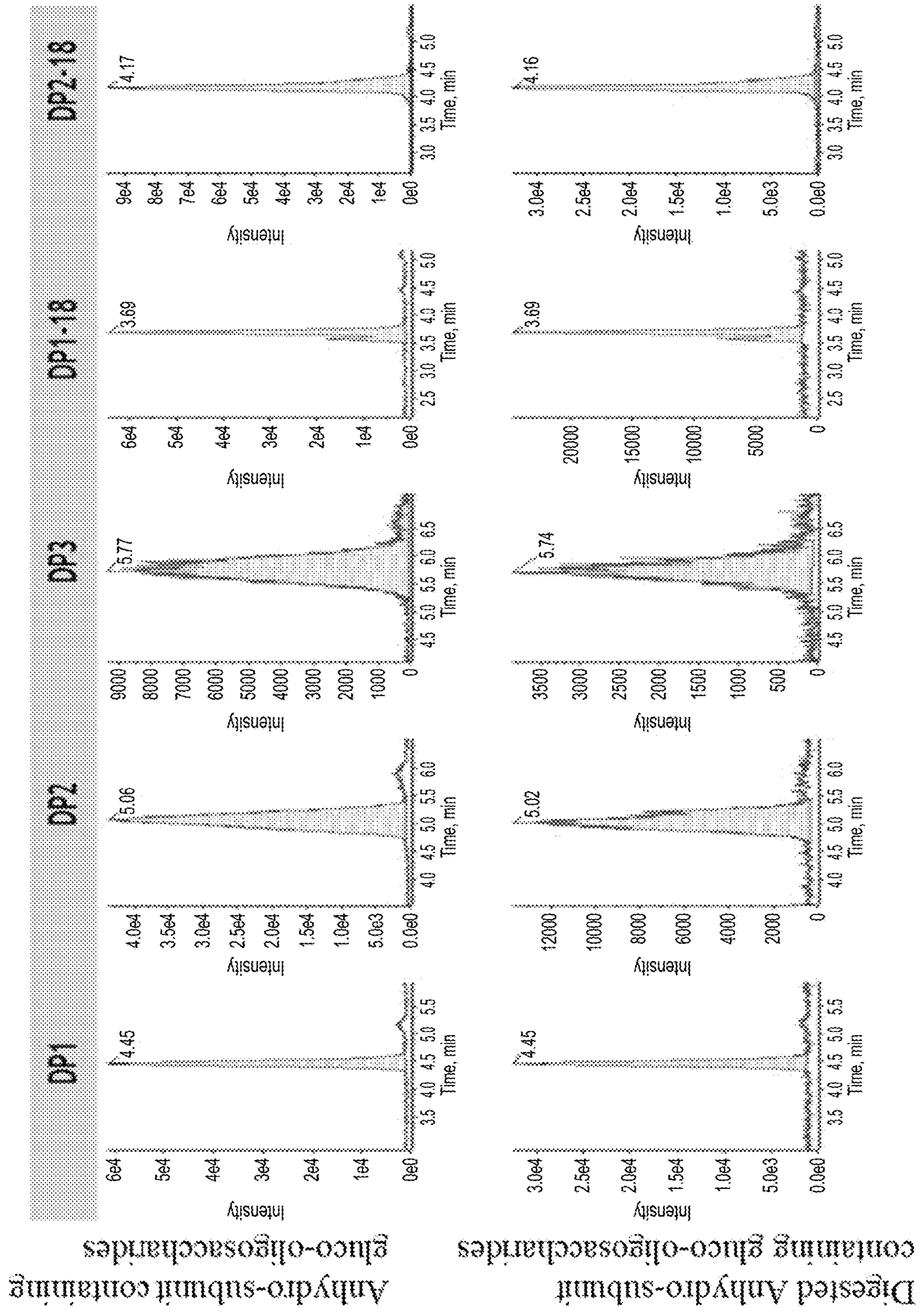
FIG. 14 illustrates mass chromatograms of anhydro-subunit containing oligosaccharides (top) and digested anhydro-subunit containing oligosaccharides (bottom) at selected MRMs.

Diffusion-Ordered NMR Spectroscopy (DOSY) was performed to separate the NMR signals of different species according to diffusion coefficient and thus MW. Signals at the upper part of the DOSY spectra in FIG. 12 correspond to high DP species, while lower DPs species appear below. FIG. 12 illustrates an overlay of $^1$H DOSY spectra of three anhydro-subunit containing oligosaccharides in Table 8.

Example 21

Semi-Preparative Isolation of DP1 & DP2 Fraction

Preparative isolation of the DP1 fraction was performed by preparative HPLC using a Waters BEH Amide 19×150 mm column. As mobile phase water was used as solvent A and Acetonitrile as solvent B, each with 0.1% ammonia. The applied gradient is shown in Table 9. The collected DP1 fraction of 8 separations were pooled, dried and resolubilized in 0.75 ml $D_2O$ for NMR analysis as described before.

For the characterization of the DP2 fraction a 2-step purification was done. The first step was performed on a flash chromatography system, using an ELSD (Evaporative light scattering detector). 2 ml (2.65 g) of an oligosaccharide preparation were diluted with 1 ml DMSO, 0.5 ml water and 0.5 ml Acetonitrile. The solution was mixed and for 15 min sonicated. 1 ml of the solution was injected on a YMC DispoPackAT, NH2, spherical, 25 μm, 120 g column was used. The oligosaccharide preparation was separated running an isocratic gradient method with 75% Actonitrile in water at 40 ml/min. The DP2 containing fraction was dried with nitrogen and resolubilized in DMSO/water (80:20, v/v).

For the $2^{nd}$ purification step an analytical UPLC system with a YMC $NH_2$ 4.6×250 mm (5 μm) column at 40° was used. The DP2 fraction was purified with an isocratic gradient (Table 10) and a flow rate of 1 ml/min. A 1:5 post-column spilt was used in order to trigger the collection by ELSD. The DP2 fraction from 12 chromatographic runs were pooled, the Acetonitrile removed by heated nitrogen and the residual water by freeze-drying. The dry fraction was resolubilized for subsequent LC-MS/MS & NMR analysis.

TABLE 9

| Gradient Method | | | |
|---|---|---|---|
| Time (min) | Flow rate (ml/min) | Solvent A | Solvent B |
| 0 | 25 | 10 | 90 |
| 2.5 | 25 | 10 | 90 |
| 23 | 25 | 25 | 75 |

TABLE 9-continued

| Gradient Method | | | |
|---|---|---|---|
| Time (min) | Flow rate (ml/min) | Solvent A | Solvent B |
| 23.1 | 25 | 10 | 90 |
| 47 | 25 | 10 | 90 |

TABLE 10

| Isocratic Method | | | |
|---|---|---|---|
| Time (min) | Flow rate (ml/min) | Water (%) | ACN (%) |
| 0 | 1 | 25 | 75 |
| 15 | 1 | 25 | 75 |

Example 22

Synthesis of an Oligosaccharide Preparation with a Monotonically Decreasing DP Distribution 330 grams of D-glucose monohydrate and 0.3 grams of (+)-Camphor-10-sulfonic acid were added to a one-liter, three-neck flask with overhead mechanical mixing provided by high-torque mechanical mixer through a flex coupling. The flask was secured inside a hemispherical electric heating mantle operated by a temperature control unit via a wand thermocouple inserted into the reaction mixture. The tip of the thermocouple was adjusted to reside within the reaction mixture with several mm clearance above the mixing element. The flask was equipped with a reflux condenser cooled by a water-glycol mixture maintained below 4° C. by a recirculating bath chiller.

The reaction mixture was gradually heated to 130° C. with continuous mixing with a stir rate of 80-100 rpm. When the reaction temperature was increased to between 120° C. and 130° C., the apparatus was switched from a reflux condenser to a distillation configuration with a round bottom receiving flask placed in an ice bath. The reaction was maintained at 130° C. with 120 RPM mixing for sixty minutes and the mass of condensate collected in the receiving flask was recorded as a function time at 10 minute intervals. The reaction was quenched by adding distilled water and removing the heat. After the product mixture cooled to room temperature, an aliquot of the product syrup was diluted to about 1 Brix as determined by refractive index. The diluted aliquot was microfiltered using a 0.2 micron syringe filter and analyzed by HPLC size exclusion chromatography (SEC). SEC analysis was performed on an Agilent 1100 series HPLC with refractive index detection using an Agilent PL aquagel-OH 20 column at 40° C. with distilled water at 0.45 mL/min as the mobile phase. Retention-time to MW calibration was performed using standard solutions with known molecular weight. The DP equilibrium constant was determined to be K=3.3 and the DP distribution was found to be monotonically decreasing. FIG. 15 and FIG. 16 show the shape of the DP distribution of different oligosaccharide preparations of Example 9 as determined by HPLC-SEC.

Example 23

Synthesis of an Oligosaccharide Preparation with a Non-Monotonic DP Distribution 330 grams of D-glucose monohydrate and 0.3 grams of (+)-Camphor-10-sulfonic acid were added to a one-liter, three-neck flask with overhead mechanical mixing provided by high-torque mechanical mixer through a flex coupling. The flask was secured inside a hemispherical electric heating mantle operated by a temperature control unit via a wand thermocouple inserted into the reaction mixture. The tip of the thermocouple was adjusted to reside within the reaction mixture with several mm clearance above the mixing element. The flask was equipped with a reflux condenser cooled by a water-glycol mixture maintained below 4° C. by a recirculating bath chiller.

The reaction mixture was gradually heated to 135° C. with continuous mixing with a stir rate of 80-100 rpm. When the reaction temperature was increased to 130° C., the apparatus was switched from a reflux condenser to a distillation configuration with a round bottom receiving flask placed in an ice bath. The reaction was maintained at 135° C. with 120 RPM mixing for thirty-five minutes. The reaction was quenched by adding distilled water and removing the heat. After the product mixture cooled to room temperature, an aliquot of the product syrup was diluted to about 1 Brix as determined by refractive index. The diluted aliquot was microfiltered using a 0.2 micron syringe filter and analyzed by HPLC size exclusion chromatography (SEC). SEC analysis was performed on an Agilent 1100 series HPLC with refractive index detection using an Agilent PL aquagel-OH 20 column at 40° C. with distilled water at 0.45 mL/min as the mobile phase. Retention-time to MW calibration was performed using standard solutions with known molecular weight. The DP distribution was found to be non-monotonically decreasing. FIG. 16 illustrates that the DP3 content is greater than the DP2 content and that the DP4 and DP5 contents are essentially equal.

Example 24

Fed-Batch Synthesis of an Oligosaccharide Preparation 330 grams of D-glucose monohydrate and 0.3 grams of 2-Pyridinesulfonic acid were added to a one-liter, three-neck flask with overhead mechanical mixing provided by high-torque mechanical mixer through a flex coupling. The flask was secured inside a hemispherical electric heating mantle operated by a temperature control unit via a wand thermocouple inserted into the reaction mixture. The tip of the thermocouple was adjusted to reside within the reaction mixture with several mm clearance above the mixing element. The flask was equipped with a reflux condenser cooled by a water-glycol mixture maintained below 4° C. by a recirculating bath chiller.

The reaction mixture was gradually heated to 130° C. with continuous mixing with a stir rate of 80-100 rpm. When the reaction temperature was increased to between 120° C. and 130° C., the apparatus was switched from a reflux condenser to a distillation configuration with a round bottom receiving flask placed in an ice bath. The reaction was maintained at 130° C. with 120 RPM and the mass of condensate collected in the receiving flask was recorded as a function time at 20 minute intervals. After 210 minutes, an additional 110 grams of D-glucose monohydrate were added to the reaction. After 420 minutes, the reaction was quenched by adding distilled water and removing the heat. After the product mixture cooled to room temperature, an aliquot of the product syrup was diluted to about 1 Brix as determined by refractive index. The diluted aliquot was microfiltered using a 0.2 micron syringe filter and analyzed by HPLC size exclusion chromatography (SEC). SEC analysis was performed on an Agilent 1100 series HPLC with refractive index detection using an Agilent PL aquagel-OH 20 column at 40° C. with distilled water at 0.45 mL/min as the mobile phase. Retention-time to MW calibration was performed using standard solutions with known molecular weight. The DP equilibrium constant was determined to be K=0.8 and the DP distribution was found to be monotonically decreasing.

Example 25

Growth Performance of Commercial Broiler Chickens Fed an Oligosaccharide Preparation Broiler chickens were grown on the diets of Example 15.6 to determine the effect of the oligosaccharide preparation on the growth performance of the animals. Specifically, commercial corn-soymeal poultry feeds containing dried distillers grains with solubles (DDGS), a coccidiostat, and a standard micronutrient blend, were manufactured according to industry practices and a three phase feeding program. By proximate analysis, the feed compositions were determined as shown in Table 11.

TABLE 11

Feed Compositions

| Component | Starter | Grower | Withdrawal | Method |
|---|---|---|---|---|
| Moisture | 13.0% | 13.0% | 12.9% | AOAC 930.15 (drafted oven) |
| Crude Protein (CP) | 24.1% | 21.5% | 19.6% | AOAC 992.15; AOAC 990.03 |
| Fat (EE) | 3.2% | 3.8% | 3.9% | AOAC 920.39 (ether extraction) |
| Crude Fiber (CF) | 2.7% | 2.4% | 2.4% | AOAC 962.09 (hydrolysis) |
| Ash (AR) | 5.2% | 4.3% | 4.3% | AOAC 942.05 (muffle furnace) |
| NFE, by difference | 51.9% | 55.1% | 56.9% | Calculated: 1-CP-EE-CF-AR |
| Total | 100.0% | 100.0% | 100.0% | |

Control (CTR) and treated (TRT) diets were prepared for each phase as described in Example 15.6, where the treat diets were prepared by augmenting the control diet with one pound per treated short ton using the oligosaccharide preparation of Example 9.7. In total, about 50 short tons of each diet were manufactured.

Day-of-hatch Hubbard M99×Cobb 500 straight run chicks were obtained from a commercial poultry hatchery and placed randomly into 36 ft×40 ft pens constructed into a tunnel-ventilated, dirt-floor poultry house. Approximately 30,000 birds were placed in total, with an equal number of birds in each pen. The house bedding consisted of built-up litter top-dressed with fresh wood shavings. A standard commercial environmental and lighting program were employed. Animals and housing facilities were inspected daily, including recording the general health status, feed consumption, water supply and temperature of the facility. Any mortalities were recorded daily.

Birds in odd numbered pens were fed the treated diet (i.e., containing the feed additive at 2 lbs/ton inclusion), and birds in the even numbered pens received the control diet. All diets were provided ad libitum via automatic feeders in each pen, and on feeder trays from day one until day 7. Water was provided ad libitum from a nipple drinking line.

The starter phase took place from day 0 to day 13, the grower phase from day 14 to day 27, and the withdrawal phase from day 28 through the end of the study, day 31. Bird weights by pen were recorded on days 0 and 31. The total mass of consumed feed was recorded for each pen. Weight gain and FCR were then determined for each pen according to standard industry practices.

On day 31, six male birds were randomly selected from each pen for blood and cecal sampling. The live weight of each sampled bird was recorded. A blood sample was collected via wing puncture into vacutainer tubes and frozen following coagulation and serum separation. Each sampled bird was then euthanized via cervical dislocation followed by extraction of the ceca using standard veterinary methods. Following dissection, cecal contents were transferred to 15 mL conical tubes, the weight of the cecal contents was recorded, and the contents were flash frozen to −80° C.

From the weights of the sampled birds, the treatment group exhibited an 11 point increase in body weight, significant at $P<0.05$ (by ANOVA).

Example 26

Shotgun Sequencing of Poultry Cecal Microbiota

The relative abundances of identified taxa were determined for a total of 96 sampled birds obtained from the study of Example 25. For each microbiota sample obtained in Example 25, the cecal contents were thawed and DNA was extracted using standard methods. The extracted DNA was analyzed on an Illumina HiSeq-X instrument, with 2×150 bp reads. Standard analyses were performed to process the raw sequencing data, including: trimming (adapter, BBDuk), Entropy filtering (k=5, window=20, min=50, BBDuk), Quality filtering (mean Q20, BBDuk), *Gallus* filtering (Bowtie2).

Taxonomic assignments were made against the MetaPhlAn2 (db_v20) database.

Example 27

Microbiota Associated with Improved Growth Performance

To assess the phenotypic connection between microbiota composition and growth performance, the sampled birds of Example 25 were grouped into cohorts according to their body weight and feed efficiency. A contrast analysis was performed to identify microbiota species that differed significantly across the various cohorts.

Figure 17:
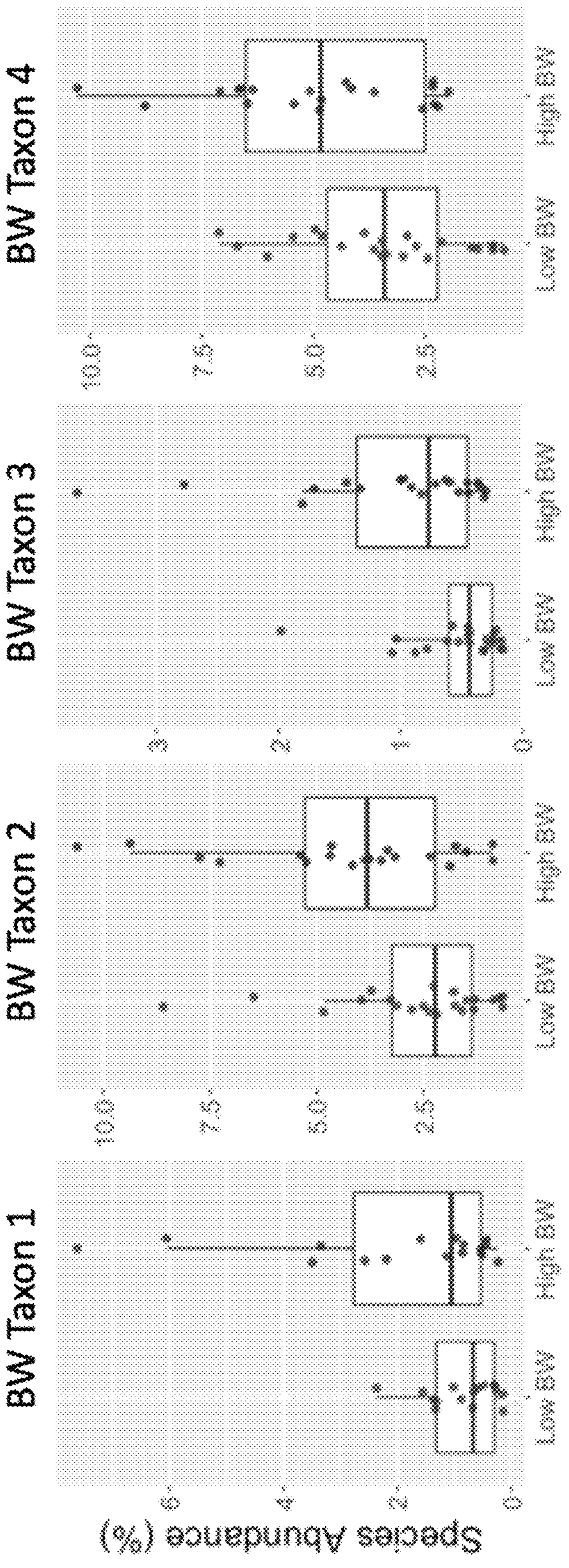
FIG. 17 shows microbial species (taxa) in the cecal microbiota associated with increased growth performance as measured by body weight.

Body Weight Effects:

First a correlation analysis was performed by regressing taxonomic abundance data versus the body weight (BW) of the bird from which the sequencing data were obtained. The correlation and P-Value of the correlation were assessed by linear regression to identify candidate genera and species positively correlated with growth performance as measured by body weight. Of the approximately 130 species isolated, fewer than thirty exhibited a positive BW correlation (FIG. 17).

The samples birds were grouped into two cohorts: (1) Low BW: the bottom quartile of sampled birds as measured by body weight; and (2) High BW: the top quartile of sampled birds as measured by body weight. The taxonomic data from Example 26 were then compared to identify species with a statically-significant difference relative abundance between the two cohorts. Specifically, for each OTU, the relative abundance of the corresponding organism was compared between the two cohorts. Species were identified which exhibited a higher relative abundance in high BW birds with $P<0.05$ as determined by ANOVA. Cecal microbiota associated with improved BW performance were characterized by an increased relative abundance of members of genera *Bacteroides, Odoribacter, Oscillibacter, Subdoligranulum, Ruminococcus*, and *Biophila*. The species *Odoribacter* splanchnicus was found to exhibit a particularly strong correlation with BW. FIG. 17 provides box and scatter plots illustrating four taxa positively associated with BW performance ($P<0.05$).

Feed Efficiency Effects:

First, a correlation analysis was performed by regressing taxonomic abundance data versus the feed conversion ratio (FCR) of the pen corresponding to the bird from which the sequencing data were obtained. The correlation and P-Value of the correlation were assessed by linear regression to identify candidate genera and species positively correlated with growth performance as measured by feed efficiency. Of the approximately 130 species isolated, fewer than twenty exhibited a positive FCR correlation.

Figure 18:
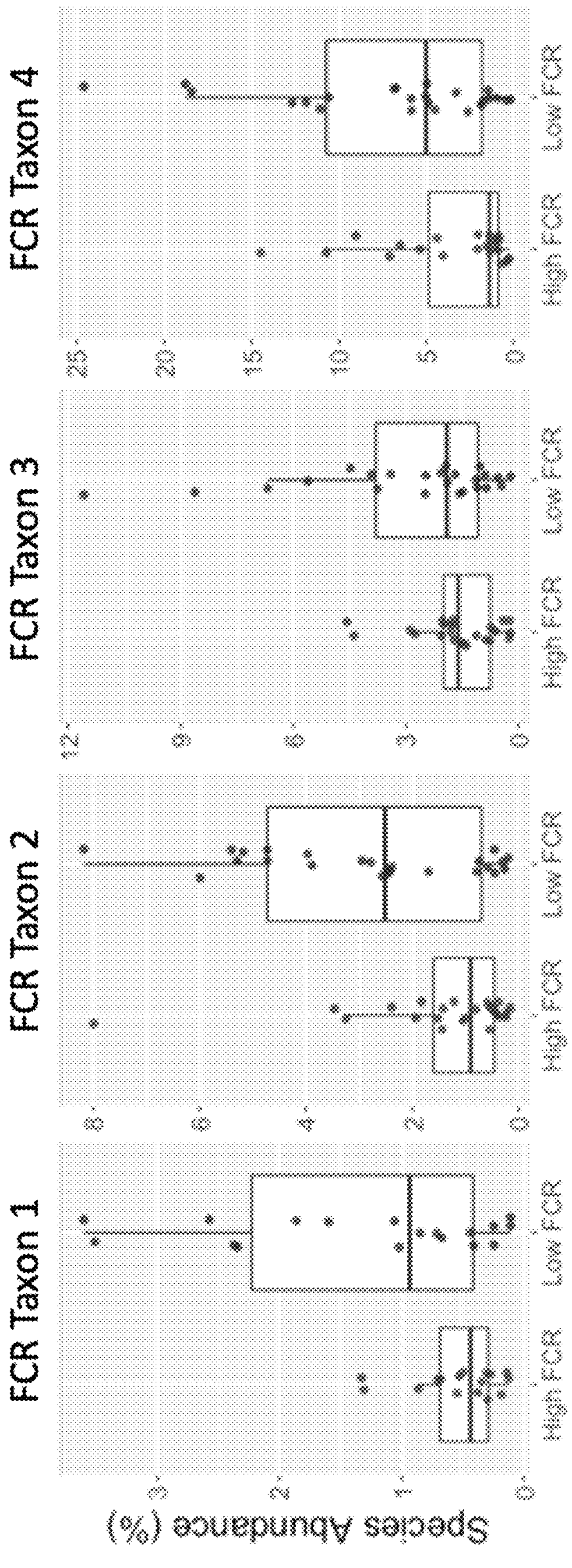
FIG. 18 shows microbial species (taxa) in the cecal microbiota associated with decreased growth performance as measured by body weight.

The samples birds were grouped into two cohorts: (1) High FCR (i.e., poor feed efficiency): the top quartile of sampled birds as measured by feed conversion ratio; and (2) Low FCR (i.e., improved feed efficiency): the bottom quartile of sampled birds as measured by feed conversion ratio. The taxonomic data from Example 26 were then compared to identify species with a statically-significant difference relative abundance between the two cohorts. Specifically, for each OTU, the relative abundance of the corresponding organism was compared between the two cohorts. Species were identified that exhibited a higher relative abundance in low FCR with $P<0.05$ as determined by ANOVA. Cecal microbiota associated with improved feed efficiency were characterized by an increased relative abundance of members of genera Parabacteroides, Akkermansia, *Subdoligranulum, Bacteroides, Barnesiella* (FIG. 18). The species *Bacteroides dorei* and *Barnesiella intestinihominis* exhibited a particularly strong associated with improved feed efficiency (FIG. 18). FIG. 18 provides box and scatter plots illustrating four taxa positively associated with feed efficiency ($P<0.05$).

Example 28

Consistency of Taxa Associations and Putative Function

The Study of Example 25 was repeated multiple times to assess the impact of different regions, diet types, coccidiosis programs, bird genetics, and grow-out durations. The cecal microbiota obtained from sampling birds and sequencing their gut microbiota according to the methods of Examples 25-25 was repeated for the various studies. The contrast analysis and correlation determinations of Example 27 were also repeated for the various studies, both independently and after pooling the data into a single set.

Taxa that exhibited a consistent association with performance across the multiple studies were identified by performing a joint cohort analysis. Table 12 shows the taxa, representative members, and putative function were obtained.

TABLE 12

| Cecal Microbiota | | |
|---|---|---|
| Taxon | Representative Members | Putative Function |
| Taxon 1 | *O. splanchnicus* | Increased body weight |
| Taxon 2 | *B. clarus* | Increased body weight<br>Reduced feed conversion ratio |
| Taxon 3 | *B. faecalis; B. dorei* | Reduced feed conversion ratio |
| Taxon 4 | *B. intestinihominis* | Reduced feed conversion ratio |
| Taxon 5 | *Oscillibacter* spp. | Increased body weight |

Furthermore, over 100 taxa were identified that exhibited either no correlation with growth performance or inconsistent association with growth performance between the various studies.

Example 29

Method of Enhancing Beneficial Taxa

The impact of the oligosaccharide preparations of Example 9 on the abundance of the beneficial taxa of Example 28 was assessed in vivo for commercial broiler chickens. Specifically, the sampled birds obtained from the study of Example 25 were grouped into two cohorts: (1) Control Group, including only those birds fed the control diets; and (2) Treated Group, including only those birds fed the treated diets containing the oligosaccharide preparation.

A contrast analysis was performed between Control Group and Treated Group cohorts. It was found that approximately twenty microbiome species exhibited a statistically significant shift in abundance as a result of feeding the oligosaccharide feed additive. Furthermore, it was found that multiple of the taxa associated with performance of Examples 27 and 28 were increased as a result of feeding the animal the oligosaccharide preparation. In particular: Taxon 4 (*Barnesiella intestinihominis*) was increased significantly ($P<0.01$, by ANOVA) and Taxon 1 (*Odoribacter* splanchnicus) was increased significantly ($P<0.1$, by ANOVA). Multiple-hypothesis testing confirmed that the beneficial taxa of Example 29 were increased significantly in the Treatment Group cohort ($Q<0.005$, by Mann-Witney-Wilcoxon Testing).

Example 30

Method of Improving Growth Performance

Animals in the study of Example 25 fed treated diets exhibited a statistically significant increase in beneficial taxa and a corresponding statistically significant increase in growth performance, as measured by a treatment effect of 11 pts in body weight relative to control ($P<0.05$).

Example 31

Upregulation of Endogenous Digestive Enzymes Expressed by the Gut Microbiome Ex vivo transcriptomics and an in vivo feed digestibility study were performed to demonstrate the ability of an oligosaccharide preparation to increase the transcription of genes known to code for enzymes that contribute to the digestion of feed and to demonstrate increased feed digestibility in broiler chickens.

Ex Vivo Transcriptomics:

A microbiota sample obtained using the methods of Example 25 was used to prepare a 20% w/v suspension in pH 7.4 phosphate buffered saline (PBS) containing 15% glycerol. Working under anaerobic conditions, an aliquot of the suspension was centrifuged at 2,000 g, the supernatant was removed by pipette, and the pellet was resuspended to form a 1% w/v cecal slurry in a sterile aqueous mixture of: 900 mg/L sodium chloride, 26 mg/L calcium chloride dihydrate, 20 mg/L magnesium chloride hexahydrate, 10 mg/L manganese chloride tetrahydrate, 40 mg/L ammonium sulfate, 4 mg/L iron sulfate heptahydrate, 1 mg/L cobalt chloride hexahydrate, 300 mg/L potassium phosphate dibasic, 1.5 g/L sodium phosphate dibasic, 5 g/L sodium bicarbonate, 0.125 mg/L biotin, 1 mg/L pyridoxine, 1 m/L pantothenate, 75 mg/L histidine, 75 mg/L glycine, 75 mg/L tryptophan, 150 mg/L arginine, 150 mg/L methionine, 150 mg/L threonine, 225 mg/L valine, 225 mg/L isoleucine, 300 mg/L leucine, 400 mg/L cysteine, and 450 mg/L proline.

Figure 19:
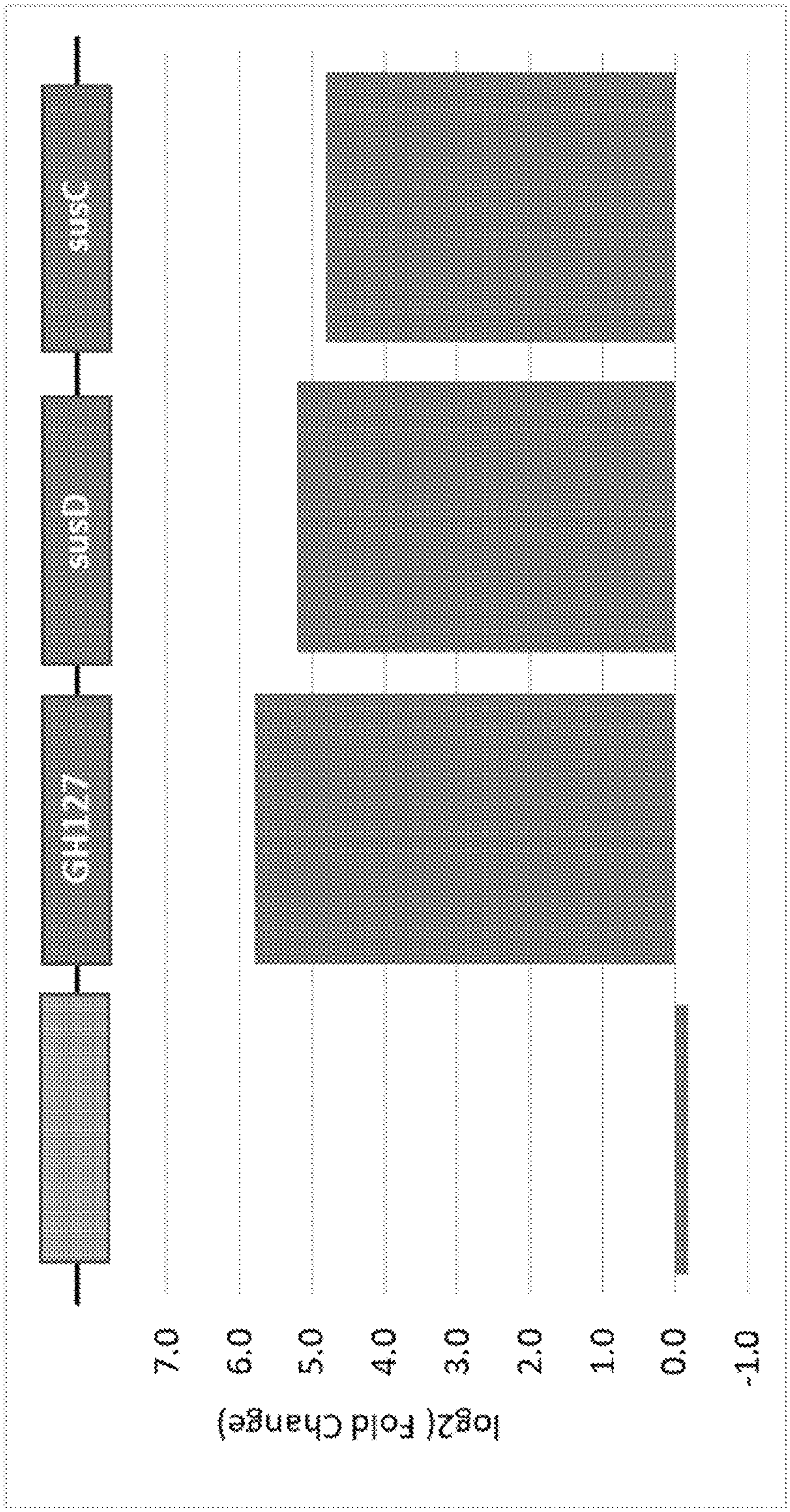
FIG. 19 is a graph showing the ex vivo increase in the transcription of hydrolytic digestive enzymes by microbiota provided with an oligosaccharide preparation of Example 9.

Deep-well microtiter plates (e.g., Costar 3958 plates) were loaded in triplicate with 250 uL of the above suspension, 50 uL of a sterile 20 wt % aqueous solution of selected oligosaccharide preparations from Example 9, and 200 uL of sterile water. Control wells were loaded with 25 uL of a sterile 20 wt % glucose solution and 200 uL of sterile water. Loaded plates were incubated at 37° C. for 45 hours under anaerobic conditions followed by RNA extraction using methods known to one skilled in the art. The effect of the oligosaccharide preparation on the polysaccharide utilization loci (PUL) of the microbiota was determined by whole transcriptome shotgun sequencing (RNA-seq). Relative to the glucose control, increased transcription of was observed in the presence of the oligosaccharide preparation for multiple genes associated with hydrolytic digestion of feed: GH127 (CAZyme α-L-arabinofuranosidase), susC (outer membrane receptor associated with the starch utilization system) and susD (starch binding protein). FIG. 19 illustrates increased transcription of hydrolytic digestive enzymes belonging to the PUL for microflora fed the oligosaccharide preparation relative to control.

In vivo increase in Feed Digestibility

Ross 308 broilers were grown for 35 days in raised floor pens on a conventional three-phase diet program. Three dietary treatment groups were compared: (1) a Negative Control Group fed an industry representative wheat-soy poultry diet; (2) a Positive Control Group fed the control diet supplemented with a conventional xylanase feed additive (AB-Vista Econase) at the recommended inclusion level; and (3) a Treatment Group fed the control diet supplemented with 500 ppm of an oligosaccharide preparation from Example 9. All diets contained an anticoccidial, industry standard levels of phytase and $TiO_2$ marker for performing the digestibility determination. Conventional environmental, lighting, and monitoring programs were employed. A randomized block study design was implemented with eight pens per treatment group with thirty-eight birds per pen.

Birds in the Treatment Group were observed to exhibit a statistically significant 2.8% increase in dry matter digestibility and a statistically significant 4.5% increase in Nitrogen digestibility relative to the Negative Control Group. The Treatment Group also outperformed the Positive Control Group fed enzyme-supplemented diets. Positive control birds exhibited a 1.4% increase in dry matter digestibility and a 1.5% increase in Nitrogen digestibility.

Example 32

Growth and Sampling Piglets Fed an Oligosaccharide Preparation

Nursery pigs were grown on the diets of Example 15 to determine the effect of an oligosaccharide preparation on the functional metagenomics of the pig ileal, cecal, and fecal microbiomes.

One hundred and forty-four Redon×Large-White weaned piglets with an initial body weight of 8.54±1.70 kg were raised for 42 days in flat-deck housing in an environmentally controlled room. The animals were allocated to 4 equal groups of 36 piglets in 9 pens of 4 animals per pen. Each pen had a plastic-coated welded wire floor and was equipped with two water nipples and two stainless-steel individualized feeders. The room humidity was maintained at 50% and the temperature was maintained initially at 27° C. and lowered weekly by about 2° C. per week to 21-22° C. The animals were fed according to a two-phase diet program formulated according to NRC (2012) nutritional recommendations using the diet constructions of Table 13.

TABLE 13

Nursery Pig Diet Compositions

| Ingredient | Pre-Starter (wt %) | Starter (wt %) |
|---|---|---|
| Corn | 52.20 | 62.25 |
| Soy Bean Meal | 26.00 | 26.00 |
| Corn Starch | 6.00 | — |
| Soy Protein Concentrate | 5.00 | 3.00 |
| Calcium Carbonate | 0.60 | 0.55 |
| Di-Calcium Phosphate | 1.7 | 1.50 |
| Sodium Bicarbonate | 0.45 | 0.40 |
| Sodium Chloride | 0.25 | 0.20 |
| L-Lysine | 0.80 | 0.65 |
| L-Threonine | 0.30 | 0.25 |
| L-Methionine | 0.20 | 0.20 |
| Soybean Oil | 3.00 | 2.00 |
| Vitamin & Mineral Premix | 3.50 | 3.00 |

Pre-starter diets were fed from day 0 to day 14; and Starter Diets were fed from day 15 until day 42. All diets were provided ad libitum as mash diet formulations. The pigs were grouped into treatment groups according to Table 14.

TABLE 14

Nursery Pig Treatment Groups

| Treatment Group | Pre-Starter Diet | Starter Diet |
|---|---|---|
| Control | Diet 15.3(CTR) | Example 15.5(CTR) |
| Test Group A | Diet 15.3(CTR) supplemented with 125 ppm of oligosaccharide preparation 9.7 | Diet 15.5(CTR) supplemented with 125 ppm of oligosaccharide preparation 9.7 |
| Test Group B | Diet 15.3(CTR) supplemented with 250 ppm of oligosaccharide preparation 9.7 | Diet 15.5(CTR) supplemented with 250 ppm of oligosaccharide preparation 9.7 |
| Treatment | Diet 15.3(TRT) | Diet 15.6(TRT) |

The average daily weight gain (ADWG) of piglets in the Treatment Group was determined to be 508.1 g/day compared to the Control Group which gained 494.9 g/day. The feed conversion ratio for the Control Group was found to be 1.781 kg/kg, while for the Treatment Group it was found to be 1.748.

Example 33

Effect of an Oligosaccharide Preparation on Functional Metagenomics

Nursery pigs were raised in pens according to the general protocol of Example 32. The pigs were grouped into two treatment groups: (1) the Control Group was fed the diets of 15.3(CTR) and 15.5(CTR); and (2) the Treatment Group was fed the diets of 15.3(CTR) and 15.5(TRT). For each treatment group, 13 animals were selected at random, euthanized, and dissected to obtain ileal, cecal, and fecal (colon) microbiota samples.

The 69 microbiota samples were prepared by SAMBO DNA extraction and sequenced by MetaQuant (MGP). 21.6M cleaned reads were generated on average per sample. Mapping and counting were performed using METEOR. Mapping with Bowtie2 (identity 95%) was performed to remove host contaminants (pig genome), and the resulting sequences were profiled against a custom gene catalog containing 9M genes (ileal, cecal, and fecal microbiomes). Biostatistical analysis was performed using MetaOMineR. Greater than $2\times10^7$ high quality reads were obtained. To avoid bias due to mapping rate variability, all samples were downsized to 10M mapped reads and gene abundances were normalized by FPKM according to gene length and sequencing depth.

Gene Richness and Functional Metagenomic Analysis:

Samples were grouped into cohorts according to treatment group and microbiome type (ileal, cecal, fecal) and a contrast analysis was performed to determine statistically-significant changes in gene richness, measured as the number of distinct genes. Animals in the treatment group exhibited a 2-5-fold increase in gene richness, significant at $P<0.006$ for the cecal microbiota and $P<0.06$ for the fecal microbiota (Wilcoxon test). A numerical increase in the ileal gene richness was also observed.

Figure 20:
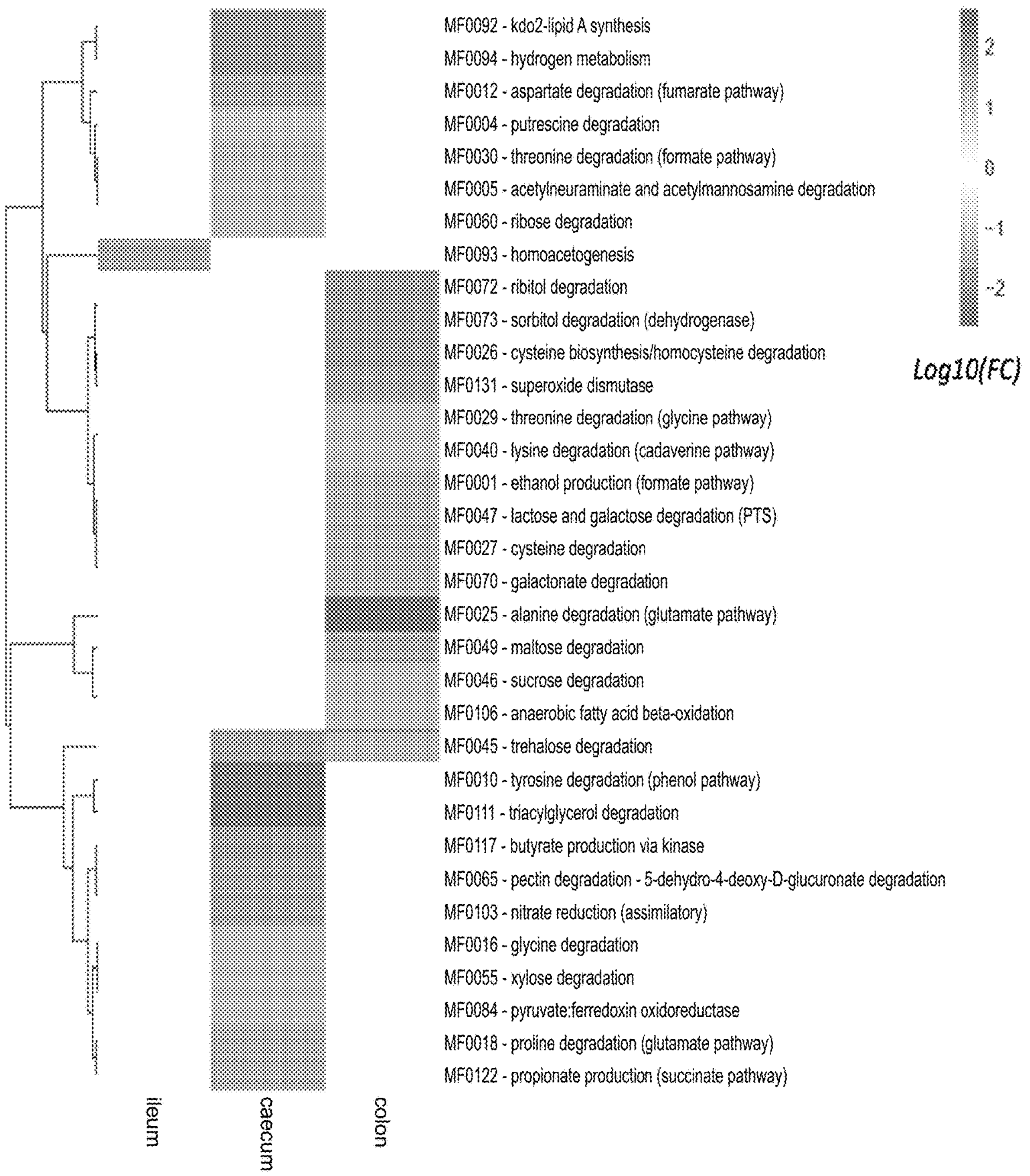
FIG. 20 is a graph showing the effect of an oligosaccharide preparation of Example 9 on the functional metagenomics of piglets.

Genes were annotated using the KEGG database (v82) and grouped according to gut metabolic modules (GMMs) [Darzi, Y. et al., The ISME Journal, 10, 1025-1028 (2015)] using an internal pipeline. A contrast analysis was performed on the GMM abundance data to determine metabolic pathways and functions that were modulated in the Treatment Group relative to the Control Group. FIG. 20 illustrates the effect of the oligosaccharide preparation on the functional metagenomics of the piglet microbiome. A statistically-significant increase in pathways associated with acetogenesis was observed in the ileum microflora. Statistically-significant increases in pathways associated with pectin degradation and SCFA production, among others, were observed in the cecum. Furthermore, SCFA pathways for the production of butyrate and propionate were enriched in the cecal microbiota for the Treatment Group.

Example 34

Reduction of Undesirable Microbial Species in the Gut Microflora

The impact of the oligosaccharide preparations of Example 9 on undesirable taxa was assessed in vivo for commercial broiler chickens. Specifically, the sampled birds obtained from the study of Example 25 were grouped into two cohorts: (1) the Control Group, including only those birds fed the control diets; and (2) the Treated Group, including only those birds fed the treated diets containing the oligosaccharide preparation.

A contrast analysis was performed between the Control Group and Treated Group cohorts to assess changes in the abundances of the taxa analyzed in Example 26. Birds fed the treated diet exhibited the following changes in microbial relative abundance as shown in Table 15.

TABLE 15

Relative Abundance of Microbial Species in Treated Group

| Microbial Species | $\log_2$ (Fold Change from Control Group) |
|---|---|
| *Campylobacter jejuni* | −1.9 ($P < 0.001$) |
| *Helicobacter pullorum* | −1.3 ($P < 0.001$) |
| *Campylobacter coli* | −0.7 ($P < 0.05$) |
| *Escherichia coli* | −0.7 ($P < 0.1$) |

Figure 21:
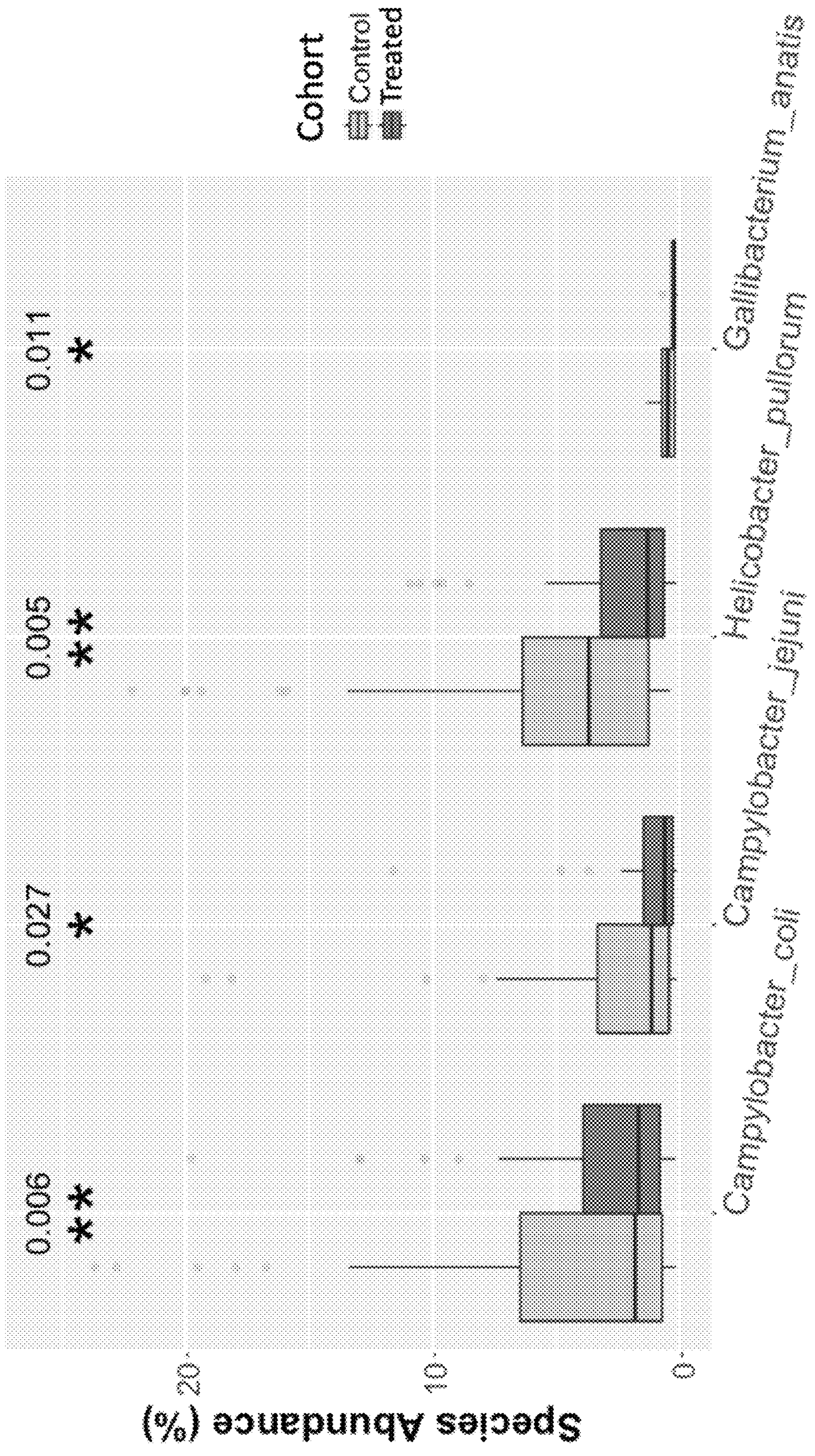
FIG. 21 shows the reduction of undesirable members of the phylum Proteobacteria in the intestinal flora of commercial broiler chickens in the Treated Group (birds fed the treated diets containing the oligosaccharide preparation) to compared to the Control Group (birds fed the control diets lacking the oligosaccharide preparation).

FIG. 21 illustrates that the species in Table 15 are reduced in the Treatment Group relative to the Control Group. By contrast, 83 species either increased or did not decrease in relative abundance. Single strain growth experiments confirmed that the oligosaccharides were not antimicrobial.

Example 35

Consistency Across Multiple Studies

The Study of Example 25 was repeated multiple times to assess the impact of different regions, diet types, coccidiosis programs, bird genetics, and grow-out durations. The cecal microbiota obtained from sampled birds in the additional studies were sequenced according to the methods of Examples 25-26. The contrast analysis of Example 34 was also repeated for the various studies, both independently and after pooling the data into a single set. A reduction in the Gram-Negative bacteria, *Campylobacter* spp., *Heliobacteria* spp., and *Escherichia* spp. was observed consistently across multiple studies. Proteobacteria *Campylobacter* species was observed consistency in all of the studies, as was an overall reduction in.

Example 36

Association Between Mortality and Intestinal Pathogen Abundance

The effect of common pathogens in the intestinal microflora on animal health was assessed in broiler chickens.

Ross 708 straight run chicks were obtained from a common breeder flock and placed into twenty-four 8 ft×6 ft floor pens situated within a single broiler house. 30 male chicks were placed per pen and bird weights by pen were recorded on Days 0. Birds were raised on built up litter top-dressed with fresh wood shavings to provide a bedding with a thickness of approximately 4 in. The temperature of the building was monitored and recorded daily. Environmental conditions during the trial followed industry practices. All birds were vaccinated following an industry-standard vaccination program and were further vaccinated for coccidiosis.

The birds were fed diets in two treatment groups according to a four-phase feeding program as shown in Table 16.

TABLE 16

Four Phase Feeding Program

| Diet Phase | Feed Type | Age (days) |
|---|---|---|
| Starter | crumble | 0-16 |
| Grower | small pellet | 16-28 |
| Finisher | pellet | 28-42 |
| Withdrawal | pellet | 42-49 |

All diets were corn-soybean meal-based and contained dried distillers grains with solubles (DDGS) and were free of antibiotic growth promotors and ionophores or other anticoccidials. Birds in the Control Group (CTR) were fed the base diet, while birds in the Treatment Group (TRT) were fed the base diets supplemented with 500 ppm of an oligosaccharide preparation from Example 9.

The diets were provided ad libitum via commercial Choretime automatic feeders in each pen. From d 1 until 7, feed was also be supplied on feeder trays, placed on the litter. Water was provided ad libitum from one nipple drinking line. Standard floor pen management practices were used throughout the experiment. Animals and housing facilities were inspected twice daily, observing, and recording the general health status, constant feed, and water supply as well as temperature, removing all dead birds, and recognizing unexpected events. Pen number and removal date was recorded for all mortalities and culled birds over the course of the study.

Figure 22:
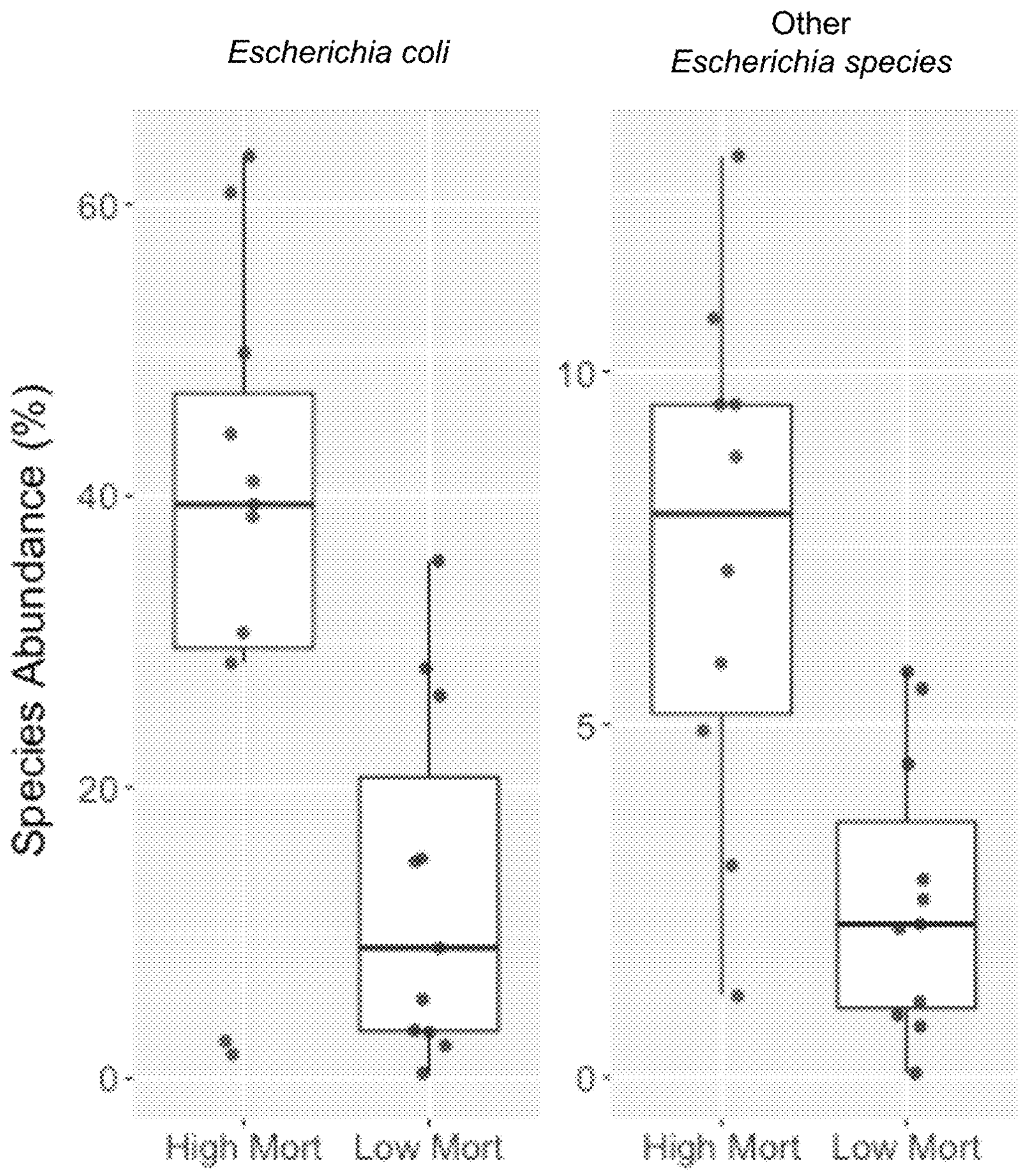
FIG. 22 is a graph showing the correlation between the relative abundance of *Escherichia coli* (left) and other *Escherichia* species (right) and mortality in commercial broiler chickens.

On Day 15, one bird selected randomly from each pen was sampled for flood and cecal microbiota following the procedure of Example 25 and the microbiota were analyzed according to the methods of Example 26. The sampled birds were grouped into two cohorts: (1) High Mortality birds were those drawn from pens in the top quartile for mortality; and (2) Low Mortality birds were those drawn from pens in the bottom quartile for mortality. A contrast analysis was performed to determine microbial species with a statistically-significant difference in abundance between the two cohorts. Approximately five species were found to correlate strongly with mortality. Little or no correlation was found for more than one hundred other cecal microbiota taxa. A particularly strong correlation was observed between the relative abundance of *Escherichia* species and mortality. FIG. 22 provides a box and scatter plot for *Escherichia coli* (left panel) and other *Escherichia* species (right panel) clearly illustrating the connection between pathogen abundance and bird mortality.

Example 37

Treatment Effect of Oligosaccharide Preparations

The sampled birds of Example 36 were analyzed by treatment group, for which a three-fold reduction was observed in the relative abundance of *Escherichia coli. Escherichia* species were reduced overall (Q=0.07, multiple comparison by Mann-Whitney-Wilcoxon testing). Furthermore, sampled birds in the treatment group exhibited a three-fold reduction in the number of pens exhibiting the apicomplexan parasite *Eimeria tenella.*

Example 38

Meta-Analysis of Live Growth Performance Studies in Broiler Chickens

The effect of oligosaccharide preparations on the live growth performance of commercial broiler chickens was assessed in vivo through a series of independent studies conducted across a variety of regions, times of year, background diet types, bird genetics, and management practices including litter handling and coccidiosis-control programs. In each study, birds were allotted to treatment groups including one control group and one or more treated groups. The control group was fed only the background diet. The treated groups were fed the background diet supplemented with a specified dose of the oligosaccharide preparations of Example 9. In selected studies, a commercial feed additive used in the poultry industry was included as a comparative example.

For each study, birds were housed in pens situated within a typical broiler house with a specified number (Hd/Rep) of birds in each pen. Statistical replications were implemented by randomly assigning pens to treatment groups, with a specified number (Reps/Trt) of replications per treatment. Table 17 summarizes the protocol details for each study included in the analysis.

TABLE 17

| Protocol | | | | | | | | | | |
|---|---|---|---|---|---|---|---|---|---|---|
| Study | Country | Season | Length | Diet Type | Reps/Trt | Hd/Rep | Genetics | Sex | Litter | Cocci Program |
| Ex. 38.1 | USA | Spring | 35 | Corn/Soy | 6 | 14 | Cobb 500 | M/F | Used | Saccox |
| Ex. 38.2 | USA | Winter | 49 | Corn/Soy | 12 | 60 | Cobb 500 | M/F | Used | Maxiban |
| Ex. 38.3 | CA | Winter | 35 | Corn/Soy | 8 | 60 | Ross 708 | M | Used | Saccox |
| Ex. 38.4 | USA | Winter | 49 | Corn/Soy | 12 | 60 | Cobb 500 | M/F | Used | Maxiban |
| Ex. 38.5 | UK | NA | NA | Wheat/Soy | NA | NA | NA | NA | Clean | None |
| Ex. 38.6 | USA | Winter | 33 | Corn/Soy | 12 | 100 | Cobb 500 | M/F | Used | Amprol |
| Ex. 38.7 | USA | Summer | 49 | Corn/Soy | 12 | 18 | Hubbard M99 | M | Used | None |
| Ex. 38.8 | C | Winter | 42 | Corn/Soy | 12 | 17 | Ross308 | Male | Used | Vaccine |
| Ex. 38.9 | GB | Autumn | 42 | Wheat/Soy | 16 | 35 | Ross308 | Male | Fresh | None |
| Ex. 38.10 | FR | Autumn | 42 | Wheat/Soy | 17 | 30 | Ross308 | Male | Fresh | None |
| Ex. 38.11 | US | Autumn | 42 | Corn/Soy | 21 | 40 | Cobb500 | Male | Used | Vaccine |
| Ex. 38.12 | FR | Summer | 36 | Corn/Soy | 12 | 18 | Cobb500 | Male | Fresh | Vaccine |
| Ex. 38.13 | CA | Spring | 42 | Corn/Soy | 10 | 20 | Ross708 | Male | Used | Vaccine |
| Ex. 38.14 | USA | Spring | 42 | Corn/Soy | 14 | 40 | Cobb500 | Male | Used | Vaccine |
| Ex. 38.15 | NZ | Spring | 35 | Wheat/Soy | 12 | 20 | Ross308 | Male | Fresh | Vaccine |

Study outcomes included bird weight (BW), feed intake (FI), feed conversion ratio (FCR), percent mortality (by head), and mortality weight. Pen was the statistical unit. Where possible, spatial blocking was implemented, and treatment groups were assigned randomly to blocks.

Background Diets:

Birds were fed in diet phases according to local industry practices for a total study length between 35 and 49 days. Starter phase diets were typically provided as crumble from bird placement through study day 15. All diets were free of antibiotic growth promoters. Starter control diet constructions are presented in Table 18 (NA=data not available from site).

TABLE 18

| Start Control Diet Constructions | | | | | | | | | |
|---|---|---|---|---|---|---|---|---|---|
| Study | % Corn Meal | % Wheat Meal | % Soy Meal | % Corn DDGS | Crude Protein | Crude Fat | AME (kcal/kg) | Lysine (SID) | Methionine (SID) |
| Ex. 38.1 | 63.5 | NA | 27.4 | NA | 22.1 | NA | 2988 | 1.35 | NA |
| Ex. 38.2 | 0 | NA | 0 | NA | NA | NA | NA | NA | NA |
| Ex. 38.3 | 63.4 | NA | 28.3 | NA | 20.9 | NA | 2940 | 1.14 | NA |
| Ex. 38.4 | NA | NA | NA | NA | NA | NA | NA | NA | NA |
| Ex. 38.5 | NA | NA | NA | NA | NA | NA | NA | NA | NA |
| Ex. 38.6 | 0 | NA | 0 | NA | NA | NA | 3011 | NA | NA |
| Ex. 38.7 | 0 | NA | 0 | NA | NA | NA | NA | NA | NA |
| Ex. 38.8 | 54.52 | 0 | 34.38 | 5 | 22.23 | 2.81 | 2900 | 1.24 | 0.63 |
| Ex. 38.9 | 0 | 51.78 | 30.5 | 0 | 21.31 | 5.74 | 2899 | 1.251 | 0.622 |
| Ex. 38.10 | 0 | 55.1 | 28 | 0 | 22.49 | 5.42 | 2899 | 1.237 | NA |
| Ex. 38.11 | 58.353 | 2.377 | 29.992 | 5 | 20.3 | NA | 2900 | 1.33 | NA |
| Ex. 38.12 | NA | NA | NA | NA | 22 | NA | 3011 | NA | NA |

TABLE 18-continued

| Start Control Diet Constructions | | | | | | | | | |
|---|---|---|---|---|---|---|---|---|---|
| Study | % Corn Meal | % Wheat Meal | % Soy Meal | % Corn DDGS | Crude Protein | Crude Fat | AME (kcal/kg) | Lysine (SID) | Methionine (SID) |
| Ex. 38.13 | 56.08 | 0 | 34.1 | 5 | 22.23 | 2.31 | 2900 | 1.24 | 0.63 |
| Ex. 38.14 | 58.353 | 0 | 29.992 | 5 | 20.3 | NA | 2900 | 1.33 | NA |
| Ex. 38.15 | 0 | 54.92 | 28.31 | 5 | NA | 6.9 | 2900 | 1.24 | NA |

Grower phase diets were provided as pellets from day 16 through day 24. Grower control diet constructions are presented in Table 19 (NA=data not available from site).

TABLE 19

| Grower Phase Control Diet Constructions | | | | | | | | | |
|---|---|---|---|---|---|---|---|---|---|
| Study | % Corn Meal | % Wheat Meal | % Soy Meal | % Corn DDGS | Crude Protein | Crude Fat | AME (kcal/kg) | Lysine (SID) | Methionine (SID) |
| Ex. 38.1 | 68.6 | NA | 22 | NA | 19.95 | NA | 3059 | 1.2 | NA |
| Ex. 38.2 | NA | NA | NA | NA | NA | NA | NA | NA | NA |
| Ex. 38.3 | 65.6 | NA | 26.3 | NA | 19.9 | NA | 2988 | 1.06 | NA |
| Ex. 38.4 | NA | NA | NA | NA | NA | NA | NA | NA | NA |
| Ex. 38.5 | NA | NA | NA | NA | NA | NA | NA | NA | NA |
| Ex. 38.6 | NA | NA | NA | NA | NA | NA | 3102 | NA | NA |
| Ex. 38.7 | NA | NA | NA | NA | NA | NA | NA | NA | NA |
| Ex. 38.8 | 54.95 | 0 | 28.31 | 10 | 20.8 | 3.88 | 3000 | 1.11 | 0.56 |
| Ex. 38.9 | 0 | 57.135 | 26 | 0 | 19.01 | 6.55 | 2997 | 1.08 | 0.533 |
| Ex. 38.10 | 0 | 55.77 | 24 | 0 | 20.94 | 7.4 | 2998 | 1.11 | NA |
| Ex. 38.11 | 65.383 | 0.344 | 20.404 | 10 | 17.5 | NA | 3040 | 1.33 | NA |
| Ex. 38.12 | NA | NA | NA | NA | 19 | NA | 3035 | NA | NA |
| Ex. 38.13 | 56.53 | 0 | 28.02 | 10 | 20.8 | 3.39 | 3000 | 1.11 | 0.56 |
| Ex. 38.14 | 65.383 | 0 | 20.404 | 5 | 17.5 | NA | 3040 | 1.14 | NA |
| Ex. 38.15 | 0 | 57.3 | 23.05 | 6 | NA | 6.27 | 3000 | 1.11 | NA |

Finisher phase diets were provided as pellets from day 16 through day 24. Finisher control diet constructions are presented in Table 20 (NA=data not available from site).

TABLE 20

| Finisher Phase Control Diet Constructions | | | | | | | | | |
|---|---|---|---|---|---|---|---|---|---|
| Study | % Corn Meal | % Wheat Meal | % Soy Meal | % Corn DDGS | Crude Protein | Crude Fat | AME (kcal/kg) | Lvsine (SID) | Methionine (SID) |
| Ex. 38.1 | 74.3 | NA | 27.4 | NA | NA | NA | 3155 | 1.06 | NA |
| Ex. 38.2 | NA | NA | NA | NA | NA | NA | NA | NA | NA |
| Ex. 38.3 | 70.8 | NA | 28.3 | NA | NA | NA | 3059 | 0.94 | NA |
| Ex. 38.4 | NA | NA | NA | NA | NA | NA | NA | NA | NA |
| Ex. 38.5 | NA | NA | NA | NA | NA | NA | NA | NA | NA |
| Ex. 38.6 | NA | NA | NA | NA | NA | NA | 3203 | NA | NA |
| Ex. 38.7 | NA | NA | NA | NA | NA | NA | NA | NA | NA |
| Ex. 38.8 | 57.37 | 0 | 24.85 | 10 | 19.4 | 5.16 | 3100 | 1.03 | 0.55 |
| Ex. 38.9 | 0 | 59.94 | 23 | 0 | 17.53 | 7.71 | 3097 | 1.003 | 0.503 |
| Ex. 38.10 | 0 | 87.67 | 21 | 0 | 19.53 | 8.88 | 3099 | 0.994 | NA |
| Ex. 38.11 | 69.41 | 0.12 | 16.879 | 10 | 16 | NA | 3084 | 1.01 | NA |
| Ex. 38.12 | NA | NA | NA | NA | NA | NA | NA | NA | NA |
| Ex. 38.13 | 58.95 | 0 | 24.56 | 10 | 19.4 | 4.66 | 3100 | 1.03 | 0.55 |
| Ex. 38.14 | 69.41 | 0 | 16.879 | 5 | 16 | NA | 3084 | 1.01 | NA |
| Ex. 38.15 | 0 | 62.02 | 17.62 | 6 | NA | 7.25 | 3100 | 0.99 | NA |

Treatment Groups:

For each study, the treatment groups were designed to compare the effect of oligosaccharide preparations versus the control diet. For selected studies, the treatment groups were designed to assess the dose-response curve for oligosaccharide preparations. Treated diets were obtained by blending a sufficient amount of the corresponding oligosaccharide preparation from Example 9 such that the final oligosaccharide content achieved the specified dose (units of ppm on a dry solids basis). In selected studies, a comparative example (Comp. Ex 36) was provided by a commercial whole yeast product (Diamond V XPC Original). Treatments were allocated according to Table 21.

TABLE 21

| Treatment Group Allocations | | | | | | | |
|---|---|---|---|---|---|---|---|
| Study | Treatment Group 1 | Treatment Group 2 | Treatment Group 3 | Treatment Group 4 | Treatment Group 5 | Treatment Group 6 | Treatment Group 7 |
| Ex. 38.1 | Control | Ex. 9.7 (500 ppm) | | | | | |
| Ex. 38.2 | Control | Ex. 9.7 (500 ppm) | | | | | |
| Ex. 38.3 | Control | Ex. 9.7 (500 ppm) | | | | | |
| Ex. 38.4 | Control | Ex. 9.7 (500 ppm) | | | | | |
| Ex. 38.5 | Control | Ex. 9.7 (100 ppm) | Ex. 9.7 (500 ppm) | Comp. Ex. 36 (1500 ppm) | | | |
| Ex. 38.6 | Control | Ex. 9.7 (500 ppm) | | | | | |
| Ex. 38.7 | Control | Ex. 9.7 (500 ppm) | | | | | |
| Ex. 38.8 | Control | Ex. 9.7 (500 ppm) | Ex. 9.3 (500 ppm) | | | | |
| Ex. 38.9 | Control | Ex. 9.7 (500 ppm) | | | | | |
| Ex. 38.10 | Control | Ex. 9.7 (500 ppm) | Ex. 9.2 (500 ppm) | Ex. 9.3 (500 ppm) | Comp. Ex. 36 (1250 ppm) | | |
| Ex. 38.11 | Control | Ex. 9.7 (500 ppm) | Ex. 9.2 (500 ppm) | Ex. 9.3 (500 ppm) | Ex. 9.4 (500 ppm) | Ex. 9.5 (500 ppm) | Comp. Ex. 36 (1250 ppm) |
| Ex. 38.12 | Control | Ex. 9.7 (500 ppm) | Ex. 9.3 (500 ppm) | | | | |
| Ex. 38.13 | Control | Ex. 9.2 (100 ppm) | Ex. 9.2 (250 ppm) | Ex. 9.2 (500 ppm) | Ex. 9.2 (750 ppm) | Ex. 9.2 (1000 ppm) | |
| Ex. 38.14 | Control | Ex. 9.3 (100 ppm) | Ex. 9.3 (250 ppm) | Ex. 9.3 (500 ppm) | Ex. 9.3 (750 ppm) | Ex. 9.3 (1000 ppm) | Ex. 9.7 (500 ppm) |
| | (continued, 8-13) | Ex. 9.2 (100 ppm) | Ex. 9.2 (250 ppm) | Ex. 9.2 (500 ppm) | Ex. 9.2 (750 ppm) | Ex. 9.2 (1000 ppm) | Comp. Ex. 36 (1250 ppm) |
| Ex. 38.15 | Control | Ex. 9.2 (100 ppm) | Ex. 9.2 (250 ppm) | Ex. 9.2 (500 ppm) | Ex. 9.3 (100 ppm) | Ex. 9.3 (250 ppm) | Ex. 9.3 (500 ppm) |

Standard equipment and methods known in the art were used to prepare both the background and treated diets. For the treated diets, oligosaccharide preparations and comparative products were formulated on top of the background diet and added to the mixer pre-pelleting. Oligosaccharide inclusion was confirmed by in-feed assaying.

Live Growth Phase and Sampling:

Feed and water were provided ad libitum. Commercial lighting and temperature programs were implemented in each study according to local industry practices for the corresponding region. Pens were inspected daily and the count and weight of any mortalities was recorded in the study log. No veterinary interventions were required.

For each diet phase, the total pen weight gain, the starting and ending number of birds, and the total feed consumption were measured for each pen. For each pen, the average bird weight (BW) was calculated by dividing the total pen weight by the number of birds in the pen at the time of weighing. For each pen, the feed conversion ratio (FCR) was calculated by dividing the total feed intake over an interval by the total weight gain of the corresponding pen. FCRs were adjusted for mortalities (FCRma) by adding back the total weight of mortalities during the period. To account for differences in pen weight, FCRma was corrected to a common body weight to obtain the corrected FCR (cFCR) for each pen using methods known in the art. The correction factor was determined for various bird genetics using published BW and FCR performance objectives as a function of growth day for the corresponding genetics.

In selected studies, one bird from each pen was selected randomly for sampling either on day 15 and/or on the final study day. For each sampled bird, 5 mL of blood was drawn from a wing vein into serum vacutainers. After coagulation, serum was recovered by centrifugation, removed, and frozen on dry ice for later processing. Each sampled bird was then euthanized according to local ethical procedures and dissected. Cecal contents were removed to 5 mL conical tubes and immediately flash frozen for microbiome whole genome sequencing and cecal metabolomics. A small resection of ileal tissue was taken, treated to deactivate RNA and frozen for later gene expression analysis.

Example 39

Study Meta-Analysis

A statistical meta-analysis of the in vivo studies of Example 38 was performed to assess the impact of oligosaccharide feed additives and comparative products on bird performance versus birds fed control diets. The analysis employed a mixed linear model with treatment group as the fixed effect and random effects for study nested with block. Statistical analysis was performed in R version 3.4.4 (2018-03-15). Outcomes were assessed by least-squares means, with statistical significance at $P<0.05$. Pairwise comparisons were performed according to Tukey's method and assigned alphabetical labels: a, b, c, d . . . . Treatments with no common letter in their Tukey grouping label differed significantly under pairwise comparison at $P<0.05$.

Feed Conversion Ratio:

Study effects for cFCR were significant at $P<0.05$. Oligosaccharide treatments provided at least 2.7 pts improvement in cFCR at 500 ppm inclusion over the control diet, versus the comparative example, which provided a 2.2 pts improvement in cFCR at 1250 ppm inclusion. The oligosaccharide of Example 9.4 provided a 6.4 pt improvement in cFCR at 500 ppm inclusion. The results of the meta-analysis for cFCR are presented in Table 22.

TABLE 22

Meta-Analysis for cFCR

| Treatment Group | cFCR (lsmean) | SE | df | Tukey Grouping | □ cFCR (pts vs control) |
|---|---|---|---|---|---|
| Control | 1.6511 | 0.043 | 14 | d | |
| Ex. 9.2 (500 ppm) | 1.6019 | 0.044 | 14 | a | −4.9 |
| Ex. 9.3 (500 ppm) | 1.6106 | 0.044 | 14 | abc | −4.1 |
| Ex. 9.4 (500 ppm) | 1.5876 | 0.044 | 14 | a | −6.4 |
| Ex. 9.5 (500 ppm) | 1.5948 | 0.044 | 14 | ab | −5.6 |
| Ex. 9.7 (500 ppm) | 1.6246 | 0.043 | 14 | bc | −2.7 |
| Comp. Ex. 36 (1250 ppm) | 1.6293 | 0.044 | 14 | c | −2.2 |

Oligosaccharide treatment groups exhibited a higher consistency of effect versus the comparative example, Comp. Ex. 38. For each oligosaccharide included in multiple studies, the consistency of its effect on cFCR was assessed by determining the fraction of studies in which a given value of cFCR improvement versus control was observed. For example, the oligosaccharide of Example 9.2 at 500 ppm inclusion provided at least a 3 pt cFCR benefit in 80% of the studies, at least a 4 pt cFCR benefit in 60% of the studies, at least a 5 pt cFCR benefit in 40% of the studies, and at least a 6 pt cFCR benefit in 40% of the studies. The comparative example at 1250 ppm inclusion provided a 3 pt cFCR benefit in only 25% of the studies and did not provide a 4 pt cFCR benefit or higher in any of the studies. The results are presented in Table 23.

TABLE 23

Consistency of Treatment Effect on cFCR

| Treatment Group | 1 pt benefit | 2 pt benefit | 3 pt benefit | 4 pt benefit | 5 pt benefit | 6 pt benefit |
|---|---|---|---|---|---|---|
| Ex. 9.2 (500 ppm) | 100% | 80% | 80% | 60% | 40% | 40% |
| Ex. 9.3 (500 ppm) | 100% | 83% | 67% | 67% | 50% | 33% |
| Ex. 9.7 (500 ppm) | 85% | 85% | 38% | 23% | 15% | 0% |
| Comp. Ex. 36 (1250 ppm) | 100% | 100% | 25% | 0% | 0% | 0% |

A clear dose response between cFCR and the inclusion rate of oligosaccharides in the diet was observed. For the oligosaccharide of Ex. 9.2, a 2.4 pt cFCR benefit was observed at 100 ppm inclusion ($P>0.05$), a 3.7 pt cFCR benefit was observed at 250 ppm inclusion ($P<0.05$), an a 6.4 pt cFCR benefit was observed at 1000 ppm inclusion ($P<0.05$).

Bird Weight:

Study effects for BW were significant at $P<0.05$. Oligosaccharide treatments provided at least 48.9 grams increased body weight over the control diet at 500 ppm inclusion, versus the comparative example which provided 39.6 grams increased body weight at 1250 ppm inclusion. The oligosaccharide of Example 9.5 provided 81.8 grams increased BW versus control at 500 ppm inclusion. The results of the meta-analysis for BW are presented in Table 24.

TABLE 24

Meta-Analysis for BW

| Treatment Group | BW (lsmean) | SE | df | Tukey Grouping | □ BW (g vs control) |
|---|---|---|---|---|---|
| Control | 2,755 | 113 | 14 | a | 0 |
| Ex. 9.2 (500 ppm) | 2,817 | 113 | 14 | b | 62.6 |
| Ex. 9.3 (500 ppm) | 2,807 | 113 | 14 | b | 52.6 |
| Ex. 9.4 (500 ppm) | 2,838 | 114 | 14 | b | 83.3 |
| Ex. 9.5 (500 ppm) | 2,837 | 114 | 14 | b | 81.8 |
| Ex. 9.7 (500 ppm) | 2,804 | 113 | 14 | b | 48.9 |
| Comp Ex. 36 (1250 ppm) | 2,794 | 113 | 14 | b | 39.6 |

Flock Uniformity:

Birds fed oligosacharide preparations at 500 ppm inclusion exhibited improved flock uniformity versus birds fed the control diet. For each treatment group, flock uniformity was assessed by calculating the fraction of bird weights that fell within a range of ±5% around the mean bird weight for its corresponding study. Averaged across all studies 36.1-36.15, 81.7% of birds fed the control diet fell within ±5% of the average bird weight while 91.3% of birds fed diets treated with the oligosaccharide of Ex. 9.2 fell within ±5% of the average bird weight. The uniformity effect was significant at $P<0.01$ as measured by the non-parametric Ansari-Bradley test.

Example 40

Microbiome Sequencing and Correlation Analysis

Cecalmicrobiome samples from Example 38 were processed and analyzed by whole genome sequencing using methods comparable to those described in Example 26. The relative abundance of identified taxa was determined and correlated against bird performance parameters including feed efficiency (FCR) and weight (BW) by linear regression. As shown in Table 25, the following taxonomic lineages provided the 94 strongest correlations against performance endpoints.

TABLE 25

Taxonomic Lineages with 94 Strongest Correlations Against Performance Endpoints

| Taxonomic Lineage | BW Correlation | FCR Correlation |
|---|---|---|
| k_Bacteria; p_Lentisphaerae; c_Lentisphaeria; o_Victivallales; f_Victivallales_unclassified; g_*Victivallales*_unclassified; s_*Victivallales_bacterium*_CCUG_44730 | 0.127342 | −0.40176 |
| k_Bacteria; p_Proteobacteria; c_Gammaproteobacteria; o_Enterobacterales; f_Enterobacteriaceae; g_*Escherichia*; s_*Escherichia_fergusonii* | 0.098983 | −0.30691 |
| k_Bacteria; p_Fusobacteria; c_Fusobacteriia; o_Fusobacteriales; f_Fusobacteriaceae; g_*Fusobactcrium*; s_*Fusobacterium*_sp_CAG_439 | −0.03954 | −0.27462 |
| k_Bacteria; p_Firmicutes; c_Negativicutes; o_Selenomonadales; f_Selenomonadaceae; g_*Megamonas*; Unclassified | 0.088303 | −0.24518 |

TABLE 25-continued

Taxonomic Lineages with 94 Strongest Correlations Against Performance Endpoints

| Taxonomic Lineage | BW Correlation | FCR Correlation |
|---|---|---|
| k_Bacteria; p_Bacteroidetes; c_Bacteroidia; o_Bacteroidales; f_Odoribacteraceae; Unclassified; Unclassified | −0.13797 | −0.21085 |
| k_Bacteria; p_Firmicutes; c_Erysipelotrichia; o_Erysipelotrichales; f_Erysipelotrichaceae; Unclassified; Unclassified | −0.07597 | −0.20076 |
| k_Bacteria; p_Firmicutes; c_Clostridia; o_Clostridiales; f_Ruminococcaceae; g_*Faecalibacterium*; s_*Faecalibacterium_prausnitzii* | −0.06693 | −0.19798 |
| k_Bacteria; p_Firmicutes; c_Clostridia; o_Clostridiales; f_Clostridiaceae; g_*Candidatus_Arthromitus*; s_*Candidatus_Arthromitus*_sp_SFB_turkey | −0.20942 | −0.19739 |
| k_Bacteria; p_Firmicutes; c_Clostridia; o_Clostridiales; f_Lachnospiraceae; g_*Lachnoclostridium*; s_*Lachnoclostridium*_sp_An14 | −0.15565 | −0.19631 |
| k_Bacteria; p_Bacteroidetes; c_Bacteroidia; o_Bacteroidales; f_Bacteroidaceae; g_*Bacteroides*; s_*Bacteroides_intestinalis* | 0.141503 | −0.19581 |
| k_Bacteria; p_Firmicutes; c_Clostridia; o_Clostridiales; f_Lachnospiraceae; g_*Lachnoclostridium*; s_*Lachnoclostridium*_sp_An_138 | −0.07409 | −0.19479 |
| k_Bacteria; p_Proteobacteria; c_Deltaproteobacteria; o_Desulfovibrionales; f_Desulfovibrionaceae; g_*Bilophila*; Unclassified | 0.252334 | −0.18335 |
| k_Bacteria; p_Proteobacteria; c_Deltaproteobacteria; o_Desulfovibrionales; f_Desulfovibrionaceae; g_Desulfovibrionaceae_unclassified; s_Desulfovibrionaceae_bacterium | −0.17096 | −0.1824 |
| k_Bacteria; p_Firmicutes; c_Clostridia; o_Clostridiales; f_Ruminococcaceae; g_*Anaerotruncus*; s_*Anaerotruncus_colihominis* | −0.11715 | −0.18239 |
| k_Bacteria; p_Firmicutes; c_Clostridia; o_Clostridiales; f_Ruminococcaceae; g_*Anaeromassilibacillus*; s_*Anaeromassilibacillus*_sp_An172 | 0.060701 | −0.18053 |
| k_Bacteria; p_Proteobacteria; c_Betaproteobacteria; o_Burkholderiales; f_Burkholderiales_unclassified; g_*Burkholderiales*_unclassified; s_*Burkholderiales_bacterium*_1_1_47 | 0.079419 | −0.18011 |
| k_Bacteria; p_Firmicutes; c_Erysipelotrichia; o_Erysipelotrichales; f_Erysipelotrichaceae; g_*Faecalitalea*; s_*Faecalitalea_cylindroides* | 0.196018 | −0.17961 |
| k_Bacteria; p_Firmicutes; Unclassified; Unclassified; Unclassified; Unclassified; Unclassified | 0.110149 | −0.16968 |
| k_Bacteria; p_Bacteroidetes; c_Bacteroidia; o_Bacteroidales; f_Bacteroidaceae; g_*Bacteroides*; s_*Bacteroides_faecis* | 0.245507 | −0.15487 |
| k_Bacteria; p_Firmicutes; c_Clostridia; o_Clostridiales; f_Ruminococcaceae; g_*Ruminococcaceae*_unclassified; s_*Clostridium_leptum* | −0.25928 | −0.14818 |
| k_Bacteria; p_Bacteroidetes; c_Bacteroidia; o_Bacteroidales; f_Odoribacteraceae; g_*Butyricimonas*; s_*Butyricimonas_virosa* | 0.147346 | −0.14584 |
| k_Bacteria; p_Firmicutes; c_Clostridia; o_Clostridiales; f_Eubacteriaceae; g_Eubacteriaceae_unclassified; s_Eubacteriaceae_bacterium_CHKCI005 | 0.104361 | −0.14004 |
| k_Bacteria; p_Firmicutes; c_Clostridia; o_Clostridiales; Unclassified; Unclassified; Unclassified | −0.1042 | −0.13951 |
| k_Bacteria; p_Bacteroidetes; c_Bacteroidia; o_Bacteroidales; f_Rikenellaceae; g_*Alistipes*; s_*Alistipes_onderdonkii* | −0.12019 | −0.12973 |
| k_Bacteria; p_Bacteroidetes; c_Bacteroidia; o_Bacteroidales; f_Bacteroidaceae; g_*Bacteroides*; s_*Bacteroides_thetaiotaomicron* | 0.091795 | −0.12878 |
| k_Bacteria; p_Actinobacteria; c_Actinobacteria; o_Bifidobacteriales; f_Bifidobacteriaceae; g_*Bifidobacterium*; s_*Bifidobacterium_longum*_CAG_69 | 0.166559 | −0.12621 |
| k_Bacteria; p_Bacteroidetes; c_Bacteroidia; o_Bacteroidales; f_Rikenellaceae; g_*Alistipes*; s_*Alistipes*_sp_HGB5 | 0.236047 | −0.12313 |
| k_Bacteria; p_Firmicutes; c_Clostridia; o_Clostridiales; f_Lachnospiraceae; g_*Anaerotignum*; s_*Anaerotignum_lactatifermentans* | 0.155753 | −0.12255 |
| k_Bacteria; p_Proteobacteria; c_Gammaproteobacteria; o_Enterobacterales; f_Enterobacteriaceae; Unclassified; Unclassified | 0.233591 | −0.12166 |
| k_Bacteria; p_Firmicutes; c_Clostridia; o_Clostridiales; f_Ruminococcaceae; g_*Anaeromassilibacillus*; Unclassified | −0.14566 | −0.1155 |
| k_Bacteria; p_Proteobacteria; c_Betaproteobacteria; o_Burkholderiales; f_Sutterellaceae; g_*Parasutterella*; s_*Parasutterella_excrementihominis* | 0.16901 | −0.1151 |
| k_Bacteria; p_Bacteroidetes; c_Bacteroidia; o_Bacteroidales; f_Bacteroidaceae; g_*Bacteroides*; s_*Bacteroides_vulgatus* | 0.230672 | −0.10698 |
| k_Bacteria; p_Bacteroidetes; c_Bacteroidia; o_Bacteroidales; f_Rikenellaceae; g_*Alistipes*; s_*Alistipes*_sp_CAG_29 | 0.238234 | −0.10519 |
| k_Bacteria; p_Firmicutes; c_Clostridia; o_Clostridiales; f_Lachnospiraceae; g_*Lachnoclostridium*; s_*Clostridium_saccharolyticum* | −0.20494 | −0.10222 |
| k_Bacteria; p_Firmicutes; c_Clostridia; o_Clostridiales; f_Lachnospiraceae; g_*Blautia*; Unclassified | −0.12726 | −0.09614 |
| k_Bacteria; p_Firmicutes; c_Clostridia; o_Clostridiales; f_Clostridiaceae; g_*Clostridium*; s_*Clostridium_leptum*_CAG_27 | −0.21692 | −0.09552 |
| k_Bacteria; p_Bacteroidetes; c_Bacteroidia; o_Bacteroidales; f_Odoribacteraceae; g_*Butyricimonas*; s_*Butyricimonas*_sp_An62 | −0.13067 | −0.08206 |
| k_Bacteria; p_Firmicutes; c_Clostridia; o_Clostridiales; f_Eubacteriaceae; Unclassified; Unclassified | 0.25026 | −0.06481 |
| k_Bacteria; p_Bacteroidetes; c_Bacteroidia; o_Bacteroidales; f_Rikenellaceae; g_*Alistipes*; s_*Alistipes_finegoldii* | 0.235859 | −0.04619 |
| k_Bacteria; p_Bacteroidetes; c_Bacteroidia; o_Bacteroidales; f_Rikenellaceae; g_*Alistipes*; s_*Alistipes_putredinis*_CAG_67 | 0.218292 | 0.055568 |
| k_Bacteria; p_Firmicutes; c_Bacilli; o_Lactobacillales; f_Lactobacillaceae; g_*Lactobacillus*; s_*Lactobacillus_salivarius* | 0.228572 | 0.058781 |

TABLE 25-continued

Taxonomic Lineages with 94 Strongest Correlations Against Performance Endpoints

| Taxonomic Lineage | BW Correlation | FCR Correlation |
|---|---|---|
| k_Bacteria; p_Proteobacteria; c_Gammaproteobacteria; o_Enterobacterales; f_Enterobacteriaceae; g_*Shigella*; Unclassified | −0.24378 | 0.063736 |
| k_Bacteria; p_Firmicutes; c_Negativicutes; Unclassified; Unclassified; Unclassified; Unclassified | −0.24202 | 0.063797 |
| k_Bacteria; p_Lentisphaerae; c_Lentisphaeria; o_Victivallales; Unclassified; Unclassified; Unclassified | 0.197695 | 0.068584 |
| k_Bacteria; p_Firmicutes; c_Clostridia; o_Clostridiales; f_Lachnospiraceae; Unclassified; Unclassified | 0.167102 | 0.080242 |
| k_Bacteria; p_Proteobacteria; c_Epsilonproteobacteria; o_Campylobacterales; f_Helicobacteraceae; g_*Helicobacter*; s_*Helicobacter_pullorum* | −0.288 | 0.080559 |
| k_Bacteria; p_Firmicutes; c_Clostridia; o_Clostridiales; f_Ruminococcaccaceae; g_*Subdoligranulum*; s_*Subdoligranulum_variabile* | 0.313342 | 0.082109 |
| k_Bacteria; p_Bacteroidetes; c_Bacteroidia; o_Bacteroidales; f_Bacteroidaceae; g_*Bacteroides*; s_*Bacteroides_massiliensis* | 0.163272 | 0.083306 |
| k_Bacteria; p_Firmicutes; c_Clostridia; o_Clostridiales; f_Ruminococcacceae; g_*Faecalibacterium*; Unclassified | 0.13539 | 0.083369 |
| k_Bacteria; p_Bacteroidetes; c_Bacteroidia; o_Bacteroidales; f_Bacteroidaceae; g_*Bacteroides*; s_*Bacteroides_uniformis* | 0.158109 | 0.084931 |
| k_Bacteria; p_Firmicutes; c_Clostridia; o_Clostridiales; f_Ruminococcaceae; g_*Anaeromassilibacillus*; s_*Anaeromassilibacillus*_sp_An250 | 0.249112 | 0.089645 |
| k_Bacteria; p_Bacteroidetes; c_Bacteroidia; o_Bacteroidales; f_Tannerellaceae; g_*Tannerella*; s_*Tannerella*_sp_6_1_58FAA_CT1 | −0.11628 | 0.090798 |
| k_Bacteria; p_Firmicutes; c_Bacilli; o_Lactobacillales; f_Lactobacillaceae; g_*Lactobacillus*; s_*Lactobacillus_johnsonii* | 0.247627 | 0.104938 |
| k_Bacteria; p_Bacteroidetes; c_Bacteroidia; o_Bacteroidales; f_Rikenellaceae; g_*Alistipes*; s_*Alistipes*_sp_CAG_268 | 0.105039 | 0.105814 |
| k_Bacteria; p_Firmicutes; c_Clostridia; o_Clostridiales; f_Ruminococcaceae; g_*Flavonifractor*; s_*Flavonifractor*_sp_An82 | −0.10307 | 0.107791 |
| k_Bacteria; p_Bacteroidetes; c_Bacteroidia; o_Bacteroidales; f_Rikenellaceae; g_*Alistipes*; s_*Alistipes*_sp_CHKCI003 | 0.21527 | 0.108887 |
| k_Bacteria; p_Firmicutes; c_Clostridia; o_Clostridiales; f_Clostridiaceae; g_*Butyricicoccus*; s_*Butyricicoccus_pullicaecorum* | −0.19161 | 0.115591 |
| k_Bacteria; p_Firmicutes; c_Clostridia; o_Clostridiales; f_Ruminococcaceae; g_*Gemmiger*; s_*Gemmiger*_sp_An50 | −0.16451 | 0.119402 |
| k_Bacteria; p_Firmicutes; c_Clostridia; o_Clostridiales; f_Eubactcriaceae; g_*Eubacterium*; s_*Eubacterium_rectale*_CAG_3_6 | −0.15551 | 0.130182 |
| k_Bacteria; p_Firmicutes; c_Clostridia; o_Clostridiales; f_Ruminococcaceae; g_*Flavonifractor*; s_*Flavonifractor*_sp_—An91 | −0.15675 | 0.130987 |
| k_Bacteria; p_Firmicutes; c_Clostridia; o_Clostridiales; f_Ruminococcaceae; g_*Drancourtella*; Unclassified | −0.10942 | 0.131152 |
| k_Bacteria; p_Proteobacteria; Unclassified; Unclassified; Unclassified; Unclassified; Unclassified | −0.30972 | 0.132825 |
| k_Bacteria; p_Firmicutes; c_Erysipelotrichia; o_Erysipelotrichales; f_Erysipelotrichaceae; g_*Massiliomicrobiota*; Unclassified | 0.203757 | 0.135764 |
| k_Bacteria; p_Firmicutes; c_Bacilli; o_Lactobacillales; f_Lactobacillaceae; g_*Lactobacillus*; s_*Lactobacillus_vaginalis* | 0.120135 | 0.142632 |
| k_Bacteria; p_Bacteroidetes; c_Bacteroidia; o_Bacteroidales; f_Bacteroidaceae; g_*Bacteroides*; s_*Bacteroides_fragilis* | −0.11504 | 0.146017 |
| k_Bacteria; p_Firmicutes; c_Clostridia; o_Clostridiales; f_Clostridiaceae; g_*Clostridium*; s_*Clostridium*_sp_ATCC_29733 | 0.174945 | 0.151387 |
| k_Bacteria; p_Bacteroidetes; c_Bacteroidia; o_Bacteroidales; f_Bacteroidaceae; g_*Bacteroides*; Unclassified | −0.06869 | 0.157261 |
| k_Bacteria; p_Bacteroidetes; c_Bacteroidia; o_Bacteroidales; f_Rikenellaceae; g_*Alistipes*; s_*Alistipes*_sp_An66 | 0.155621 | 0.15925 |
| k_Bacteria; p_Firmicutes; c_Bacilli; o_Lactobacillales; f_Lactobacillaceae; g_*Lactobacillus*; s_*Lactobacillus_reuteri* | 0.246012 | 0.162187 |
| k_Bacteria; p_Bacteroidetes; c_Bacteroidia; o_Bacteroidales; f_Bacteroidaceae; g_*Bacteroides*; s_*Bacteroides_dorei* | −0.07462 | 0.164746 |
| k_Bacteria; p_Firmicutes; c_Clostridia; o_Clostridiales; f_Eubacteriaceae; g_*Eubacterium*; s_*Eubacterium*_sp_An11 | 0.17506 | 0.165728 |
| k_Bacteria; p_Firmicutes; c_Clostridia; o_Clostridiales; f_Eubacteriaceae; g_*Eubacterium*; s_*Eubacterium*_sp_An3 | 0.188604 | 0.167651 |
| k_Bacteria; p_Firmicutes; c_Bacilli; o_Lactobacillales; f_Lactobacillaceae; g_*Lactobacillus*; s_*Lactobacillus_helveticus* | 0.158929 | 0.16852 |
| k_Bacteria; p_Firmicutes; c_Firmicutes_unclassified; o_Firmicutes_unclassified; f_Firmicutes_unclassified; g_Firmicutes_unclassified; Unclassified | −0.17633 | 0.172219 |
| k_Bacteria; p_Firmicutes; c_Clostridia; o_Clostridiales; f_Ruminococcaceae; g_*Flavonifractor*; s_*Flavonifractor*_sp_—An_10 | −0.06748 | 0.177671 |
| k_Bacteria; p_Firmicutes; c_Clostridia; o_Clostridiales; f_Ruminococcaceae; g_*Pseudoflavonifractor*; s_*Pseudoflavonifractor*_sp_An85 | 0.118547 | 0.185369 |
| k_Bacteria; p_Firmicutes; c_Clostridia; o_Clostridiales; f_Clostridiales_unclassified; g_Clostridiales_unclassified; s_Clostridiales_bacterium_CHKCI001 | 0.067653 | 0.185637 |
| k_Bacteria; p_Firmicutes; c_Clostridia; o_Clostridiales; f_Lachnospiraceae; g_*Blautia*; s_*Blautia*_sp_An81 | 0.161327 | 0.187129 |

TABLE 25-continued

Taxonomic Lineages with 94 Strongest Correlations Against Performance Endpoints

| Taxonomic Lineage | BW Correlation | FCR Correlation |
|---|---|---|
| k_Bacteria; p_Bacteroidetes; c_Bacteroidia; o_Bacteroidales; f_Rikenellaceae; g_*Alistipes*; Unclassified | −0.10556 | 0.192622 |
| k_Bacteria; p_Firmicutes; c_Clostridia; o_Clostridiales; f_Ruminococcaceae; g_*Pseudoflavonifractor*; s_*Pseudoflavonifractor*_sp_An187 | 0.234653 | 0.206078 |
| k_Bacteria; p_Bacteroidetes; c_Bacteroidia; o_Bacteroidales; f_Rikenellaceae; g_*Alistipes*; s_*Alistipes_indistinctus* | 0.273404 | 0.213441 |
| k_Bacteria; p_Firmicutes; c_Clostridia; o_Clostridiales; f_Lachnospiraceae; g_*Tyzzerella*; s_*Tyzzerella*spAn114 | −0.0804 | 0.218662 |
| k_Bacteria; p_Firmicutes; c_Bacilli; o_Lactobacillales; f_Lactobacillaceae; g_*Lactobacillus*; s_*Lactobacillus_aviarius* | 0.089093 | 0.2243 |
| k_Bacteria; p_Firmicutes; c_Bacilli; o_Lactobacillales; f_Lactobacillaceae; g_*Lactobacillus*; s_*Lactobacillus_ingluviei* | 0.231413 | 0.225168 |
| k_Bacteria; p_Firmicutes; c_Clostridia; o_Clostridiales; f_Eubacteriaceae; g_Eubacteriaceae_unclassified; s_Eubacteriaceae_bacterium_CHKCI004 | 0.105658 | 0.228612 |
| k_Bacteria; p_Firmicutes; c_Clostridia; o_Clostridiales; f_Eubacteriaceae; g_*Eubacterium*; Unclassified | 0.085665 | 0.262875 |
| k_Bacteria; p_Bacteroidetes; c_Bacteroidia; o_Bacteroidales; f_Rikenellaceae; g_*Alistipes*; s_*Alistipes*_sp_An54 | 0.07405 | 0.266283 |
| k_Bacteria; p_Firmicutes; c_Clostridia; o_Clostridiales; f_Clostridiales_unclassified; g_Clostridiales_unclassified; s_Clostridiales_bacterium_CHKCI006 | 0.148222 | 0.269782 |
| k_Bacteria; p_Bacteroidetes; c_Bacteroidia; o_Bacteroidales; f_Odoribacteraceae; g_*Odoribacter*; s_*Odoribacter*_sp_CAG_788 | −0.11429 | 0.270529 |
| k_Bacteria; p_Firmicutes; c_Clostridia; o_Clostridiales; f_Ruminococcaceae; g_*Flavonifractor*; s_*Flavonifractor_plautii* | −0.14162 | 0.276379 |
| k_Bacteria; p_Firmicutes; c_Clostridia; o_Clostridiales; f_Clostridiaceae; g_*Clostridium*; s_*Clostridium*_sp_CAG_678 | 0.081329 | 0.278429 |
| k_Bacteria; p_Bacteroidetes; c_Bacteroidia; o_Bacteroidales; f_Rikenellaceae; g_*Alistipes*; s_*Alistipes_timonensis* | 0.135766 | 0.279078 |
| k_Bacteria; p_Bacteroidetes; c_Bacteroidia; o_Bacteroidales; f_Bacteroidaceae; g_*Bacteroides*; s_*Bacteroides*_sp_D2 | 0.067539 | 0.298525 |
| k_Bacteria; p_Firmicutes; c_Erysipelotrichia; o_Erysipelotrichales; f_Erysipelotrichaceae; g_*Massiliomicrobiota*; s_*Massiliomicrobiota*_sp_An80 | 0.177296 | 0.318597 |

Performance Grouping and SIMPER Analysis:

Taxa were assigned into four performance correlation groups: Group 1 taxa were associated with improved FCR and improved BW; Group 2 taxa were associated with improved FCR but decreased BW; Group 3 taxa were associated with increased BW but poorer FCR; Group 4 taxa were associated with poorer FCR and deceased BW. Taxa assignments were made by a performing Similarity Percentage (SIMPER) analysis (see for example, Clarke, K. R. (1993). Non-parametric multivariate analyses of changes in community structure. Australian Journal of Ecology, 18(1), 117-143.). A separate analysis was performed for young animals (Day 15 samplings in Example 36) and later phase animals (Study Endpoint sampling in Example 36). Significance was assessed by running 100 SIMPER permutations.

SIMPER analysis of young birds (starter phase, day 15 of growth) identified the following taxonomic allocations to performance correlation groups (Table 26).

TABLE 26

Taxonomic Lineages with Performance Correlations

| Performance Group | Taxonomic Lineage | SIMPER Contribution | Significance |
|---|---|---|---|
| Group 1 | k_Bacteria; p_Bacteroidetes; c_Bacteroidia; o_Bacteroidales; f_Rikenellaceae; g_*Alistipes*; s_*Alistipes*_sp_HGB5 | 0.023 | |
| | k_Bacteria; p_Bacteroidetes; c_Bacteroidia; o_Bacteroidales; f_Tannerellaceae; g_*Parabacteroides*; s_*Parabacteroides_distasonis* | 0.020 | P < 0.01 |
| | k_Bacteria; p_Bacteroidetes; c_Bacteroidia; o_Bacteroidales; f_Tannerellaceae; g_*Parabacteroides*; s_*Parabacteroides_merdae* | 0.014 | |
| Group 2 | k_Bacteria; p_Proteobacteria; c_Gammaproteobacteria; o_Enterobacterales; f_Enterobacteriaceae; g_*Escherichia*; s_*Escherichia_coli* | 0.018 | |
| | k_Bacteria; p_Bacteroidetes; c_Bacteroidia; o_Bacteroidales; f_Barnesiellaceae; g_*Barnesiella*; s_*Barnesiella_intestinihominis* | 0.014 | |
| | k_Bacteria; p_Proteobacteria; c_Gammaproteobacteria; o_Enterobacterales; f_Enterobacteriaceae; g_*Escherichia*; s_*Escherichia_coli* | 0.030 | P < 0.01 |
| | k_Bacteria; p_Bacteroidetes; c_Bacteroidia; o_Bacteroidales; f_Barnesiellaceae; g_*Barnesiella*; s_*Barnesiella_intestinihominis* | 0.025 | |
| Group 3 | k_Bacteria; p_Bacteroidetes; c_Bacteroidia; o_Bacteroidales; f_Rikenellaceae; g_*Alistipes*; s_*Alistipes*_sp_CHKCI003 | 0.093 | |

TABLE 26-continued

Taxonomic Lineages with Performance Correlations

| Performance Group | Taxonomic Lineage | SIMPER Contribution | Significance |
|---|---|---|---|
| | k_Bacteria; p_Bacteroidetes; c_Bacteroidia; o_Bacteroidales; f_Bacteroidaceae; g_*Bacteroides*; s_*Bacteroides_xylanisolvens* | 0.020 | |
| | k_Bacteria; p_Bacteroidetes; c_Bacteroidia; o_Bacteroidales; f_Rikenellaceae; g_*Alistipes*; s_*Alistipes*_sp_CHKCI003 | 0.108 | |
| | k_Bacteria; p_Bacteroidetes; c_Bacteroidia; o_Bacteroidales; f_Bacteroidaceae; g_*Bacteroides*; s_*Bacteroides_xylanisolvens* | 0.016 | |
| | k_Bacteria; p_Bacteroidetes; c_Bacteroidia; o_Bacteroidales; f_Bacteroidaceae; g_*Bacteroides*; s_*Bacteroides_uniformis* | 0.015 | P < 0.05 |
| Group 4 | k_Bacteria; p_Bacteroidetes; c_Bacteroidia; o_Bacteroidales; f_Barnesiellaceae; g_*Barnesiella*; s_*Barnesiella*_sp_An22 | 0.085 | |
| | k_Bacteria; p_Bacteroidetes; c_Bacteroidia; o_Bacteroidales; f_Bacteroidaceae; g_*Bacteroides*; s_*Bacteroides_fragilis* | 0.075 | |
| | k_Bacteria; p_Proteobacteria; c_Epsilonproteobacteria; o_Campylobacterales; f_Helicobacteraceae; g_*Helicobacter*; s_*Helicobacter_pullorum* | 0.043 | |
| | k_Bacteria; p_Proteobacteria; c_Gammaproteobacteria; o_Enterobacterales; f_Enterobacteriaceae; g_*Shigella*; s_*Shigella_sonnei* | 0.013 | |
| | k_Bacteria; p_Bacteroidetes; c_Bacteroidia; o_Bacteroidales; f_Barnesiellaceae; g_*Barnesiella*; s_*Barnesiella*_sp_An22 | 0.089 | |
| | k_Bacteria; p_Bacteroidetes; c_Bacteroidia; o_Bacteroidales; f_Bacteroidaceae; g_*Bacteroides*; s_*Bacteroides_fragilis* | 0.071 | |
| | k_Bacteria; p_Proteobacteria; c_Epsilonproteobacteria; o_Campylobacterales; f_Helicobacteraceae; g_*Helicobacter*; s_*Helicobacter_pullorum* | 0.036 | |
| | k_Bacteria; p_Proteobacteria; c_Gammaproteobacteria; o_Enterobacterales; f_Enterobacteriaceae; g_*Shigella*; s_*Shigella_sonnei* | 0.022 | P < 0.05 |

SIMPER analysis of birds at the end of their grow-out identified the following taxonomic assignments to performance correlation groups is presented in Table 27.

TABLE 27

Taxonomic Assignments to Performance Correlation Groups

| Correlation Group | Taxonomic Lineage | SIMPER Contribution | Significance |
|---|---|---|---|
| Group 1 | k_Bacteria; p_Bacteroidetes; c_Bacteroidia; o_Bacteroidales; f_Tannerellaceae; g_*Parabacteroides*; s_*Parabacteroides_distasonis* | 0.058 | P < 0.01 |
| | k_Bacteria; p_Bacteroidetes; c_Bacteroidia; o_Bacteroidales; f_Tannerellaceae; g_*Parabacteroides*; s_*Parabacteroides_merdae* | 0.020 | |
| | k_Bacteria; p_Bacteroidetes; c_Bacteroidia; o_Bacteroidales; f_Bacteroidaceae; g_*Bacteroides*; s_*Bacteroides_vulgatus* | 0.013 | |
| | k_Bacteria; p_Bacteroidetes; c_Bacteroidia; o_Bacteroidales; f_Tannerellaceae; g_*Parabacteroides*; s_*Parabacteroides_distasonis* | 0.051 | |
| | k_Bacteria; p_Bacteroidetes; c_Bacteroidia; o_Bacteroidales; f_Tannerellaceae; g_*Parabacteroides*; s_*Parabacteroides_merdae* | 0.012 | |
| | k_Bacteria; p_Bacteroidetes; c_Bacteroidia; o_Bacteroidales; f_Rikenellaceae; g_*Alistipes*; s_*Alistipes*_sp_HGB5 | 0.009 | |
| Group 2 | k_Bacteria; p_Bacteroidetes; c_Bacteroidia; o_Bacteroidales; f_Barnesiellaceae; g_*Barnesiella*; s_*Barnesiella_intestinihominis* | 0.015 | |
| | k_Bacteria; p_Bacteroidetes; c_Bacteroidia; o_Bacteroidales; f_Barnesiellaceae; g_*Barnesiellai*; s_*Barnesiella_intestinihominis* | 0.041 | |
| | k_Bacteria; p_Bacteroidetes; c_Bacteroidia; o_Bacteroidales; f_Odoribacteraceae; g_*Butyricimonas*; s_*Butyricimonas*_sp_An62 | 0.011 | P < 0.05 |
| Group 3 | k_Bacteria; p_Bacteroidetes; c_Bacteroidia; o_Bacteroidales; f_Rikenellaceae; g_*Alistipes*; s_*Alistipes*_sp_CHKCI003 | 0.044 | |
| | k_Bacteria; p_Verrucomicrobia; c_Verrucomicrobiae; o_Venucomicrobiales; f_Akkermansiaceae; g_*Akkermansia*; s_*Akkermansia_muciniphila* | 0.022 | |

TABLE 27-continued

Taxonomic Assignments to Performance Correlation Groups

| Correlation Group | Taxonomic Lineage | SIMPER Contribution | Significance |
|---|---|---|---|
| | k_Bacteria; p_Bacteroidetes; c_Bacteroidia; o_Bacteroidales; f_Rikenellaceae; g_*Alistipes*; s_*Alistipes*_sp_An54 | 0.011 | |
| | k_Bacteria; p_Bacteroidetes; c_Bacteroidia; o_Bacteroidales; f_Rikenellaceae; g_*Alistipes*; s_*Alistipes*_sp_CHKCI003 | 0.048 | |
| | k_Bacteria; p_Verrucomicrobia; c_Verrucomicrobiae; o_Venucomicrobiales; f_Akkermansiaceae; g_*Akkermansia*; s_*Akkermansia_muciniphila* | 0.020 | |
| | k_Bacteria; p_Firmicutes; c_Firmicutes_unclassified; o_Firmicutes_unclassified; f_Firmicutes unclassified; g_Firmicutes_unclassified; s_Firmicutes_bacterium_CAG_94 | 0.014 | P < 0.01 |
| | k_Bacteria; p_Bacteroidetes; c_Bacteroidia; o_Bacteroidales; f_Rikenellaceae; g_*Alistipes*; s_*Alistipes*sp_An54 | 0.012 | |
| Group 4 | k_Bacteria; p_Bacteroidetes; c_Bacteroidia; o_Bacteroidales; f_Barnesicllaceae; g_*Barnesiella*; s_*Barnesiella*sp_An22 | 0.124 | |
| | k_Bacteria; p_Bacteroidetes; c_Bacteroidia; o_Bacteroidales; f_Odoribacteraceae; g_*Odoribacter*; s_*Odoribacter*_sp_CAG_788 | 0.075 | P < 0.01 |
| | k_Bacteria; p_Proteobacteria; c_Epsilonproteobacteria; o_Campylobacterales; f_Helicobacteraceae; g_*Helicobacter*; s_*Helicobacter_pullorum* | 0.067 | |
| | k_Bacteria; p_Bacteroidctcsic_Bacteroidia; o_Bacteroidales; f_Bacteroidaceae; g_*Bacteroides*; s_*Bacteroides_dorei* | 0.016 | |
| | k_Bacteria; p_Bactcroidetes; c_Bacteroidia; o_Bacteroidales; f_Bacteroidaceae; g_*Bacteroides*; s_*Bacteroides_clarus* | 0.016 | |
| | k_Bacteria; p_Bactcroidctcsi; c_Bacteroidia; o_Bacteroidales; f_Barnesiellaceae; g_*Barnesiella*; s_*Barnesiella*_sp_An22 | 0.113 | |
| | k_Bacteria; p_Proteobacteria; c_Epsilonproteobacteria; o_Campylobacterales; f_Helicobacteraceae; g_*Helicobacter*; s_*Helicobacter_pullorum* | 0.070 | |
| | k_Bacteria; p_Bacteroidetes; c_Bacteroidia; o_Bacteroidales; f_Odoribacteraceae; g_*Odoribacter*; s_*Odoribacter*_sp_CAG_788 | 0.067 | |
| | k_Bacteria; p_Bacteroidetes; c_Bacteroidia; o_Bacteroidales; f_Bacteroidaceae; g_*Bacteroides*; s_*Bacteroides_clarus* | 0.015 | |
| | k_Bacteria; p_Bacteroidetes; c_Bacteroidia; o_Bacteroidales; f_Bacteroidaceae; g_*Bacteroides*; s_*Bacteroides_dorei* | 0.012 | |

It was observed that different oligosaccharide treatments resulted in distinct shifts in abundance between the various Performance Correlation Groups.

Example 41

Method of Modulating Taxonomic Performance Groups

Birds are fed a diet comprising an oligosaccharide preparation of Example 9, where the oligosaccharide identity is selected to increase the abundance of taxa in Group 1, Group 2 and/or Group 3 of Example 40.

Birds are fed diets comprising an oligosaccharide preparation of Example 9, where the oligosaccharide identity is selected to decrease the abundance of taxa in Group 4 of Example 40.

Example 42

Replicate Batches Scale-Up for Manufacturing

The production scale of oligosaccharide preparations was increased to that of a 720 L overhead-stirred tank reactor. Twelve batch reactions using a scaled-up procedure derived from those of Example 9.2 were performed at the 720 L scale. The resulting oligosaccharide preparations were characterized against pre-determined QC acceptance criteria to perform batch qualification and to assess the process stability.

For the twelve batches, process conditions such as temperature, reaction time, and reaction pressure were varied intentionally in a range around the nominal conditions of Example 9.2 to assess the sensitivities of the resulting product to reasonable variations in the process conditions that might be expected in a typical manufacturing environment. For select batches, an in situ viscosity probe was used to monitor the time dependence of the viscosity of the reactor contents. In certain batches, the reaction stopping time employed an in-process control (IPC) based on the continuous viscosity measurement. Material amounts, including the dispensed quantities of reactants, distillation water, and evolved condensate were measured either by mass via load cells on the reactor and auxiliary tanks or volumetric flow and time.

The final water content of the reactor product was measured by Karl Fisher titration for a representative aliquot of the reactor contents drawn at the end of the reaction, i.e., prior to pH neutralization and dilution. At a reaction temperature of 120° C., the water content of the reaction product was determined to be 8 and 9 wt % water on an as-is basis. At a reaction temperature of 130° C., the water content of the reaction product was determined to be between 5 and 7 wt % water on an as-is basis.

The resulting oligosaccharide syrup appearance of all the batches was determined by visual inspection as a caramel syrup. The total dissolved solids content was determined by Karl-Fisher titration, the residual monomer content, MWn and MWw were determined by HPLC/GPC chromatography, the pH was determined by calibrated pH meter and the anhydro-DP2 content was determined by LC-MS/MS. As shown in Table 29, the following batch characterization data were obtained (N/R="data not reported"):

TABLE 29

| Characterization of Oligosaccharide Preparations | | | | | | | |
|---|---|---|---|---|---|---|---|
| Batch | wt % DS | pH | Residual Catalyst | wt % DP1 | MWn | MWw | Anhydro DP2 Content (g Anhydro DP2/ g total DP2) |
| 27.1 | 66.4 | N/D | N/R | 17.5 | 777 | 1218 | 0.84% |
| 27.2 | 68.8 | 3.3 | N/R | 17.9 | 735 | 1091 | 0.91% |
| 27.3 | 69.4 | 3.1 | 0.095 | 14.8 | 807 | 1276 | N/R |
| 27.4 | 71.0 | N/D | 0.068 | 15.5 | 793 | 1241 | 1.04% |
| 27.5 | 70.9 | 3.2 | 0.057 | 15.8 | 777 | 1196 | 1.15% |
| 27.6 | 70.9 | 3.3 | N/R | 16.3 | 773 | 1170 | N/R |
| 27.7 | 70.7 | 3.0 | N/R | 15.7 | 783 | 1226 | 1.13% |
| 27.8 | 70.5 | 3.9 | N/R | 16.1 | 785 | 1182 | 1.09% |
| 27.9 | 71.1 | 4.1 | N/R | 17.1 | 761 | 1169 | 1.09% |
| 27.10 | 70.4 | 4.1 | N/R | 16.3 | 778 | 1193 | 1.15% |
| 27.11 | 70.5 | 4.7 | N/R | 18.6 | 696 | 995 | 1.33% |
| 27.12 | 70.9 | 3.9 | N/R | 16.7 | 769 | 1194 | 1.12% |

Example 43 pH Adjustment of an Oligosaccharide Preparation

The pH of the oligosaccharide preparation of Example 9.2 at 50 wt % solids content was determined in triplicate by diluting 5.00±0.05-gram aliquots of the oligosaccharide preparation with 1.80±0.02 mL of deionized water and mixing by vortex agitation to obtain a uniform concentration. The pH of each aliquot was measured with a calibrated pH meter (VWR, Symphony B30PCI) to obtain an average reading of 2.4 pH units.

To 1.2 kg of the oligosaccharide preparation of Example 9.2 was added 6.53 mL of 1.0 molar aqueous sodium hydroxide solution. The resulting mixture was mixed vigorously to achieve a uniform pH-adjusted syrup. The pH of the resulting adjusted syrup at 50 wt % solids content was then determined in triplicate as described above to obtain an average of 4.1 pH units.

The pH adjustment procedure was repeated for replicate batch syntheses at various scales, but with certain variations in the procedure by which the base was provided to the product oligosaccharide composition. For one batch, the pH adjustment was performed as the final step of the reaction, prior to the dilution of reaction water. In another batch, the pH adjustment was performed concurrently with the dilution step by first dissolving the required amount of base in the dilution water; the base and dilution water were therefore added together to quench the reaction a single step to produce a final syrup at the desired pH. In another batch, the base was provided as food-grade sodium hydroxide pellets. In another batch, 10 ppm of a food-grade silicone emulsion (Dow Xiameter AFE-0100) was added to the reaction prior to dilution and pH adjustment.

Example 44

Preparation of a Glass Powder Formulation of an Oligosaccharide Preparation

Approximately 50 grams of the oligosaccharide preparation of Example 9.1 was dispensed onto a drying tray and placed in a forced-air convection heater at 60° C. to produce a caramel colored brittle glass. The glass was removed from the drying tray and ground with a shear rotary mill to yield a light-orange colored flowable powder. The particle size of the powder was determined by sieving to be between 100 and 2000 microns, with 90% of the mass below 1350 microns. The true density of the coarse milled powder was determined by Helium Pyncnometry to be 1.3063 g/mL. The resulting powder was observed to be flowable.

The formulation procedure was repeated using a hammer mill to obtain a fine powder with 90% of the mass of the powder exhibiting a particle size below 196 microns. The true density of the fine milled powder was determined to be 1.5263 g/mL. The resulting powder was neither stable nor flowable.

DSC measurements were performed on the powders using two temperature cycling programs. In the first program, temperature was ramped to 160° C. from 0° C. at a rate of 5° C./min, then annealed back to 0° C. at a rate of −5° C./min, followed by a final heating back to 160° C. In the second program, the temperature was ramped to 50° C. from −50° C. at a rate of 5° C./min, annealed to −60° C. at a rate of −5° C./min and then heated to 60° C. at a rate of 5° C./min. The powder was observed to exhibit a glass transition temperature of between 20 and 40° C., dependent on the residual water content of the solid between 5 and 10 wt % moisture.

The milling formulation process was repeated for each of the oligosaccharide preparations of Example 9.2, Example 9.3, Example 9.4, and Example 9.5. The powders readily re-dissolved in water and alcohol-water mixtures, but were insoluble in acetone, methanol, and anhydrous ethanol.

Example 45

Preparation of a Carrier-Loaded Powder Formulation

Equal masses of a 70 wt % aqueous syrup of the oligosaccharide preparation of Example 9.2 and diatomaceous earth were combined at room temperature to yield a stable, flowable powder. The resulting powder comprised about 35 wt % adsorbed oligosaccharide (dry solids basis) and about 50 wt % carrier. The particle size distribution of the powder was measured by sieving. 10% by weight of the powder exhibited a particle size below 290 micrometers, 50% by weight of the powder exhibited a particle size below 511 micrometers, and 90% by weight of the powder exhibited a particle size below 886 micrometers. The powder was stable to segregation and cohesion, as determined using standard aeration and compressibility tests. The true density of the resulting powder was measured by Helium pynenometry to be 1.8541 g/mL.

The carrier loading formulation was repeated using feed-grade silica to yield a stable, flowable powder with a loading of at least 50 wt % oligosaccharide preparation (dry solids basis) with respect to the final powder. The true density of the resulting powder was measured to be 1.5562 g/mL.

Example 46

Preparation of an Extruded Solid Form

A solid extruded product was prepared by blending 20% of the oligosaccharide preparation of Example 9.2 with semolina and formulated the mixture through a jacketed twin-screw dye extruder to form a flowable powder with a particle size between 0.2 mm and 3.0 mm, with 90% of the mass below 2 mm particle size. The resulting powder was observed to be free-flowing and stable.

Example 47

Preparation of Stable Powder Formulations

The solid formulations, including those of Examples 44-46, were assessed to determine their stability and hygroscopicity. The powders of Examples 45 and 46 were observed to be stable to segregation and agglomeration, while the coarse milled powder of Example 44 was observed to be unstable with respect to segregation.

Sample of each powder formulation to be tested were placed in a sealed climate chambers at 50% relative humidity and 65% relative humidity for up to two-weeks exposure at 25° C. Of the forms tested, several exhibited little or no mass gain upon exposure to humidity and remained flowable after the two-week exposure period. The fine-milled powder of Example 45 was found to be unstable with exposure to humidity.

Example 48

Determination of Residual Catalyst in Oligosaccharide Preparations

The residual acid catalyst content of oligosaccharides preparations was determined by Ion Chromatography. Between 80 and 100 milligrams of a powder formulation of the oligosaccharide preparation (obtained for example as described in Example 44) were dissolved in exactly 1.00 milliliter and centrifuged to remove particulates if necessary. The resulting solution was analyzed by ion chromatography at 30° C. using a Thermo Dionex ICS-3000 System equipped with conductivity detection, a 4×250 mm Ion Pac AS19A column, an Ion Pac AS19G 50 4×50 mm pre-column and a continuously regenerated CR-ATC anion trap column using KOH in water as the eluent. Elution was conducted at 10 mM KOH for the first ten minutes after injection followed by a gradient elution increasing linearly to 55 mM KOH at 25 minutes, then decreasing to 10 mM KOH at 26 minutes, and remaining at 10 mM KOH until the end of the program.

For the oligosaccharide preparation of Example 9.2, the concentration of residual catalyst was determined by reference to a standard calibration curve generated using an authentic sample of (+)-camphor-10-sulfonic acid. A representative batch of the oligosaccharide preparation of Example 9.2 was analyzed and the residual catalyst concentration was determined to be 0.62 mg per gram of 70 wt % syrup.

Example 49

Qualification of the Residual Catalyst Concentration for Batch Acceptance

The residual catalyst determination of Example 48 was compared against a batch acceptance criterion to determine suitability of the batch for further use. The acceptance limit for the concentration of residual catalyst in the product oligosaccharide preparation was preestablished to be <1.0 mg per gram product syrup. The measured value of the residual catalyst was 0.62 mg per gram of product syrup. Therefore, the acceptance criterion was met for the tested batch and the batch was accepted for further use.

Example 50

Formulation of a Syrup Product

The oligosaccharide preparation of Example 9.7 was pH adjusted to a pH of 4.2 with food grade sodium hydroxide according to the procedure of Example 43. The resulting syrup was packaged into a 20 liter carboy with a tamper-resistant cap. Immediately prior to sealing the container, a 500 gram sample was taken and subjected to quality testing. The total solids content of the syrup was confirmed to be greater than 70 wt %, per the methods of FCC APPENDIX X: Carbohydrates (Starches, Sugars, and Related Substances): TOTAL SOLIDS. The reducing sugar content was confirmed to be less than 50% as D-glucose on a dry weight basis according to the method of FCC APPENDIX X: Carbohydrates (Starches, Sugars, and Related Substances): REDUCING SUGARS ASSAY. Sulfated ash was confirmed to be less than 1% on a dry weight basis using the method of FCC APPENDIX II: Physical Tests and Determinations: C. OTHERS: RESIDUE ON IGNITION (Sulfated Ash) Method II (for Liquids). The sulfur dioxide content was confirmed below 40 mg/kg using an optimized Monier Williams method. The lead content was confirmed to be below 1 mg/kg using the method of AOAC International Official Method 2013.06. The total aerobic plate count was confirmed to be below 1000 cfu/g using the methods of CMMEF Chapter 7. Total yeast and mold were confirmed below 100 cfu/g using the method of AACC International Approved Method 42-50. Coliforms were confirmed below 10 MPN/g using the method of the FDA BAM Chapter 4. *E. coli* was confirmed below 3 MPN/g using the method of FDA BAM Chapter 4. *Salmonella* was confirmed to be not detected per a 25 gram sample according to the method of FDA BAM Chapter 5. *Staphylococcus aureus* was confirmed to be below 10 cfu/g using the method of FDA BAM Chapter 12. Color was confirmed by visual inspection to be caramel. The container was sealed, the remaining retention sample was frozen and stored for future reference, and a certificate of analysis was issued for the resulting lot.

Example 51

Preparation of Treated Drinking Water

Drinking water containing 250 ppm of the oligosaccharide preparation of Example 9.7 was prepared as follows. 37 mL of the oligosaccharide syrup of Example 50 and 40 grams of potassium sorbate were added gradually to 50 gallons of potable tap water in a 55 gallon blue-poly drum. The solution was mixed manually using a paddle for 10 minutes at room temperature.

The method was repeated without the incorporation of potassium sorbate.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein can be employed in practicing the invention. It is therefore contemplated that the invention shall also cover any such alternatives, modifications, variations or equivalents.

What is claimed is:

1. A method of modulating the growth of at least one bacterial species in the gastrointestinal tract of a bird, said method comprising: administering a nutritional composition comprising a base nutritional composition and a synthetic oligosaccharide preparation to a bird, wherein said synthetic oligosaccharide preparation comprises at least n fractions of oligosaccharides each having a distinct degree of polymerization selected from 1 to n (DP1 to DPn fractions), wherein n is an integer greater than 3; and wherein each of a DP1 and DP2 fraction independently comprises from about 0.5% to about 15% of anhydro-subunit containing oligosaccharides by relative abundance as determined by mass spectrometry, wherein a level of at least one bacterial species in a gastrointestinal sample from said bird is increased or decreased relative to a level of said at least one bacterial species in a gastrointestinal sample from said bird prior to said administering said nutritional composition to said bird, and wherein said at least one bacterial species is selected from the group consisting of *Odoribacter splanchnicus, Bacteroides dorei, Barnesiella intestinthominis, Bacillus clarus, Butyricimonas faecalis, Oscillibacter* spp., *Campylobacter jejuni, Helicobacter pullorum, Campylobacter coli*, and *Escherichia coli.*

2. A method of modulating the growth of at least one bacterial species in the gastrointestinal tract of a bird, said method comprising: administering a nutritional composition comprising a base nutritional composition and a synthetic oligosaccharide preparation to a bird, wherein said synthetic oligosaccharide preparation comprises at least n fractions of oligosaccharides each having a distinct degree of polymerization selected from 1 to n (DP1 to DPn fractions), wherein n is an integer greater than 3; and wherein each of a DP1 and DP2 fraction independently comprises from about 0.5% to about 15% of anhydro-subunit containing oligosaccharides by relative abundance as determined by mass spectrometry, wherein a level of at least one bacterial species in a gastrointestinal sample from said bird is increased or decreased relative to a level of said at least one bacterial species in a gastrointestinal sample from a comparable control bird, that has been administered a comparable nutritional composition lacking said synthetic oligosaccharide preparation, and wherein said at least one bacterial species is selected from the group consisting of *Odoribacter splanchnicus, Bacteroides dorei, Barnesiella intestinthominis, Bacillus clarus, Butyricimonas faecalis, Oscillibacter* spp., *Campylobacter jejuni, Helicobacter pullorum, Campylobacter coli*, and *Escherichia coli.*

3. The method of claim 2, wherein said method comprises promoting the growth of said at least one bacterial species, and wherein said level of at least one bacterial species in said gastrointestinal sample is increased relative to a level of said at least one bacterial species in a gastrointestinal sample from a comparable control bird, that has been administered a comparable nutritional composition lacking said synthetic oligosaccharide preparation.

4. A method of modulating expression of at least one bacterial protein within the gastrointestinal tract of a bird, said method comprising: administering a nutritional composition comprising a base nutritional composition and a synthetic oligosaccharide preparation to a bird, wherein said synthetic oligosaccharide preparation comprises at least n fractions of oligosaccharides each having a distinct degree of polymerization selected from 1 to n (DP1 to DPn fractions), wherein n is an integer greater than 3; and wherein each of a DP1 and DP2 fraction independently comprises from about 0.5% to about 15% of anhydro-subunit containing oligosaccharides by relative abundance as determined by mass spectrometry, wherein a level of at least one bacterial protein in a gastrointestinal sample is increased or decreased relative to a level of said at least one bacterial protein in a gastrointestinal sample from said bird prior to administration of said nutritional composition to said bird, and wherein said at least one bacterial protein is selected from the group consisting of CAZyme a-L-arabinofuranosidase (GH127), outer membrane receptor associated with the starch utilization system (susC), and starch binding protein (susD).

5. A method of modulating expression of at least one bacterial protein within the gastrointestinal tract of a bird, the method comprising: administering a nutritional composition comprising a base nutritional composition and a synthetic oligosaccharide preparation to a bird, wherein said synthetic oligosaccharide preparation comprises at least n fractions of oligosaccharides each having a distinct degree of polymerization selected from 1 to n (DP1 to DPn fractions), wherein n is an integer greater than 3; and wherein each of a DP1 and DP2 fraction independently comprises from about 0.5% to about 15% of anhydro-subunit containing oligosaccharides by relative abundance as determined by mass spectrometry, and wherein a level of at least one bacterial protein in a gastrointestinal sample is increased or decreased relative to a level of said at least one protein in a gastrointestinal sample from a comparable control bird, that has been administered a comparable nutritional composition lacking said synthetic oligosaccharide preparation, and wherein said at least one bacterial protein is selected from the group consisting of CAZyme a-L-arabinofuranosidase (GH127), outer membrane receptor associated with the starch utilization system (susC), and starch binding protein (susD).

6. The method of claim 4, wherein said level of said at least one bacterial protein in said gastrointestinal sample is decreased relative to said level of said at least one bacterial protein in a gastrointestinal sample from said bird prior to administration of said nutritional composition to said bird.

7. The method of claim 5, wherein said level of said at least one bacterial protein in said gastrointestinal sample is decreased relative to said level of said at least one bacterial protein in a gastrointestinal sample from said a comparable control bird prior to administration of said nutritional composition to said bird.

8. The method of claim 4, wherein said bacterial protein is CAZyme a-L-arabinofuranosidase (GH127).

9. The method of claim 5, wherein said bacterial protein is CAZyme a-L-arabinofuranosidase (GH127).

* * * * *